(12) United States Patent
Bratton et al.

(10) Patent No.: US 7,244,763 B2
(45) Date of Patent: Jul. 17, 2007

(54) COMPOUNDS THAT MODULATE PPAR ACTIVITY AND METHODS OF PREPARATION

(75) Inventors: Larry D. Bratton, Whitmore Lake, MI (US); Xue-Min Cheng, Ann Arbor, MI (US); Noe Erasga, Ann Arbor, MI (US); Gary F. Filzen, Ann Arbor, MI (US); Andrew G. Geyer, Novi, MI (US); Chitase Lee, Ann Arbor, MI (US); Bharat K. Trivedi, Farmington Hills, MI (US); Paul C. Unangst, Ann Arbor, MI (US)

(73) Assignee: Warner Lambert Company LLC, Morris Plains, NJ (US)

( * ) Notice: Subject to any disclaimer, the term of this patent is extended or adjusted under 35 U.S.C. 154(b) by 295 days.

(21) Appl. No.: 10/774,260

(22) Filed: Feb. 6, 2004

(65) Prior Publication Data

US 2004/0209936 A1   Oct. 21, 2004

Related U.S. Application Data

(60) Provisional application No. 60/463,641, filed on Apr. 17, 2003.

(51) Int. Cl.
| | |
|---|---|
| *A61K 31/235* | (2006.01) |
| *A61K 31/38* | (2006.01) |
| *A61K 31/35* | (2006.01) |
| *C07D 405/00* | (2006.01) |
| *C07D 261/06* | (2006.01) |

(52) U.S. Cl. .................. 514/532; 514/448; 514/443; 514/378; 514/336; 514/456; 560/9; 549/51; 549/70; 549/399; 548/247; 546/282.7

(58) Field of Classification Search .......... 560/9; 549/70, 51, 399; 548/247; 546/282.7; 514/532, 514/448, 443, 378, 336, 456
See application file for complete search history.

(56) References Cited

U.S. PATENT DOCUMENTS

| | | | | |
|---|---|---|---|---|
| 6,699,904 | B2 * | 3/2004 | Hayward et al. | 514/535 |
| 6,723,740 | B2 * | 4/2004 | Chao et al. | 514/365 |
| 6,787,552 | B2 * | 9/2004 | Sakuma et al. | 514/256 |
| 6,867,224 | B2 * | 3/2005 | Cheng et al. | 514/365 |
| 6,964,983 | B2 * | 11/2005 | Auerbach et al. | 514/568 |
| 6,987,118 | B2 * | 1/2006 | Chang | 514/307 |
| 7,005,440 | B1 * | 2/2006 | Jayyosi et al. | 514/375 |
| 2003/0207915 | A1 | 11/2003 | Cheng et al. | |
| 2003/0207924 | A1 | 11/2003 | Cheng et al. | |
| 2003/0225158 | A1 | 12/2003 | Auerbach et al. | |

FOREIGN PATENT DOCUMENTS

| | | |
|---|---|---|
| EP | 0028063 A1 | 8/2000 |
| EP | 0930299 A1 | 9/2003 |
| GB | 2058785 | 5/2000 |
| WO | WO 97/28137 A1 | 10/1997 |
| WO | WO 97/28149 | 10/1997 |
| WO | WO 01/00603 A1 | 6/2001 |
| WO | WO 01/16120 A1 | 10/2001 |
| WO | WO 02/16331 A1 | 3/2002 |
| WO | WO 02/50047 A1 | 5/2002 |
| WO | WO 02/50048 A1 | 5/2002 |
| WO | WO 02/100403 | 5/2002 |
| WO | WO02/50047 A1 | 6/2002 |
| WO | WO 02/062774 A1 | 6/2002 |
| WO | WO 02/092590 A1 | 9/2002 |
| WO | WO 02/096904 A1 | 9/2002 |
| WO | WO02/18355 A1 | 10/2002 |
| WO | WO 02/102780 A1 | 10/2002 |
| WO | WO 03/011842 A1 | 1/2003 |
| WO | WO 03/024395 A2 | 2/2003 |
| WO | WO 2004/000315 A1 | 3/2004 |
| WO | WO 2004/000762 A2 | 7/2004 |
| WO | WO 2004/000785 A2 | 7/2004 |

OTHER PUBLICATIONS

G. Romussi et al., Spectral Properties of Mono- and Dihydroxychromones, J Heterocyclic Chem vol. 13, p. 211 (1976).
T. Gordon et al., High Density Lipoprotein As A Protective Factor Against Coronary Heart Disease, The American Journal of Medicine, vol. 62, May 1977 707-714.
W.R. Oliver et al., A selective peroxisome proliferator-activated receptor delta agonist promotes reverse cholesterol transport, PNAS, vol. 98 No. 9 5306-5311, 1998.

\* cited by examiner

*Primary Examiner*—Deborah C. Lambkin
(74) *Attorney, Agent, or Firm*—Mehdi Ganjeizadeh; Michelle Sherwood; Charles W. Ashbrook

(57) ABSTRACT

This invention relates to compounds that alter PPAR activity. The invention also relates to pharmaceutically acceptable salts of the compounds, pharmaceutically acceptable compositions comprising the compounds or their salts, and methods of using them as therapeutic agents for treating or preventing dyslipidemia, hypercholesterolemia, obesity, hyperglycemia, atherosclerosis, hypertriglyceridemia and hyperinsulinemia in a mammal. The present invention also relates to methods for making the disclosed compounds.

46 Claims, No Drawings

COMPOUNDS THAT MODULATE PPAR ACTIVITY AND METHODS OF PREPARATION

CROSS REFERENCE TO RELATED APPLICATION

This Utility application claims benefit of U.S. Provisional Application Ser. No. 60/463,641 filed Apr. 17, 2003.

FIELD OF THE INVENTION

The present invention relates to compounds and pharmaceutical formulations that can be used to treat conditions mediated by nuclear hormone receptors, more specifically, to compounds and pharmaceutical formulations that modulate Peroxisome Proliferator Activation Receptor, ("PPAR") activity.

BACKGROUND OF THE INVENTION

Hypercholesterolemia, hyperlipidemia, and diabetes are well recognized risk factors in the onset of atherosclerosis and coronary heart disease. Hypercholesterolemia and hyperlipidemia are characterized by excessively high levels of blood cholesterol and lipids. The blood cholesterol pool is generally dependent on dietary uptake of cholesterol from the intestine and biosynthesis of cholesterol throughout the body, especially the liver. The majority of cholesterol in plasma is carried on apolipoprotein B-containing lipoproteins, such as low-density lipoproteins (LDL) and very-low-density lipoproteins (VLDL). The risk of coronary artery disease in man increases when LDL and VLDL levels increase. Conversely, high levels of cholesterol carried in high-density lipoproteins (HDL) is protective against coronary artery disease (Am. J. med., 1977; 62:707–714).

The statins represent perhaps the most important class of lipid-lowering drugs. These compounds inhibit HMG-CoA reductase which is implicated in the rate-limiting step in cellular cholesterol biosynthesis. Representative statins include atorvastatin, lovastatin, pravastatin, and simvastatin. The effectiveness of these compounds depends on LDL receptor regulation. Other important antilipidemia drugs include fibrates such as gemfibril and clofibrate, bile acid sequestrants such as cholestyramine and colestipol, probucol, and nicotinic acid analogs.

To date, a number of oral antidiabetic agents have been developed. The most commonly used hypoglygemic drugs are the sulfonylureas. Sulfonylureas are generally used to stimulate insulin. The biguanide metformin is generally used to improve insulin sensitivity and to decrease hepatic glucose output. Acarbose is used to limit postprandial hyperglycemia. Thiazolidine 2,4 diones are used to enhance insulin action without increasing insulin secretion.

Peroxisome Proliferator Activation Receptors (PPAR) are implicated in a number of biological processes and disease states including hypercholesterolemia, hyperlipidemia, and diabetes. PPARs are members of the nuclear receptor superfamily of transcription factors that includes steroid, thyroid, and vitamin D receptors. They play a role in controlling expression of proteins that regulate lipid metabolism. Furthermore, the PPARs are activated by fatty acids and fatty acid metabolites. There are three PPAR subtypes PPAR α, PPAR β (also referred to as PPAR δ), and PPAR γ. Each receptor shows a different pattern of tissue expression, and differences in activation by structurally diverse compounds. PPAR γ, for instance, is expressed most abundantly in adipose tissue and at lower levels in skeletal muscle, heart, liver, intestine, kidney, vascular endothelial and smooth muscle cells as well as macrophages. PPAR receptors are associated with the regulation of insulin sensitivity and blood glucose levels, macrophage differentiation, inflammatory response, and cell differentiation. Accordingly, PPARs have been associated with obesity, diabetes, carcinogenesis, hyperplasia, atherosclerosis, hyperlipidemia, and hypercholesterolemia.

In addition, PPARα agonists lower plasma triglycerides and LDL cholesterol and are therefore useful in treating hypertriglyceridemia, hyperlipidemia and obesity. PPAR γ is associated with the development of non-insulin-dependent diabetes mellitus (NIDDM), hypertension, coronary artery disease, hyperlipidemia and certain malignancies. Finally, activation of PPAR β has been demonstrated to increase HDL levels. (Leibowitz, WO97/28149, August 1997.) More recently, a PPAR β selective agonist was reported to have shown a dose-related increase in serum HDL-C and decrease in LDL-C and VLDL-TG in insulin-resistant middle aged rhesus monkeys. (W. R. Oliver et al., PNAS, v. 98, pp. 5306–5311, 2001)

Antilipidemic and antidiabetic agents are still considered to have non-uniform effectiveness. The effectiveness of antidiabetic and antilipidemic therapies is limited, in part because of poor patient compliance due to unacceptable side effects. These side effects include diarrhea and gastrointestinal discomfort, and in the case of antidiabetics, edema, hypoglycemia and hepatoxicity. Furthermore, each type of drug does not work equally well in all patients.

For the reasons set forth above, there is a need for novel antilipidemic and antidiabetic agents that can be used alone or in combination. Furthermore, activation of PPARβ alone or in combination with the simultaneous activation of PPAR α and/or PPAR γ may be desirable in formulating a treatment for hyperlipidemia in which HDL is increased and LDL lowered.

SUMMARY OF THE INVENTION

The present invention provides compounds capable of modulating PPAR activity. More specifically, the present invention provides a compound having a Formula (I),

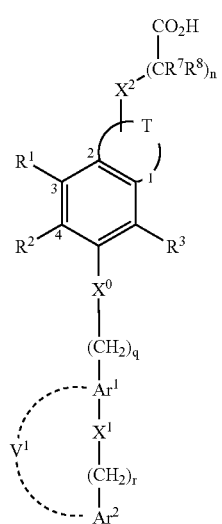

Formula I a pharmaceutically acceptable salt, ester, amide or prodrug thereof, or a pharmaceutically acceptable salt of the prodrug wherein:

$X^0$ and $X^1$ are each independently absent, O, S, $NR^4$, —$CH_2$—$CH_2$—, —CH=CH, or —C≡C—; $Ar^1$ and $Ar^2$ are each independently absent or unsubstituted or substituted aryl or heteroaryl,

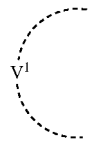

is absent; or when present,

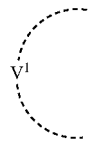

is a saturated or unsaturated hydrocarbon chain which is substituted or unsubstituted, wherein said chain has from 1 to 4 atoms so that

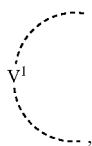

$Ar^1$, $X^1$, $(CH_2)_r$ and $Ar^2$, together form a five to eight membered ring; T is a saturated or unsaturated, substituted or unsubstituted hydrocarbon chain or hydrocarbon-heteroatom chain having from 3 to 6 atoms wherein the carbon atom of position 1 is connected to the carbon atom of position 2 to form a five to eight member ring wherein the

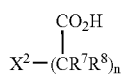

is attached to a substitutionally available position of said ring; $X^2$ is absent, O, S, or $NR^4$; $R^1$, $R^2$, and $R^3$ are independently hydrogen, lower alkyl, lower alkoxy, lower thioalkoxy, —$O(CH_2)_pCF_3$, halogen, nitro, cyano, —OH, —SH, —$CF_3$, $S(O)_p$Alkyl, $S(O)_p$Aryl, —$(CH_2)_nOR^4$, or —$(CH_2)_mNR^5R^6$, $COR^4$, —$CONR^5R^6$, —$CO_2R^4$, or —$NR^5R^6$ or $R^1$ and $R^2$ are joined together to form a substituted or unsubstituted, saturated or unsaturated cyloalkyl or heterocycloalkyl ring; $R^4$ is hydrogen, alkyl, alkenyl, alkynyl, acyl, $SO_2$Aryl, $SO_2$Alkyl or aryl; $R^5$ and $R^6$ are independently hydrogen, alkyl, alkenyl, alkynyl, cycloalkyl, $SO_2$Alkyl aryl or $SO_2$Aryl, or joined together to form a 4 to 7 member ring having 0 to 3 heteroatoms; $R^7$ and $R^8$ are independently H, lower alkyl, halo, or $R^7$ and $R^8$ taken together form a 3–6 membered hydrocarbon ring, optionally containing a heteroatom;

m is an integer from 0 to 5; n is an integer from 0 to 5; and p is an integer from 0 to 2.

q is an integer from 0 to 10; and r is an integer from 0 to 10.

The present invention further provides a compound having a Formula II:

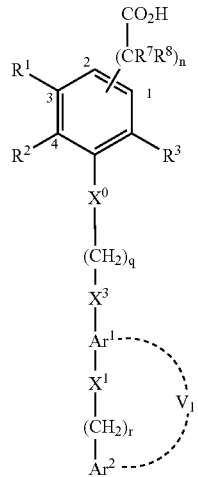

Formula (II)

a pharmaceutically acceptable salt, ester, amide or prodrug thereof, or a pharmaceutically acceptable salt of the prodrug wherein:

$X^3$ is O, C=O, S, $CHOR^{11}$, absent or $NR^4$; $R^{11}$ is lower alkyl, aryl, acyl, —$SO_2$Alkyl- or —$SO_2$Aryl, absent or $NR^4$; and $R^1$, $R^2$, $R^3$, $R^4$, $R^5$, $R^6$, $R^7$, $R^8$, $X^0$, $X^1$, an $X^2$, $Ar^1$, $Ar^2$,

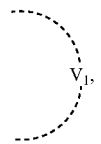

n, r and q are as defined above.

The present invention further provides a pharmaceutical composition containing a compound of Formula I or Formula II as set forth above, or the pharmaceutically acceptable salt, ester, amide or prodrug thereof, or the pharmaceutically acceptable salt of the prodrug and a pharmaceutically acceptable carrier, diluent, or vehicle.

Further, the present invention provides a method of treating, preventing or controlling non-insulin dependent diabetes mellitus, hyperglycemia, obesity, atherosclerosis, hyperlipidemia, hypercholesterolemia, hypertryglyceridemia, hyperinsulinemia, and various glucose related disorders in a mammal by administering to the mammal in need thereof a therapeutically effective amount of a compound of Formula I or Formula II as set forth above, or the pharmaceutically acceptable salt, ester, amide or prodrug thereof, or the pharmaceutically acceptable salt of the prodrug.

Further, the present invention provides inter alia the following compounds: [6-(4'-Trifluoromethyl-biphenyl-4-ylmethylsulfanyl)-chroman-2-yl]-acetic acid; {6-[4-(5-Trifluoromethyl-pyridin-2-yl)-benzylsulfanyl]-chroman-2-yl}- acetic acid; {6-[4-(2,5-Dichloro-benzyloxy)-benxylsulfa-nyl]-chroman-2-yl}-acetic acid; {6-[4-(4-Trifluoromethyl-benzyloxy)-benzylsulfanyl]-chroman-2-yl}-acetic acid; {6-[5-(4-Trifluoromethyl-phenyl)-isoxazol-3-ylmethylsulfany]-chroman-2-yl}-acetic acid; {6-[3-(4-Trifluoromethyl-benzyloxy)-benzylsulfanyl]-chroman-2-yl}-acetic acid; {6-[2-(4-Trifluoromethyl-phenyl)-thiazol-4-ylmethoxy]-benzo[b]thiophen-3-yl}-acetic acid; {6-[4-(4-Trifluoromethyl-benzyloxy)-benzyloxy]-benzo[b]thiophen-3-yl}-acetic acid; {6-[2-(4-Trifluoromethyl-benzyloxy)-benzyloxy]-benzo[b]thiophen-3-yl}-acetic acid; and pharmaceutically acceptable salts thereof.

Further, the present invention provides a compound having a formula (IA),

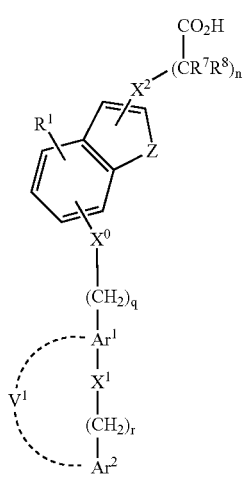

Formula (IA)

a pharmaceutically acceptable salt, ester, amide, or prodrug thereof, or a pharmaceutically acceptable salt of the prodrug wherein: Z=S, O or $NR^4$, and $Ar^1$, $Ar^2$,

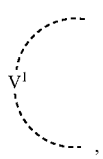

$X^0$, $X^1$, $X^2$, $R^1$, $R^4$, $R^7$, $R^8$, n, q and r are as defined for Formula I above.

Further, the present invention provides inter alia the following compounds: {6-[4-(4-Trifluoromethyl-benzyloxy)-benzyloxy]-benzo[b]thiophen 3-yl}-acetic acid; {6-[5-(4-Trifluoromethyl-phenyl)-isoxazol-3-ylmethoxy]-benzo[b]thiophen-3-yl}-acetic acid; {6-[3-(4-Trifluoromethyl-benzyloxy)-benzyloxy]-benzo[b]thiphen-3-yl}-acetic acid; {6-[2-(4-Trifluoromethyl-phenyl)-thiazol-4-ylmethoxy]-benzo[b]thiophen-3-yl}-acetic acid; {6-[5-(4-Chloro-phenyl)-isoxazol-3-ylmethoxy]-benzo[b]thiophen-3-yl}-acetic acid; and pharmaceutically acceptable salts thereof.

Further, the present invention provides a compound having a Formula III,

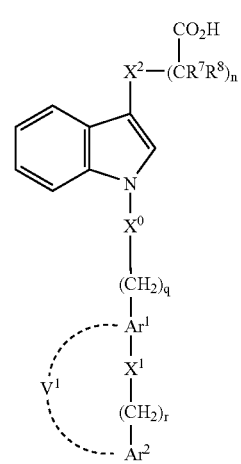

Formula (III)

a pharmaceutically salt, ester amide or prodrug thereof, or a pharmaceutically acceptable salt of the prodrug wherein: $Ar^1$, $Ar^2$,

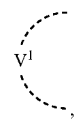

$X^0$, $X^1$, $X^2$, $R^7$, $R^8$, n q and r are as defined above for Formula I.

Further, the present invention provides inter alia the following compounds: 3-{1-[3-(4-Trifluoromethyl-benzyloxy)-benzyl]-1H-indol-3yl}-propionic acid; 3-{1-[4-(4-Trifluoromethyl-benzyloxy)-benzyl]-1H-indol-3-yl}-propionic acid; 3-[1-(4'-Trifluoromethyl-biphenyl-4-ylmethyl)-1H-indol-3-yl]-propionic acid; {1-[3-(4-Trifluoromethyl-benzyloxy)-benzyl]-1H-indol-3-yl}-acetic acid, and pharmaceutically acceptable salts thereof.

Further, the present invention provides a compound havingFormula IV,

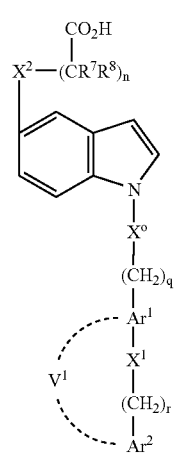

Formula (IV)

a pharmaceutically acceptable salt, ester, amide, or prodrug thereof, or a pharmaceutically acceptable salt of the prodrug wherein: Ar¹, Ar²,

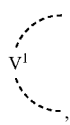

X⁰, X¹, X², R⁷, R⁸, n, q and r are as defined above for Formula I.

Further still, the present invention provides inter alia the following compounds: [1-(4'-Trifluoromethyl-biphenyl-4-ylmethyl)-1H-indol-5-yloxyl]-acetc acid, [1-(4'-Trifluoromethyl-biphenyl-4-ylmethyl)-1H-indol-4-yloxy]-acetic acid; [6-(4'-Trifluoromethyl-biphenyl-4-ylmethylsulfanyl)-chroman-2-yl]-acetic acid; {6-[5-(4-Trifluoromethyl-phenyl)-isoxazol-3-ylmethylsulfany]-chroman-2-yl}-acetic acid; {6-[2-(4-Trifluoromethyl-phenyl)-thiazol-4-ylmethoxy]-benzo[b]thiophen-3-yl}-acetic acid; and pharmaceutically acceptable salts thereof.

Yet further, the present invention provides a compound having a Formula IIA,

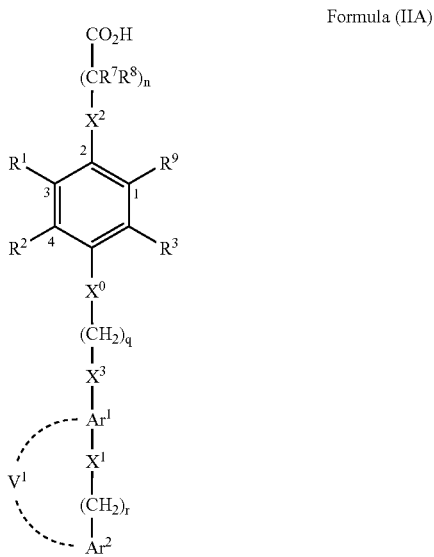

Formula (IIA)

a pharmaceutically acceptable salt, amide, ester or prodrug thereof, or a pharmaceutically acceptable salt of the prodrug wherein: $X^1$ and $X^3$ are each independently O, C=O, S, CHOR¹¹, absent or NR⁴; R¹, R², R³ and R⁹ are independently hydrogen, lower alkyl, lower alkoxy, lower thioalkoxy, —O(CH₂)$_p$CF₃, halogen, nitro, cyano, —OH, —SH, —CF₃, S(O)$_p$Alkyl, S(O)$_p$Aryl, —(CH₂)$_m$OR⁴, or —(CH₂)$_m$NR¹R⁶, —COR⁴, —CO₂H, —CO₂R!, or —NR⁵R⁶, or R¹ and R² are joined together to form a substituted or unsubstituted, saturated or unsaturated cycloalkyl or heterocycloalkyl ring; R¹¹ is lower alkyl, aryl, acyl, —SO₂Alkyl- or —SO₂Aryl, absent or NR⁴; and R⁴, R⁵, R⁶, R⁷, R⁸, Ar¹, Ar², X¹, X², m, n, p, q and r are as defined above for Formula I.

Further, the invention provides inter alia the following compounds: {6-[5-(4-Methoxymethyl-phenyl)-isoxazol-3-ylmethoxy]-benzo[b]thiophen-3-yl}-acetic acid; {6-[5-(3-Methoxymethyl-phenyl)-isoxazol-3-ylmethoxy-benzo[b]thiophen-3-yl}-acetic acid; {6-[5-(4-Methanesulfonyloxy-phenyl)-isoxazol-3-ylmethoxy]-benzo[b]thiophen-3-yl}-acetic acid; {6-[5-(3-Methanesulfonyloxy-phenyl)-isoxazol-3-ylmethoxy]-benzo[b]thiophen-3-yl}-acetic acid; {6-[5-(4-Methoxymethyl-phenyl)-isoxazol-3-ylmethoxy]-4-methyl-benzo[b]thiophen-3-yl}-acetic acid; {6-[5-(3-Methoxymethyl-phenyl)-isoxazol-3-ylmethoxy]-4-methyl-benzo[b]thiophen-3-yl}-acetic acid; {6-[5-(4-Methanesulfonyloxy-phenyl)-isoxazol-3-ylmethoxy]-4-methyl-benzo[b]thiophen-3-yl}-acetic acid; {6-[5-(3-Methanesulfonyloxy-phenyl)-isoxazol-3-ylmethoxy]-4-methyl-benzo[b]thiophen-3-yl}-acetic acid; {5-Methoxy-6-[5-(4-methoxymethyl-phenyl)-isoxazol-3-ylmethoxy]-benzo[b]thiophen-3-yl}-acetic acid; {5-Methoxy-6-[5-(3-methoxymethyl-phenyl)-isoxazol-3-ylmethoxy]-benzo[b]thiophen-3-yl}-acetic acid; {6-[5-(4-Methanesulfonyloxy-phenyl)-isoxazol-3-ylmethoxy]-5-methoxy-benzo[b]thiophen-3-yl}-acetic acid; {6-[5-(3-Methanesulfonyloxy-phenyl)-isoxazol-3-ylmethoxy]-5-methoxy-benzo[b]thiophen-3-yl}-acetic acid; {6-[5-(4-Methoxymethyl-phenyl)-isoxazol-3-ylmethoxy]-benzofuran-3-yl}-acetic acid; {6-[5-(3-Methoxymethyl-phenyl)-isoxazol-3-ylmethoxy]-benzofuran-3-yl}-acetic acid; {6-[5-(4-Methanesulfonyloxy-phenyl)-isoxazol-3-ylmethoxy]-benzofuran-3-yl}-acetic acid; {6-[5-(3-Methanesulfonyloxy-phenyl)-isoxazol-3-ylmethoxy]-benzofuran-3-yl}-acetic acid; {6-[5-(4-Methoxymethyl-phenyl)-isoxazol-3-ylmethoxy]-4-methyl-benzofuran-3-yl}-acetic acid; {6-[5-(3-Methoxymethyl-phenyl)-isoxazol-3-ylmethoxy]-4-methyl-benzofuran-3-yl}-acetic acid; {6-[5-(4-Methanesulfonyloxy-phenyl)-isoxazol-3-ylmethoxy]-4-methyl-benzofuran-3-yl}-acetic acid; {6-[5-(3-Methanesulfonyloxy-phenyl)-isoxazol-3-ylmethoxy]-4-methyl-benzofuran-3-yl}-acetic acid; {5-Methoxy-6-[5-(4-methoxymethyl-phenyl)-isoxazol-3-ylmethoxy]-benzofuran-3-yl}-acetic acid; {5-Methoxy-6-[5-(3-methoxymethyl-phenyl)-isoxazol-3-ylmethoxy]-benzofuran-3-yl}-acetic acid; {6-[5-(4-Methanesulfonyloxy-phenyl)-isoxazol-3-ylmethoxy]-5-methoxy-benzofuran-3-yl}-acetic acid; {6-[5-(3-Methanesulfonyloxy-phenyl)-isoxazol-3-ylmethoxy]-5-methoxy-benzofuran-3-yl}-acetic acid; {7-[5-(4-Methoxymethyl-phenyl)-isoxazol-3-ylmethoxy]-indan-4-yloxy}-acetic acid; {7-[5-(3-Methoxymethyl-phenyl)-isoxazol-3-ylmethoxy]-indan-4-yloxy}-acetic acid; {7-[5-(4-Methanesulfonyloxy-phenyl)-isoxazol-3-ylmethoxy]-indan-4-yloxy}-acetic acid; {7-[5-(3-Methanesulfonyloxy-phenyl)-isoxazol-3-ylmethoxy]-indan-4-yloxy}-acetic acid; {4-[5-(4-Methoxymethyl-phenyl)-isoxazol-3-ylmethoxy]-2-methyl-phenoxy}-acetic acid; {4-[5-(3-Methoxymethyl-phenyl)-isoxazol-3-ylmethoxy]-2-methyl-phenoxy}-acetic acid; {4-[5-(4-Methanesulfonyloxy-phenyl)-isoxazol-3-ylmethoxy]-2-methyl-phenoxy}-acetic acid; {4-[5-(3-Methanesulfonyloxy-phenyl)-isoxazol-3-ylmethoxy]-2-methyl-phenoxy}-acetic acid; and pharmaceutically acceptable salts thereof.

DETAILED DESCRIPTION OF THE INVENTION

The present invention provides a compound having a Formula (I),

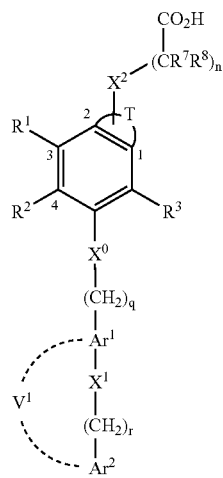

Formula I a pharmaceutically acceptable salt, ester, amide or prodrug thereof, or a pharmaceutically acceptable salt of the prodrug wherein: $X^0$ and $X^1$ are each independently absent, O, S, $NR^4$, —CH2—CH$_2$—, —CH=CH—, or —C≡C—; $Ar^1$ and $Ar^2$ are each independently absent or unsubstituted or substituted aryl or heteroaryl,

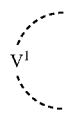

is absent; or when present,

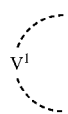

is a saturated or unsaturated hydrocarbon chain which is substituted or unsubstituted, wherein said chain has from 1 to 4 atoms so that

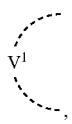

$Ar^1$, $X^1$, $(CH_2)_r$ and $Ar^2$, together form a five to eight membered ring; T is a saturated or unsaturated, substituted or unsubstituted hydrocarbon chain or hydocarbon-heteroatom chain having from 3 to 6 atoms wherein the carbon atom of position 1 is connected to the carbon atom of position 2 to form a five to eight member ring wherein the

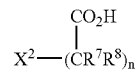

is attached to a substitutionally available position of said ring; $X^2$ is absent, O, S, or $NR^4$; $R^1$, $R^2$, and $R^3$ are independently hydrogen, lower alkyl, lower alkoxy, lower thioalkoxy, —O(CH$_2$)$_p$CF$_3$, halogen, nitro, cyano, —OH, —SH, —CF$_3$, S(O)$_p$Alkyl, S(O)$_p$Aryl, —(CH$_2$)$_m$OR$^4$, or —(CH$_2$)$_m$NR$^5$R$^6$, COR$^4$, —CONR$^5$R$^6$, —CO$_2$R$^4$, or —NR$^5$R$^6$ or $R^1$ and $R^2$ are joined together to form a substituted or unsubstituted, saturated or unsaturated cyloalkyl or heterocycloalkyl ring; $R^4$ is hydrogen, alkyl, alkenyl, alkynyl, acyl, SO$_2$Aryl, SO$_2$Alkyl or aryl; $R^5$ and $R^6$ are independently hydrogen, alkyl, alkenyl, alkynyl, cycloalkyl, SO$_2$Alkyl aryl or SO$_2$Aryl, or joined together to form a 4 to 7 member ring having 0 to 3 heteroatoms; $R^7$ and $R^8$ are independently H, lower alkyl, halo, or $R^7$ and $R^8$ taken together form a 3–6 membered hydrocarbon ring, optionally containing a heteroatom;

m is an integer from 0 to 5; n is an integer from 0 to 5; p is an integer from 0 to 2; q is an integer from 0 to 10; and r is an integer from 0 to 10.

The present invention further provides a compound having a Formula II:

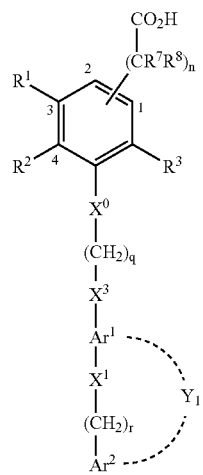

Formula (II)

a pharmaceutically acceptable salt, amide, ester or prodrug thereof, or a pharmaceutically acceptable salt of the prodrug wherein $X^3$ is O, C=O, S, CHOR$^{11}$, where $R^{11}$ is lower alkyl, aryl, acyl, —SO$_2$Alkyl, —SO$_2$Aryl, absent or NR$^4$; and $R^1$, $R^2$, $R^3$, $R^4$, $R^5$, $R^6$, $R^7$, $R^8$, $X^0$, $X^1$, $X^2$, $Ar^1$, $Ar^2$,

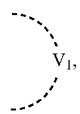

n, r and q are as defined above for Formula I.

The present invention further provides a compound having a Formula I as described above, the pharmaceutically acceptable salt, ester, amide or prodrug thereof, or the pharmaceutically acceptable salt of the prodrug, wherein $X^0$ is S or O; $X^1$ is absent O or S; $Ar^1$ and $Ar^2$ are each independently absent, or unsubstituted or substituted aryl or heteroaryl;

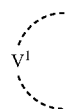

is absent; q is 1; and r is 0 or 1. The present invention further provides the compound, pharmaceutically acceptable salt, ester, amide or prodrug thereof, or the pharmaceutically acceptable salt of the prodrug, wherein T is substituted with 1 or more substituents selected from the group consisting of lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$-C$_6$ alkyl, —NH$_2$, —NHC$_1$-C$_6$ alkyl, —CONR'R", or —N(C$_1$-C$_6$alkyl)$_2$; and R' and R" are independently alkyl, akenyl, alkynyl, aryl, or joined together to form a 4 to 7 member ring.

The present invention further provides a compound having a Formula I as described above, the pharmaceutically acceptable salt, ester, amide or prodrug thereof, or the pharmaceutically acceptable salt of the prodrug, wherein $X^0$ is S or O; $X^1$ is 0 or absent; and $Ar^1$ and $Ar^2$ are each independently unsubstituted or substituted aryl or heteroaryl.

The present invention further provides a compound having a Formula I as described above, the pharmaceutically acceptable salt, ester, amide or prodrug thereof, or the pharmaceutically acceptable salt of the prodrug, wherein T is —CH$_2$CH$_2$CO—O—, —CH$_2$—CH$_2$—O—CO—, —CH$_2$—CH$_2$—CH$_2$—CH$_2$—, —HC=CH—HC=CH—, —N=CH—HC=CH—, —HC=N—HC=CH—, —HC=CH—N=CH—, —HC=CH—HC=N—, —CH$_2$—CH$_2$—CH$_2$—, —CH$_2$—CH$_2$—O—CH$_2$—, —CH$_2$—HC=CH—, —CH$_2$CH$_2$—NH—CH$_2$—, —COCH=CH—O—, —O—CH=CH—CO—, —O—CH=CH—, —CH=CH—O—, —O—CH$_2$—CH=CH—, —CH=CH—CH$_2$—O—, —CH$_2$—CH$_2$—CO—NR$^4$, —CH$_2$—CH$_2$—CO—CH$_2$—, —CH$_2$—CH$_2$—NR$^4$—CH$_2$—, —CH$_2$—CH$_2$—NR$^4$—CH$_2$—CH$_2$—, —CH=CH—NR$^4$—, —NR$^4$—CH=CH—, —CH=CH—CH$_2$—, —CH$_2$—CH$_2$—NR$^4$—, —NR$^4$—CH$_2$—CH$_2$—, —O—CH$_2$—CH$_2$—, —O—CH$_2$—CH$_2$—CH$_2$—, —CH$_2$—CH$_2$—O—, —CH$_2$—CH$_2$—CH$_2$—O—, —O—CH(CH$_3$)—CH$_2$—CH$_2$—, —CH$_2$—CH$_2$—CH(CH$_3$)—O—, —CH$_2$—CH$_2$—CH$_2$—NR$^4$—, —NR$^4$—CH$_2$—CH$_2$—CH$_2$—, —CH$_2$—CH$_2$—CO—NR$^4$—, —NR$^4$—CO—CH$_2$—CH$_2$—, —O—NR$^4$—CO—, —CO—NR$^4$—O—, —O—CH$_2$—CH$_2$—CH$_2$—, —CH$_2$—CH$_2$—CH$_2$—O—, —CH$_2$—CH$_2$—NR$^4$—CO—, —CH$_2$—CH$_2$—CH$_2$—CO—, —CO—CH$_2$—CH$_2$—CH$_2$—, —NR$^4$—CO—CH$_2$—CH$_2$—, —CO—NR$^4$—CH$_2$—CH$_2$—, —CH$_2$—CH$_2$—CO—, —CH$_2$—CO—CH$_2$—, —CO—CH$_2$—CH$_2$—, —S—C=C—, —C=C—S—, —S—C—C, —C=C—S—, —S—C=C—C—, —C=C—C—S—, —C=C—C—S—, —C—C=C—S—, —S—C=C—C—, or —S—C=C=C—.

The present invention further provides a compound having a Formula I as described above, the pharmaceutically acceptable salt, ester, amide or prodrug thereof, or the pharmaceutically acceptable salt of the prodrug, wherein $X^0$ is S; $X^1$ is absent; $Ar^1$ is substituted phenyl;

$Ar^2$ is phenyl;

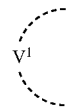

is absent; q is 1; and r is 0 or 1.

The present invention further provides a compound having a Formula I as described above, the pharmaceutically acceptable salt, ester, amide or prodrug thereof, or the pharmaceutically acceptable salt of the prodrug, wherein q is 1.

The present invention further provides a compound having a Formula I as described above, the pharmaceutically acceptable salt, ester, amide or prodrug thereof, or the pharmaceutically acceptable salt of the prodrug, wherein $Ar^1$ is substituted or unsubstituted phenyl.

The present invention further provides a compound having a Formula I as described above, the pharmaceutically acceptable salt, ester, amide or prodrug thereof, or the pharmaceutically acceptable salt of the prodrug, wherein $Ar^2$ is 4-trifluoromethylphenyl.

The present invention further provides a compound having a Formula I as described above, the pharmaceutically acceptable salt, ester, amide or prodrug thereof, or the pharmaceutically acceptable salt of the prodrug, wherein

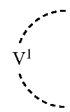

is absent.

The present invention further provides a compound having a Formula I as described above, the pharmaceutically acceptable salt, ester, amide or prodrug thereof, or the pharmaceutically acceptable salt of the prodrug, wherein

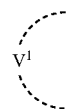

is (CH$_2$)$_t$ and t is an integer from 1 to 4.

The present invention further provides a compound having a Formula I as described above, the pharmaceutically acceptable salt, ester, amide or prodrug thereof, or the pharmaceutically acceptable salt of the prodrug, wherein

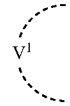

is substituted with at least one substituent selected from the group consisting of lower alkyl, lower alkoxy, lower thioalkoxy, —O(CH$_2$)$_{0-2}$CF$_3$, halogen, nitro, cyano, =O, =S, —OH, —SH, —CF$_3$, —OCF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring.

The present invention further provides a pharmaceutical composition comprising a compound having a Formula I or a Formula II as described above, or the pharmaceutically acceptable salt, ester, amide or prodrug thereof, or the pharmaceutically acceptable salt of the prodrug and a pharmaceutically acceptable carrier, diluent, or vehicle.

The present invention further provides a method of treating, preventing or controlling non-insulin dependent diabetes mellitus in a mammal comprising administering to the mammal in need thereof a therapeutically effective amount of a compound of Formula I or Formula II as described above, or the pharmaceutically acceptable salt, ester, amide or prodrug thereof, or the pharmaceutically acceptable salt of the prodrug.

The present invention further provides a method of treating, preventing or controlling obesity in a mammal comprising administering to the mammal in need thereof a therapeutically effective amount of a compound of Formula I or Formula II as described above, or the pharmaceutically acceptable salt, ester, amide or prodrug thereof, or the pharmaceutically acceptable salt of the prodrug.

The present invention further provides a method of treating, preventing or controlling hyperglycemia in a mammal comprising administering to the mammal in need thereof a therapeutically effective amount of a compound of Formula I or Formula II as described above, or the pharmaceutically acceptable salt, ester, amide or prodrug thereof, or the pharmaceutically acceptable salt of the prodrug.

The present invention further provides a method of treating, preventing or controlling hyperlipidemia in a mammal comprising administering to the mammal in need thereof a therapeutically effective amount of a compound of Formula I or Formula II as described above, or the pharmaceutically acceptable salt, ester, amide or prodrug thereof, or the pharmaceutically acceptable salt of the prodrug.

The present invention further provides a method of treating, preventing or controlling hypercholesteremia in a mammal comprising administering to the mammal in need thereof a therapeutically effective amount of a compound of Formula I or Formula II as described above, or the pharmaceutically acceptable salt, ester, amide or prodrug thereof, or the pharmaceutically acceptable salt of the prodrug.

The present invention further provides a method of treating, preventing or controlling atherosclerosis in a mammal comprising administering to the mammal in need thereof a therapeutically effective amount of a compound of Formula I or Formula II as described above, or the pharmaceutically acceptable salt, ester, amide or prodrug thereof, or the pharmaceutically acceptable salt of the prodrug.

The present invention further provides a method of treating, preventing or controlling hypertriglyceridemia in a mammal comprising administering to the mammal in need thereof a therapeutically effective amount of a compound of Formula I or Formula II as described above, or the pharmaceutically acceptable salt, ester, amide or prodrug thereof, or the pharmaceutically acceptable salt of the prodrug.

The present invention further provides a method of treating, preventing or controlling hyperinsulinemia in a mammal comprising administering to the mammal in need thereof a therapeutically effective amount of a compound of Formula I or Formula II as described above, or the pharmaceutically acceptable salt, ester, amide or prodrug thereof, or the pharmaceutically acceptable salt of the prodrug.

The present invention further provides a method of treating a patient exhibiting glucose disorders associated with circulating glucocorticoids, growth hormone, catecholamines, glucagon, or parathyroid hormone, comprising administering to the patient a therapeutically effective amount of a compound of Formula I or Formula II as described above, or the pharmaceutically acceptable salt, ester, amide or prodrug thereof, or the pharmaceutically acceptable salt of the prodrug.

The present invention further provides a compound of Formula II as described above, the pharmaceutically acceptable salt, ester, amide or prodrug thereof, or the pharmaceutically acceptable salt of the prodrug, wherein X$^3$ is NR$^4$ or C=O.

The present invention further provides the compound of Formula II as described above, the pharmaceutically acceptable salt, ester, amide or prodrug thereof, or the pharmaceutically acceptable salt of the prodrug, wherein Ar$^2$ is chloro-phenyl, dichloro-phenyl-, trichlorophenyl, fluorophenyl-, difluorophenyl, trifluorophenyl, trifluoromethylphenyl, or fluoro-trifluoromethyl-phenyl-; and wherein Ar$^1$ is absent.

The present invention further provides a compound having Formula 1a, Formula 1b, Formula 1c, Formula 1d, Formula 1e, Formula 1f, Formula 1g, or Formula 1h, the pharmaceutically acceptable salt, ester, amide or prodrug thereof, or the pharmaceutically acceptable salt of the prodrug:

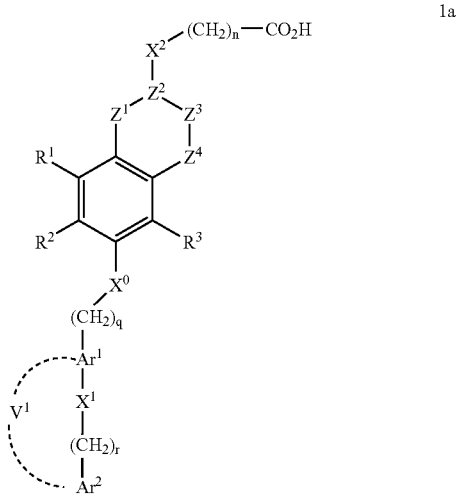

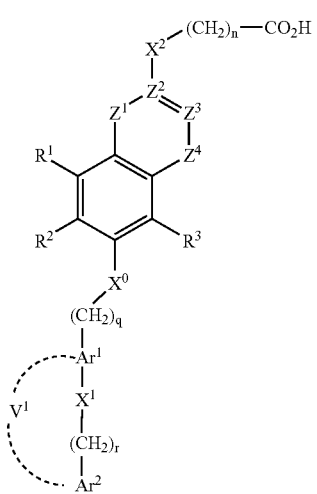
1b
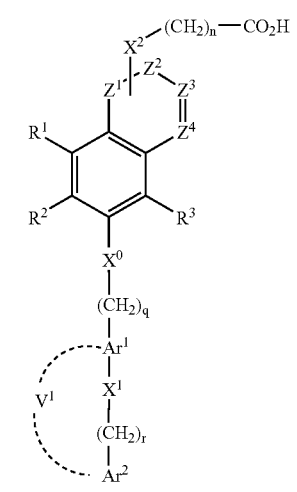
1c
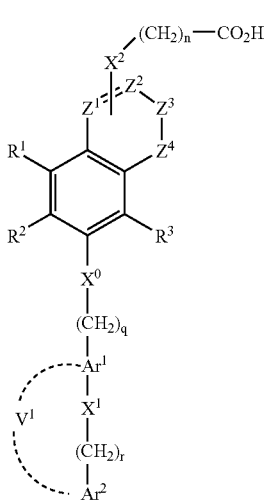
1d
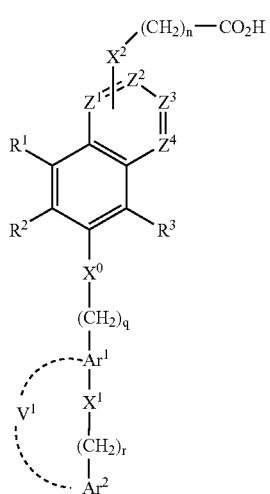
1e
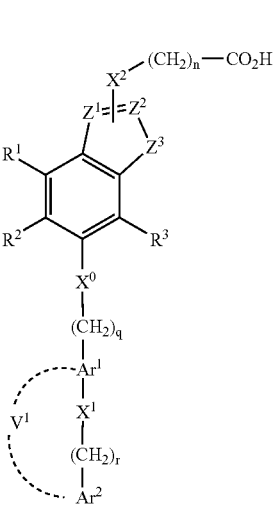
1f
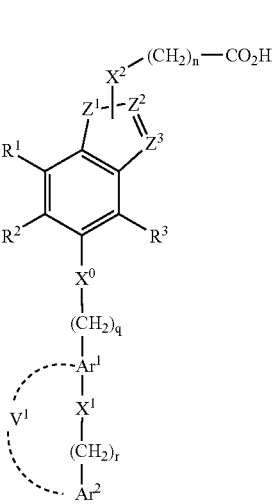
1g -continued

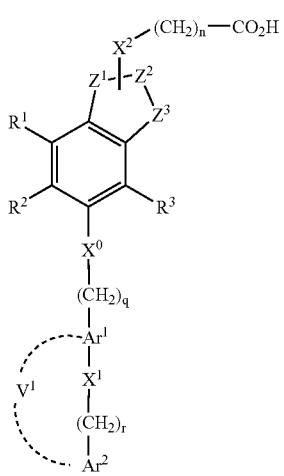

wherein $X^0$ is O or S; $X^2$ is absent, O, S, or $NR^4$; $R^1$, $R^2$, and $R^3$ are independently hydrogen, lower alkyl, lower alkoxy, lower thioalkoxy, —O(CH$_2$)$_p$CF$_3$, halogen, nitro, cyano, —OH, —SH, —CF$_3$, S(O)$_p$Alkyl, S(O)$_p$Aryl, —(CH$_2$)$_m$OR$^4$, or —(CH$_2$)$_m$NR$^5$R$^6$, COR$^4$, —CO$_2$H, —CO$_2$R$^4$, or —NR$^5$R$^6$ or $R^1$ and $R^2$ are joined together to form a substituted or unsubstituted, saturated or unsaturated cyloalkyl or heterocycloalkyl ring; $R^4$ is hydrogen, alkyl, alkenyl, alkynyl, acyl, SO$_2$Aryl, SO$_2$Alkyl or aryl; $R^5$ and $R^6$ are independently hydrogen, alkyl, alkenyl, alkynyl, cycloalkyl, SO$_2$Alkyl or, SO$_2$Aryl, or joined together to form a 4 to 7 member ring having 0 to 3 heteroatoms; m is an integer from 0 to 5; n is an integer from 0 to 5; p is an integer from 0 to 2; $Z^1$, $Z^2$, $Z^3$, and $Z^4$ are independently O, S, CR$^5$R$^6$, NR$^{11}$, or N; $R^{11}$ is lower alkyl, acyl, aryl, —SO$_2$alkyl, or —SO$_2$Ar, and wherein $Z^1$, $Z^2$, $Z^3$, and $Z^4$ are bonded to a sufficient number of hydrogen atoms or substituents to complete the valency of each atom with the proviso that $Z^1$, $Z^2$, $Z^3$, and $Z^4$ are not all heteroatoms and that not more than two adjacent atoms in $Z^1$, $Z^2$, $Z^3$, and $Z^4$ are heteroatoms and that in Formulae 1b, 1c, 1d, 1f, and 1g, $Z^1$, $Z^2$, $Z^3$, and $Z^4$ are not all carbon atoms; and $X^1$, Ar$^1$, Ar$^2$,

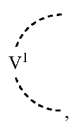

and r and q are as defined above for Formula I.

The present invention further provides a compound of Formula I as described above, the pharmaceutically acceptable salt, ester, amide or prodrug thereof, or the pharmaceutically acceptable salt of the prodrug, wherein $R^1$, $R^2$, and $R^3$ are independently hydrogen, alkyl, or alkoxy.

The present invention further provides a compound of Formula I as described above, the pharmaceutically acceptable salt, ester, amide or prodrug thereof, or the pharmaceutically acceptable salt of the prodrug, wherein $R^1$ and $R^3$ are hydrogen; and $R^2$ is alkyl or alkoxy.

The present invention further provides a compound of Formula I as described above, the pharmaceutically acceptable salt, ester, amide or prodrug thereof, or the pharmaceutically acceptable salt of the prodrug, wherein $R^1$ and $R^3$ are hydrogen; and $R^2$ is alkoxy.

The present invention further provides a compound of Formula I as described above, the pharmaceutically acceptable salt, ester, amide or prodrug thereof, or the pharmaceutically acceptable salt of the prodrug, wherein $R^1$ and $R^3$ are independently hydrogen, methyl, ethyl, isopropyl, n-propyl, t-butyl, n-butyl, or isobutyl; and $R^2$ is methyoxy, ethoxy, isopropoxy, n-propoxy, t-butoxy, n-butoxy, or isobutoxy.

The present invention further provides inter alia the following compounds: [6-(4'-Trifluoromethyl-biphenyl-4-ylmethylsulfanyl)-chroman-2-yl]-acetic acid; {6-[4-(5-Trifluoromethyl-pyridin-2-yl)-benzylsulfanyl]-chroman-2-yl}-acetic acid; {6-[4-(2,5-Dichloro-benzyloxy)-benxylsulfanyl}-chroman-2-yl}-acetic acid; {6-[4-(4-Trifluoromethyl-benzyloxy)-benzylsulfanyl]-chroman-2-yl}-acetic acid; {6-[5-(4-Trifluoromethyl-phenyl)-isoxazol-3-ylmethylsulfany]-chroman-2-yl}-acetic acid; {6-[3-(4-Trifluoromethyl-benzyloxy)-benzylsulfanyl]-chroman-2yl}-acetic acid; {6-[2-(4-Trifluoromethyl-phenyl)-thiazol-4-ylmethoxy]-benzo[b]thiophen-3-yl}-acetic acid; {6-[4-(4-Trifluoromethyl-benzyloxy)-benzyloxy]-benzo[b]thiophen-3-yl}-acetic acid; {6-[2-(4-Trifluoromethyl-benzyloxy)-benzyloxy]-benzo[b]thiophen-3-yl}-acetic acid; and pharmaceutically acceptable salts thereof.

The present invention further provides a compound having a formula (IA),

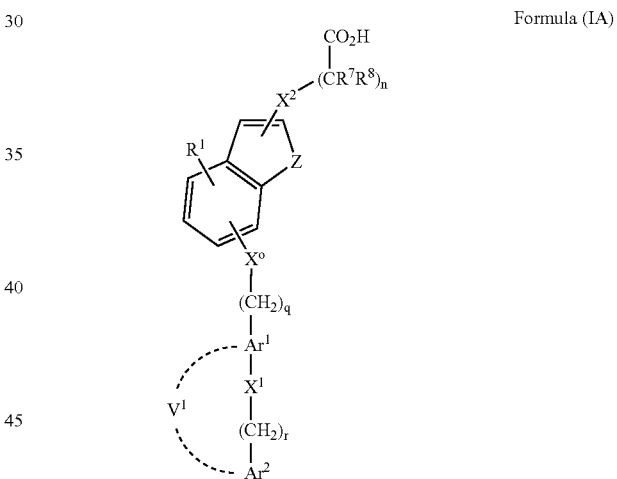

Formula (IA)

a pharmaceutically acceptable salt, ester, amide, or prodrug thereof, or a pharmaceutically acceptable salt of the prodrug wherein Z=S O or NR$^4$, and Ar$^1$, Ar$^2$,

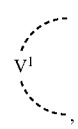

$X^0$, $X^1$, $X^2$, $R^1$, $R^4$, $R^7$, $R^8$, n, q and r are as defined above for Formula I. The present invention further provides a compound having a formula IA, as described above, the pharmaceutically acceptable amide ester or prodrug thereof, or the pharmaceutically acceptable salt of the prodrug wherein $X^0$ is oxygen; $X^1$ is absent or O; Ar$^1$ is a substituted or unsubstituted aryl or heteroaryl; $Ar^2$ is a substituted phenyl;

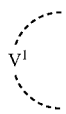

is absent; $X^2$ is absent; n is an integer from 0 to 5; q is an integer from 0 to 3; and r is an integer from 0 to 3.

The present invention further provides inter alia the following compounds: {6-[4-(4-Trifluoromethyl-benzyloxy)-benzyloxy]-benzo[b]thiophen 3-yl}-acetic acid; {6-[5-(4-Trifluoromethyl-phenyl)-isoxazol-3-ylmethoxy]-benzo[b]thiophen-3-yl}-acetic acid; {6-[3-(4-Trifluoromethyl-benzyloxy)-benzyloxy]-benzo[b]thiphen-3-yl}-acetic acid; {6-[2-(4-Trifluoromethyl-phenyl)-thiazol-4-ylmethoxy]-benzo[b]thiophen-3-yl}-acetic acid; {6-[5-(4-Chloro-phenyl)-isoxazol-3-ylmethoxy]-benzo[b]thiophen-3-yl}-acetic acid; and pharmaceutically acceptable salts thereof.

The present invention further provides a compound having a Formula III,

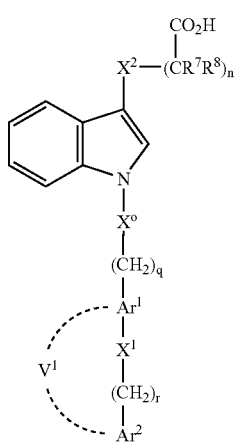

Formula (III)

a pharmaceutically acceptable salt, ester, amide or prodrug thereof, or a pharmaceutically acceptable salt of the prodrug wherein $Ar^1$, $Ar^2$,

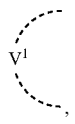

$X^0$, $X^1$, $X^2$, $R^7$, $R^8$, n q and r are as defined above for Formula I.

The present invention further provides inter alia the following compounds: 3-{1-[3-(4-Trifluoromethyl-benzyloxy)-benzyl]-1H-indol-3yl}-propionic acid; 3-{1-[4-(4-Trifluoromethyl-benzyloxy)-benzyl]-1H-indol-3-yl}-propionic acid; 3-[1-(4'-Trifluoromethyl-biphenyl-4-ylmethyl)-1H-indol-3-yl]-propionic acid; {1-[3-(4-Trifluoromethyl-benzyloxy)-benzyl]-1H-indol-3-yl}-acetic acid, and pharmaceutically acceptable salts thereof.

The present invention further provides a compound having a Formula IV,

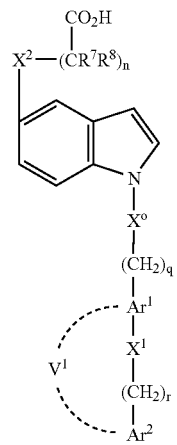

Formula (IV)

a pharmaceutically acceptable salt, ester, amide, or prodrug thereof, or a pharmaceutically acceptable salt of the prodrug wherein $Ar^1$, $Ar^2$,

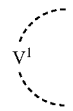

$X^0$, $X^1$, $X^2$, $R^7$, $R^8$, n, q and r are as defined above for Formula I.

The present invention also provides a compound having a Formula IV as described above, a pharmaceutically acceptable salt, amide, ester or prodrug thereof, or a pharmaceutically acceptable salt of the prodrug wherein Xo is absent; $X^1$ is absent or O; $Ar^1$ is a substituted or unsubstituted phenyl; $Ar^2$ is 4-trifluoromethylphenyl;

is absent; $X^2$ is absent, O, or S; n is an integer from 0 to 5; q is an integer from 0 to 3; and r is an integer from 0 to 3.

The present invention further provides a compound having a Formula IV as described above, a pharmaceutically acceptable salt, amide, ester or prodrug thereof, or a pharmaceutically acceptable salt of the prodrug wherein $X^0$ is absent; $X^1$ is absent or O; $Ar^1$ is a substituted or unsubstituted phenyl; $Ar^2$ is 4-trifluoromethylphenyl;

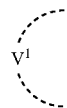

is absent; $X^2$ is absent, O, or S; n is an integer from 0 to 5; q is an integer from 0 to 3; and r is an integer from 0 to 3.

The present invention further provides a compound having a Formula IV as described above, a pharmaceutically acceptable salt, amide, ester, prodrug thereof, or a pharmaceutically acceptable salt of the prodrug, wherein $X^0$ and $X^1$ are absent; $Ar^1$ is a substituted or unsubstituted phenyl; $Ar^2$ is 4-trifluoromethylphenyl;

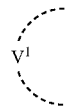

is absent; $X^2$ is absent, O or S; n is an integer from 0 to 5; q is an integer from 0 to 3; and r is an integer from 0 to 3.

The present invention further provides a compound having a Formula IV, a pharmaceutically acceptable salt, ester, amide or prodrug thereof, or a pharmaceutically acceptable salt of the prodrug, wherein $Ar^2$ is trifluoromethyl-phenyl.

The present invention further provides inter alia the following compounds: [1-(4'-Trifluoromethyl-biphenyl-4-ylmethyl)-1H-indol-5-yloxyl]-acetc acid, [1-(4'-Trifluoromethyl-biphenyl-4-ylmethyl)-1H-indol-4-yloxy]-acetic acid; [6-(4'-Trifluoromethyl-biphenyl-4-ylmethylsulfanyl)-chroman-2-yl]-acetic acid; {6-[5-(4-Trifluoromethyl-phenyl)-isoxazol-3-ylmethylsulfany]-chroman-2-yl}-acetic acid; {6-[2-(4-Trifluoromethyl-phenyl)-thiazol-4-ylmethoxy]-benzo[b]thiophen-3-yl}-acetic acid; [1-(4'-Trifluoromethyl-biphenyl-4-ylmethyl)-1H-indol-5-yloxyl]-acetc acid, [1-(4'-Trifluoromethyl-biphenyl-4-ylmethyl)-1H-indol-4-yloxy]-acetic acid; [6-(4'-Trifluoromethyl-biphenyl-4-ylmethylsulfanyl)-chroman-2-yl]-acetic acid; {6-[5-(4-Trifluoromethyl-phenyl)-isoxazol-3-ylmethylsulfany]-chroman-2-yl}-acetic acid; {6-[2-(4-Trifluoromethyl-phenyl)-thiazol-4-ylmethoxy]-benzo[b]thiophen-3-yl}-acetic acid; and pharmaceutically acceptable salts thereof.

The present invention further provides a method of making a compound having the Formula (I):

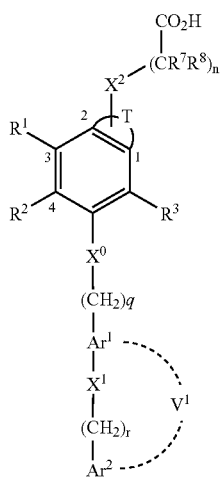

Formula (I)

comprising reacting a compound of Formula A,

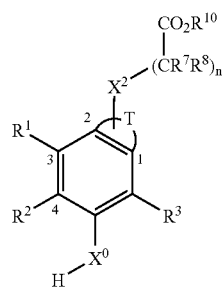

Formula (A)

wherein $R^{10}$ is a lower alkyl, with a compound of Formula B,

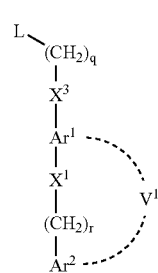

Formula (B)

where L is an appropriate leaving group and $X^3$ is absent, to form a compound having a Formula C,

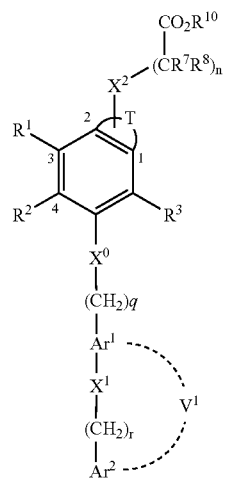

Formula (C)

and subsequently saponifying the compound having a Formula C to form the compound having the Formula I.

The present invention further provides a compound having a Formula IIA,

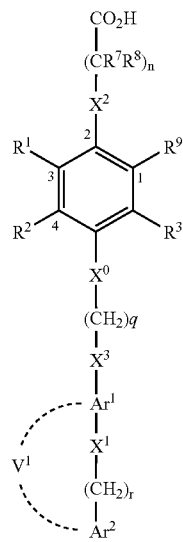

Formula (IIA)

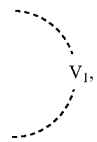

q and r are as defined above for Formula I.

The present invention further provides a method of making a compound having the Formula IIB,

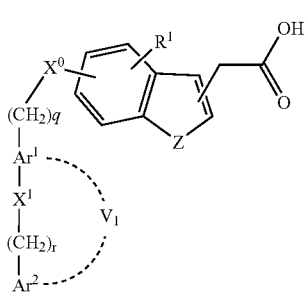

Formula (IIB)

a pharmaceutically acceptable salt, amide ester or prodrug thereof, or a pharmaceutically acceptable salt of the prodrug wherein $X^1$ and $X^3$ are each independently O, C=O, S, CHOR$^9$, absent or NR$^4$; R$^1$, R$^2$, R$^3$ and R$^9$ are independently hydrogen, lower alkyl, lower alkoxy, lower thioalkoxy, —O(CH$_2$)$_p$CF$_3$, halogen, nitro, cyano, —OH, —SH, —CF$_3$, S(O)$_p$Alkyl, S(O)$_p$Aryl, —(CH$_2$)$_m$OR$^4$, or —(CH$_2$)$_m$NR$^5$R$^6$, —COR$^4$, —CO$_2$H, —CO$_2$R$^4$, or —NR$^5$R$^6$, or R$^1$ and R$^2$ are joined together to form a substituted or unsubstituted, saturated or unsaturated cycloalkyl or heterocycloalkyl ring; and R$^4$, R$^5$, R$^6$, R$^7$, R$^8$, Ar$^1$, Ar$^2$, X$^0$, X$^2$, m, n, p, q and r are as defined above for Formula I.

The present invention further provides a compound having the Formula IIB, comprising reacting a compound of Formula H wherein R$^{10}$ is a lower alkyl,

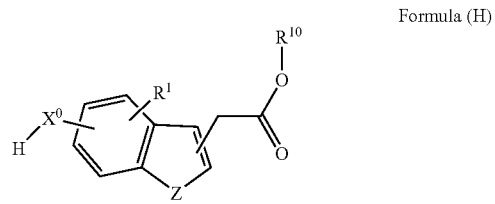

Formula (H)

with a compound of Formula B wherein X$^3$ is absent:

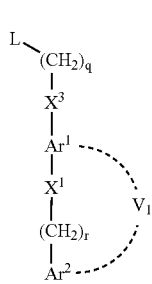

Formula (B)

L = leaving group

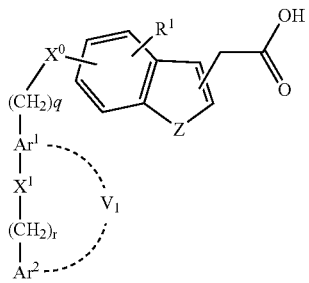

Formula (IIB)

a pharmaceutically acceptable salt, ester, or amide thereof, or a pharmaceutically acceptable salt of the prodrug wherein Z is NR$^4$, S, or O; and R$^1$, R$^4$, X$^0$, X$^1$, Ar$^1$, Ar$^2$, to form a compound of Formula J:

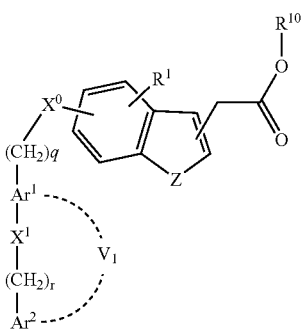

Formula (J)

and subsequently saponifying the compound of Formula J to form the compound IIB.

The present invention provides inter alia the following compounds:

{6-[5-(4-Methoxymethyl-phenyl)-isoxazol-3-ylmethoxy]-benzo[b]thiophen-3-yl}-acetic acid;
{6-[5-(3-Methoxymethyl-phenyl)-isoxazol-3-ylmethoxy]-benzo[b]thiophen-3-yl}-acetic acid;
{6-[5-(4-Methanesulfonyloxy-phenyl)-isoxazol-3-yl-methoxy]-benzo[b]thiophen-3-yl}-acetic acid;
{6-[5-(3-Methanesulfonyloxy-phenyl)-isoxazol-3-yl-methoxy]-benzo[b]thiophen-3-yl}-acetic acid;
{6-[5-(4-Methoxymethyl-phenyl)-isoxazol-3-ylmethoxy]-4-methyl-benzo[b]thiophen-3-yl}-acetic acid;
{6-[5-(3-Methoxymethyl-phenyl)-isoxazol-3-ylmethoxy]-4-methyl-benzo[b]thiophen-3-yl}-acetic acid;
{6-[5-(4-Methanesulfonyloxy-phenyl)-isoxazol-3-yl-methoxy]-4-methyl-benzo[b]thiophen-3-yl}-acetic acid;
{6-[5-(3-Methanesulfonyloxy-phenyl)-isoxazol-3-yl-methoxy]-4-methyl-benzo[b]thiophen-3-yl}-acetic acid;
{5-Methoxy-6-[5-(4-methoxymethyl-phenyl)-isoxazol-3-ylmethoxy]-benzo[b]thiophen-3-yl}-acetic acid;
{5-Methoxy-6-[5-(3-methoxymethyl-phenyl)-isoxazol-3-ylmethoxy]-benzo[b]thiophen-3-yl}-acetic acid;
{6-[5-(4-Methanesulfonyloxy-phenyl)-isoxazol-3-yl-methoxy]-5-methoxy-benzo[b]thiophen-3-yl}-acetic acid;
{6-[5-(3-Methanesulfonyloxy-phenyl)-isoxazol-3-yl-methoxy]-5-methoxy-benzo[b]thiophen-3-yl}-acetic acid;
{6-[5-(4-Methoxymethyl-phenyl)-isoxazol-3-ylmethoxy]-benzofuran-3-yl}-acetic acid;
{6-[5-(3-Methoxymethyl-phenyl)-isoxazol-3-ylmethoxy]-benzofuran-3-yl}-acetic acid;
{6-[5-(4-Methanesulfonyloxy-phenyl)-isoxazol-3-yl-methoxy]-benzofuran-3-yl}-acetic acid;
{6-[5-(3-Methanesulfonyloxy-phenyl)-isoxazol-3-yl-methoxy]-benzofuran-3-yl}-acetic acid;
{6-[5-(4-Methoxymethyl-phenyl)-isoxazol-3-ylmethoxy]-4-methyl-benzofuran-3-yl}-acetic acid;
{6-[5-(3-Methoxymethyl-phenyl)-isoxazol-3-ylmethoxy]-4-methyl-benzofuran-3-yl}-acetic acid;
{6-[5-(4-Methanesulfonyloxy-phenyl)-isoxazol-3-yl-methoxy]-4-methyl-benzofuran-3-yl}-acetic acid;
{6-[5-(3-Methanesulfonyloxy-phenyl)-isoxazol-3-yl-methoxy]-4-methyl-benzofuran-3-yl}-acetic acid;
{5-Methoxy-6-[5-(4-methoxymethyl-phenyl)-isoxazol-3-ylmethoxy]-benzofuran-3-yl}-acetic acid;
{5-Methoxy-6-[5-(3-methoxymethyl-phenyl)-isoxazol-3-ylmethoxy]-benzofuran-3-yl}-acetic acid;
{6-[5-(4-Methanesulfonyloxy-phenyl)-isoxazol-3-yl-methoxy]-5-methoxy-benzofuran-3-yl}-acetic acid;
{6-[5-(3-Methanesulfonyloxy-phenyl)-isoxazol-3-yl-methoxy]-5-methoxy-benzofuran-3-yl}-acetic acid;
{7-[5-(4-Methoxymethyl-phenyl)-isoxazol-3-ylmethoxy]-indan-4-yloxy}-acetic acid;
{7-[5-(3-Methoxymethyl-phenyl)-isoxazol-3-ylmethoxy]-indan-4-yloxy}-acetic acid;
{7-[5-(4-Methanesulfonyloxy-phenyl)-isoxazol-3-yl-methoxy]-indan-4-yloxy}-acetic acid;
{7-[5-(3-Methanesulfonyloxy-phenyl)-isoxazol-3-yl-methoxy]-indan-4-yloxy}-acetic acid;
{4-[5-(4-Methoxymethyl-phenyl)-isoxazol-3-ylmethoxy]-2-methyl-phenoxy}-acetic acid;
{4-[5-(3-Methoxymethyl-phenyl)-isoxazol-3-ylmethoxy]-2-methyl-phenoxy}-acetic acid;
{4-[5-(4-Methanesulfonyloxy-phenyl)-isoxazol-3-yl-methoxy]-2-methyl-phenoxy}-acetic acid; and
{4-[5-(3-Methanesulfonyloxy-phenyl)-isoxazol-3-yl-methoxy]-2-methyl-phenoxy}-acetic acid.

The following definitions are used, unless otherwise described. Halo is fluoro, chloro, bromo or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically recited.

The term "alkyl" as used herein refers to a straight or branched hydrocarbon of from 1 to 11 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents selected from lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring. Useful alkyl groups have from 1 to 6 carbon atoms (C$_1$–C$_6$ alkyl).

The term "lower alkyl" as used herein refers to a subset of alkyl which means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like. Optionally, lower alkyl is referred to as "C$_1$–C$_6$alkyl."

The term "haloalkyl" as used herein refers to a lower alkyl radical, as defined above, bearing at least one halogen substituent, for example, chloromethyl, fluoroethyl, trifluoromethyl, or 1,1,1-trifluoroethyl and the like. Haloalkyl can also include perfluoroalkyl wherein all hydrogens of a loweralkyl group are replaced with fluorine atoms.

The term "alkenyl" means a straight or branched unsaturated hydrocarbon radical having from 2 to 12 carbon atoms and includes, for example, ethenyl, 1-propenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

The term "alkynyl" means a straight or branched hydrocarbon radical having of 2 to 12 carbon atoms having at least one triple bond and includes, for example, 3-propynyl, 1-butynyl, 3-butynyl, 1-pentynyl, 3-pentynyl, 3-methyl-3-butynyl, 1-hexynyl, 3-hexynyl, 3-hexynyl, 3-heptynyl, 1-octynyl, 1-nonynyl, 1-decynyl, 1-undecynyl, 1-dodecynyl, and the like.

The term "alkylene" as used herein refers to a divalent group derived from a straight or branched chain saturated hydrocarbon having from 1 to 10 carbon atoms, for example methylene, 1,2-ethylene, 1,1-ethylene, 1,3-propylene, 2,2-dimethylpropylene, and the like. The alkylene groups of this invention can be optionally substituted with one or more of the substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring. Useful alkylene groups have from 1 to 6 carbon atoms (C$_1$–C$_6$ alkylene).

The term "heteroatom" as used herein represents oxygen, nitrogen, or sulfur (O, N, or S) as well as sulfoxyl or sulfonyl (SO or SO$_2$) unless otherwise indicated.

The term "hydrocarbon chain" as used herein refers to a straight hydrocarbon of from 2 to 6 carbon atoms. The hydrocarbon chain is optionally substituted with one or more substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring.

The term "hydrocarbon-heteroatom chain" as used herein refers to a hydrocarbon chain wherein one or more carbon atoms are replaced with a heteroatom. The hydrocarbon-heteroatom chain is optionally substituted with one or more substituents selected from lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NH(C$_1$–C$_6$ alkyl), —CONR'R", or —N(C$_1$–C$_6$alkyl)$_2$ where R' and R" are independently alkyl, akenyl, alkynyl, aryl, or joined together to form a 4 to 7 member ring.

The term "heteroalkylene" as used herein, refers to an alkylene radical as defined above that includes one or more heteroatoms such as oxygen, sulfur, or nitrogen (with valence completed by hydrogen or oxygen) in the carbon chain or terminating the carbon chain.

The terms "lower alkoxy" and "lower thioalkoxy" as used herein refers to O-alkyl or S-alkyl of from 1 to 6 carbon atoms as defined above for "lower alkyl."

The term "aryl" as used herein refers to an aromatic ring which is unsubstituted or optionally substituted by 1 to 4 substituents selected from lower alkyl, lower alkoxy, lower thioalkoxy, —O(CH$_2$)$_p$CF$_3$, halogen, nitro, cyano —OH, —SH, —CF$_3$, —CO$_2$H, —CO$_2$C$_1$–C$_6$ alkyl, —NH$_2$, —NHC$_1$–C$_6$ alkyl, —SO$_2$alkyl, —SO$_2$NH$_2$, —CONR'R", or —N(C$_1$–C$_6$alkyl)$_2$ where R' and R" are independently alkyl, akenyl, alkynyl, aryl, or joined together to form a 4 to 7 member ring. Examples include, but are not limited to phenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-chloro-3-methylphenyl, 2-chloro-4-methylphenyl, 2-chloro-5-methylphenyl, 3-chloro-2-methylphenyl, 3-chloro-4-methylphenyl, 4-chloro-2-methylphenyl, 4-chloro-3-methylphenyl, 5-chloro-2-methylphenyl, 2,3-dichlorophenyl, 2,5-dichlorophenyl, 3,4-dichlorophenyl, 2,3-dimethylphenyl, 3,4-dimethylphenyl, or the like. Further, The term "aryl" means a cyclic or polycyclic aromatic ring having from 5 to 12 carbon atoms, and being unsubstituted or substituted with up to 4 of the substituent groups recited above for alkyl, alkenyl, and alkynyl.

The term "heteroaryl" means an aromatic ring containing one or more heteroatoms. The heteroaryl is optionally substituted with one or more groups enumerated for aryl. Examples of heteroaryl include, but are not limited to thienyl, furanyl, pyrrolyl, pyridyl, pyrimidyl, imidazoyl, pyrazinyl, oxazolyl, thiazolyl, benzothienyl, benzofuranyl, indolyl, quinolinyl, isoquinolinyl, and quinazolinyl, and the like. Further, the term "heteroaryl" means an aromatic mono-, bi-, or or polycyclic ring incorporating one or more (i.e. 1–4) heteroatoms selected from N, O, and S. It is understood that a heterocycle is optionally substituted with —OH, —O(alkyl), SH, S(alkyl), amine, halogen, acid, ester, amide, amidine, alkyl ketone, aldehyde, nitrile, fluoroalkyl, nitro, sulphone, sulfoxide or C1–6 alkyl. Examples of suitable monocyclic heteroaryl include, but are not limited to substituted or unsubstituted thienyl, furanyl, pyrrolyl, imidazolyl, pyrazolyl, isothiazolyl, isoxazolyl, triazolyl, tetrazolyl, pyridinyl, pyrazinyl, pyrimidinyl, piperidinyl, pyrrolidinyl, piperazinyl, azetidinyl, aziridinyl, morpholinyl, thietanyl, oxetaryl. Preferred monocyclic diheterocycles include, but are not limited to 1-, 2-, 4-, or 5-imidazolyl, I—, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 1,3-, or 5-triazolyl, 1-, 2-, or 3-tetrazolyl, 2-pyrazinyl, 2-, 4-, or 5-pyrimidinyl, 1- or 2-piperazinyl, 2-, 3-, or 4-morpholinyl. Examples of suitable bicyclic and polyclic heteroaryl groups include, but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4aH carbazolyl, 1-, 2-, 3-, 4-, 5-, 6-, 7-, or 8-carbzaolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 5-4H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteoary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

The term "heterocycle" means a saturated or unsaturated mono- or polycyclic (i.e. bicyclic) ring incorporating one or more (i.e. 1–4) heteroatoms selected from N, O, and S. It is understood that a heterocycle is optionally substituted with —OH, —O(alkyl), SH, S(alkyl), amine, halogen, acid, ester, amide, amidine, alkyl ketone, aldehyde, nitrile, fluoroalkyl, nitro, sulphone, sulfoxide or C1–6 alkyl. Examples of suitable monocyclic heterocycles include, but are not limited to substituted or unsubstituted thienyl, furanyl, pyrrolyl, imidazolyl, pyrazolyl, thiazolyl, isothiazolyl, oxazolyl, isoxazolyl, triazolyl, tetrazolyl, pyridinyl, pyrazinyl, pyrimidinyl, piperidinyl, pyrrolidinyl, piperazinyl, azetidinyl, aziridinyl, morpholinyl, thietanyl, oxetaryl. Examples of monocyclic diheterocycles include, but are not limited to, 1-, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 1,3-, or 5-triazolyl, 1-, 2-, or 3-tetrazolyl, 2-pyrazinyl, 2-, 4-, or 5-pyrimidinyl, 1- or 2-piperazinyl, 2-, 3-, or 4-morpholinyl. Examples of suitable bicyclic heterocycles include, but are not limited to indolizinyl, isoindolyl, benzofuranyl, benzothienyl, benzoxazolyl, benzimidazolyl, quinolinyl, isoquinolinyl, quinazolinyl, 1-, 2-, 3-, 4-, 5-, 6-, or 7-indolyl, 1-, 2-, 3-, 5-, 6-, 7-, or 8-indolizinyl, 1-, 2-, 3-, 4-, 5-, 6-, or 7-isoindolyl, 2-, 3-, 4-, 5-, 6-, or 7-benzothienyl, 2-, 4-, 5-, 6-, or 7-benzoxazolyl, 1-, 2-, 4-, 5-, 6-, or 7-benzimidazolyl, 2-, 3-, 4-, 5-, 6-, 7-, or 8-quinolinyl, and 1-, 3-, 4-, 5-, 6-, 7-, or 8-isoquinolinyl.

Further, the term "heterocycloalkyl" means a monocyclic, fused, bridged, or spiro bicyclic heterocyclic ring systems. Monocyclic heterocyclic rings contain from about 3 to 12 ring atoms, with from 1 to 5 heteroatoms selected from N, O, and S, and preferably from 3 to 7 member atoms, in the ring. Bicyclic heterocyclics contain from 7 to 17 member atoms, preferably 7 to 12 member atoms, in the ring. Bicyclic heterocyclics rings may be fused, spiro, or bridged ring systems. Examples of heterocyclic groups include cyclic ethers (oxiranes) such as ethyleneoxide, tetrahydrofuran, dioxane, and substituted cyclic ethers, wherein the substituents are those described above for the alkyl and cycloalkyl groups. Typical substituted cyclic ethers include propyleneoxide, phenyloxirane (styrene oxide), cis-2-butene-oxide (2,3-dimethyloxirane), 3-chlorotetrahydrofuran, 2,6-dimethyl-1,4-dioxane, and the like. Heterocycles containing nitrogen are groups such as pyrrolidine, piperidine, piperazine, tetrahydrotriazine, tetrahydropyrazole, and substituted groups such as 3-aminopyrrolidine, 4-methylpiperazin-1-yl, and the like. Typical sulfur containing heterocycles include tetrahydrothiophene, dihydro-1,3-dithio]-2-yl, and hexahydrothiepin-4-yl. Other commonly employed heterocycles include dihydro-oxathiol-4-yl, tetrahydro-oxazolyl, tetrahydro-oxadiazolyl, tetrahydro-dioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothiophene. Further examples of heterocycloalkyl, include, but are not limited to, 2- or 3-tetrahydrothieno, 2- or 3-tetrahydrofurano, 2- or 3-pyrrolidino, 2-, 4-, or 5-thiazolidino, 2-, 4-, or 5-oxazolidino, 2-, 3-, or 4-piperidino, N-morpholinyl or N-thiamorpholinyl or tetrahydropyrano.

The term "cycloalkyl" means a saturated hydrocarbon ring. Further, the term "cycloalkyl" means a hydrocarbon ring containing from 3 to 12 carbon atoms, for example, cyclopropyl, cyclobutyl, cyclopentyl, cyclohexyl, cycloheptyl, cyclooctyl, decalinyl, norpinanyl, and adamantyl. The cycloalkyl ring may be unsubstituted or substituted by 1 to 3 substituents selected from alkyl, alkoxy, thioalkoxy, hydroxy, thiol, nitro, halogen, amino, alkyl and dialkylamino, formyl, carboxyl, CN, —NH—CO—R—CO—NHR—, —$CO_2$R—, —COR—, aryl, or heteroaryl, wherein alkyl, aryl, and heteroaryl are as defined herein. Examples of substituted cycloalkyl groups include fluorocyclopropyl, 2-iodocyclobutyl, 2,3-dimethylcyclopentyl, 2,2-dimethoxycyclohexyl, and 3-phenylcyclopentyl.

The term "cycloalkenyl" means a cycloalkyl group having one or more carbon-carbon double bond. Example includes cyclobutene, cyclopentene, cyclohexene, cycloheptene, cyclobutadiene, cyclopentadiene, and the like.

The term "patient" means all mammals including humans. Examples of patients include humans, cows, dogs, cats, goats, sheep, pigs, and rabbits.

A "therapeutically effective amount" is an amount of a compound of the present invention that when administered to a patient ameliorates a symptom of dyslipidemia, non-insulin dependent diabetes mellitus, obesity, hyperglycemia, hypercholesteremia, hyperlipidemia, atherosclerosis, hypertriglyceridemia, or hyperinsulinemia.

The term "a pharmaceutically acceptable salt, ester, amide, or prodrug" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "a pharmaceutically acceptable salt" refers to the relatively non-toxic, inorganic and organic acid or base addition salts of compounds of the present invention. These salts can be prepared in situ during the final isolation and purification of the compounds or by separately reacting the purified compound in its free form with a suitable organic or inorganic acid or base and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977;66:1–19, which is incorporated herein by reference.) The free base form may be regenerated by contacting the salt form with a base. While the free base may differ from the salt form in terms of physical properties, such as solubility, the salts are equivalent to their respective free bases for the purposes of the present invention.

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

"Prodrugs" are intended to include any covalently bonded carrier which releases the active parent drug according to Formulas I–IV in vivo. Further, the term "prodrug" refers to compounds that are transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference. Examples of prodrugs include acetates, formates, benzoate derivatives of alcohols, and amines present in compounds of Formulas I through IV.

In some situations, compounds may exist as tautomers. All tautomers are included within Formulas I through IV and are provided by this invention.

Certain compounds of the present invention can exist in unsolvated form as well as solvated form including hydrated form. In general, the solvated form including hydrated form is equivalent to unsolvated form and is intended to be encompassed within the scope of the present invention.

Certain of the compounds of the present invention possess one or more chiral centers and each center may exist in the R or S configuration. The present invention includes all diastereomeric, enantiomeric, and epimeric forms as well as the appropriate mixtures thereof. Stereoisomers may be obtained, if desired, by methods known in the art as, for example, the separation of stereoisomers by chiral chromatographic columns. Additionally, the compounds of the present invention may exist as geometric isomers. The present invention includes all cis, trans, syn, anti, entgegen (E), and zusammen (Z) isomers as well as the appropriate mixtures thereof.

The compounds of the present invention are suitable to be administered to a patient for the treatment, control, or prevention of non-insulin dependent diabetes mellitus, hypercholesteremia, hyperlipidemia, obesity, hyperglycemia, hyperlipidemia, atherosclerosis, hypertriglyceridemia, and hyperinsulinemia. Accordingly, the compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

Preparation of Compounds of the Invention

The present invention contains compounds that can be synthesized in a number of ways familiar to one skilled in organic synthesis. The compounds outlined herein can be synthesized according to the methods described below, along with methods typically utilized by a synthetic chemist, and combinations or variations of those methods, which are generally known to one skilled in the art of synthetic chemistry. The synthetic route of compounds in the present invention is not limited to the methods outlined below. It is assumed one skilled in the art will be able to use the schemes outlined below to synthesize compounds claimed in this invention. Individual compounds may require manipulation of the conditions in order to accommodate various functional groups. A variety of protecting groups generally known to one skilled in the art may be required. Purification, if necessary, can be accomplished on a silica gel column eluted with the appropriate organic solvent system. Also, reverse phase HPLC or recrystallization may be employed.

A compound of Formula I or Formula II may be made by reacting a compound of Formula A,

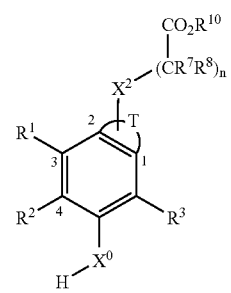

Formula (A)

or a compound of Formula D,

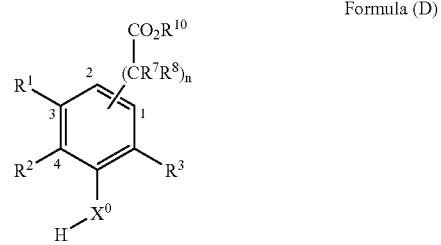

Formula (D)

wherein $R^{10}$ is a lower alkyl or $C_1$–$C_6$ alkyl; $X^2$ is absent, O, S, or $NR^4$; $X^0$ is absent, O, S, —$CH_2$—$CH_2$—, —CH=CH—, or —CH=CH—; T is a saturated or unsaturated, substituted or unsubstituted hydrocarbon chain or hydrocarbon-heteroatom chain having from 3 to 6 atoms wherein the carbon atom of position 1 is connected to the carbon atom of position 2 to form a five to eight member ring wherein the

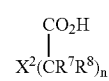

is attached to a substitutionally available position of said ring; $R^1$, $R^2$ and $R^3$ are independently hydrogen, lower alkyl, lower alkoxy, lower thioalkoxy, $O(CH_2)_pCF_3$, halogen, nitro, cyano, —OH, —SH, —$CF_3$, $S(O)_p$Alkyl, $S(O)_p$Aryl, —$(CH_2)_mOR^4$, or —$(CH_2)_mNR^5R^6$, $COR^4$, —$CO_2H$, —$CO_2R^4$, or —$NR^5R^6$ or $R^1$ and $R^2$ are joined together to form a substituted or unsubstituted, saturated or unsaturated cyloalkyl or heterocycloalkyl ring;

$R^4$ is hydrogen, alkyl, alkenyl, alkynyl, or aryl;

$R^5$ and R are independently hydrogen, alkyl, alkenyl, alkynyl, cycloalkyl, $SO_2$Alkyl or, $SO_2$Aryl, or joined together to form a 4 to 7 member ring having 0 to 3 heteroatoms;

$R^7$ and $R^8$ are independently H, $CH_3$ Halo, or $R^7$ and $R^8$ taken together form a 3–6 membered hydrocarbon ring, optionally containing a heteroatom.

m is an integer from 0 to 5;

n is an integer from 0 to 5; and p is an integer from 0 to 2;

in an appropriate solvent in the presence of a base such as cesium carbonate, with a compound of Formula E, Formula (B)

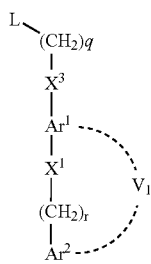

wherein L is an appropriate leaving group; $Ar^1$ and $Ar^2$ are each independently absent or unsubstituted or substituted aryl or heteroaryl,

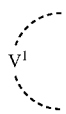

is absent; or when present,

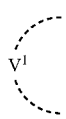

is a saturated or unsaturated hydrocarbon chain which is substituted or unsubstituted, wherein said chain has from 1 to 4 atoms so that

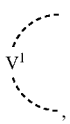

$Ar^1$, $X^1$, $(CH_2)_r$ and $Ar^2$, together form a five to eight membered ring; $X^1$ is absent, O, S, —$CH_2$—$CH_2$—, —CH=CH—, or —C≡C—; $X^3$ is O, C=O, S, $CHOR^9$, absent or $NR^4$; q is an integer from 0 to 10; and r is an integer from 0–10.

The resulting ester may then be saponified to form a compound of Formula I or Formula II.

"An appropriate leaving group" as used herein and above means a substituent group that can leave as a relatively stable, weakly basic molecule or ion, such as for example, bromide, chloride, or mesylate. "Appropriate solvents" as used herein means polar aprotic solvents such as, for example, acetonitrile or tetrahydrofuran.

A compound of Formula IA, for example, may be made by reacting a compound of Formula H, Formula (H)

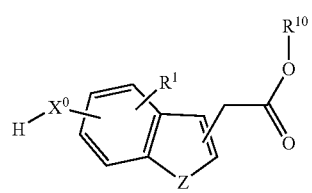

wherein $R^{10}$ is a lower alkyl or $C_1$–$C_6$ alkyl; Z is $NR^5$, S, or O; and $X^0$ and $R^1$ are as above-defined, with a compound of Formula B, shown above, wherein $X^3$ is absent, to form a compound of Formula J:

Formula (J)

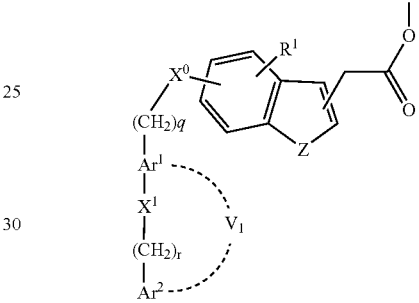

and subsequently saponifying the compound of Formula J to form the compound of Formula IA.

Specifically, compounds of Formulas I through IV may be prepared using the synthetic routes outlined in Scheme 1–6. With reference to the schemes that follow, any one of d, d.3, f.1, f.2, g, j, n, or u may be reacted with any one of Y, CC, FF, or JJ in the presence of a base such as cesium carbonate to give an intermediate product which may be then saponified with lithium hydroxide to give the final product.

Compounds of the general formula d are either commercially available or can be prepared as described in Scheme 1. Compounds with an appropriate protecting group of the general formula a are alkylated with compounds of the general formula b in the presence of a base such as cesium carbonate to give compounds of the general formula c. Subsequent cyclization of c in the presence of an acid such as methanesulfonic acid followed by deprotection give compounds of the general formula d.

Scheme 1

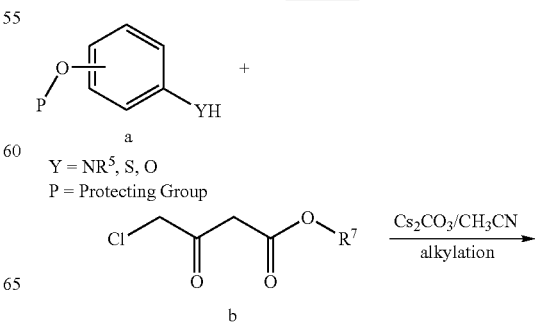

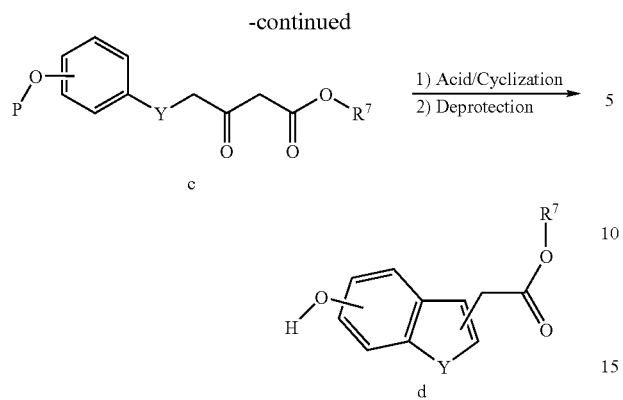

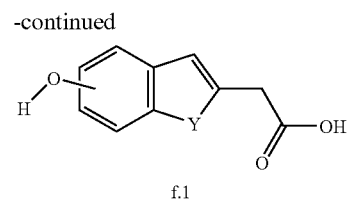

Compounds of the general formula f.1 are either commercially available or can be prepared as described in Scheme 1.1. Compounds with an appropriate protecting group of the general formula a.1 are reacted with maleic anhydride (b.1) in the presence of a catalytic amount of base such as triethylamine to give compounds of the general formula c.1. Intra-molecular Friedel-Crafts acylation with a Lewis acid such as aluminum trichloride or zinc chloride may give compounds of the general formula d.1. Reduction of d.1 with sodium cyanoborohydride or sodiumborohydride and subsequent dehydration of the intermdiate alcohol may give compounds of the general formula e.1. Deprotection may then give compounds of the general formula f.1.

Compounds of the general formula g.2 are either commercially available or can be prepared as described in Scheme 1.2. Compounds with an appropriate protecting group of the general formula a.2 are condensed with a pyruvate ester (b.2) in the presence of a catalytic amount of acid such as hydrochloric acid to give compounds of the general formula c.2. Fischer indole cyclization with a Lewis acid such zinc chloride or poly phosphoric acid, may give compounds of the general formula d.2. De-carboxylation with copper powder in quinoline and subsequent de-protection may give compounds of the general formula f.2. Selective O-alkylation using a base such as cesium carbonate may give compounds of the general formula g.2.

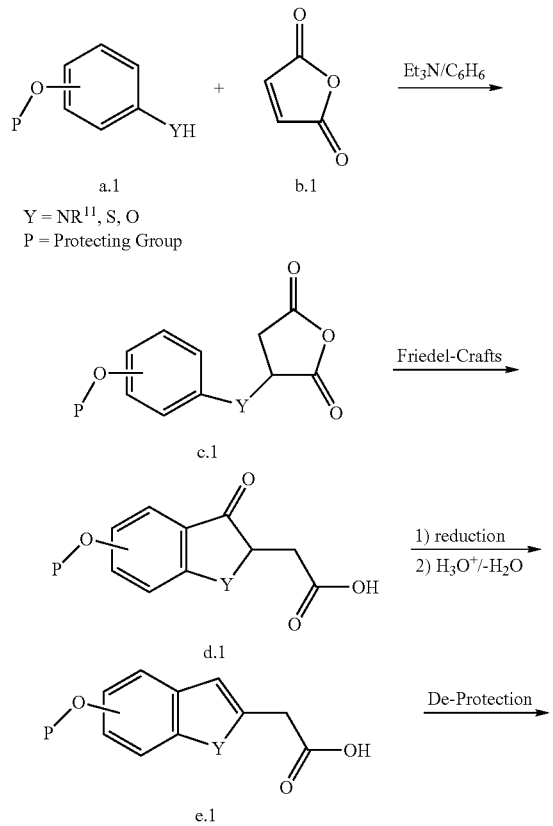

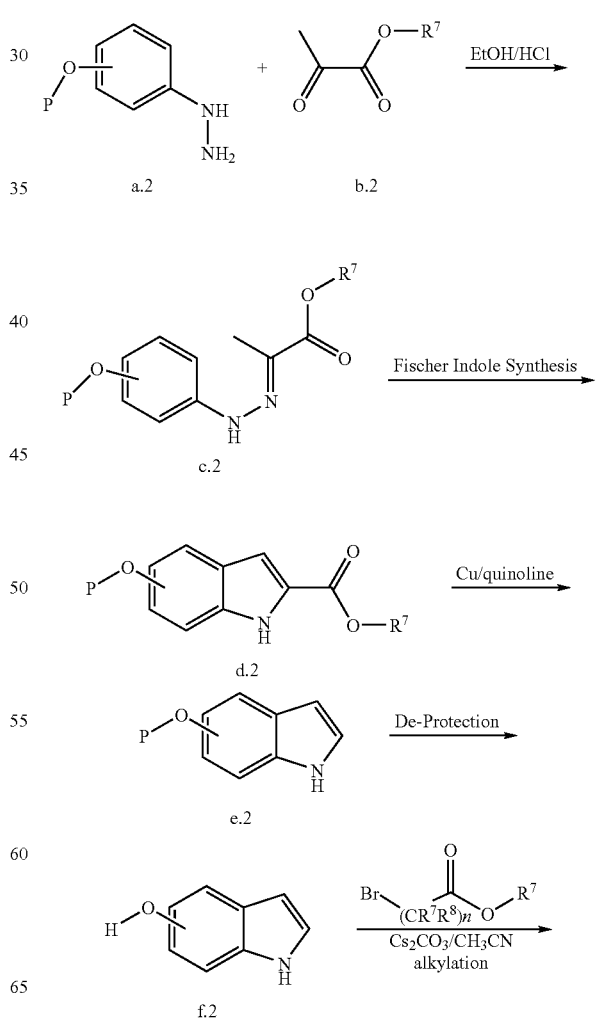

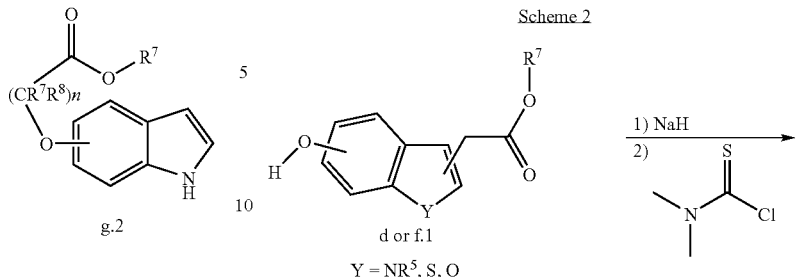

Compounds of the general formula d.3 are either commercially available or can be prepared as described in Scheme 1.3. Compounds of the general formula a.3 are condensed with an aldehyde (b.3) in the presence of a catalytic amount of acid such as hydrochloric acid to give compounds of the general formula c.3. Fischer indole cyclization with a Lewis acid such zinc chloride or poly phosphoric acid, may give compounds of the general formula d.3.

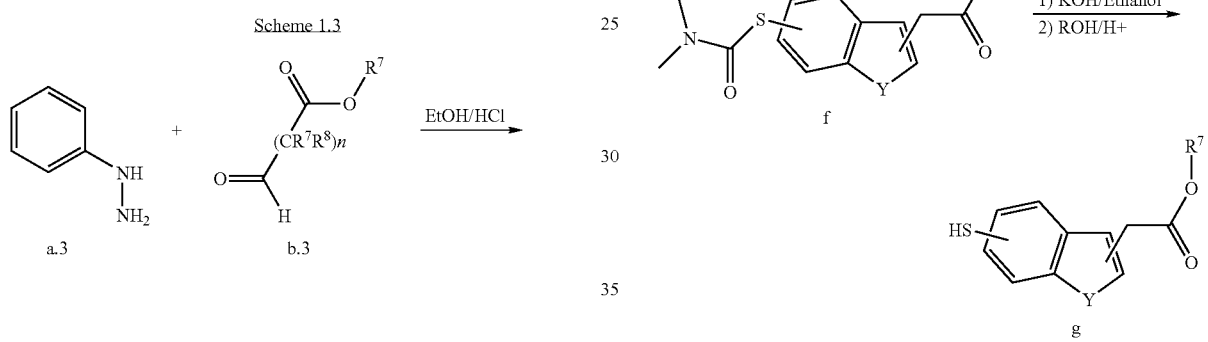

Compounds of the general formula g can be prepared as described in Scheme 2. Compound e may be prepared by thiocarbamoylation of compound d or f.1. Compound f may be prepared by a Newman-Kwart rearrangement of compound e in refluxing diphenyl ether. Saponification and re-esterification of compound f then gives compound g.

Compounds of the general formula j may be prepared as described in scheme 3. Compounds of the general formula h are commercially available or their preparation is obvious to one skilled in the art. h may be reacted with chlorosulfonic acid to give i followed by reduction with, for example, tin, zinc or Lithium Aluminum Hydride (LAH) to give a thiol j.

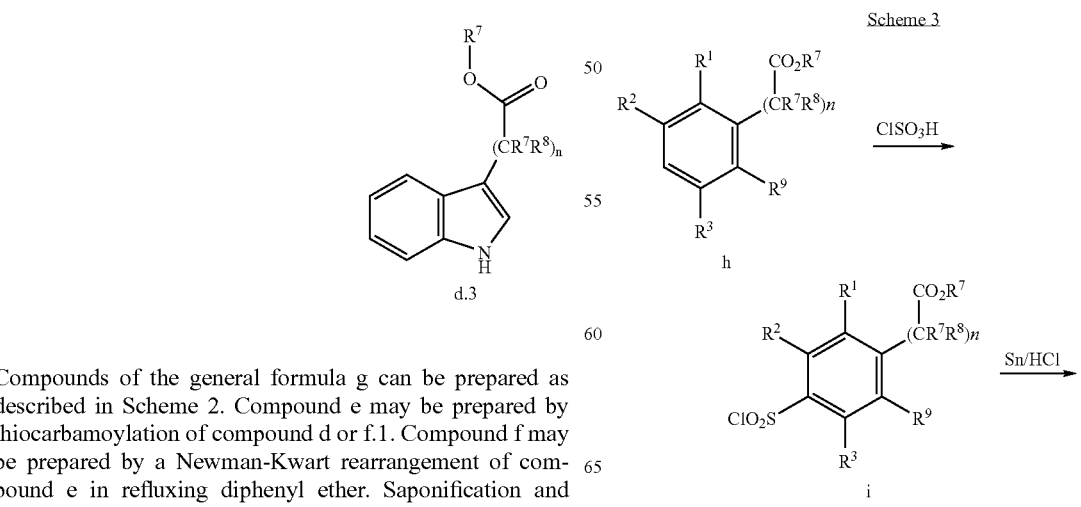

-continued

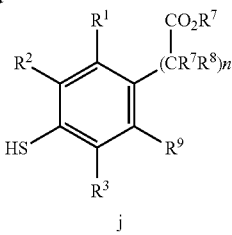

j

With reference to Scheme 4, compounds of the general formula k may be thiocyanated with, for example, a mixture of bromine and sodium thiocyanate to give compounds of the general formula 1. Compounds of the general formula I may be alkylated with a haloester to give compounds of the general formula m. A preferred haloester is bromoester. Compounds of the general formula n may be prepared by reduction of m with, for example, dithiothreitol in methanol or mercaptoacetic acid in methanol.

erably methyl ester to give compounds of the general formula p. Compounds of the general formula p may be thiocyanated with a mixture of bromine and sodium thiocyanate to give compounds of the general formula q, which may be then reduced with for example, dithiothreitol in methanol or mercaptoacetic acid in methanol to give r. Ring closure may be effected by refluxing r in toluene in the presence of an acid such as, trifluoroacetic acid to give s. Compounds of the general formula s may be reduced to give t followed by a Wittig or Horner-Emmons reaction to give compounds of the general formula u.

Scheme 4

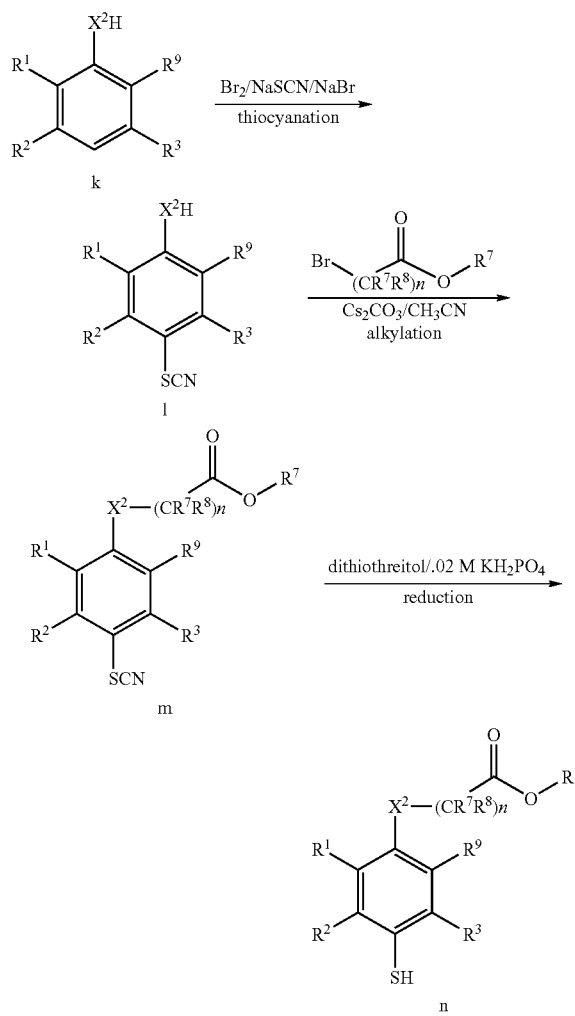

Scheme 5

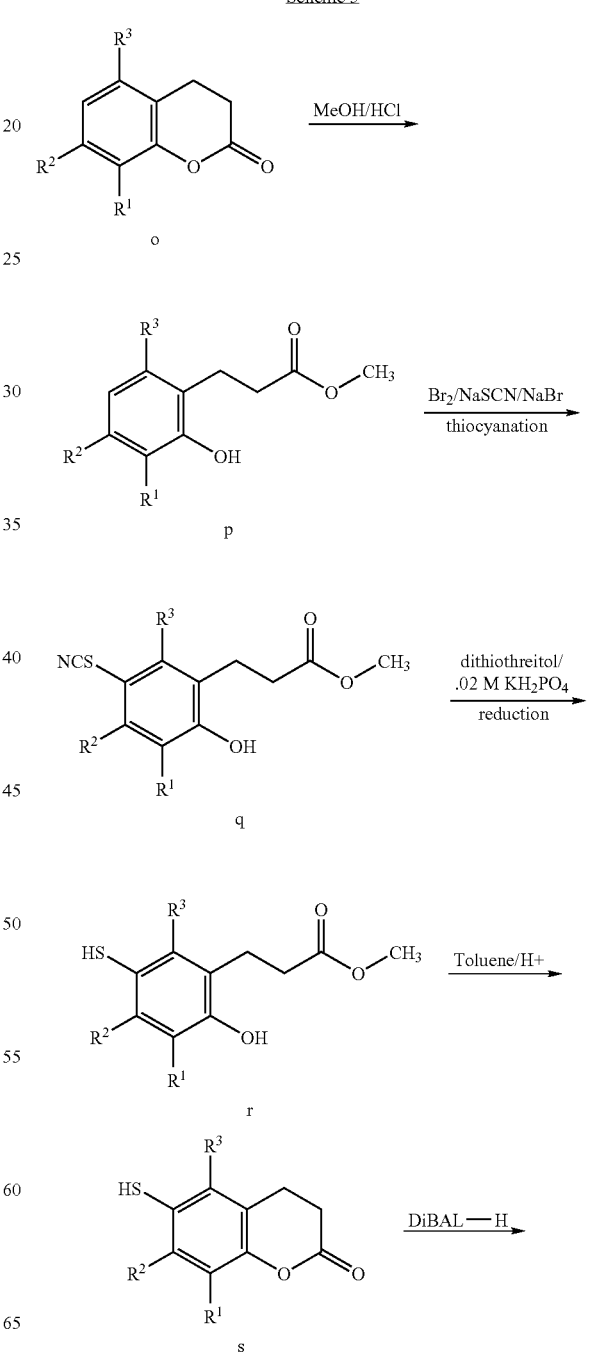

With reference to Scheme 5, compounds of the general formula o, may be esterified to the appropriate ester, pref-

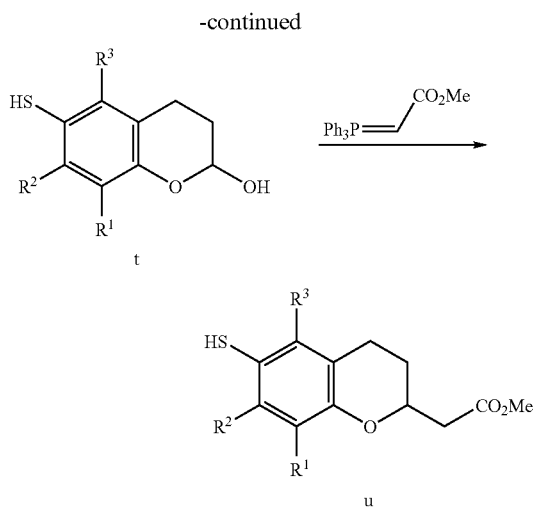

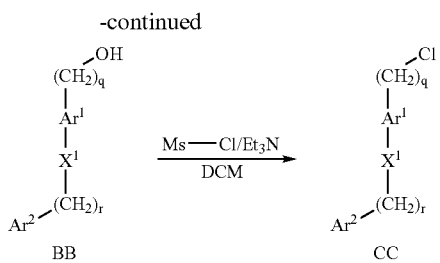

With reference to Scheme 8, compounds of the general formula FF can be prepared by reacting an appropriately substituted aryl amine DD under Sandmeyer conditions followed by heating to give intermediate EE. The resulting intermediate EE may then be reacted with a chlorinating agent such as methanesulfonyl chloride to give chlorides of the general formula FF.

With reference to Scheme 6, compounds of the general formula x are prepared by reacting an appropriate aryl boronic acid, such as hydroxymethylphenyl boronic acid w with, for example, aryl bromide v in the presence of Pd(0) and cesium carbonate. Compounds of the general formula x may be reacted with a chlorinating agent such as methanesulfonyl chloride to give chlorides of the general formula y.

Scheme 8

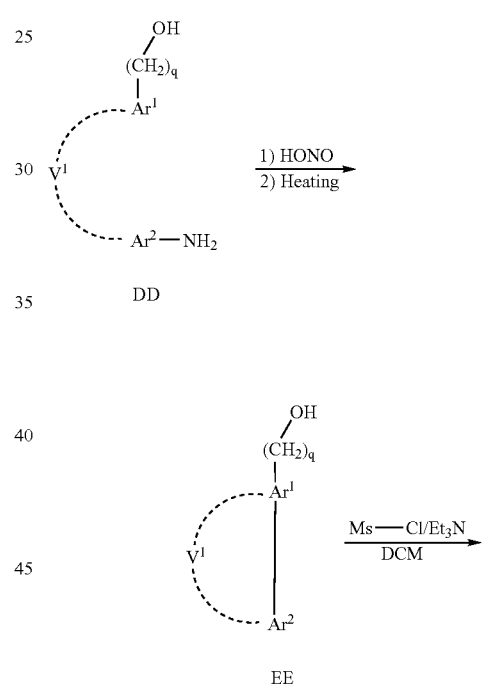

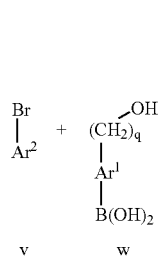

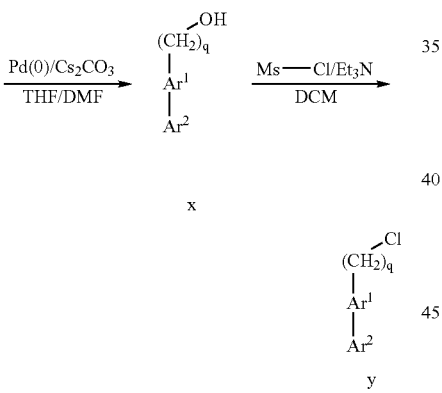

With reference to Scheme 7, compounds of the general formula CC may be prepared wherein an appropriate hydroxy benzyl alcohol AA is alkylated with an appropriate bromide Z. The resulting compound BB is then reacted with a chlorinating agent such as methanesulfonyl chloride to give chlorides of the general formula CC.

Scheme 7

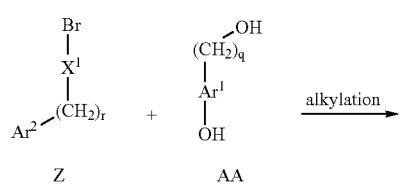

With reference to Scheme 9, compounds of the general formula GG may be alkylated with a diesterified oxalic acid, for example, diethyl oxalate to give HH. Compounds of the general formula HH may then be cyclized in the presence of hydroxylamine hydrochloride to give II. Compounds of the general formula II may then be reduced and chlorinated as described previously to give JJ.

Scheme 9

GG

HH

II

JJ

Finally, any one of d, d.3, f.1, g.2, g, j, n, or u may be reacted with any one of Y, CC, FF, or JJ in the presence of a base such as cesium carbonate to give an intermediate product which may be then saponified with lithium hydroxide to give the final product. This is depicted in scheme 10 and scheme 11.

Scheme 10 d, d.3, f.1, g.2, g, j, n, u + Y, CC, FF, JJ $\xrightarrow[\text{LiOH/THF/H}_2\text{O}]{\text{Cs}_2\text{CO}_3/\text{CH}_3\text{CN}}$ Scheme 11

L = leaving group

-continued

The following non-limiting descriptions also demonstrate methods for the synthesis of compounds of the invention.

EXAMPLE 1

Synthesis of {7-[4-(4-Chloro-phenyl)-4-oxo-butylsulfanyl]-indan-4-yloxy}-acetic acid (Compound 1)

Step 1. Preparation of Indan-4-ol (Compound 1A)

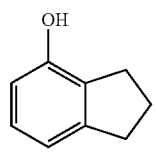

A mixture of 4-hydroxy-indan-1-one (5.0 g, 33.7 mmol), sodium cyanoborohydride (6.4 g, 101.1 mmol), and zinc iodide (32.3 g, 101.1 mmol) in dichloroethane, was heated at reflux for two hours. The reaction mixture was then filtered through 50 g SiO$_2$ while still warm, eluting further with dichloroethane. The filtrate was collected and concentrated under vacuum. The residue was added to diethyl ether and the resulting white precipitate was filtered off. The filtrate was collected and concentrated in vacuo to give 4.2 g of the title compound with purity high enough for subsequent use. 400 MHz $^1$H NMR (DMSO-d$_6$) δ 9.06 (s, 1H), 6.86 (t, 1H, J=7.8 Hz), 6.59 (d, 1H, J=7.8 Hz), 6.48 (d, 1H, J=7.8 Hz), 2.75 (t, 2H, J=7.3 Hz), 2.67 (t, 2H, J=7.3 Hz), 1.92 (m, 2H).

Step 2. Preparation of 7-Thiocyanato-indan-4-ol (Compound 1B)

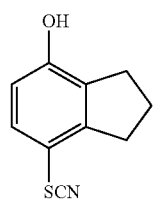

The product from Example 1A (2.75 g, 20.5 mmol), sodium thiocyanate (4.98 g, 61.6 mmol), and sodium bromide (2.1 g, 20.5 mmol) were dissolved in 80 ml anhydrous methanol. Bromine (3.28 g, 20.5 mmol) was added drop wise over 15 minutes and allowed to stir at ambient temperature for 1 h. Brine was added (50 ml) and the crude product was extracted into ethyl acetate (3×100 ml). The combined organic extracts were washed with brine, dried over anhydrous sodium sulfate, decanted, and concentrated to afford the title product in good purity. MS m/z 192 (M+1).

Step 3. Preparation of (7-Thiocyanato-indan-4-yloxy)-acetic acid methyl ester (Compound 1C)

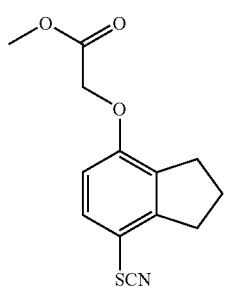

7-Thiocyanato-indan-4-ol (Example 1B) (3.23 g, 16.89 mmol), cesium carbonate (11 g, 33.8 mmol) and methyl bromoacetate (2.58 g, 16.89 mmol) were stirred in 20 ml acetonitrile at ambient temperature for 4 h. The reaction was filtered and concentrated. The crude product was recrystallized from ethyl acetate/heaxanes to afford the title product. MS m/z 239 (M+1).

Step 4. Preparation of (7-Mercapto-indan-4-yloxy)-acetic acid methyl ester (Compound 1D)

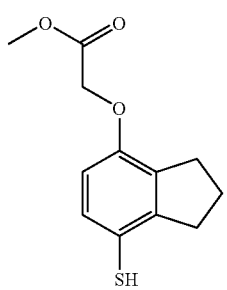

(7-Thiocyanato-indan-4-yloxy)-acetic acid methyl ester (Example 1C) (3.09 g, 12.9 mmol) was dissolved in 30 ml methanol. Dithiothreitol (2.6 g) was added followed by sodium borohydride (200 mg). The reaction was stirred for 1 hour followed by concentration to an oil. The crude product was dissolved in 200 ml dichloromethane and filtered through silica gel and eluted with 200 ml dichloromethane. The product was then recrystallized from ethyl acetate/heaxanes to afford the title product. MS m/z 239 (M+1).

Step 4. Preparation of {7-[4-(4-Chloro-phenyl)-4-oxo-butyl-sulfanyl]-indan-4-yloxy}-acetic acid methyl ester (Compound 1E)

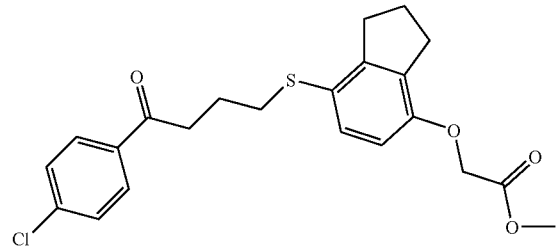

Compound 1D (300 mg, 1.26 mmol), 4-chloro-1-(4-chloro-phenyl)-butan-1-one (327 mg, 1.51 mmol), and cesium carbonate (616 mg, 1.89 mmol) in 10 ml anhydrous acetonitrile were stirred at ambient temperature for 72 hours. The reaction was then run through 0.5 g SiO$_2$ eluting with Et$_2$O. The eluant was collected and concentrated to give the title compound, pure enough for subsequent use. MS m/z 419 (M+1).

Step 5. Preparation of {7-[4-(4-Chloro-phenyl)-4-oxo-butyl-sulfanyl]-indan-4-yloxy}-acetic acid (Compound 1)

The product from Example 1E (528 mg, 1.26 mmol) and lithium hydroxide monohydrate (264 mg, 6.3 mmol) were dissolved in 5 ml THF/water solution (5:1). The reaction then stirred at ambient temperature for one hour followed by blowing to dryness with a stream of $N_2$. The crude residue was then taken up in EtOAc, and acidified with 6N HCl. The organic layer was then separated, dried ($Na_2SO_4$) and concentrated in vacuo. Recrystallisation from acetonitrile/water afforded the title compound (200 mg, 39%). 400 MHz $^1$H NMR (DMSO-$d_6$) δ 12.95 (br(s), 1H), 7.87 (d, 2H, J=8.8 Hz), 7.52 (d, 2H, J=8.8 Hz), 7.07 (d, 1H, J=8.6 Hz), 6.58 (d, 1H, J=8.6 Hz), 4.62 (s, 2H), 3.09 (t, 2H, J=7.1 Hz), 2.79 (m, 6H), 1.95 (m, 2H), 1.78 (m, 2H). MS m/z 405 (M+1). Anal. Calc'd for $C_{21}H_{21}Cl_1O_4S_1$ C, 62.29; H, 5.23; found: C, 62.12; H, 4.88.

EXAMPLE 2

Synthesis of {7-[4-(4-Bromo-phenyl)-4-oxo-butylsulfanyl]-indan-4-yloxy}-acetic acid (Compound 2)

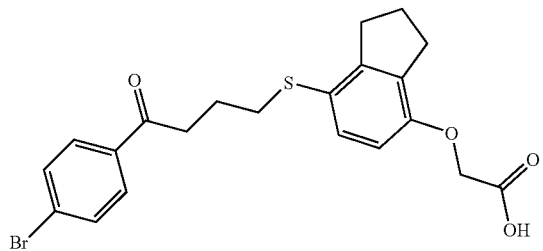

2

Compound 2 was made in a similar manner as described for compound 1. 400 MHz $^1$H NMR (DMSO-$d_6$) δ 12.95 (br(s), 1H), 7.80 (d, 2H, J=8.5 Hz), 7.67 (d, 2H, J=8.5 Hz), 7.07 (d, 1H, J=8.5 Hz), 6.57 (d, 1H, J=8.5 Hz), 4.61 (s, 2H), 3.08 (t, 2H, J=7.1 Hz), 2.78 (m, 6H), 1.95 (m, 2H), 1.77 (m, 2H). MS m/z 451 (M+1). Anal. Calc'd for $C_{21}H_{21}Br_1O_4S$] C, 56.13; H, 4.71; found: C, 55.57; H, 4.27.

EXAMPLE 3

Synthesis of {7-[4-(4-Fluoro-phenyl)-4-oxo-butylsulfanyl]-indan-4-yloxy}-acetic acid (Compound 3)

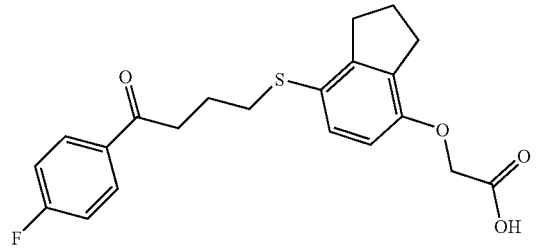

3

Compound 3 was made in a similar manner as described for compound 1. 400 MHz $^1$H NMR (DMSO-$d_6$) δ 7.96 (m, 2H), 7.29 (m, 2H), 7.08 (d, 1H, J=8.4 Hz), 6.58 (d, 1H, J=8.4 Hz), 4.60 (s, 2H), 3.09 (t, 2H, J=6.9 Hz), 2.79 (m, 6H), 1.95 (m, 2H), 1.78 (m, 2H). MS m/z 398 (M+1).

EXAMPLE 4

Synthesis of [7-(4-Oxo-4-thiophen-2-yl-butylsulfanyl)-indan-4-yloxy]-acetic acid (Compound 4)

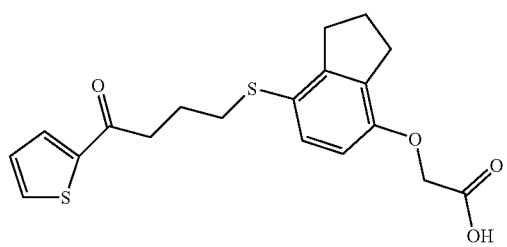

4

Compound 4 was made in a similar manner as described for compound 1. 400 MHz $^1$H NMR (DMSO-$d_6$) δ 7.94 (d, 1H, J=4.9 Hz), 7.86 (d, 1H, J=4.9 Hz), 7.18 (d, 1H, J=4.9 Hz), 7.07 (d, 1H, J=8.5 Hz), 6.58 (d, 1H, J=8.5 Hz), 4.62 (s, 2H), 3.04 (t, 2H, J=7.1 Hz), 2.79 (m, 6H), 1.95 (m, 2H), 1.77 (m, 2H). MS m/z 377 (M+1). Anal. Calc'd for $C_{19}H_{20}O_4S_2$ C, 60.61; H, 5.35; found: C, 60.31; H, 4.97.

EXAMPLE 5

Synthesis of {6-[4-(4-Trifluoromethyl-benzyloxy)-benzyloxy]-benzo[b]thiophen-3-yl}-acetic acid (Compound 5)

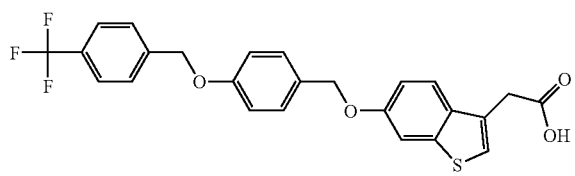

5

Step 1. Preparation of 4-(3-Methoxy-phenylsulfanyl)-3-oxo-butyric acid methyl ester (Compound 5A)

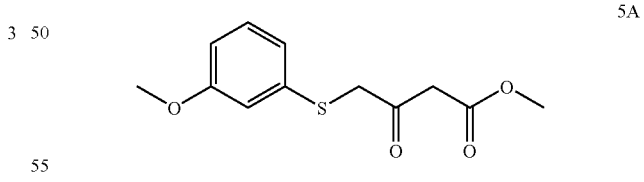

5A

A solution of methyl 2-chloroacetoacetate (15.0 g, 0.10 mol) in 20 ml of acetonitrile was added dropwise to a mixture of 3-methoxythiophenol (14.0 g, 0.10 mol) and cesium carbonate (65.2 g, 0.20 mol) in 400 ml of acetonitrile over 30 min. The mixture was stirred at room temperature for 2 hours, then filtered through Celite®. The filtrate was concentrated and purified using normal phase chromatography. 400 MHz $^1$H NMR (DMSO-$d_6$) δ 7.21 (dt, 1H), 6.95–6.85 (m, 2H), 6.78 (dd, 1H), 3.82 (s, 2H), 3.80 (s, 3H), 3.74 (s, 3H), 3.65 (s, 2H), MS (ES (M–1)=253).

Step 2. Preparation of (6-methoxybenzo[b]thiophen-3-yl) acetic acid methyl ester (Compound 5B)

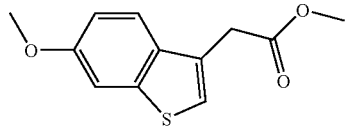

The product from example 5A (2.54 g, 0.01 mol) was added dropwise to 25 ml of methanesulfonic acid at room temperature, and the solution was stirred at the same temperature for 15 minutes, then the reaction mixture was added to 250 ml of ice-water. The aqueous mixture was extracted with ethyl acetate. The organic phase was washed with brine, sodium bicarbonate, dried over sodium sulfate, and concentrated to give 5B in good purity. 400 MHz $^1$H NMR (DMSO-$d_6$) δ 7.64 (d, 1H), 7.32 (d, 1H), 7.18 (s, 1H), 7.04 (dd, 1H), 3.88 (s, 3H), 3.82 (s, 2H), 3.71 (s, 3H), MS (ES (M+1)=236).

Step 3. Preparation of (6-hydroxy-benzo[b]thiophen-3-yl) acetic acid methyl ester (Compound 5C)

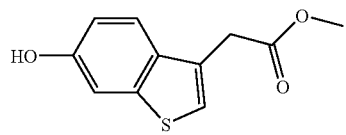

To a stirred solution of the product from example 5B (2.20 g, 9.32 mmol) in 50 ml of dichloromethane at −78° C. was added dropwise a solution of boron tribromide (11.68 g, 46.6 mmol) in 50 ml of dichloromethane. After the completion of the addition of boron tribromide, the reaction mixture was maintained at −78° C. for 1 h, then allowed to reach room temperature and stirred at the same temperature overnight. The mixture was cooled to 0° C., carefully quenched with 100 ml of water, extracted with ethyl acetate, washed with brine, dried over sodium sulfate, concentrated, and purified using normal phase chromatography to afford the title product. 400 MHz $^1$H NMR (DMSO-$d_6$) δ 7.59 (d, 1H), 7.25 (d, 1H), 7.16 (s, 1H), 6.92 (dd, 1H), 5.20 (brs, 1H), 3.82 (s, 2H), 3.71 (s, 3H), MS (ES (M+1)=223).

Step 4. Preparation of [4-(4-Trifluoromethyl-benzyloxy)-phenyl]-methanol (Compound 5D)

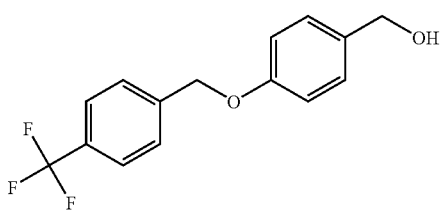

4-Hydroxymethyl-phenol (1 g, 8.06 mmol), 1-Chloromethyl-4-trifluoromethyl-benzene (1.57 g, 8.06 mmol), and cesium carbonate (5.26 g, 16.12 mmol) were refluxed in acetonitrile for 20 h, cooled, filtered, and concentrated to give the title compound. MS m/z 265 (M−$H_2O$+1).

Step 5. Preparation of 1-(4-trifluoromethyl-benzyloxy)-4-chloromethyl-benzene (Compound 5E)

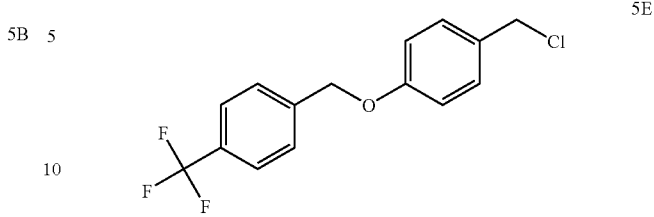

To a cooled (0° C.) solution of the product from Example 5D (10 g, 37 mmoles) in 138 mL of anhydrous dichloromethane was added 12.8 mL of triethylamine (9.3 g, 92 mmoles), followed by 5.7 mL of methanesulfonyl chloride (8.4 g, 73 mmoles). The reaction mixture was stirred at 0° C. for 1 hr and then at room temperature for 18 hrs. The reaction mixture was evaporated onto 8 g of silica gel and chromatographed (silica gel, 10% ethyl acetate in hexane) to provide analytically pure product. MS m/z 265 (M−Cl+1).

Step 6. Preparation of {6-[4-(4-Trifluoromethyl-benzyloxy)-benzyloxy]-benzo[b]thiophen-3-yl}-acetic acid methyl ester (Compound 5F)

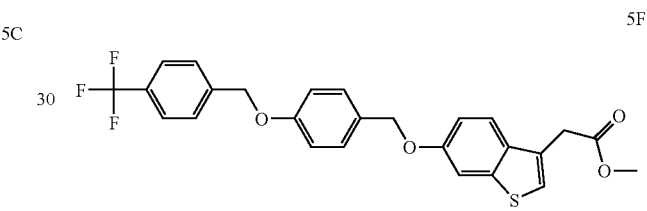

Compounds 5C, 5E and cesium carbonate in 10 mL AcCN stirred at 60° C. for 18 hours. The reaction was then cooled, diluted with $Et_2O$ and filtered through Celite®. The filtrate was collected and concentrated in vacuo. Recrystalisation from $CHCl_3$/Hexanes gave 340 mg (62%) of the title compound. MS m/z 487 (M+1).

Step 7. Preparation of {6-[4-(4-Trifluoromethyl-benzyloxy)-benzyloxy]-benzo[b]thiophen-3-yl}-acetic acid (Compound 5)

The title compound was prepared from compound 5F in a manner analogous to compound 1. 400 MHz $^1$H NMR (DMSO-$d_6$) δ 12.39 (s(br), 1H), 7.71 (d, 2H, J=8.0 Hz), 7.58 (m, 3H), 7.36 (d, 2H, J=8.8 Hz), 7.30 (s, 1H), 7.00 (m, 4H), 5.19 (s, 2H), 5.03 (s, 2H), 3.73 (s, 2H); MS m/z 473 (M+1). Anal. Calc'd for $C_{25}H_{19}F_3O_4S_1$ C, 63.55; H, 4.05; found: C, 63.35; H, 3.73.

EXAMPLE 6

Synthesis of {6-[3-(4-Trifluoromethyl-benzyloxy)-benzyloxy]-benzo[b]thiophen-3-yl}-acetic acid (Compound 6)

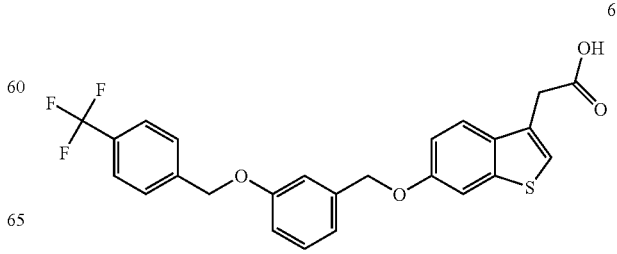

Step 1. Preparation of [3-(4-trifluoromethyl-benzyloxy)-phenyl]-methanol (Compound 6A)

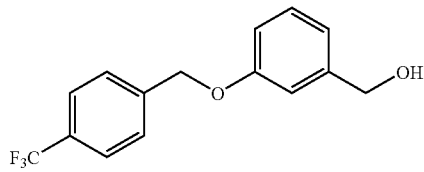

6A

The title compound was prepared in the manner analogous to example 5D using 1-bromomethyl-4-trifluoromethyl-benzene and 3-hydroxymethyl-phenol. MS m/z 265 (M–OH).

Step 2. Preparation of 1-(4-trifluoromethyl-benzyloxy)-3-chloromethyl-benzene (Compound 6B)

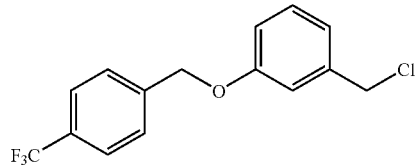

6B

The title compound was prepared in the manner analogous to example 5E using the product from example 6A. MS m/z 265 (M–Cl).

Step 3. Preparation of {6-[3-(4-Trifluoromethyl-benzyloxy)-benzyloxy]-benzo[b]thiophen-3-yl}-acetic acid methyl ester (Compound 6C)

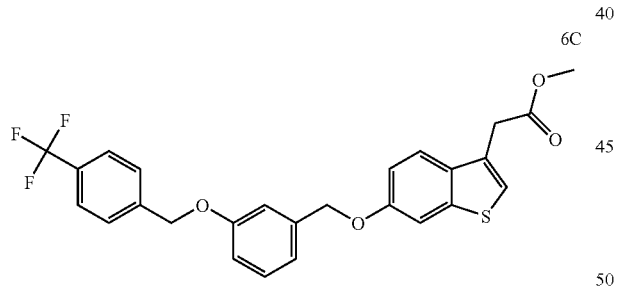

6C

The title compound was prepared from compounds 6B and 5C in a manner analogous to compound 5F. MS m/z 487 (M+1).

Step 4. Preparation of {6-[3-(4-Trifluoromethyl-benzyloxy)-benzyloxy]-benzo[b]thiophen-3-yl}-acetic acid (Compound 6)

The title compound was prepared from compound 6C in a manner analogous to compound 1. 400 MHz $^1$H NMR (DMSO-$d_6$) δ 7.70 (d, 2H, J=8.3 Hz), 7.59 (m, 3H), 7.31 (s, 1H), 7.27 (t, 1H, J=7.8 Hz), 7.05 (s, 1H), 7.02 (m, 3H), 6.92 (dd, 1H, J=8.3 Hz, J=2.0 Hz), 5.19 (s, 2H), 5.10 (s, 2H), 3.73 (s, 2H); MS m/z 473 (M+1). Anal. Calc'd for $C_{25}H_{19}F_3O_4S_1 \cdot 0.5H_2°$ C., 62.36; H, 4.19; found: C, 62.12; H, 3.79.

EXAMPLE 7

Synthesis of {6-[2-(4-Trifluoromethyl-benzyloxy)-benzyloxy]-benzo[b]thiophen-3-yl}-acetic acid (Compound 7)

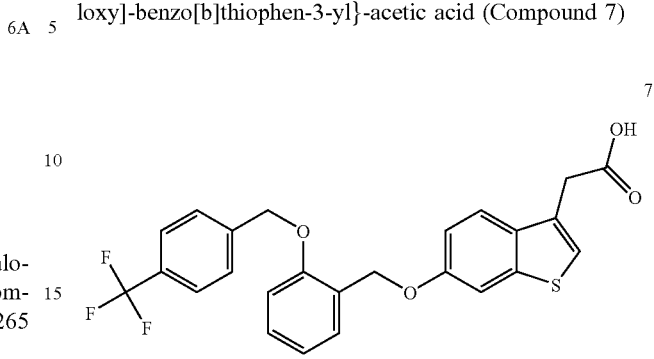

7

Step 1. Preparation of [2-(4-Trifluoromethyl-benzyloxy)-phenyl]-methanol (Compound 7A)

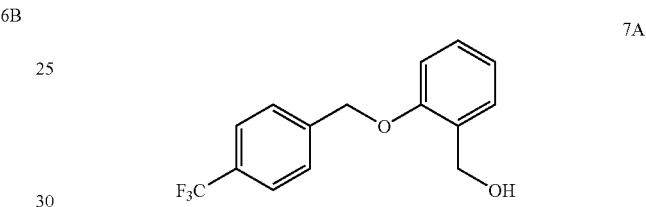

7A

The title compound was prepared in the manner analogous to example 5D using 1-bromomethyl-4-trifluoromethyl-benzene and 2-hydroxymethyl-phenol. MS m/z 265 (M–OH).

Step 2. Preparation of 1-(4-trifluoromethyl-benzyloxy)-2-chloromethyl-benzene (Compound 7B)

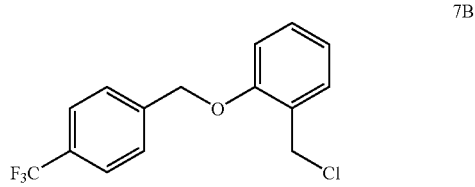

7B

The title compound was prepared in the manner analogous to example 5E using the product from example 7A. MS m/z 265 (M–Cl).

Step 3. Preparation of {6-[2-(4-Trifluoromethyl-benzyloxy)-benzyloxy]-benzo[b]thiophen-3-yl}-acetic acid methyl ester (Compound 7C)

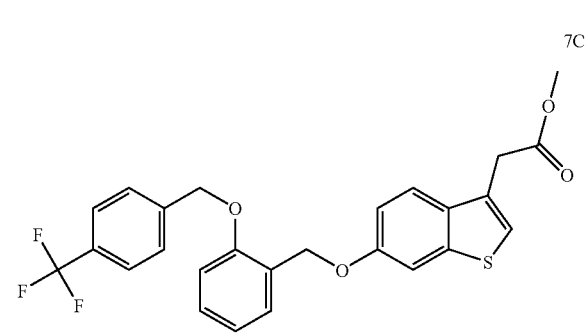

7C

The title compound was prepared from compounds 7B and 5C in a manner analogous to compound 5F. MS m/z 487 (M+1).

Step 4. Preparation of {6-[2-(4-Trifluoromethyl-benzyloxy)-benzyloxy]-benzo[b]thiophen-3-yl}-acetic acid (Compound 7)

The title compound was prepared from compound 7C in a manner analogous to compound 1. 400 MHz $^1$H NMR (DMSO-d$_6$) δ 12.38 (s, (br) 1H), 7.62 (m, 6H), 7.42 (d, 1H, J=7.6 Hz), 7.31 (s, 1H), 7.27 (t, 1H, J=8.3 Hz), 7.04 (m, 2H), 6.94 (t, 1H, J=6.6 Hz), 5.27 (s, 2H), 5.17 (s, 2H), 3.73 (s, 2H); MS m/z 473 (M+1). Anal. Calc'd for C$_{25}$H$_{19}$F$_3$O$_4$S$_1$C, 63.55; H, 4.05; found: C, 63.29; H, 3.72.

EXAMPLE 8

Synthesis of {6-[5-(4-Chloro-phenyl)-isoxazol-3-yl-methoxy]-benzo[b]thiophen-3-yl}-acetic acid (Compound 8)

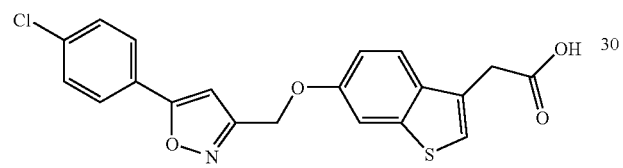

8

Step 1. Preparation of {6-[5-(4-Chloro-phenyl)-isoxazol-3-ylmethoxy]-benzo[b]thiophen-3-yl}-acetic acid methyl ester (Compound 8A)

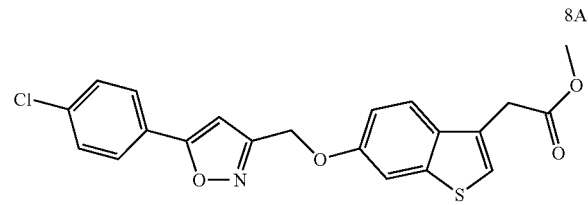

8A

The title compound was prepared from compound 5C and commercially available 3-chloromethyl-5-(4-chloro-phenyl)-isoxazole in the manner analogous to example 5F. MS m/z 414 (M+1).

Step 2. Preparation of {6-[5-(4-Chloro-phenyl)-isoxazol-3-ylmethoxy]-benzo[b]thiophen-3-yl}-acetic acid (Compound 8)

The title compound was prepared from compound 8A in a manner analogous to compound 1. 400 MHz $^1$H NMR (DMSO-d$_6$) δ ppm 7.88 (m, 2H), 7.65 (m, 2H), 7.56 (m, 2H), 7.35 (s, 1H), 7.21 (s, 1H), 7.09 (dd, J=8.8, 2.4 Hz, 1H), 5.27 (s, 2H), 3.74 (s, 2H); MS m/z 400 (M+1).

EXAMPLE 9

Synthesis of {4-Chloro-6-[5-(4-chloro-phenyl)-isoxazol-3-ylmethoxy]-benzo[b]thiophen-3-yl}-acetic acid (Compound 9)

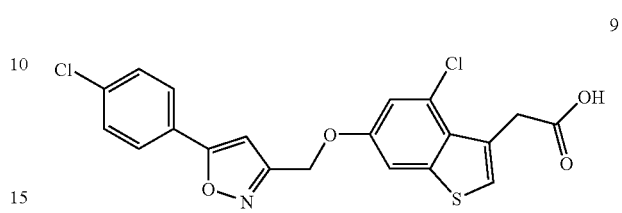

9

Step 1. Preparation of Dimethyl-thiocarbamic acid S-(3-chloro-5-methoxy-phenyl) ester (Compound 9A)

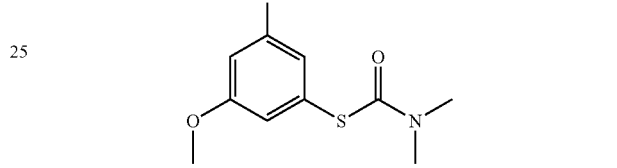

9A

A solution of 3-chloro-5-methoxy-phenol (15.0 g, 94.6 mmol) in 20 mL dry DMF was treated portionwise with NaH (2.7 g of a 95% dispersion in mineral oil, 114 mmol). After 30 min, dimethylthiocarbamoyl chloride (12.9 g, 104 mmol) was added and the reaction stirred at ambient temperature for 3 hours. The solvent was then removed in vacuo, the residue taken up in Et$_2$O and washed 1×2 M HCl, 1× brine, dried (Na$_2$SO$_4$) and concentrated. The crude material was run through 200 g SiO$_2$, eluting with 1.5 L 30% EtoAc/Hex to give 19.4 g of the intermediate product dimethyl-thiocarbamic acid O-(3-chloro-5-methoxy-phenyl) ester pure enough for subsequent use. MS m/z 246 (M+1). The intermediate was then taken up in 50 mL diphenyl ether and added to 60 mL refluxing diphenyl ether. After 50 minutes, reaction was cooled and run through 500 g SiO$_2$ to remove the diphenyl ether. Subsequent elution with 100% Et$_2$O gave 18.7 g of the title compound pure enough for subsequent use. MS m/z 246 (M+1).

Step 2. Preparation of 3-Chloro-5-methoxy-benzenethiol (Compound 9B)

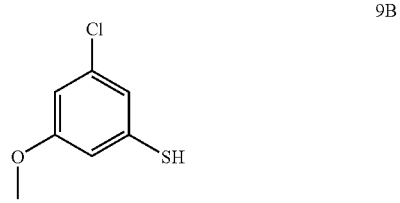

9B example 9A (18.7 g, 76.1 mmol) and KOH (381 mmols) in 150 mL 3:1 EtOH/water, heated at reflux for 5H. The reaction was then cooled, concentrated to about 50 mL, taken up in EtOAc and quenched carefully with conc. HCL.

The organic layer was then washed 1×H$_2$O, dried (Na$_2$SO$_4$) and solvent removed in vacuo. Purification by flash column chromtography (gradient elution) 5% EtOAc/Hex to 35% EtOAc/Hex gave 9.8 g product. MS m/z 173 (M−1)

Step 3. Preparation of 4-(3-Chloro-5-methoxy-phenylsulfanyl)-3-oxo-butyric acid methyl ester (Compound 9C)

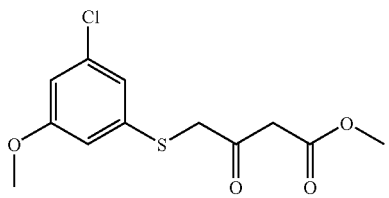

The title compound was made from example 9B in a similar manner as described for example 5A. MS m/z 286 (M−1).

Step 4. Preparation of (4-Chloro-6-methoxy-benzo[b]thiophen-3-yl)-acetic acid methyl ester (Compound 9D)

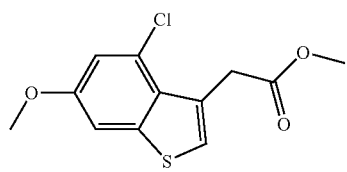

The title compound was made from example 9C in a similar manner as described for example 5B. MS m/z 271 (M+1).

Step 5. Preparation of (4-Chloro-6-hydroxy-benzo[b]thiophen-3-yl)-acetic acid methyl ester (Compound 9E)

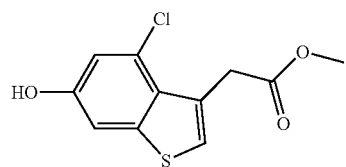

The title compound was made from example 9D in a similar manner as described for example 5C. MS m/z 255 (M−1).

Step 6. Preparation of {4-Chloro-6-[5-(4-chloro-phenyl)-isoxazol-3-ylmethoxy]-benzo[b]thiophen-3-yl}-acetic acid methyl ester (Compound 9F)

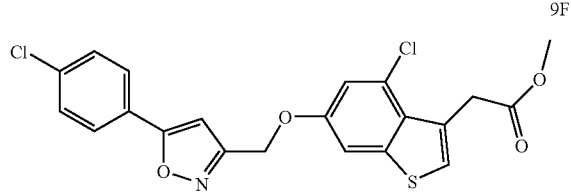

The title compound was made from example 9E and commercially available 3-chloromethyl-5-(4-chloro-phenyl)-isoxazole in the manner analogous to example 5F. MS m/z 447 (M−1).

Step 7. Preparation of {4-Chloro-6-[5-(4-chloro-phenyl)-isoxazol-3-ylmethoxy]-benzo[b]thiophen-3-yl}-acetic acid (Compound 9)

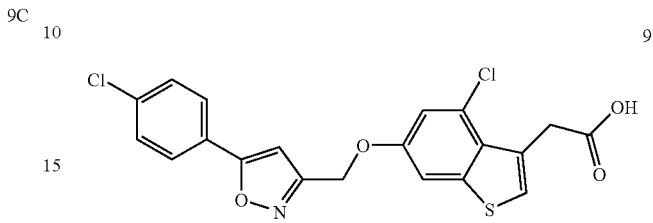

The title compound was made from example 9F in a manner analogous to example 5. 400 MHz $^1$H NMR (DMSO-d$_6$) δ ppm 3.95 (s, 2H) 5.30 (s, 2H) 7.15 (d, J=2.20 Hz, 1H) 7.20 (s, 1H) 7.44 (s, 1H) 7.56 (d, J=8.79 Hz, 2H) 7.69 (d, J=2.20 Hz, 1H) 7.87 (d, J=8.79 Hz, 2H). MS m/z 433 (M−1).

EXAMPLE 10

Synthesis of {6-[4-(5-Trifluoromethyl-pyridin-2-yl)-benzylsulfanyl]-chroman-2-yl}-acetic acid (Compound 10)

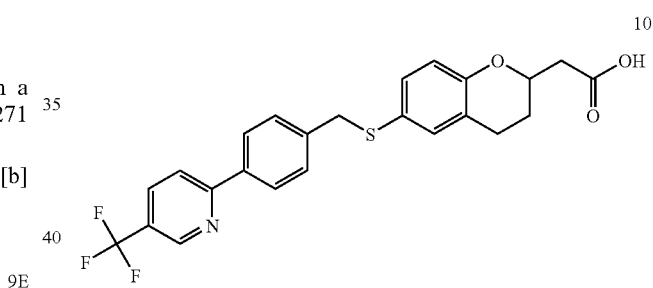

Step 1. Preparation of 5-(2-Hydroxy-5-thiocyanato-phenyl)-pent-2-enoic acid ethyl ester (Compound 10A)

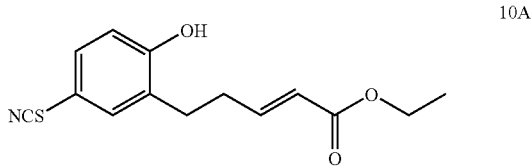

The title compound was prepared from 5-(2-Hydroxyphenyl)-pent-2-enoic acid methyl ester in the manner analogous to example 1B. MS m/z 278 (M+1).

Step 2. Preparation of (6-Thiocyanato-chroman-2-yl)-acetic acid ethyl ester (Compound 10B)

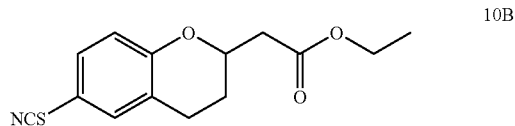

The product from example 10A (2.4 g, 9.1 mmol) was dissolved in 20 ml acetonitrile. Cesium carbonate (2.97 g, 9.12 mmol), was added. The reaction was stirred for 6 h followed by filtration through Celite and concentration. The products was purified by MPLC to give a clear, colorless oil. MS m/z 278 (M+1).

Step 3. Preparation of (6-Mercapto-chroman-2-yl)-acetic acid ethyl ester (Compound 10C)

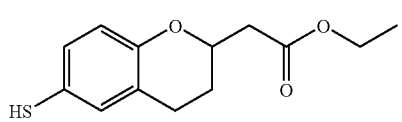

10C

The title compound was prepared in the manner analogous to example 1D using the product from example 10B MS m/z 253 (M+1)

Step 4. Preparation of [4-(5-Trifluoromethyl-pyridin-2-yl)-phenyl]-methanol (Compound 10D)

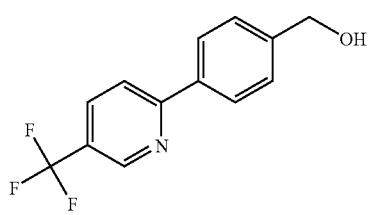

10D

The title compound was made in a similar manner as described for example 36D. 400 MHz ¹H NMR (DMSO-d₆) δ 8.98 (s, 1H), 8.2 (dd, 1H, J=2.4 Hz, J=8.4 Hz), 8.09 (m, 3H), 7.42 (d, 2H, J=8.54 Hz), 5.23 (t, 1H), 4.54 (d, 2H, J=6 Hz); MS m/z 254 (M+1).

Step 5. Preparation of 2-(4-Chloromethyl-phenyl)-5-trifluoromethyl-pyridine (Compound 10E)

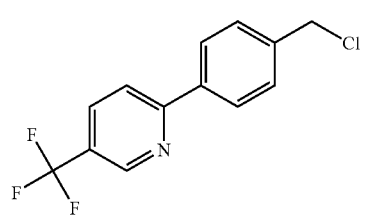

10E

The title compound was prepared in the manner analogous to example 5E using 10D. MS m/z 272 (M+1).

Step 6. Preparation of {6-[4-(5-Trifluoromethyl-pyridin-2-yl)-benzylsulfanyl]-chroman-2-yl}-acetic acid ethyl ester (Compound 10F)

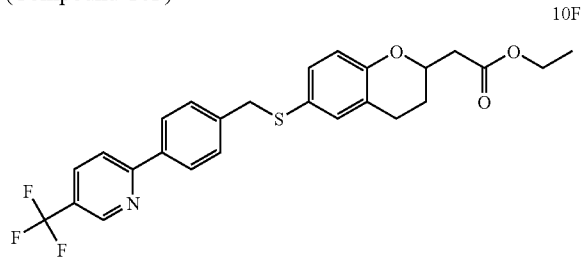

10F

The title compound was prepared in the manner analogous to example 1E using the products from example 10C and example 10E. MS m/z 488 (M+1).

Step 7. Preparation of {6-[4-(5-Trifluoromethyl-pyridin-2-yl)-benzylsulfanyl]-chroman-2-yl}-acetic acid (Compound 10)

The title compound was prepared in the manner analogous to example 1 using the product from example 10D 400 MHz ¹H NMR (DMSO-d₆) δ 8.97 (m, 1H), 8.22 (m, 1H), 8.13 (m, 1H), 8.03 (m, 2H), 7.36 (d, 2H, J=8.5 Hz), 7.02 (m, 2H), 6.59 (d, 1H, J=8.5 Hz), 4.27 (m, 1H), 4.11 (s, 2H), 2.71 (m, 1H), 2.53 (m, 3H), 1.94 (m, 1H), 1.60 (m, 1H). MS m/z 460 (M+1).

EXAMPLE 11

Synthesis of {6-[4-(2,5-Dichloro-benzyloxy)-benzylsulfanyl]-chroman-2-yl}-acetic acid (Compound 11)

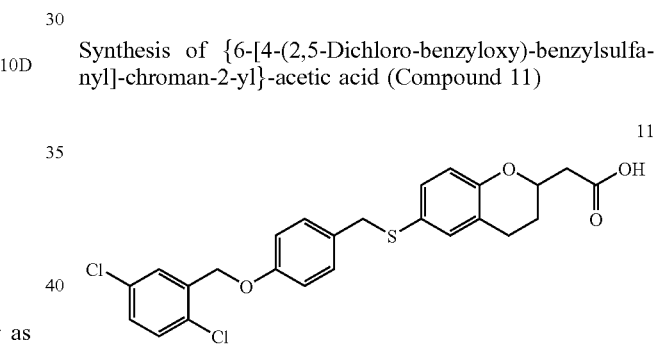

11

Step 1. Preparation f 1,4-dichloro-2-(4-chloromethyl-phenoxymethyl)-benzene (Compound 11A)

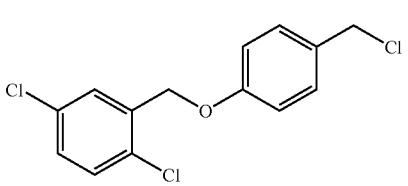

11A

The title compound was made in a similar manner as described for example 5E. MS m/z 265 (M–Cl).

Step 2. Preparation of {6-[4-(2,5-Dichloro-benzyloxy)-benzylsulfanyl]-chroman-2-yl}-acetic acid ethyl ester (Compound 11B)

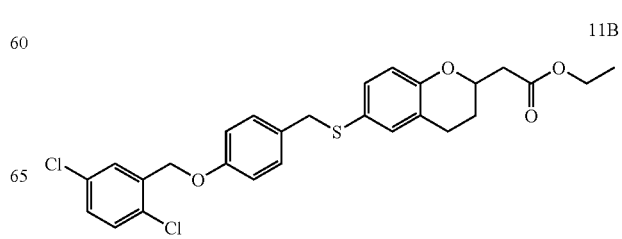

11B

The title compound was prepared in the manner analogous to example 1E using the products from example 10C and example 11A. MS m/z 517 (M).

Step 2. Preparation of {6-[4-(2,5-Dichloro-benzyloxy)-benzylsulfanyl]-chroman-2-yl}-acetic acid (Compound 11)

The title compound was prepared in the manner analogous to example 1 using the product from example 11B. 400 MHz $^1$H NMR (DMSO-$d_6$) δ 7.60 (d, 1H, J=2.2 Hz), 7.50 (m, 1H), 7.43 (m, 1H), 7.14 (m, 2H), 6.98 (m, 2H), 6.89 (m, 2H), 6.58 (d, 1H, J=8.5 Hz), 5.06 (s, 2H), 4.28 (m, 1H), 3.98 (s, 2H), 2.71 (m, 1H), 2.55 (m, 3H), 1.94 (m, 1H), 1.60 (m, 1H). MS m/z 487 (M−2).

EXAMPLE 12

Synthesis of {6-[4-(4-Trifluoromethyl-benzyloxy)-benzylsulfanyl]-chroman-2-yl}-acetic acid (Compound 12)

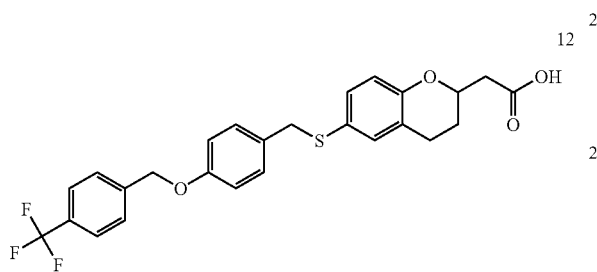

Step 1. Preparation of {6-[4-(4-Trifluoromethyl-benzyloxy)-benzylsulfanyl]-chroman-2-yl}-acetic acid ethyl ester (Compound 12A)

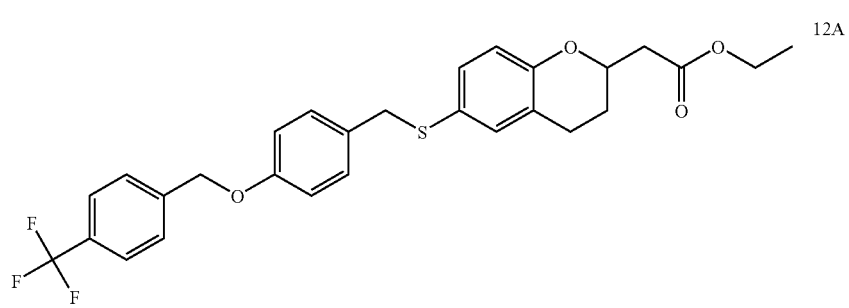

The title compound was prepared in the manner analogous to example 1E using the products from example 10C and example 5E. MS m/z 515 (M−1).

Step 2. Preparation of {6-[4-(4-Trifluoromethyl-benzyloxy)-benzylsulfanyl]-chroman-2-yl}-acetic acid (Compound 12)

The title compound was prepared in the manner analogous to example 1 using the product from example 12A. 400 MHz $^1$H NMR (DMSO-$d_6$) δ 12.32 (br(s), 1H), 7.70 (d, 2H, J=8.1 Hz), 7.60 (d, 2H, J=8.1 Hz), 7.12 (m, 2H), 6.98 (m, 2H), 6.88 (m, 2H), 6.58 (d, 1H, J=8.3 Hz), 5.14 (s, 2H), 4.28 (m, 1H), 3.97 (s, 2H), 2.71 (m, 1H), 2.55 (m, 3H), 1.95 (m, 1H), 1.58 (m, 1H). MS m/z 487 (M−1).

EXAMPLE 13

Synthesis of {6-[5-(4-Trifluoromethyl-phenyl)-isoxazol-3-ylmethylsulfanyl]-chroman-2-yl}-acetic acid (Compound 13)

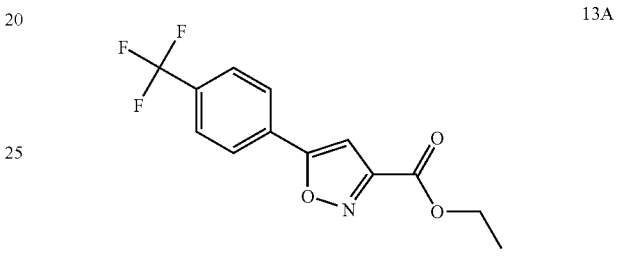

Step 1. Preparation of 5-(4-Trifluoromethyl-phenyl)-isoxazole-3-carboxylic acid ethyl ester (Compound 13A)

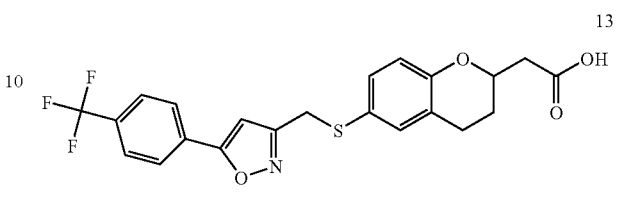

Sodium hydride (1.6 g, 63.7 mmol, 95%) was added to a solution of 1-(4-trifluoromethyl-phenyl)-ethanone (10.0 g, 53.1 mmol) and oxalic acid diethyl ester (8.7 mL, 63.7 mmol) in 75 mL dry DMF at 0° C. The reaction was allowed to come to room temperature and then heated to 45° C. for 45 minutes. The reaction was then cooled, concentrated in vacuo, and the residue taken up in EtOAc. The organic layer was then washed with 2 M HCl (1×100 mL), dried (Na$_2$SO$_4$) and the solvent removed in vacuo. Purification by flash column chromatography (gradient elution: 5% EtOAc/hexane to 55% EtOAc/hexane) gave the intermediate 2,4-dioxo-4-(4-trifluoromethyl-phenyl)-butyric acid ethyl ester (12.2 g, 80%) which was then taken up in EtOH and refluxed in the presence of hydroxylamine hydrochloride (10.2 g, 132.3 mmol) for 3H. The reaction was then cooled, diluted with EtOAc, washed with dilute NaHCO$_3$, brine, dried (Na$_2$SO$_4$), and concentrated in vacuo. Recrystallization from EtOAc/hexane gave 5.2 g of the title compound. MS m/z 286 (M+1).

Step 2. Preparation of [5-(4-Trifluoromethyl-phenyl)-isoxazol-3-yl]-methanol (Compound 13B)

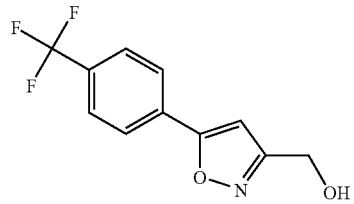

13B

A solution of 13A (14.1 g, 49.4 mmol) in 3:1 THF/MeOH, was treated with NaBH$_4$ (5.6 g, 148 mmol) at ambient temperature. The reaction was then stired for 3H, followed by concentrating in vacuo to about 50 mL, quenching with 2 M HCl, extract 1×150 mL EtOAC, dry (Na$_2$SO$_4$) and concentrate in vacuo to give 11.8 g of the title compound pure enough for subsequent use. MS m/z 244 (M+1).

Step 3. Preparation of 3-chloromethyl-5-(4-trifluoromethyl-phenyl)-isoxazole (Compound 13C)

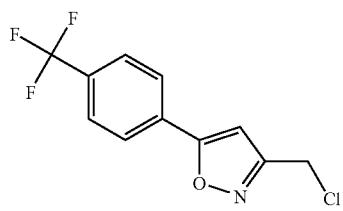

13C

The title compound was prepared in a manner analogous to Example 5E using 13B. MS m/z 262 (M+1).

Step 4. Preparation of {6-[5-(4-Trifluoromethyl-phenyl)-isoxazol-3-ylmethylsulfanyl]-chroman-2-yl}-acetic acid ethyl ester (Compound 13D)

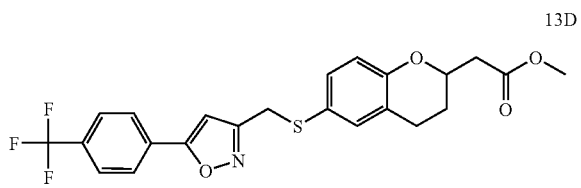

13D

The title compound was prepared in the manner analogous to example 1E using the products from example 10C and example 13C. MS m/z 464 (M+1).

Step 5. Preparation of {6-[5-(4-Trifluoromethyl-phenyl)-isoxazol-3-ylmethylsulfanyl]-chroman-2-yl}-acetic acid (Compound 13)

The title compound was prepared in the manner analogous to example 1 using the product from example 13D 400 MHz $^1$H NMR (DMSO-d$_6$) δ 12.33 (br(s), 1H), 8.01 (d, 2H, J=8.8 Hz), 7.84 (d, 2H, J=8.8 Hz), 7.12 (s, 1H), (7.11 (m, 1H), 7.05 (dd, 1H, J=2.4 Hz, J=8.5 Hz), 6.61 (d, 1H, J=8.5 Hz), 4.28 (m, 1H), 4.12 (s, 2H), 2.73 (m, 1H), 2.60 (m, 1H), 2.55 (m, 2H), 1.93 (m, 1H), 1.60 (m, 1H). MS m/z 450 (M+1).

EXAMPLE 14

Synthesis of {6-[3-(4-Trifluoromethyl-benzyloxy)-benzylsulfanyl]-chroman-2-yl}-acetic acid (Compound 14)

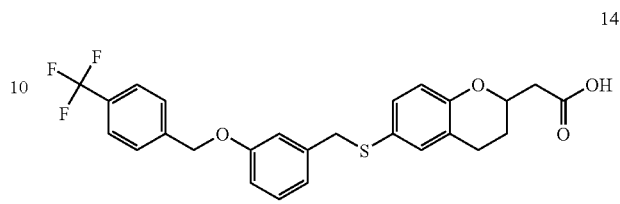

14

Step 1. Preparation of {6-[3-(4-Trifluoromethyl-benzyloxy)-benzylsulfanyl]-chroman-2-yl}-acetic acid methyl ester (Compound 14A)

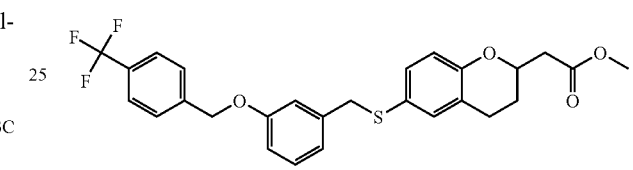

14A

The title compound was prepared in the manner analogous to example 1E using the products from example 10C and example 6B. MS m/z 503 (M+1).

Step 2. Preparation of {6-[3-(4-Trifluoromethyl-benzyloxy)-benzylsulfanyl]-chroman-2-yl}-acetic acid (Compound 14)

The title compound was prepared in the manner analogous to example 1 using the product from example 14A. 400 MHz $^1$H NMR (DMSO-d$_6$) δ 12.33 (br(s), 1H), 7.71 (d, 2H, J=8.1 Hz), 7.59 (d, 2H, J=8.1 Hz), 7.14 (t, 1H, J=8.1 Hz), 6.98 (m, 2H), 6.81 (m, 3H), 6.58 (d, 1H, J=8.3 Hz), 5.11 (s, 2H), 4.26 (m, 1H), 3.99 (s, 2H), 2.68 (1H), 2.55 (m, 3H), 1.94 (m, 1H), 1.59 (m, 1H). MS m/z 489 (M+1).

EXAMPLE 15

Synthesis of 1-{4-[2-(4-Trifluoromethyl-benzyloxy)-benzyloxy]-phenyl}-cyclopropanecarboxylic acid (Compound 15)

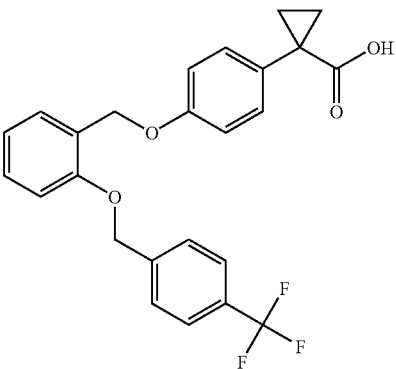

15

Step 1. Preparation of 1-(4-Hydroxy-phenyl)-cyclopropanecarboxylic acid methyl ester (Compound 15A)

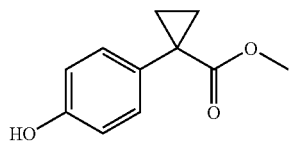

1-(4-Methoxy-phenyl)-cyclopropanecarboxylic acid methyl ester (2.08 g, 10.1 mmol) was dissolved in 25 ml DCM and cooled over an ice bath to ca. 5 deg. C. BBr3 (3.03 g, 12.01 mmol) was added followed by stirring for 2 h. 25 ml 2N HCl was added followed by stirring for 10 minutes. The DCM layer was seperated, dried over sodium sulfate, decanted and concentrated. 100 MeOH and 5 drops conc. sulfuric acid were added followed by heating at 50 deg. C for 2 days. The reaction was concentrated, dissolved in 50 ml ethyl acetate, washed 1×20 ml brine, dried over sodium sulfate, decanted, and concentrated. MPLC gave the desired phenol as a clear colorless oil. MS m/z 193 (M+1).

Step 2. 1-{4-[2-(4-Trifluoromethyl-benzyloxy)-benzyloxy]-phenyl}-cyclopropanecarboxylic acid methyl ester (Compound 15B)<

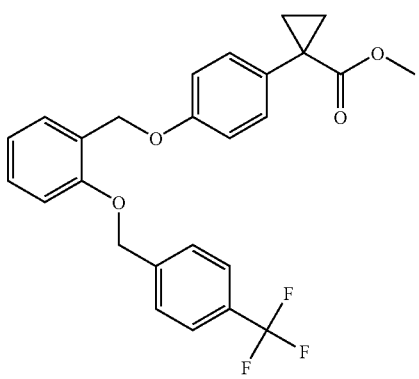

The title compound was prepared in the manner analogous to example 1E using the products from example 15A and example 7B. MS m/z 457 (M+1).

Step 3. Preparation of 1-{4-[2-(4-Trifluoromethyl-benzyloxy)-benzyloxy]-phenyl}-cyclopropanecarboxylic acid (Compound 15)

The title compound was prepared in the manner analogous to example 1 using the product from example 15B 400 MHz $^1$H NMR (DMSO-$d_6$) δ 12.16 (br(s), 1H), 7.65 (m, 4H), 7.35 (dd, 1H, J=1.7 Hz, J=7.56), 7.26 (m, 1H), 7.16 (m, 2H), 7.05 (d, 1H, J=8.05), 6.93 (m, 1H), 6.86 (m, 2H), 6.26 (s, 2H), 5.08 (s, 2H), 1.35 (m, 2H), 1.01 (m, 2H). MS m/z 441 (M−1).

EXAMPLE 16

Synthesis of {6-[5-(4-Trifluoromethyl-phenyl)-isoxazol-3-ylmethoxy]-benzo[b]thiophen-3-yl}-acetic acid (Compound 16)

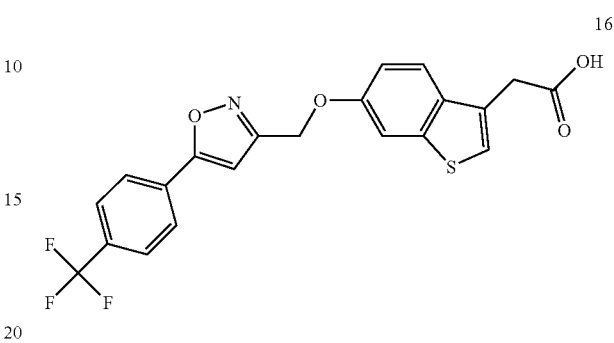

Step 1. Preparation of {{6-[5-(4-Trifluoromethyl-phenyl)-isoxazol-3-ylmethoxy]-benzo[b]thiophen-3-yl}-acetic acid methyl ester (Compound 16A)

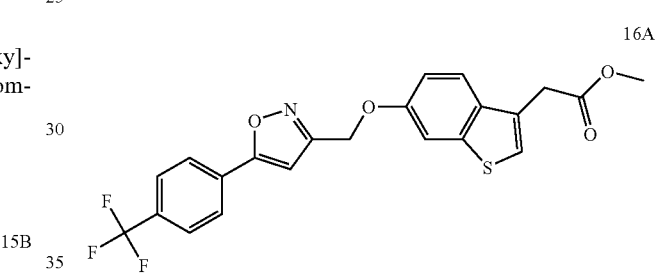

The title compound was prepared in the manner analogous to example 1E using the product from example 5C and the product from example 13C. MS m/z 448 (M+1).

Step 2. Preparation of {{6-[5-(4-Trifluoromethyl-phenyl)-isoxazol-3-ylmethoxy]-benzo[b]thiophen-3-yl}-acetic acid (Compound 16)

The title compound was prepared in the manner analogous to example 1 using the product from example 16A 400 MHz $^1$H NMR (DMSO-$d_6$) δ 12.40 (br(s), 1H), 8.09 (d, 2H, J=8.3 Hz), 7.86 (d, 2H, J=8.3 Hz), 7.65 (m, 2H), 7.36 (m, 2H), 7.10 (dd, 1H, J=2.44, J=8.8 Hz), 5.30 (s, 2H), 3.75 (s, 2H). MS m/z 434 (M+1).

EXAMPLE 17

Synthesis of {4-Methyl-6-[4-methyl-2-(4-trifluoromethyl-phenyl)-thiazol-5-ylmethoxy]-benzo[b]thiophen-3-yl}-acetic acid (Compound 17)

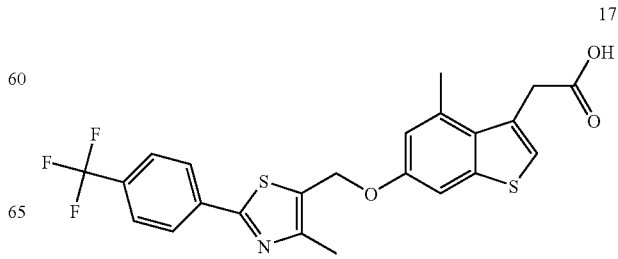

Step 1. Preparation of (6-Hydroxy-4-methyl-benzo[b]thiophen-3-yl)-acetic acid ethyl ester (Compound 17A)

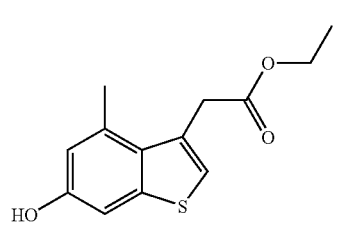

17A

The title compound was prepared in the manner analogous to example 5C starting with 3 3-methoxy-5-methyl-benzenethiol and the 4-chloro-3-oxo-butyric acid ethyl ester. MS m/z 251 (M+1).

Step 2. Preparation of {4-Methyl-6-[4-methyl-2-(4-trifluoromethyl-phenyl)-thiazol-5-ylmethoxy]-benzo[b]thiophen-3-yl}-acetic acid ethyl ester (Compound 17B)

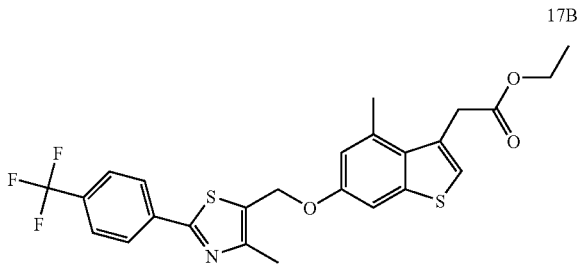

17B

The title compound was prepared in the manner analogous to example 1E using 3-chloromethyl-5-(4-trifluoromethyl-phenyl)-isoxazole and the product from example 17A MS m/z 506 (M+1).

Step 3. Preparation of {4-Methyl-6-[4-methyl-2-(4-trifluoromethyl-phenyl)-thiazol-5-ylmethoxy]-benzo[b]thiophen-3-yl}-acetic acid (Compound 17)

The title compound was prepared in the manner analogous to example 1 using the product from example 17B 400 MHz $^1$H NMR (DMSO-$d_6$) δ 12.40 (br(s), 1H), 8.06 (d, 2H, J=8.19), 7.78 (d, 2H, J=8.19 Hz), 7.47 (d, 1H, J=2.34 Hz), 7.26 (s, 1H), 6.80 (dd, 1H, J=2.44 Hz, J'=0.88 Hz), 5.34 (s, 2H), 3.91 (s, 2H), 2.54 (s, 3H), 2.43 (s, 3H). MS m/z 478 (M+1).

EXAMPLE 18

Synthesis of {4-Methyl-6-[3-(4-trifluoromethyl-benzyloxy)-benzyloxy]-benzo[b]thiophen-3-yl}-acetic acid (Compound 18)

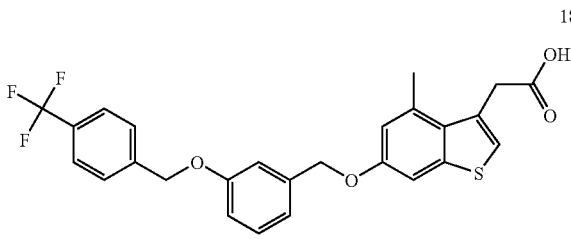

18

Step 1. Preparation of {4-Methyl-6-[3-(4-trifluoromethyl-benzyloxy)-benzyloxy]-benzo[b]thiophen-3-yl}-acetic acid ethyl ester (Compound 18A)

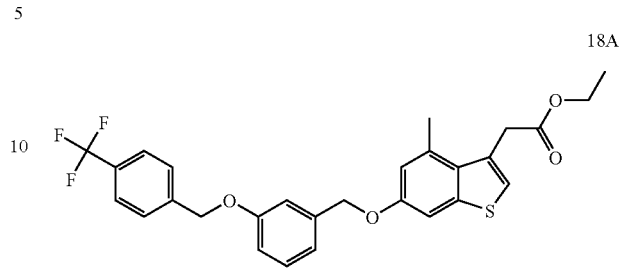

18A

The title compound was prepared in the manner analogous to example 1E using the products from example 17A and example 6B. MS m/z 515 (M+1).

Step 2. Preparation of {{4-Methyl-6-[3-(4-trifluoromethyl-benzyloxy)-benzyloxy]-benzo[b]thiophen-3-yl}-acetic acid (Compound 18)

The title compound was prepared in the manner analogous to example 1 using the product from example 18A. 400 MHz $^1$H NMR (DMSO-$d_6$) δ 12.39 (br(s), 1H), 7.70 (d, 2H, J=8.05 Hz), 7.62 (d, 2H, J=8.05 Hz), 7.37 (d, 1H, 2.20 Hz), 7.26 (m, 2H), 7.07 (m, 1H), 7.00 (d, 1H, J=8.06 Hz), 6.92 (m, 1H), 6.78 (m, 1H), 5.19 (s, 3H), 5.07 (s, 2H), 3.90 (s, 2H), 2.53 (s, 3H). MS m/z 487 (M+1).

EXAMPLE 19

Synthesis of {4-Methyl-6-[5-(4-trifluoromethyl-phenyl)-isoxazol-3-ylmethoxy]-benzo[b]thiophen-3-yl}-acetic acid (Compound 19)

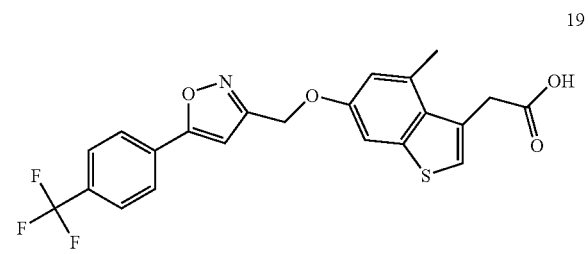

19

Step 1. Preparation of {4-Methyl-6-[3-(4-trifluoromethyl-benzyloxy)-benzyloxy]-benzo[b]thiophen-3-yl}-acetic acid ethyl ester (Compound 19A)

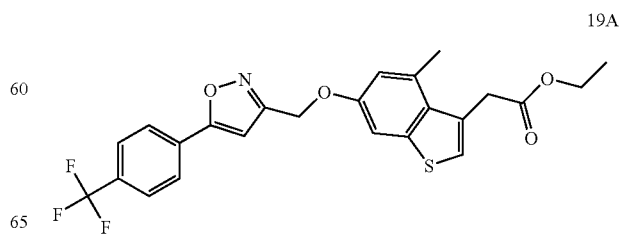

19A

The title compound was prepared in the manner analogous to example 1E using the products from example 17A and example 13C. MS m/z 476 (M+1).

Step 2. Preparation of {4-Methyl-6-[5-(4-trifluoromethyl-phenyl)-isoxazol-3-ylmethoxy]-benzo[b]thiophen-3-yl}-acetic acid (Compound 19)

The title compound was prepared in the manner analogous to example 1 using the product from example 19A 400 MHz $^1$H NMR (DMSO-d$_6$) δ 7.67 (m, 2H), 7.56 (m, 2H), 7.46 (d, 1H, J=1.95 Hz), 7.27 (s, 1H), 7.16 (s, 1H), 5.23 (s, 2H), 3.91 (s, 2H), 2.55 (s, 3H). MS m/z 448 (M+1).

EXAMPLE 20

Synthesis of {6-[5-(4-Chloro-phenyl)-isoxazol-3-ylmethoxy]-4-methyl-benzo[b]thiophen-3-yl}-acetic acid (Compound 20)

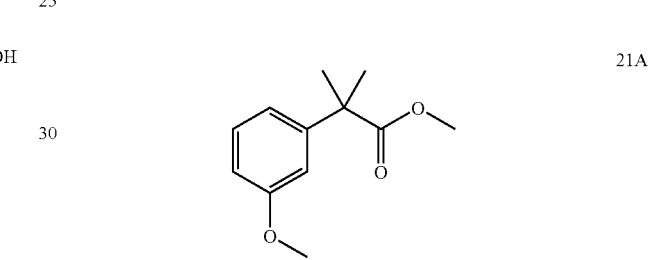

Step 1. Preparation of {{6-[5-(4-Chloro-phenyl)-isoxazol-3-ylmethoxy]-4-methyl-benzo[b]thiophen-3-yl}-acetic acid ethyl ester (Compound 20A)

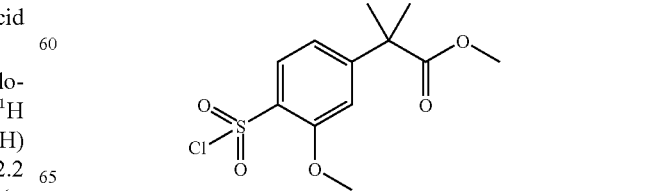

The title compound was prepared in the manner analogous to example 1E using the products from example 17A and commercially available 3-chloromethyl-5-(4-chlorophenyl)-isoxazole. MS m/z 442 (M).

Step 2. Preparation of {6-[5-(4-Chloro-phenyl)-isoxazol-3-ylmethoxy]-4-methyl-benzo[b]thiophen-3-yl}-acetic acid (Compound 20)

The title compound was prepared in the manner analogous to example 1 using the product from example 20A. $^1$H NMR (400 MHz, DMSO-D6) □ ppm 2.6 (s, 3H) 3.9 (s, 2H) 5.3 (s, 2H) 6.8 (m, 1H) 7.3 (s, 1H) 7.3 (s, 1H) 7.5 (d, J=2.2 Hz, 1H) 7.9 (d, J=8.3 Hz, 2H) 8.1 (d, J=8.1 Hz, 2H) 12.4 (s, 1H). MS m/z 414 (M+1).

EXAMPLE 21

Synthesis of 2-{3-Methoxy-4-[4-(5-trifluoromethyl-pyridin-2-yl)-benzylsulfanyl]-phenyl}-2-methyl-propionic acid (Compound 21)

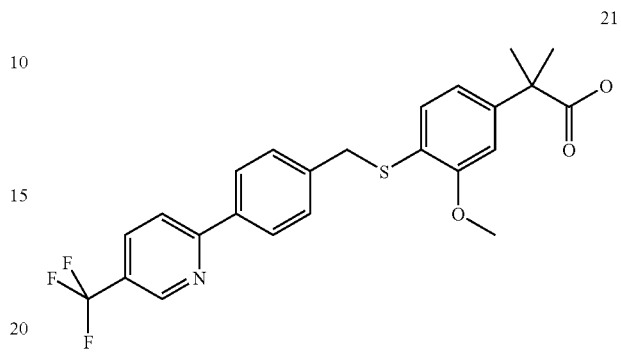

Step 1. Preparation of 2-(3-Methoxy-phenyl)-2-methyl-propionic acid methyl ester (Compound 21A)

21A

3-Methoxy phenyl acetic acid (10 g, 60 mmol) was dissolved in MeOH (100 mL) and was then treated with H$_2$SO$_4$ (5 μL). The reaction mixture was refluxed overnight. MeOH was evaporated and the residue was diluted with water and ether. The layers were separated and the aqueous layer was extracted with ether (2×30 mL). The combined organics were dried with MgSO$_4$ and condensed to afford the product in quantitative yield (10.91 g) as a light yellow oil. MS m/z 181 (M+1).

To a suspension of NaH (3.66 g, 91.5 mmol) in THF (75 mL) was added a solution of the above ester (5.5 g, 30.5 mmol) in THF (25 mL) followed by dropwise addition of methyl iodide (10.4 g, 73.2 mmol). The mixture was stirred at RT overnight. The solids were filtered from the reaction mixture and the filtrate evaporated to give a clear oil as the desired product (4.6 g, 72%). MS m/z 209 (M+1).

Step 2. Preparation of 2-(4-Chlorosulfonyl-3-methoxy-phenyl)-2-methyl-propionic acid methyl ester (Compound 21B).

21B

Chlorosulfonic acid (11.5 mL) was cooled to 0° C. Then compound 21A (4.6 g, 22 mmol) was added over 15 min. The mixture was stirred at RT for 3 h and then poured into ice (100 g). The cloudy solution was extracted with $CH_2Cl_2$ (2×50 mL) The extracts were dried with $MgSO_4$ and concentrated to give a purple oil which was passed through a short pad of silica gel to afford the desired product 21B (2.43 g 36%) as an orange oil. MS m/z 271 (M−Cl).

Step 3. Preparation of 2-(4-Mercapto-3-methoxy-phenyl)-2-methyl propionic acid methyl ester (Compound 21C)

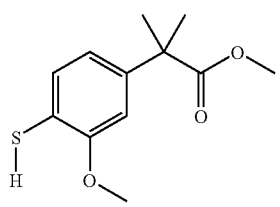

21C

The product from example 21B (2.43 g, 7.92 mmol) was refluxed with tin powder (4.7 g, 39.6 mmol) in MeOH (40 mL) and 4M HCL/dioxane (40 mL). After 3 h, the reaction mixture was poured into ice with $CH_2Cl_2$ (100 mL). The phases were separated and the aqueous layer was extracted with $CH_2Cl_2$ (2×50 mL). The combined organic layers were dried with magnesium sulfate, filtered and evaporated to give the thiol compound 21C as a yellow oil (1.82 g, 96%). MS m/z 239 (M−1).

Step 4. Preparation of 2-{3-Methoxy-4-[4-(5-trifluoromethyl-pyridin-2-yl)-benzylsulfanyl]-phenyl}-2-methyl-propionic acid methyl ester (Compound 21D)

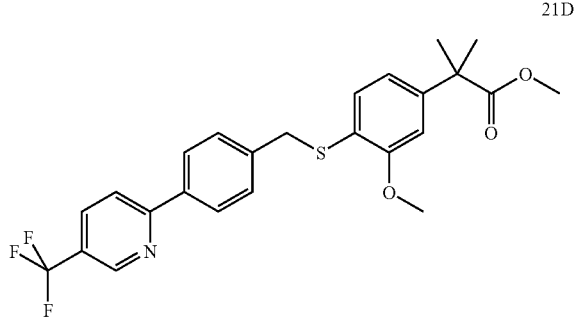

21D

The product from example 21C (264 mg, 1.1 mmol) was dissolved in acetonitrile (15 mL) with 10E (271 mg, 1.0 mmol) and $Cs_2CO_3$ (720 mg, 2.2 mmol). The reaction mixture was stirred at RT for 3 h. Ether (15 mL) and water were added and the stirring was continued for another 5 min. The layers were separated and the aqueous layer was extracted with ether (2×15 mL) The combined organics were dried over $MgSO_4$ and concentrated to tan solids. The crude product was purified by column chromatography eluted with EtOAc and hexanes to give the desired product, compound 1D, as white solid (150 mg, 32%); MS m/z 476 (M+1).

Step 5. Preparation of 2-{3-Methoxy-4-[4-(5-trifluoromethyl-pyridin-2-yl)-benzylsulfanyl]-phenyl}-2-methyl-propionic acid (Compound 21)

To the solution of the above methyl ester, compound 21D (0.15 g, 0.32 mmol) in MeOH (10 mL) was added LiOH.$H_2O$ (80 mg, 1.89 mmol). After refluxing for 3 h, the solution was cooled to RT and solvents were removed by rotovap. The residue was dissolved in water and neutralized with 1N HCl. The cloudy solution was extracted with ether (2×25 mL) and the extracts were dried with $MgSO_4$ then concentrated to white solids. The solids were further washed with ether and then dried to yield the desired product as white solids (52 mg, 36%). MS m/z 462 (M+1). Anal Calc'd for $C_{24}H_{22}NO_3SF_3$. C 62.46, H 4.80, N 3.03, found C, 62.23; H, 4.84; N, 2.80.

EXAMPLE 22

Synthesis of {4-[4-(5-Chloro-indan-1-yloxy)-benzylsulfanyl]-2-methyl-phenoxy}-acetic acid (Compound 2)

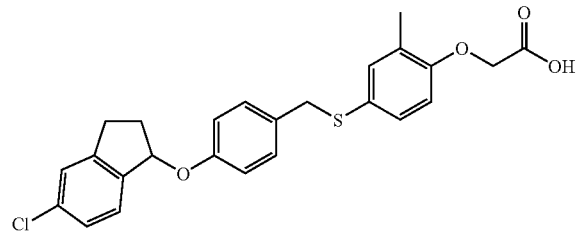

22

Step 1. Preparation of [4-(4-Acetoxy-benzylsulfanyl)-2-methyl-phenoxy]-acetic acid methyl ester (Compound 22A)

22A

The title compound was prepared in the manner analogous to example 1E using acetic acid 4-chloromethyl-phenyl ester and the product from example TB. MS m/z 361 (M+1).

Step 2. Preparation of [4-(4-Hydroxy-benzylsulfanyl)-2-methyl-phenoxy]-acetic acid (Compound 22B)

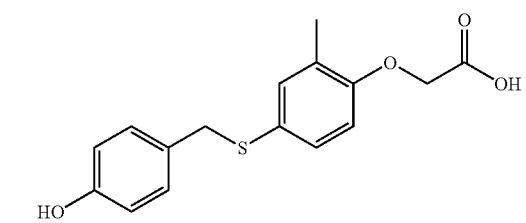

22B

The title compound was prepared in the manner analogous to example 1 using the product from example 22A. MS m/z 303 (M−1).

Step 3. Preparation of [4-(4-Hydroxy-benzylsulfanyl)-2-methyl-phenoxy]-acetic acid methyl ester (Compound 22C)

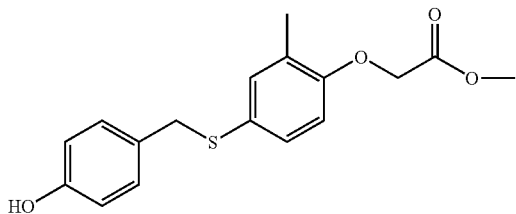

22C

To a solution of the product from example 22B (3.0 g, 9.8 mmol) in 98 mL of 2,2-dimethoxy propane was added 9.8 mL of concentrated hydrochloric acid. The reaction mixture was stirred at room temperature for 18 hours. The reaction mixture was evaporated to give a residue, which was dissolved in a mixture of 50 mL of water and 50 mL of ethyl acetate. The aqueous layer was extracted with ethyl acetate (2×50 mL) and then the organic layers were combined and washed with 5% sodium bicarbonate (3×50 mL), followed with 50 mL of brine. The organic layer was separated, dried (sodium sulfate), filtered, and evaporated to give a brown residue. The residue was flash chromatography (silica gel, 30% ethyl acetate in hexane) to provide semi-pure product, which was triturated in 30% ethyl acetate in hexane to afford the title compound. MS m/z 317 (M−1).

Step 4. Preparation of 5-Chloro-indan-1-ol (Compound 22D)

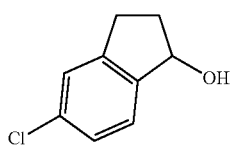

22D

To a precooled (5–10° C.) solution of 5-chloro-indan-1-one (2.0 g, 12 mmoles) in 33 mL of anhydrous methanol was added sodium borohydride (0.43 g, 11 mmoles). The reaction mixture was stirred at 10° C. for 2 hrs and then at room temperature for 18 hrs. The reaction mixture was evaporated to afford a yellow residue. The residue was dissolved in 200 mL of diethyl ether and then washed with water (2×100 mL), with 0.10 N hydrochloric acid (2×100 mL), and then with brine (100 mL). The organic layer was separated, dried (sodium sulfate), filtered, and the filtrate was evaporated to provide the title compound in good purity. MS m/z 167 (M−1).

Step 5. Preparation of {4-[4-(5-Chloro-indan-1-yloxy)-benzylsulfanyl]-2-methyl-phenoxy}-acetic acid methyl ester (Compound 22E)

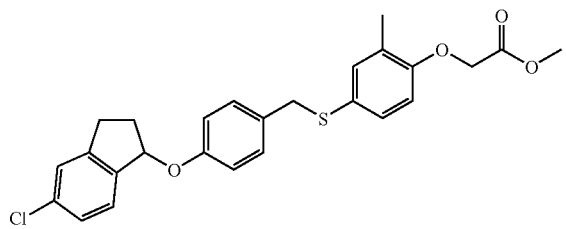

22E

The products from example 22C (0.60 g, 1.9 mmoles) and example 22D (0.35 g, 2.1 mmoles), triphenyl phosphine (0.60 g, 2.3 mmoles), and 0.36 mL of diethyl azodicarboxylate (0.40 g, 2.3 mmoles) were dissolved in 13 mL of tetrahydrofuran. The reaction mixture was stirred at room temperature under nitrogen for 3 d. The reaction mixture was evaporated to give a residue, which was flash chromatographed (silica gel, 20% ethyl acetate in hexane) to afford the title compound in good purity. MS m/z 469 (M+1).

Step 6. Preparation of {4-[4-(5-Chloro-indan-1-yloxy)-benzylsulfanyl]-2-methyl-phenoxy}-acetic acid (Compound 22)

The title compound was prepared in the manner analogous to example 1 using the product from example 22E. mp 130–131° C.; IR (KBr) cm$^{-1}$: 3070, 3034, 1750, 1494, 1229, 1194; 400 MHz $^1$H NMR (DMSO-d$_6$): δ 12.96 (br(s), 1H), 7.28–7.37 (m, 2H), 7.04–7.25 (m, 5H), 6.85–6.92 (m, 2H), 6.70 (d, 1H, J=8.5 Hz), 5.69–5.78 (m, 1H), 4.62 (s, 2H), 4.02 (s, 2H), 2.91–3.04 (m, 1H), 2.76–2.88 (m, 1H), 2.39–2.55 (m, 1H), 2.09 (s, 3H), 1.89–2.02 (m, 1H); MS m/z 453 (M−1). Anal. Calc'd for C$_{25}$H$_{23}$ClO$_4$S: C, 66.00; H, 5.10; found: C, 65.79; H, 4.91.

EXAMPLE 23

Synthesis of {7-[4-(5-Chloro-indan-1-yloxy)-benzylsulfanyl]-indan-4-yloxy}-acetic acid (Compound 23)

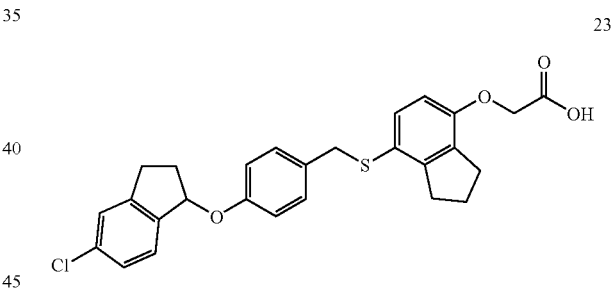

23

Step 1. Preparation of [7-(4-Acetoxy-benzylsulfanyl)-indan-4-yloxy]-acetic acid methyl ester (Compound 23A)

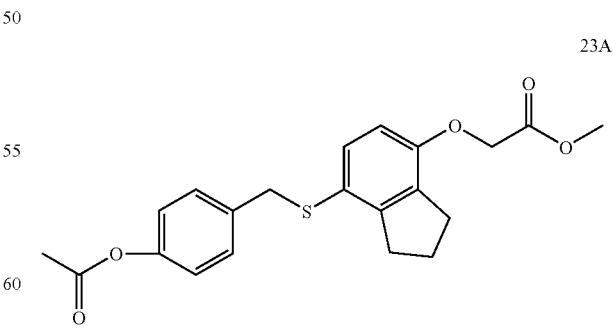

23A

The title compound was prepared in the manner analogous to example 22A using acetic acid 4-chloromethyl-phenyl ester and the product from example 1D. MS m/z 387 (M+1).

Step 2. Preparation of [7-(4-Hydroxy-benzylsulfanyl)-indan-4-yloxy]-acetic acid (Compound 3B)

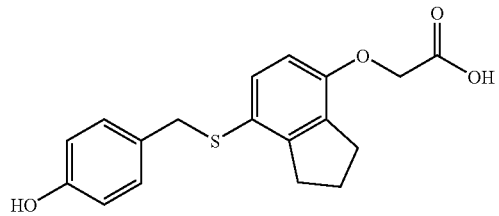
23B

The title compound was prepared in the manner analogous to example 22B using the product from example 23A. MS m/z 391 (M−1).

Step 3. Preparation of [7-(4-Hydroxy-benzylsulfanyl)-indan-4-yloxy]-acetic acid methyl ester (Compound 23C)

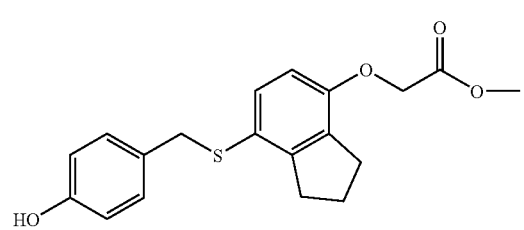
23C

The title compound was prepared in the manner analogous to example 22C using the product from example 23B. MS m/z 237 (M−107).

Step 4. Preparation of {7-[4-(5-Chloro-indan-1-yloxy)-benzylsulfanyl]-indan-4-yloxy}-acetic acid methyl ester (Compound 23D)

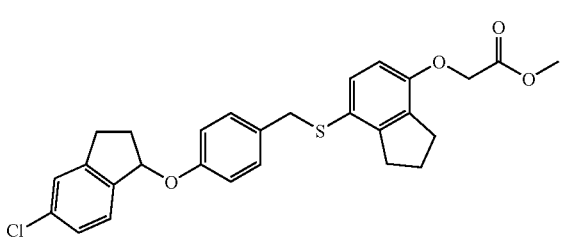
23D

The title compound was prepared in a manner analogous to example 22E using the products from example 22D and example 23C. MS m/z 495 (M+1).

Step 5. Preparation of {7-[4-(5-Chloro-indan-1-yloxy)-benzylsulfanyl]-indan-4-yloxy}-acetic acid (Compound 23)

The title compound was prepared in the manner analogous to example 1 using the product from example 23D. mp 169–170° C.; IR (KBr) cm$^{-1}$: 3030, 1739, 1713, 1505, 1474, 1244; 400 MHz $^1$H NMR (DMSO-d$_6$): δ 12.95 (br(s), 1H), 7.28–7.37 (m, 2H), 7.19–7.25 (m, 1H), 7.03–7.16 (m, 3H), 6.84–6.92 (m, 2H), 6.58 (d, 1H, J=8.5 Hz), 5.71–5.77 (m, 1H), 4.61 (s, 2H), 3.95 (s, 2H), 2.92–3.03 (m, 1H), 2.79–2.88 (m, 1H), 2.76 (t, 2H, J=7.5 Hz), 2.69 (t, 2H, 7.5 Hz), 2.41–2.56 (m, 1H), 1.84–2.01 (m, 3H); HPLC: area %=92.78, r.t. =6.078 min., λ=214 nm, mobile phase=acetonitrile/water with 0.10% TFA; MS m/z 481 (M+1). Anal. Calc'd for C$_{27}$H$_{25}$ClO$_4$S: C, 67.42; H, 5.24; found: C, 66.58; H, 4.93.

EXAMPLE 24

Synthesis of {6-[5-(4-Chloro-phenyl)-isoxazol-3-yl-methoxy]-benzofuran-3-yl}-acetic acid (Compound 24)

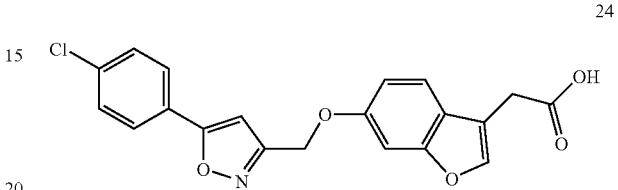
24

Step 1. Preparation of (6-Hydroxy-benzofuran-3-yl)-acetic acid methyl ester (Compound 24A)

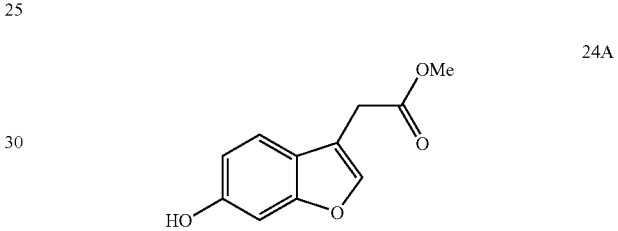
24A

A solution (6-hydroxy-benzofuran-3-yl)-acetic acid (Fall Y., et al., *Heterocycles*, 1995; 41:647; 4.1 g, 21.0 mmol) in 50 ml of tetrahydrofuran was treated with lithium hydroxide monohydrate (0.90 g, 21 mmol), and the mixture was stirred at room temperature for 30 minutes. Dimethyl sulfate (2.1 ml; 2.8 g, 22 mmol) was added, and the mixture was stirred at reflux for 3 hours. The bulk of the solvent was evaporated, and the residue was partitioned between 200 ml of ethyl acetate and 150 ml of 5% aqueous sodium bicarbonate solution. The layers were separated, and the aqueous layer was extracted with fresh ethyl acetate (2×100 ml). The combined organic layers were back-washed with brine (2×200 ml), then dried over anhydrous sodium sulfate and concentrated. The crude product was purified by normal phase chromatography. mp 75–79° C.; MS m/z 206 (M).

Step 2. Preparation of {6-[5-(4-Chloro-phenyl)-isoxazol-3-ylmethoxy]-benzofuran-3-yl}-acetic acid methyl ester (Compound 24B)

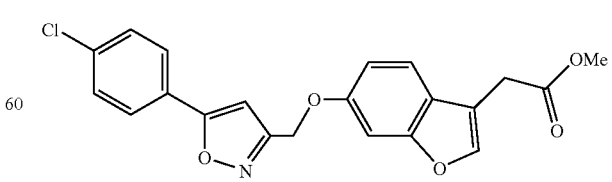
24B

A solution of (6-hydroxy-benzofuran-3-yl)-acetic acid methyl ester (0.41 g, 2.0 mmol) and commercially available 3-(chloromethyl)-5-(4-chlorophenyl)isoxazole (0.46 g, 2.0 mmol) were combined in 15 ml of acetonitrile. The mixture was stirred at room temperature for 64 hours and filtered. The insoluble material was washed on the funnel several times with fresh acetonitrile. The bulk of the solvent was evaporated, and the residue was partitioned between 200 ml of ethyl acetate and 150 ml of brine. The layers were separated, and the aqueous layer was extracted with fresh ethyl acetate (2×100 ml). The combined organic layers were back-washed with brine (2×150 ml), then dried over anhydrous sodium sulfate and concentrated. The crude product was purified by normal phase chromatography. mp 136–137° C.; MS m/z 397 (M−1).

Step 3. Preparation of {6-[5-(4-Chloro-phenyl)-isoxazol-3-ylmethoxy]-benzofuran-3-yl}-acetic acid (Compound 24)

A solution of {6-[5-(4-chloro-phenyl)-isoxazol-3-yl-methoxy]-benzofuran-3-yl}-acetic acid methyl ester (0.20 g, 0.50 mmol) in 8.0 ml of tetrahydrofuran was treated with lithium hydroxide monohydrate (0.10 g, 2.4 mmol), followed by 2.5 ml of water. The mixture was stirred at room temperature for 16 hours and added to 75 ml of water. The solution was made strongly acidic by the addition of 4.0 N hydrochloric acid. The precipitated product was extracted with ethyl acetate (4×75 ml). The combined organic layers were washed with brine (2×150 ml), then dried over anhydrous sodium sulfate and evaporated to a white solid. The crude product was recrystallized from aqueous acetonitrile. mp 193–194° C.; IR (thin film) cm$^{-1}$: 1716, 1611, 1434, 1288, 1224, 1146; 400 MHz $^1$H NMR (DMSO-d$_6$) ☐12.39 (br s, 1H), 7.87 (d, 2H, J=8.8 Hz), 7.73 (s, 1H), 7.55 (d, 2H, J=8.8 Hz), 7.44 (d, 1H, J=8.6 Hz), 7.28 (d, 1H, J=2.0 Hz), 7.19 (s, 1H), 6.93–6.96 (m, 1H), 5.24 (2, 2H), 3.59 (s, 2H); MS m/z 382 (M−1). Anal. Calc'd for C$_{20}$H$_{14}$ClNO$_5$: C, 62.59; H, 3.68; N, 3.65; found: C, 62.87; H, 3.67; N, 3.61.

EXAMPLE 25

Synthesis of {6-[4-(4-Trifluoromethyl-benzyloxy)-benzyloxy]-benzofuran-3-yl}-acetic acid (Compound 25)

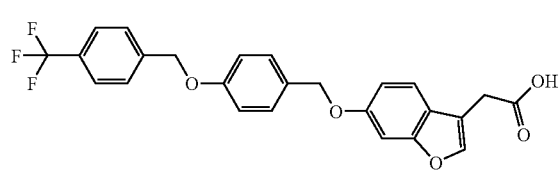

25

Step 1. Preparation of {6-[4-(4-Trifluoromethyl-benzyloxy)-benzyloxy]-benzofuran-3-yl}-acetic acid methyl ester (Compound 25A)

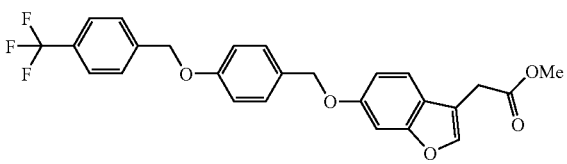

25A

The title compound was prepared in the manner analogous to example 1E using (6-hydroxy-benzofuran-3-yl)-acetic acid methyl ester (example 24A) and 1-(4-trifluoromethyl-benzyloxy)-4-chloromethyl-benzene (example 5E). MS m/z 471 (M+1).

Step 2. Preparation of {6-[4-(4-Trifluoromethyl-benzyloxy)-benzyloxy]-benzofuran-3-yl}-acetic acid (Compound 25)

The title compound was prepared in the manner analogous to example 1 using {6-[4-(4-trifluoromethyl-benzyloxy)-benzyloxy]-benzofuran-3-yl}-acetic acid methyl ester and lithium hydroxide. mp 161–163° C.; IR (thin film) cm$^{-1}$: 1715, 1514, 1331, 1226, 1119, 1069; 400 MHz $^1$H NMR (DMSO-d$_6$) ☐12.38 (br s, 1H), 7.68–7.72 (m, 3H), 7.61 (d, 2H, J=8.1 Hz), 7.29–7.41 (m, 3H), 7.18 (d, 1H, J=2.2 Hz), 6.96–7.00 (m, 2H), 6.87–6.89 (m, 1H), 5.19 (s, 2H), 5.01 (s, 2H), 3.58 (s, 2H); MS m/z 455 (M−1). Anal. Calc'd for: C$_{25}$H$_{19}$F$_3$O$_5$: C, 65.79; H, 4.20; found: C, 65.54; H, 4.02.

EXAMPLE 26

Synthesis of [7-(3-naphthalen-2-yl-propylsulfanyl)-indan-4-yloxy]-acetic acid (Compound 26)

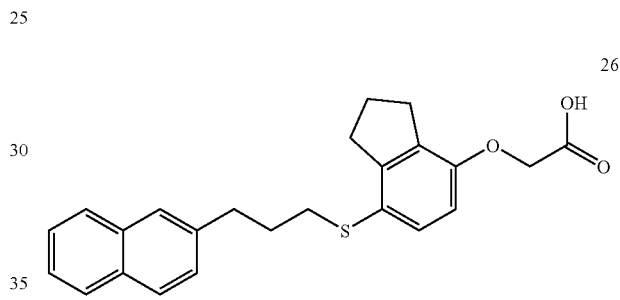

Step 1. Preparation of Methanesulfonic acid 3-naphthalen-2-yl-propyl ester (Compound 26A)

3-Naphthalen-2-yl-propan-1-ol (0.708 g, 3.8 mmol) was dissolved in 25.3 mL dichloromethane. morpholinomethyl polystyrene HL resin (2.8 g, 4.0 mmol/g, 11.6 mmol) and methane sulfonyl chloride (0.9 mL, 11.6 mmol) were added to the alcohol solution. The slurry was shaken at ambient temperature for 16H. The reaction was filtered, washing the solids well with dichloromethane. The filtrate was concentrated. The resulting crude product was dissolved in ethyl acetate and washed with a 50% sodium bicarbonate solution, brine, and dried over anhydrous magnesium sulfate. The resulting solution was concentrated in vacuo and used for the next step without further purification. 400 MHz $^1$H NMR (CDCl$_3$) δ 7.80 (m, 3H), 7.63 (s, 1H), 7.47 (m, 2H), 7.32 (dd, 1H, J=8, 2 Hz), 4.26 (t, 2H, J=6 Hz), 2.98 (s, 3H), 2.92 (t, 2H, J=8 Hz), 2.18 (m, 2H).

Step 2. Preparation of [7-(3-naphthalen-2-yl-propylsulfanyl)-indan-4-yloxy]-acetic acid methyl ester (Compound 26B)

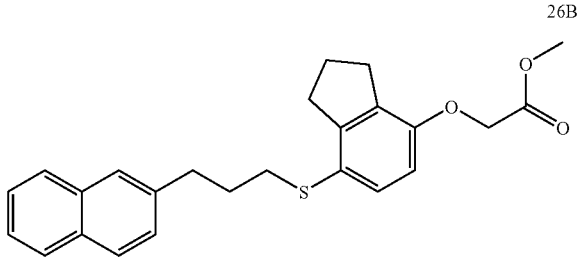

The product from example 26A (0.256 g, 0.973 mmol) was dissolved in 6.5 mL anhydrous acetonitrile. (7-Mercapto-indan-4-yloxy)-acetic acid methyl ester (example 1D) (0.232 g, 0.973 mmol) was dissolved in 6.5 mL anhydrous acetonitrile and added to the activated alcohol solution. Cesium carbonate (0.760 g, 2.34 mmol) was added and the reaction was shaken at 60° C. for 3.5H, followed by 16H of shaking at ambient temperature. The reaction was filtered, washing solids well with acetonitrile. The solvent was removed under a stream of nitrogen and the crude product was used in the next step without further purification. MS m/z 406.1 (M+1).

Step 3. Preparation of [7-(3-naphthalen-2-yl-propylsulfanyl)-indan-4-yloxy]-acetic acid (Compound 26)

The product from example 26B was dissolved in 24 mL of a 0.5M solution of LiOH in 4:1 methoxyethanol:water. The solution was heated at 60° C. for 3H. The reaction was cooled and ~10 mL 1N HCL was added to attain a solution pH of 7. 10 mL of brine was added to the reaction. The crude product was extracted with ethyl acetate (2×35 mL). The reaction was submitted to reverse phase HPLC purification. LCMS m/z 393.1 (M+1), 3.64 min.

EXAMPLE 27

Synthesis of [2-Methyl-4-(3-naphthalen-2-yl-propylsulfanyl)-phenoxy]-acetic acid (Compound 27)

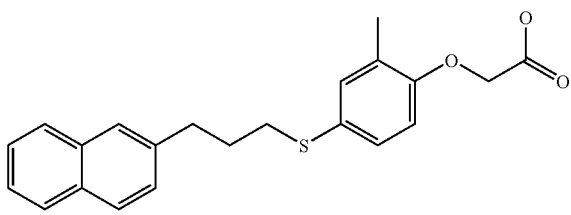

Compound 27 was made in a similar manner as described for compound 26. LCMS m/z 365.1 (M−1), 3.47 min.

EXAMPLE 28

Synthesis of {4-[3-(Biphenyl-4-yl-ethyl-amino)-propylsulfanyl]-2-methyl-phenoxy}-acetic acid (Compound 28)

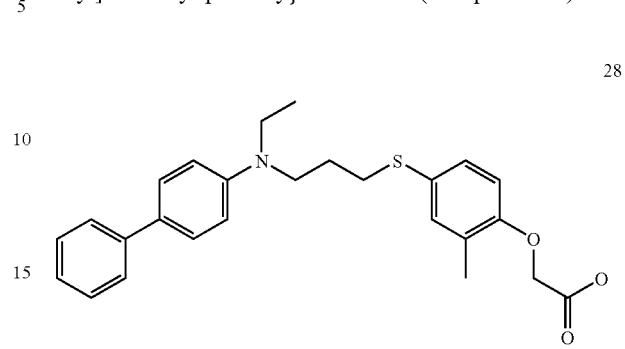

Step 1. Preparation of Methanesulfonic acid 3-(biphenyl-4-yl-ethyl-amino)-propyl ester (Compound 28A)

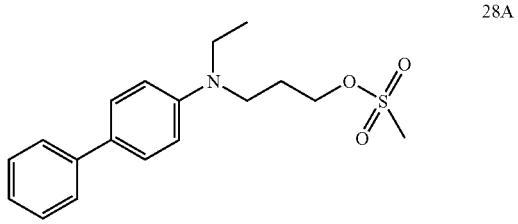

The title compound was prepared in the manner analogous to example 26A. 400 MHz
$^1$H NMR (CDCl$_3$): δ 7.53(m, 2H), 7.48 (m, 2H), 7.41 (m, 2H), 7.25 (m, 1H), 6.77 (br(d), 2H, J=6.5 Hz), 4.32 (t, 1H, J=6 Hz), 3.61(t, 1H, J=3.2 Hz), 3.48 (m, 2H), 3.43 (m, 2H), 3.01, (s, 2H), 2.09 (m, 2H), 1.20 (m, 3H).

Step 2. Preparation of {4-[3-(Biphenyl-4-yl-ethyl-amino)-propylsulfanyl]-2-methyl-phenoxy}-acetic acid methyl ester (Compound 28B)

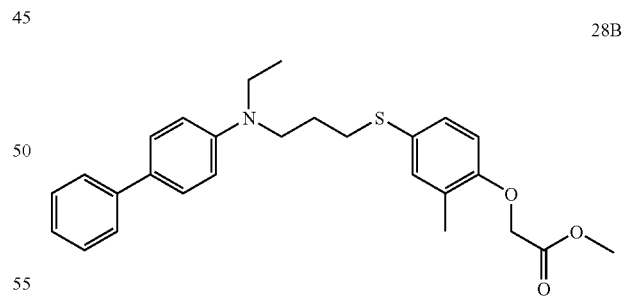

The title compound was prepared in the manner analogous to example 26B using the product from example 28A and 4-mercapto-2-methyl-phenoxy)-acetic acid methyl ester (example TB). MS m/z 450.1 (M+1)

Step 3. Preparation of {4-[3-(Biphenyl-4-yl-ethyl-amino)-propylsulfanyl]-2-methyl-phenoxy}-acetic acid (Compound 28)

The title compound was prepared in the manner analogous to example 26 using the product from example 28B. LCMS m/z 436.2 (M+1), 3.33 min

EXAMPLE 29

Synthesis of {7-[3-Biphenyl-4-yl-ethyl-amino)-propylsulfanyl]-indan-4-yloxy}-acetic acid (Compound 29)

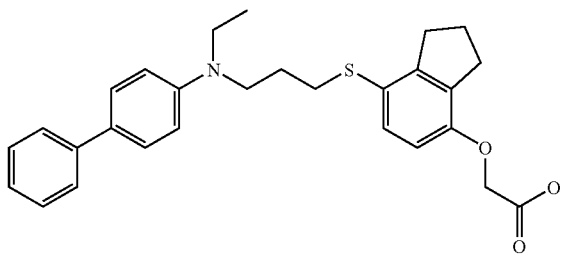

Compound 29 was prepared in a similar manner as described for compound 28. LCMS m/z 462.3 (M+1), 3.59 min

EXAMPLE 30

Synthesis of {4-[4-(2,4-Dichloro-phenoxy)-butylsulfanyl]-5-methoxy-2-methyl-phenoxy)-acetic acid (Compound 30)

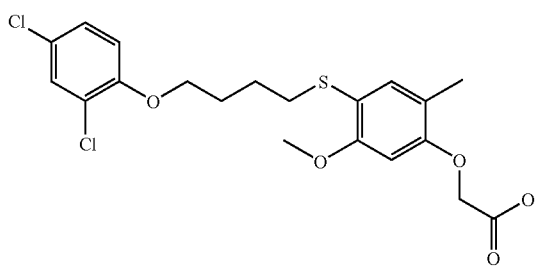

Step 1. Preparation of Methanesulfonic acid 4-(2,4-dichlorophenoxy)-butyl ester (Compound 30A)

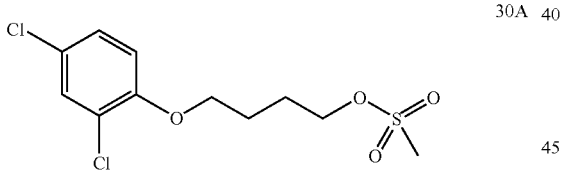

The title compound was prepared in the manner analogous to example 26A. 400 MHz $^1$H NMR (CDCl$_3$): δ 7.35 (d, 1H, J=2.5 Hz), 7.17 (dd, 1H, J=9, 2.5 Hz), 6.82 (d, 1H, J=9 Hz), 4.34 (t, 2H J=6 Hz), 4.04 (t, 2H, J=6 Hz), 3.01 (s, 3H), 1.99 (m, 4H).

Step 2. Preparation of {4-[4-(2,4-Dichloro-phenoxy)-butylsulfanyl]-5-methoxy-2-methyl-phenoxy)-acetic acid methyl ester (Compound 30B)

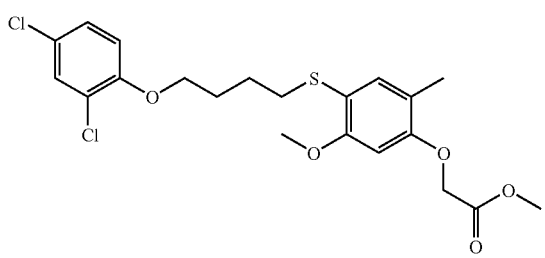

The title compound was prepared in the manner analogous to example 26B using the product from example 30A and (4-mercapto-5-methoxy-2-methyl-phenoxy)-acetic acid methyl ester (example TA). MS m/z 459.0 (M+1)

Step 3. Preparation of {4-[4-(2,4-Dichloro-phenoxy)-butylsulfanyl]-5-methoxy-2-methyl-phenoxy)-acetic acid (Compound 30)

The title compound was prepared in the manner analogous to example 26 using the product from example 30B. LCMS m/z 444.1 (M+1), 3.47 min

EXAMPLE 31

Synthesis of {4-[4-(2,4-Dichloro-phenoxy)-butylsulfanyl]-2-methyl-phenoxy}-acetic acid (Compound 31)

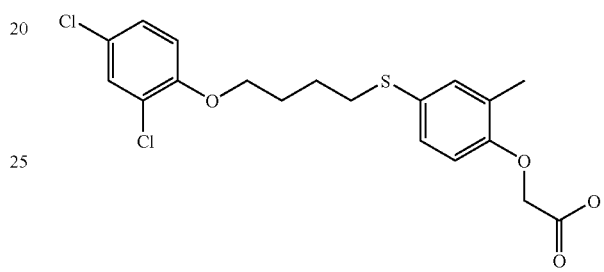

Compound 31 was prepared in a similar manner as described for compound 30. LCMS m/z 414.05 (M+1), 3.52 min

EXAMPLE 32

Synthesis of {7-[4-(2,4-Dichloro-phenoxy)-butylsulfanyl]-indan-4-yloxy}-acetic acid (Compound 32)

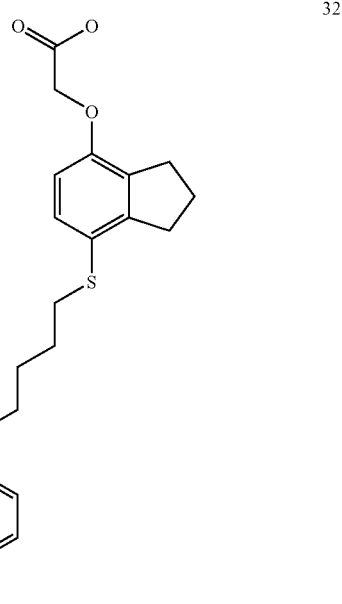

Compound 32 was prepared in a similar manner as described for compound 30. LCMS m/z 440.0 (M−1), 3.67 min

EXAMPLE 33

Synthesis of {4-[2-(2,4-Dichloro-phenoxy)-ethylsulfanyl]-5-methoxy-2-methyl-phenoxy}-acetic acid (Compound 33)

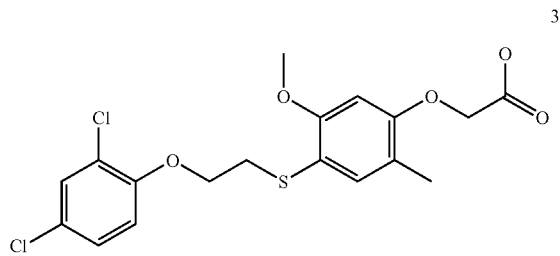

Step 1. Preparation of Methanesulfonic acid 2-(2,4-dichloro-phenoxy)-ethyl ester (Compound 33A)

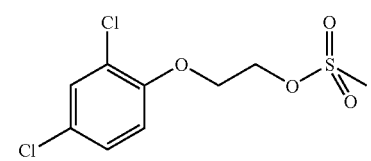

The title compound was prepared in the manner analogous to example 26A. 400 MHz $^1$H NMR (CDCl$_3$): δ 7.38 (s, 1H), 7.20 (dd, 1H, J=9, 2.5 Hz), 6.86 (d, 1H, J=9 Hz), 4.60 (m, 2H), 4.27 (m, 2H), 3.13 (s, 3H).

Step 2. Preparation of {4-[2-(2,4-Dichloro-phenoxy)-ethylsulfanyl]-5-methoxy-2-methyl-phenoxy}-acetic acid methyl ester (Compound 33B)

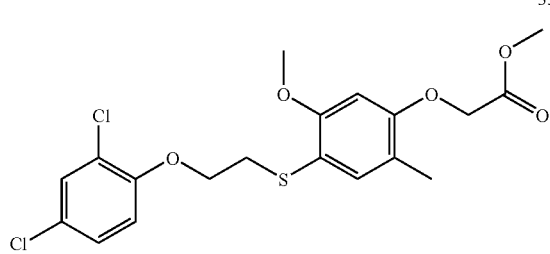

The title compound was prepared in the manner analogous to example 26B using the product from example 33A and (4-mercapto-5-methoxy-2-methyl-phenoxy)-acetic acid methyl ester (example TB). MS m/z 429.9 (M+1)

Step 3. Preparation of {4-[2-(2,4-Dichloro-phenoxy)-ethylsulfanyl]-5-methoxy-2-methyl-phenoxy}-acetic acid (Compound 33)

The title compound was prepared in the manner analogous to example 26 using the product from example 33B. LCMS m/z 415.0 (M−1), 3.30 min

EXAMPLE 34

Synthesis of {7-[2-(2,4-Dichloro-phenoxy)-ethylsulfanyl]-indan-4-yloxy}-acetic acid (Compound 34)

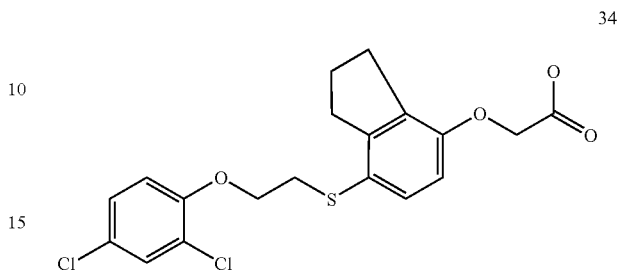

Compound 34 was made in a similar manner as described for compound 33. LCMS m/z 411.0 (M−1), 3.49 min

EXAMPLE 35

Synthesis of {4-[2-(2,4-Dichloro-phenoxy)-ethylsulfanyl]-2-methyl-phenoxy}-acetic acid (Compound 35)

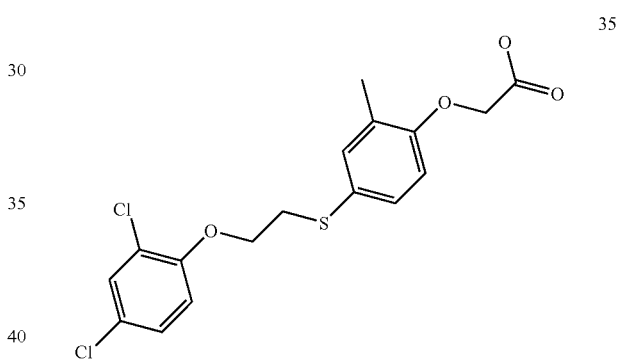

Compound 35 was made in a similar manner as described for compound 33. LCMS m/z 385.0 (M−1), 3.33 min

EXAMPLE 36

Synthesis of 1-[4-(4'-Trifluoromethyl-biphenyl-4-ylmethylsulfanyl)-phenyl]-cyclopropanecarboxylic acid (Compound 36)

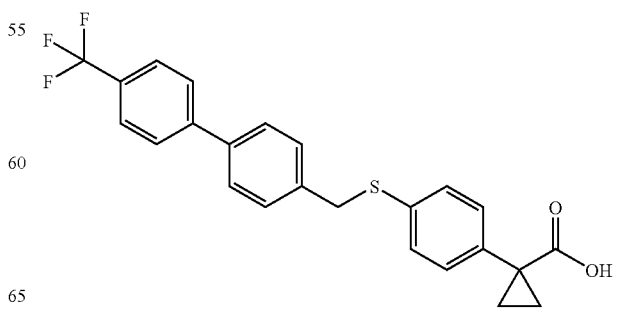

Step 1. Preparation of 1-Phenyl-cyclopropanecarboxylic acid methyl ester (Compound 36A)

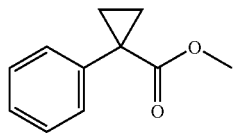

36A

1-Phenyl-cyclopropanecarboxylic acid (5 g, 30.86 mmol) was dissolved in MeOH (100 mL) and was then treated with $H_2SO_4$ (2 mL). The reaction mixture was refluxed overnight. MeOH was evaporated and the residue was diluted with water and ether. Layers were separated and the aqueous layer was extracted with ether (2×30 mL). The combined organics were dried with $MgSO_4$ and condensed to afford the product (5.3 g, 97%) as white crystals. MS: 177 (M+1)+

Step 2. Preparation of 1-(4-Chlorosulfonyl-phenyl)-cyclopropanecarboxylic acid methyl ester (Compound 36B)

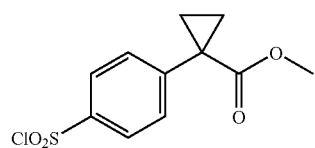

36B

Chlorosulfonic acid (10 mL) was cooled to 0° C. Then compound 36A (6.80 g, 38.6 mmol) was added over 30 min. The mixture was stirred at RT for 3 h and was poured into ice (~500 g). The cloudy solution was extracted with ether (2×200 mL). The extracts were dried with magnesium sulfate and concentrated to give a brown oil which was passed through a short pad of silica gel to afford the desired product 36B (6.05 g, 57%) as white plates. MS: 239 (M−Cl)+.

Step 3. Preparation of 1-(4-Mercapto-phenyl)-cyclopropanecarboxylic acid methyl ester (Compound 36C)

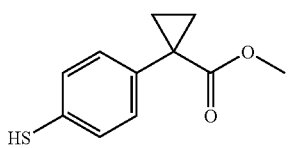

36C

The above product 36B (1.0 g, 3.64 mmol) was refluxed with tin powder (2.2 g, 18.8 mmol) in MeOH (10 mL) and 4M HCl/dioxane (10 mL). After 3 h, the reaction mixture was poured into ice with $CH_2Cl_2$ (100 mL). The phases were separated and the aqueous layer was extracted with $CH_2Cl_2$ (2×50 mL). The combined organic layers were dried with magnesium sulfate, filtered and evaporated to give the thiol compound 36C as a yellow oil (650 mg, 86%). MS: 207 (M−1)+

Step 4. Preparation of (4'-Trifluoromethyl-biphenyl-4-yl)-methanol (compound 36D)

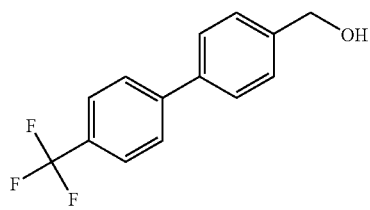

36D

1-Bromo-4-trifluoromethyl-benzene (814 mg, 3.62 mmol), 4-hydroxymethylphenylboronic acid (600 mg, 3.98 mmol), cesium carbonate (2.36 g, 7.24 mmol), and $PdCl_2$ (dppf) (132 mg, 0.181 mmol) were added to 10 ml of a 1:1 solution of DMF/THF. The reaction was flushed with nitrogen and heated to 90° C. for 1 h. The reaction was cooled, poured into diethyl ether and washed with water (2×50 ml), brine (1×50 ml) and dried over anhydrous sodium sulfate. The crude product was filtered through silica gel, eluted with diethyl ether, and concentrated to provide the title compound. MS m/z 251 (M−1).

Step 5. Preparation of 4-Chloromethyl-4'-trifluoromethyl-biphenyl (compound 36E)

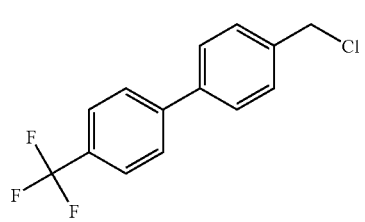

36E

The product from Example 36D was dissolved in 10 ml methylene chloride. Triethylamine (468 mg, 4.62 mol) and methanesulfonyl chloride (422 mg, 3.68 mmol) were then added and stirred for 18 h. The reaction was poured into water and extracted with methylene chloride. The organic solution was dried over anhydrous sodium sulfate, decanted and concentrated to provide the title compound that was used without further purification. MS m/z 235 (M−Cl+1).

Step 6. Preparation of 1-[4-(4'-Trifluoromethyl-biphenyl-4-ylmethylsulfanyl)-phenyl]-cyclopropane-carboxylic acid methyl ester (Compound 36F):

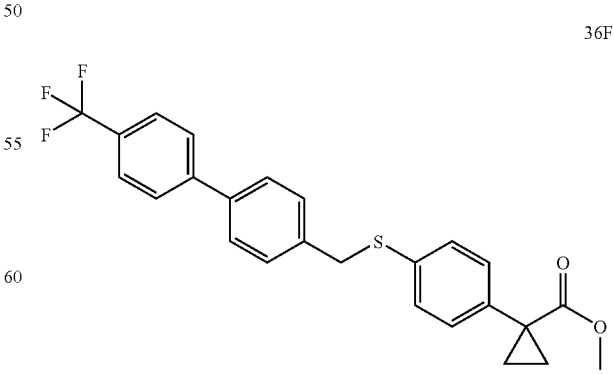

36F

Compound 36C (416 mg, 2.0 mmol) was dissolved in acetonitrile (50 mL) with example 36E (568 mg, 2.1 mmol)

and Cs₂CO₃ (1.3 g, 4.0 mmol). The reaction mixture was stirred at RT overnight. Ether (50 mL) and H₂O were added and stirring was continued for another 5 min. The layers were separated and the aqueous layer was extracted with ether (2×100 mL). The combined organics was dried over MgSO₄ and concentrated to an oil. The crude product was purified by column chromatography eluted with EtOAc and hexanes to give the desired product, compound 36F as a thick yellow oil (597 g, 68%).

MS: 443 (M+1)⁺

Step 7. Preparation of 1-[4-(4'-Trifluoromethyl-biphenyl-4-ylmethylsulfanyl)-phenyl]-cyclopropane-carboxylic acid (Compound 36) To the solution of the above methyl ester, compound 36F (597 mg, 1.35 mmol) in MeOH (10 mL) and THF (10 mL) was added LiOH.H₂O (170 mg, 4.0 mmol). After refluxing overnight, the solution was cooled to RT and solvents were removed by rotavap. The residue was dissolved in water and neutralized with 1N HCl. The cloudy solution was extracted with EtOAc (3×50 mL) and the extracts were dried with MgSO₄, and concentrated. The crude product was purified by chromatography to afford a yellow solid, which was further washed with ether to yield the desired product as yellowish crystals (486 mg, 84%). MS: 427 (M−1)⁺. Anal. Calc'd for C₂₄H₁₉F₃O₂S C, 67.28; H, 4.47; found: C, 67.37; H, 4.26.

EXAMPLE 37

Synthesis of 1-{4-[4-(5-Trifluoromethyl-pyridin-2-yl)-benzylsulfanyl]-phenyl}-cyclopropanecarboxylic acid (Compound 37)

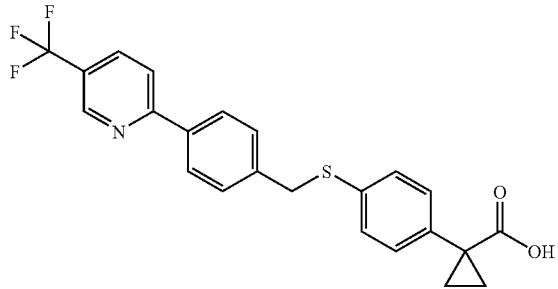

37

Step 1. Preparation of 1-{4-[4-(5-Trifluoromethyl-pyridin-2-yl)-benzylsulfanyl]-phenyl}-cyclopropane-carboxylic acid methyl ester (Compound 37A)

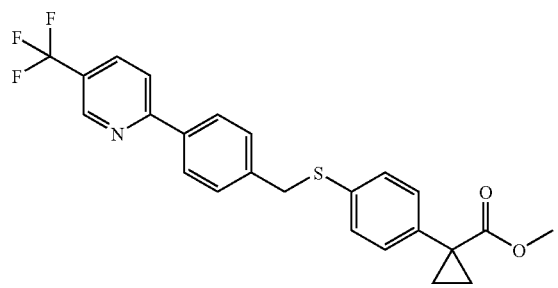

37A

The ester was synthesized with the same procedure as used for synthesis of compound 36F in 64% yield. MS: 444 (M+1)⁺.

Step 2. Preparation of 1-{4-[4-(5-Trifluoromethyl-pyridin-2-yl)-benzylsulfanyl]-phenyl}-cyclopropane-carboxylic acid (Compound 37)

The acid was synthesized with the same procedure as used for synthesis of example 36 in 74% yield. MS: 430 (M+1)⁺. Anal. Calc'd for C₂₃H₁₈F₃NO₂S: C, 64.33; H, 4.22; N, 3.26; found: C, 64.15; H, 4.11, N, 3.21.

EXAMPLE 38

Synthesis of 1-{4-[3-(4-Trifluoromethyl-benzyloxy)-benzylsulfanyl]-phenyl}-cyclopropanecarboxylic acid (Compound 38)

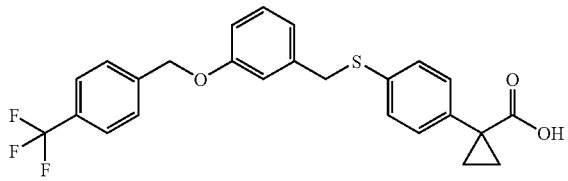

38

Step 1. Preparation of 1-{4-[3-(4-Trifluoromethyl-benzyloxy)-benzylsulfanyl]-phenyl}-cyclopropanecarboxylic acid methyl ester (Compound 38A)

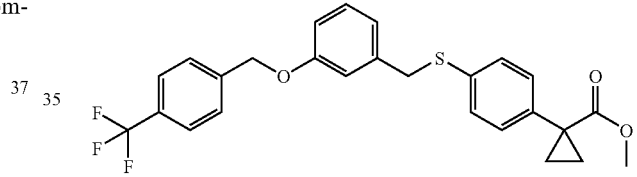

38A

The ester was synthesized with the same procedure as used for synthesis of compound 36F in 58% yield. MS: 473 (M+1)⁺.

Step 2. Preparation of 1-{4-[3-(4-Trifluoromethyl-benzyloxy)-benzylsulfanyl]-phenyl}-cyclopropanecarboxylic acid (Compound 38)

The acid was synthesized with the same procedure as used for example 36 in 99% yield. MS: 457 (M−1)⁺. Anal. Calc'd for C₂₅H₂₁F₃O₃S. C, 65.49; H, 4.62; found: C, 65.12; H, 4.45.

EXAMPLE 39

Synthesis of 1-{4-[5-(4-Chloro-phenyl)-isoxazol-3-ylmethylsulfanyl]-phenyl}-cyclopropanecarboxylic acid (Compound 39)

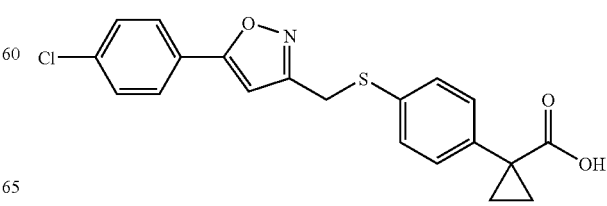

39

Step 1. Preparation of 1-{4-[5-(4-Chloro-phenyl)-isoxazol-3-ylmethylsulfanyl]-phenyl}-cyclopropanecarboxylic acid methyl ester (Compound 39A)

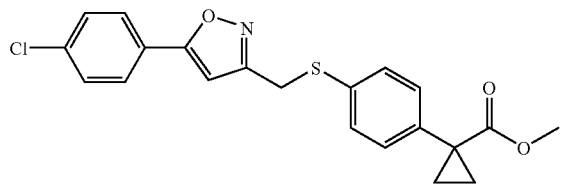

39A

The ester was synthesized with the same procedure as used for synthesis of compound 36F in 70% yield. MS: 400 (M+1)+.

Step 2. Preparation of 1-{4-[5-(4-Chloro-phenyl)-isoxazol-3-ylmethylsulfanyl]-phenyl}-cyclopropanecarboxylic acid (Compound 39)

The acid was synthesized with the same procedure as used for synthesis of example 36 in 98% yield. MS: 386 (M−1)+. Anal. Calc'd for $C_{20}H_{16}ClNO_3S$: C, 62.25; H, 4.18; N, 3.63; found: C, 62.05; H, 4.05, N, 3.58.

EXAMPLE 40

Synthesis of 1-{4-[4-(2,5-Dichloro-benzyloxy)-benzylsulfanyl]-phenyl}-cyclopropanecarboxylic acid (Compound 40)

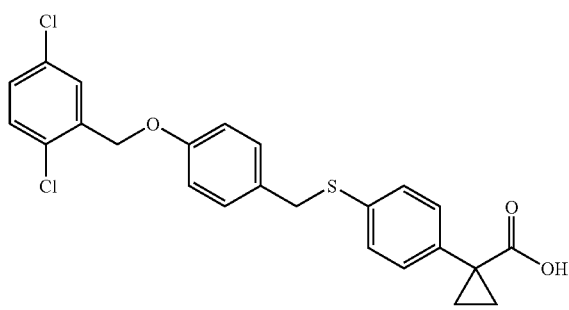

40

Step 1. Preparation of 1-{4-[4-(2,5-Dichloro-benzyloxy)-benzylsulfanyl]-phenyl}-cyclopropanecarboxylic acid methyl ester (Compound 40A)

40A

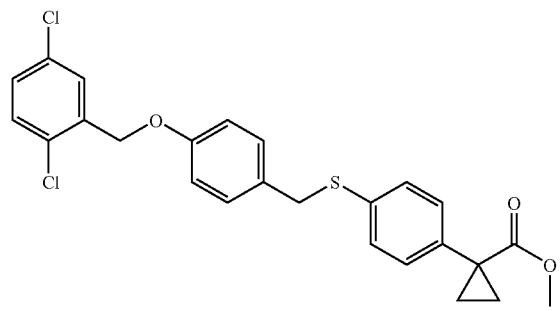

The ester was synthesized with the same procedure as used for synthesis of compound 36F in 70% yield. MS: 473 (M−1)+.

Step 2. Preparation of 1-{4-[4-(2,5-Dichloro-benzyloxy)-benzylsulfanyl]-phenyl}-cyclopropanecarboxylic acid (Compound 40) The acid was synthesized with the same procedure as used for synthesis of example 36 in 94% yield. MS: 457 (M−1)+. Anal. Calc'd for $C_{24}H_2O Cl_2O_3S$: C, 62.75; H, 4.39; found: C, 62.62; H, 4.23.

EXAMPLE 41

Synthesis of 1-{4-[4-(4-Trifluoromethyl-benzyloxy)-benzylsulfanyl]-phenyl}-cyclopropanecarboxylic acid (Compound 41)

41

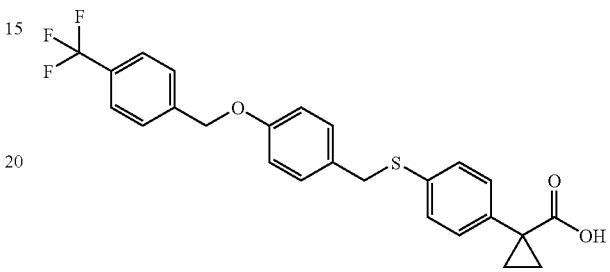

Step 1. Preparation of 1-{4-[4-(4-Trifluoromethyl-benzyloxy)-benzylsulfanyl]-phenyl}-cyclopropanecarboxylic acid methyl ester (Compound 41A)

41A

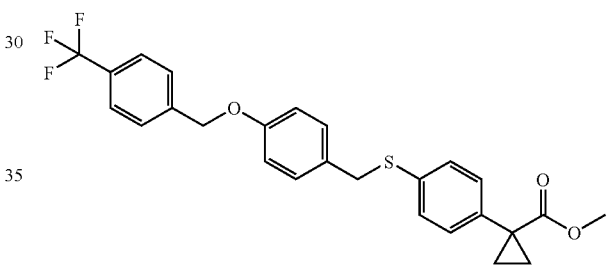

The ester was synthesized with the same procedure as used for synthesis of compound 36F in 81% yield. MS: 473 (M+1)+.

Step 2. Preparation of 1-{4-[4-(4-Trifluoromethyl-benzyloxy)-benzylsulfanyl]-phenyl}-cyclopropanecarboxylic acid (Compound 41)

The acid was synthesized with the same procedure as used for synthesis of example 36 in 60% yield. MS: 457 (M+1)+. Anal. Calc'd for $C_{25}H_{21}F_3O_3S$: C, 65.49; H, 4.62; found: C, 65.04; H, 4.34.

EXAMPLE 43

Synthesis of 1-{4-[4-(4-Fluoro-3-trifluoromethyl-benzyloxy)-benzylsulfanyl]-phenyl}-cyclopropanecarboxylic acid (Compound 43)

43

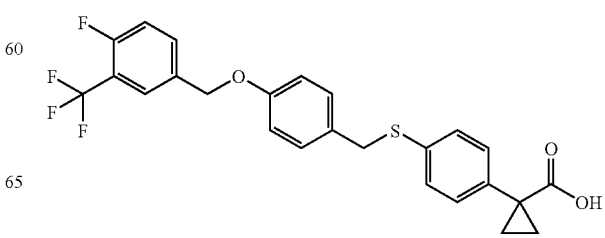

Step 1. Preparation of 1-{4-[4-(4-Fluoro-3-trifluoromethyl-benzyloxy)-benzylsulfanyl]-phenyl}-cyclopropanecarboxylic acid methyl ester (Compound 43A)

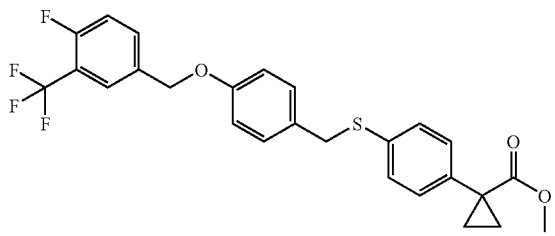

43A

The ester was synthesized with the same procedure as used for synthesis of compound 36F in 72% yield. MS: 507 (M+1)⁺.

Step 2. Preparation of 1-{4-[4-(4-Fluoro-3-trifluoromethyl-benzyloxy)-benzylsulfanyl]-phenyl}-cyclopropanecarboxylic acid (Compound 43)

The acid was synthesized with the same procedure as used for synthesis of example 36 in 56% yield. MS: 491 (M−1)⁺. Anal. Calc'd for $C_{25}H_{20}ClF_3O_3S$: C, 60.91; H, 4.09; found: C, 60.93; H, 3.83.

EXAMPLE 44

Synthesis of 1-{4-[4-(2,5-Difluoro-benzyloxy)-benzylsulfanyl]-phenyl}-cyclopropanecarboxylic acid (Compound 44)

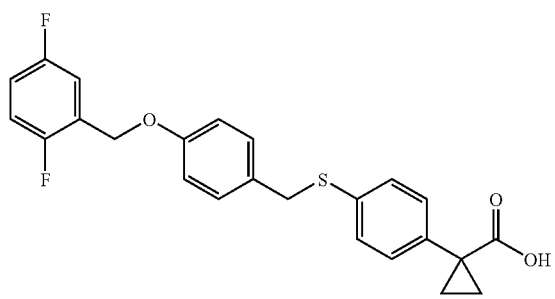

44

Step 1. Preparation of 1-{4-[4-(2,5-Difluoro-benzyloxy)-benzylsulfanyl]-phenyl}-cyclopropanecarboxylic acid methyl ester (Compound 44A)

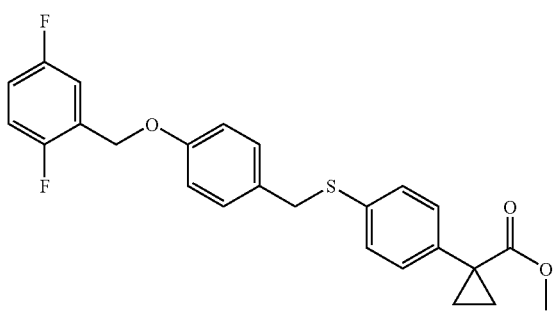

44A

The ester was synthesized with the same procedure as used for synthesis of compound 36F in 82% yield. MS: 441 (M+1)⁺.

Step 2. Preparation of 1-{4-[4-(2,5-Difluoro-benzyloxy)-benzylsulfanyl]-phenyl}-cyclopropanecarboxylic acid (Compound 44)

The acid was synthesized with the same procedure as used for synthesis of example 36 in 60% yield. MS: 425 (M−1)⁺. Anal. Calc'd for $C_2H_2O\,F_2O_3S$: C, 67.59; H, 4.73; found: C, 67.55; H, 4.37.

EXAMPLE 45

Synthesis of 1-{4-[2-(4-Trifluoromethyl-benzyloxy)-benzylsulfanyl]-phenyl}-cyclopropanecarboxylic acid (Compound 45)

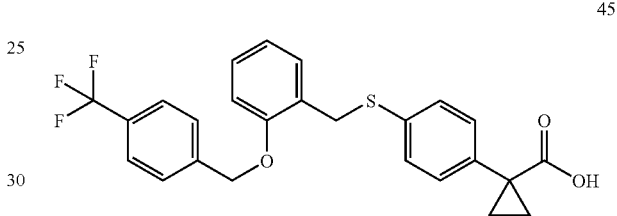

45

Step 1. Preparation of 1-{4-[2-(4-Trifluoromethyl-benzyloxy)-benzylsulfanyl]-phenyl}-cyclopropanecarboxylic acid methyl ester (Compound 45A)

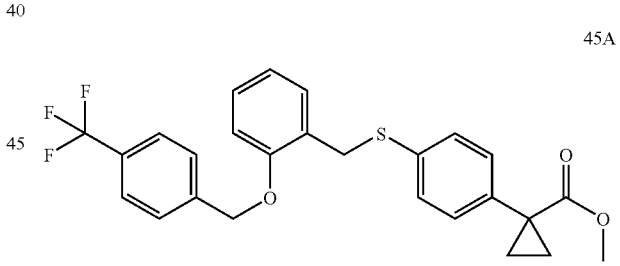

45A

The ester was synthesized with the same procedure as used for synthesis of compound 36F in 65% yield. MS: 473 (M+1)⁺.

Step 2. Preparation of 1-{4-[2-(4-Trifluoromethyl-benzyloxy)-benzylsulfanyl]-phenyl}-cyclopropanecarboxylic acid (Compound 45)

The acid was synthesized with the same procedure as used for synthesis of example 36 in 52% yield. MS: 457 (M−1)⁺. Anal. Calc'd for $C_{25}H_{21}F_3O_3S$: C, 65.49; H, 4.62; found: C, 64.91; H, 4.33.

EXAMPLE 46

Synthesis of 1-{4-[5-(4-Trifluoromethyl-phenyl)-isoxazol-3-ylmethylsulfanyl]-phenyl}-cyclopropanecarboxylic acid (Compound 46)

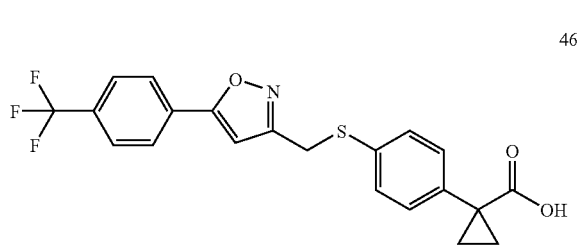

Step 1. Preparation of 1-{4-[5-(4-Trifluoromethyl-phenyl)-isoxazol-3-ylmethylsulfanyl]-phenyl}-cyclopropanecarboxylic acid methyl ester (Compound 46)

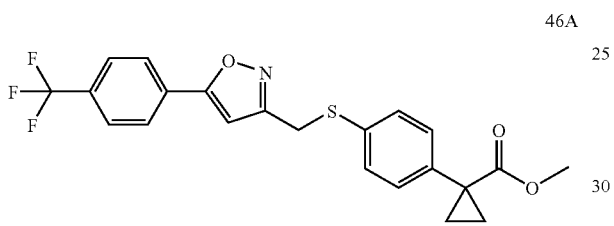

The ester was synthesized with the same procedure as used for synthesis of compound 36F in 65% yield. MS: 434 (M+1)+.

Step 2. Preparation of 1-{4-[5-(4-Trifluoromethyl-phenyl)-isoxazol-3-ylmethylsulfanyl]-phenyl}-cyclopropanecarboxylic acid (Compound 46)

The acid was synthesized with the same procedure as used for example 36 in 59% yield. MS: 420 (M+1)+. Anal. Calc'd for $C_{21}H_{16}F_3NO_3S$: C, 60.14; H, 3.85; found: C, 59.64; H, 3.63.

EXAMPLE 47

Synthesis of 2-[3-Methoxy-4-(4'-trifluoromethyl-biphenyl-4-ylmethylsulfanyl)-phenyl]-2-methyl-propionic acid (Compound 47)

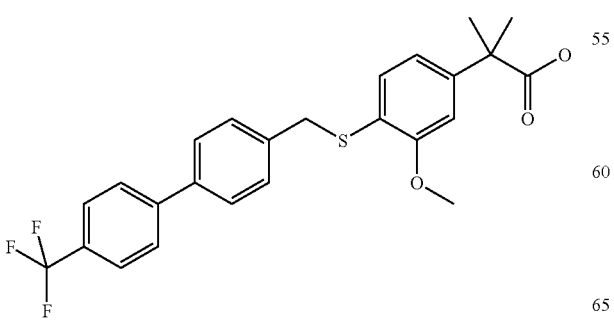

Step 1. Preparation of 2-[3-Methoxy-4-(4'-trifluoromethyl-biphenyl-4-ylmethylsulfanyl)-phenyl]-2-methyl-propionic acid methyl ester (Compound 47A)

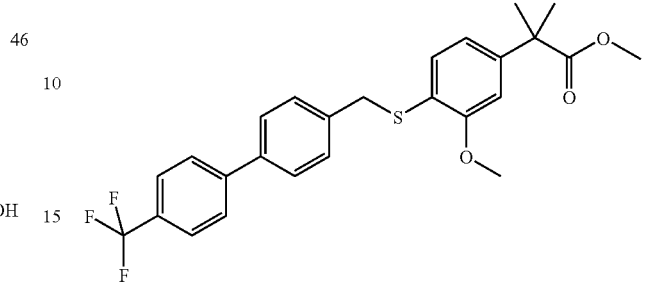

Compound 47A was prepared analogously to compound 21D using the product prepared from compound 21C. Yield was 34% after flash column purification. MS m/z 475 (M+1).

Step 2. Preparation 2-[3-Methoxy-4-(4'-trifluoromethyl-biphenyl-4-ylmethylsulfanyl)-phenyl]-2-methyl-propionic acid (Compound 47)

Compound 47 was prepared analogously to compound 21 in 61% yield. MS m/z 461 (M+1). Anal. Calc'd for $C_{25}H_{23}O_3SF_3$ C, 65.20; H, 5.03; found: C, 65.43; H, 4.97.

EXAMPLE 48

Synthesis of 2-{4-[4-(2,4-Dichloro-benzyloxy)-benzylsulfanyl]-3-methoxy-phenyl}-2-methyl-propionic acid (Compound 48).

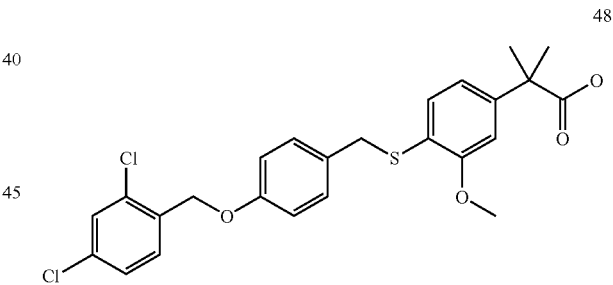

Step 1. Preparation of 2-{4-[4-(2,4-Dichloro-benzyloxy)-benzylsulfanyl]-3-methoxy-phenyl}-2-methyl-propionic acid methyl ester (Compound 48A).

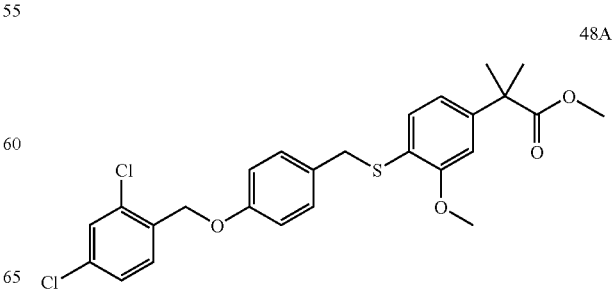

Compound 48A was prepared analogously to compound 21D using the products prepared from example 21C. Yield was 34% after flash column purification. MS m/z 504 (M−1).

Step 2. Preparation 2-{4-[4-(2,4-Dichloro-benzyloxy)-benzylsulfanyl]-3-methoxy-phenyl}-2-methyl-propionic acid (Compound 48)

Compound 48 was prepared analogously to compound 21 in 28% yield. MS m/z 490 (M−1). Anal. Calc'd for $C_{25}H_{24}O_4SCl_2$ C, 61.10; H, 4.92; found: C, 61.07; H, 4.79.

EXAMPLE 49

Synthesis of {2-Oxo-6-[4-(4-trifluoromethyl-benzyloxy)-benzylsulfanyl]-3,4-dihydro-2H-quinolin-1-yl}-acetic acid (Compound 49)

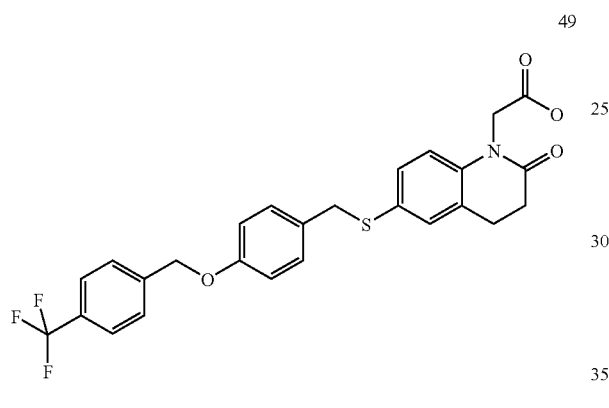

Step 1. Preparation of (2-Oxo-3,4-dihydro-2H-quinolin-1-yl)-acetic acid methyl ester (Compound 49A).

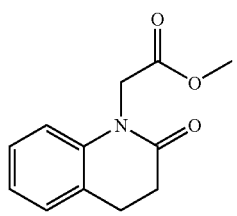

Methyl bromoacetate (5.72 g, 37.4 mmol) was slowly added to a stirred solution of sodium hydride (1.5 g, 37.4 mmol) and 3,4-dihydro-2 (1H)-quinolinone (5.0 g, 34 mmol) in THF. The mixture was stirred at RT for 3 h. After removing the solvent, the residue was diluted with water and ether. The layers were separated and the aqueous layer was extracted with ether (3×50 mL). The combined organics were dried with $MgSO_4$ and condensed to afford the desired product, compound 49A (7.06 g, 95%) as a yellow solid. MS m/z 220 (M+1).

Step 2. Preparation of (6-Chlorosulfonyl-2-oxo-3,4-dihydro-2H-quinolin-1-yl) acetic acid methyl ester (Compound 49B).

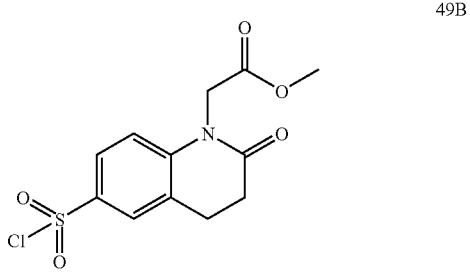

Compound 49B was prepared analogously to compound 21B using the product prepared from compound 49A. Yield was 28%. MS m/z 318 (M+1).

Step 3. Preparation of (6-Mercapto-2-oxo-3,4-dihydro-2H-quinolin-1-yl)-acetic acid methyl ester (Compound 49C).

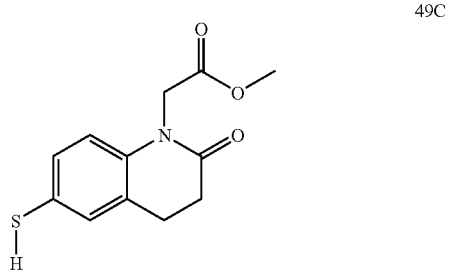

Compound 49C was prepared analogously to compound 21C using the product prepared from compound 49B. Yield was quantitative MS m/z 252 (M+1).

Step 4. Preparation of {2-Oxo-6-[4-(4-trifluoromethyl-benzyloxy)-benzylsulfanyl]-3,4-dihydro-2H-quinolin-1-yl}-acetic acid methyl ester (Compound 49D).

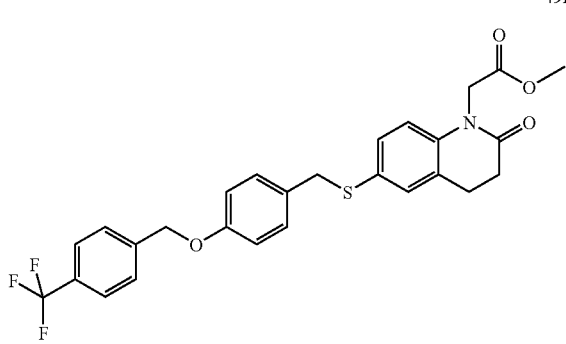

Compound 49D was prepared analogously to compound 21D using the product prepared from compound 49C. Yield was 17% after flash column purification. MS m/z 516 (M+1).-

Step 5. Preparation {2-Oxo-6-[4-(4-trifluoromethyl-benzyloxy)-benzylsulfanyl]-3,4-dihydro-2H-quinolin-1-yl}-acetic acid (Compound 49).

Compound 49 was prepared analogously to compound 21 in 98% yield. MS m/z 502 (M+1). Anal. Calc'd for $C_{26}H_{22}NO_4SF_3$ C, 62.27; H, 4.42; N 2.79, found: C, 62.11; H, 4.72, N 2.72.

EXAMPLE 50

Synthesis of {2-Oxo-6-[2-(4-trifluoromethyl-benzyloxy)-benzylsulfanyl]-3,4-dihydro-2H-quinolin-1-yl}-acetic acid (Compound 50)

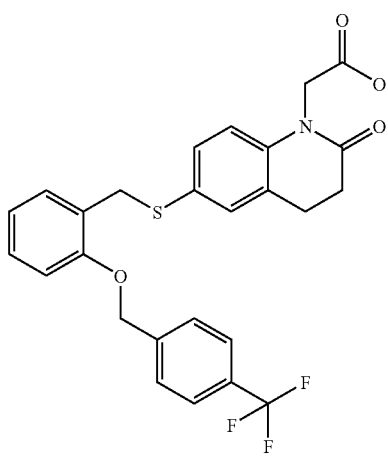

Step 1. Preparation of {2-Oxo-6-[2-(4-trifluoromethyl-benzyloxy)-benzylsulfanyl]-3,4-dihydro-2H-quinolin-1-yl}-acetic acid methyl ester (Compound 50A).

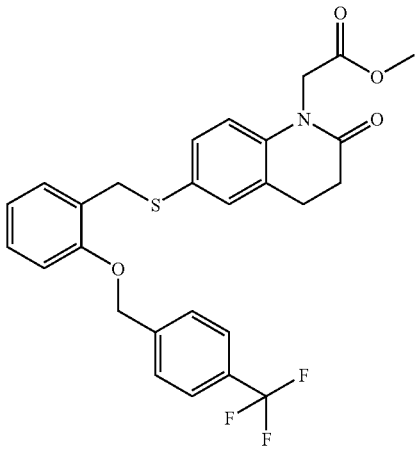

Compound 50A was prepared analogously to compound 21D using the product prepared from compound 49C. Yield was 33% after flash column purification. MS m/z 516 (M+1).

Step 2. Preparation {2-Oxo-6-[2-(4-trifluoromethyl-benzyloxy)-benzylsulfanyl]-3,4-dihydro-2H-quinolin-1-yl}-acetic acid (Compound 50).

Compound 50 was prepared analogously to compound 21 in 63% yield. MS m/z 502 (M+1). Anal. Calc'd for $C_{26}H_{22}NO_4SF_3$ C, 62.27; H, 4.42; N 2.79, found: C, 62.26; H, 4.29, N 2.73.

EXAMPLE 51

Synthesis of {2-Oxo-6-[3-(4-trifluoromethyl-benzyloxy)-benzylsulfanyl]-3,4-dihydro-2H-quinolin-1-yl}-acetic acid (Compound 51)

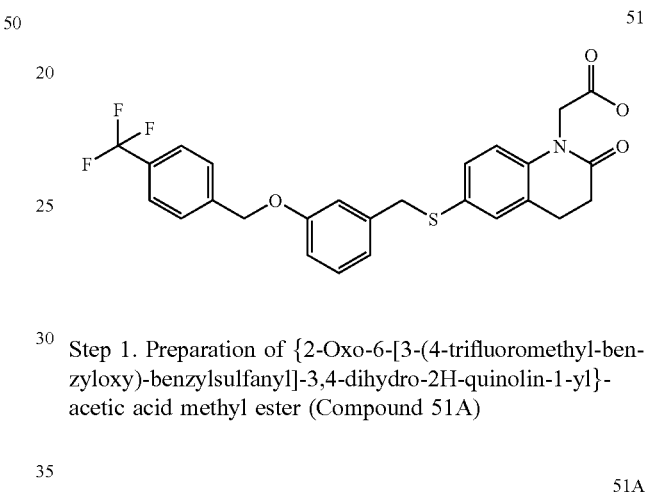

Step 1. Preparation of {2-Oxo-6-[3-(4-trifluoromethyl-benzyloxy)-benzylsulfanyl]-3,4-dihydro-2H-quinolin-1-yl}-acetic acid methyl ester (Compound 51A)

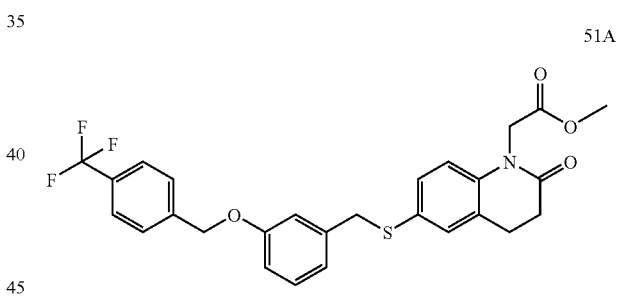

The product from example 49C (500 mg, 1.1 mmol) was dissolved in acetonitrile (20 mL) with 6B (540 mg, 1.0 mmol) and $Cs_2CO_3$ (1.3 g, 2.2 mmol). The reaction mixture was stirred at RT for 3 h. Ether (15 mL) and water were added and the stirring was continued for another 5 min. The layers were separated and the aqueous layer was extracted with ether (2×15 mL). The combined organics was dried over $MgSO_4$ and concentrated to an oil. The crude product was purified by column chromatography eluted with EtOAc and hexanes to give the desired product, compound 51A as a yellow oil (130 mg, 14%). MS m/z 516 (M+1).

Step 2. Preparation of {2-Oxo-6-[3-(4-trifluoromethyl-benzyloxy)-benzylsulfanyl]-3,4-dihydro-2H-quinolin-1-yl}-acetic acid (Compound 51)

Compound 51 was prepared analogously to compound 21 in 99% yield. MS m/z 500 (M−1). Anal. Calc'd for $C_{26}H_{22}NO_4SF_3$ C 62.27; H 4.42; N 2.79; found: C 62.63, H 4.32, N 2.60.-

Synthesis of {5-[4-(4-Trifluoromethyl-benzyloxy)-benzyloxy]-indan-1-yl}-acetic acid (Compound 52)

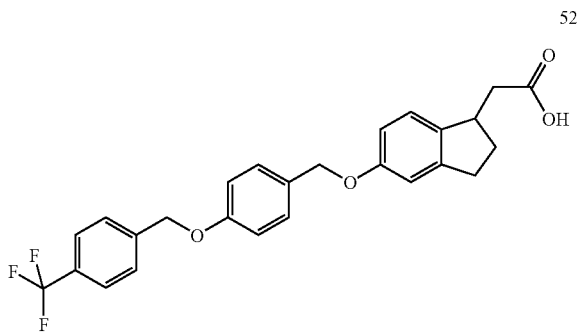

Step 1. Preparation of 5-[4-(4-Trifluoromethyl-benzyloxy)-benzyloxy]-indan-1-one (Compound 52A)

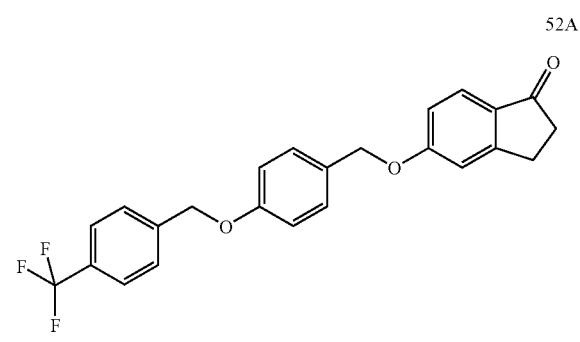

5-Hydroxyindanone (1.0 g, 1.1 mmol) was dissolved in acetonitrile (40 nL) with 5E (1.8 g, 1.0 mmol) and Cs$_2$CO$_3$ (4.4 g, 2.2 mmol). The reaction mixture was stirred at RT for 3 h. Ether (25 mL) and water were added and the stirring was continued for another 5 min. The layers were separated and the aqueous layer was extracted with ether (2×20 mL). The combined organics was dried over MgSO$_4$ and concentrated to a tan solid. The crude product was purified by column chromatography eluted with EtOAc and hexanes to give the desired product, compound 52A as a tan solid (1.26 g, 50%). MS m/z 413 (M+1).

Step 2. Preparation of {5-[4-(4-Trifluoromethyl-benzyloxy)-benzyloxy]-indan-1-yl}-acetic acid ethyl ester (Compound 52B).

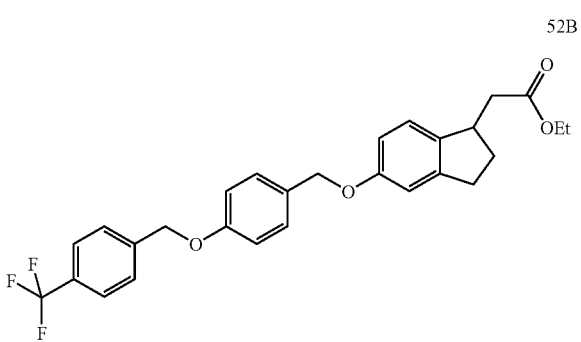

The product from example 52A (1.25 g, 3.03 mmol) and triethyl phosphonoacetate (1.36 g, 6.06 mmol) in THF (15 ml) was added to a stirred solution of sodium hydride (240 mg, 6.06 mmol) and ethanol (104 mg, 2.27 mmol) in THF (20 mL). The mixture was heated at 80° C. overnight. After removing the solvent in vacuo, the residue was diluted with water (50 ml) and layered with ether (50 ml). The layers were separated and the aqueous layer extracted with ether (2×25 ml). The combined organics were dried with MgSO$_4$ and condensed to give a crude dark oil. It was purified by column chromatography eluted with 10% EtOAc and hexanes to afford the yellow solids in 20% yield. Compound 52B was then prepared by hydrogenation of the unsaturated solid catalyzed by Pd/C (10%) in 86% yield. MS: 485 (M+1).

Step 3. Preparation of {5-[4-(4-Trifluoromethyl-benzyloxy)-benzyloxy]-indan-1-yl}-acetic acid (Compound 52)

Compound 52 was prepared analogously to compound 21 in 20% yield. MS m/z 455 (M−1). Anal. Calc'd for C$_{26}$H$_{23}$O$_4$F$_3$ C 68.41; H 5.08; N 0.0; found: C, 68.20; H, 4.92; N, 0.05. There is no Example 53.

EXAMPLE 54

Synthesis of {4-Chloro-6-[5-(4-chloro-phenyl)-isoxazol-3-ylmethoxy]-benzo[b]thiophen-3-yl}-acetic acid (Compound 54)

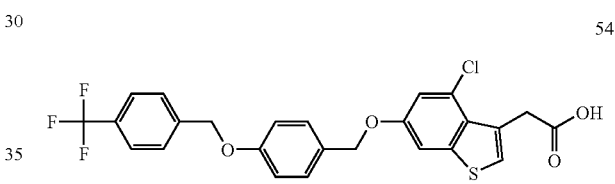

Step 1. Preparation of {4-Chloro-6-[4-(4-trifluoromethyl-benzyloxy)-benzyloxy]-benzo[b]thiophen-3-yl}-acetic acid methyl ester (Compound 54A)

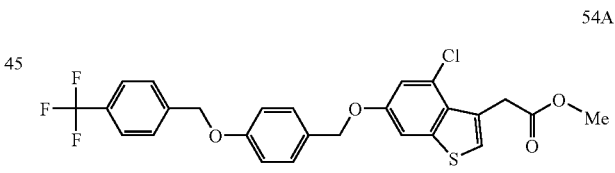

The title compound was made from example 9E and 5E in the manner analogous to example 5F. MS m/z 521 (M+1).

Step 2. Preparation of {4-Chloro-6-[5-(4-chloro-phenyl)-isoxazol-3-ylmethoxy]-benzo[b]thiophen-3-yl}-acetic acid (Compound 54)

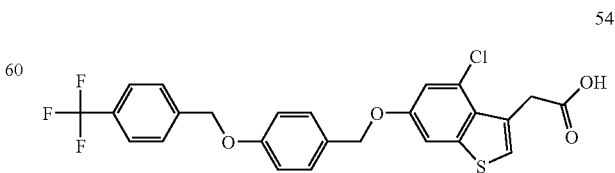

The title compound was prepared from compound 54A in a manner analogous to compound 1. 400 MHz $^1$H NMR (DMSO-d$_6$) δ 7.70 (d, 2H, J=8.3 Hz), 7.61 (d, 2H, J=8.3 Hz), 7.61 (s, 1H), 7.40 (s, 1H), 7.36 (d, 2H, J=8.8 Hz), 7.05 (d, 1H, J=2.2 Hz), 6.99 (d, 2H, J=8.8 Hz), 5.19 (s, 2H), 5.05 (s, 2H), 3.94 (s, 2H); MS m/z 505 (M−1). Anal. Calc'd for C$_{25}$H$_{18}$Cl$_1$F$_3$O$_4$S C, 59.23; H, 3.58; found: C, 58.62; H, 3.20.

EXAMPLE 55

Synthesis of {4-Chloro-6-[5-(4-trifluoromethyl-phenyl)-isoxazol-3-ylmethoxy]-benzo[b]thiophen-3-yl}-acetic acid (Compound 55)

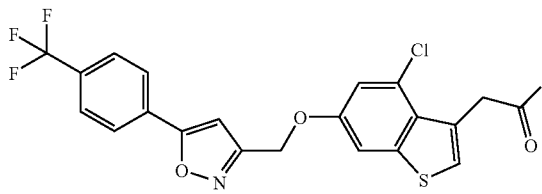

Step 1. Preparation of {4-Chloro-6-[5-(4-trifluoromethyl-phenyl)-isoxazol-3-ylmethoxy]-benzo[b]thiophen-3-yl}-acetic acid methyl ester (Compound 55A)

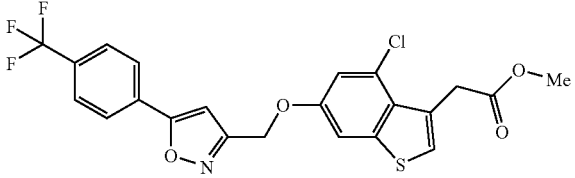

The title compound was made from example 9E and 13C in the manner analogous to example 5F. MS m/z 480 (M−1).

Step 2. Preparation of {4-Chloro-6-[5-(4-trifluoromethyl-phenyl)-isoxazol-3-ylmethoxy]-benzo[b]thiophen-3-yl}-acetic acid (Compound 55)

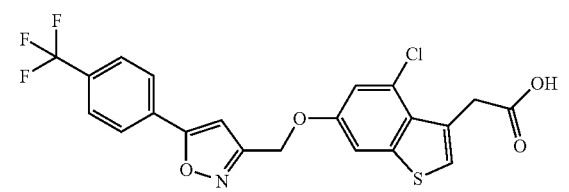

The title compound was prepared from compound 55A in a manner analogous to compound 1. 400 MHz $^1$H NMR (DMSO-d$_6$) δ 8.07 (d, 2H, J=8.1 Hz), 7.86 (d, 2H, J=8.1 Hz), 7.70 (d, 2H, J=2.4 Hz), 7.45 (s, 1H), 7.35 (s, 1H), 7.16 (d, 1H, J=2.4 Hz), 6.99 (d, 2H, J=8.8 Hz), 5.33 (s, 2H), 3.96 (s, 2H); MS m/z 466 (M−1). Anal. Calc'd for C$_{21}$H$_{13}$Cl$_1$F$_3$N$_1$O$_4$S C, 53.91; H, 2.80; found: C, 53.72; H, 2.59.

EXAMPLE 56

Synthesis of {2-Oxo-6-[5-(4-trifluoromethyl-phenyl)-isoxazol-3-ylmethylsulfanyl]-3,4-dihydro-2H-quinolin-1-yl}-acetic acid (Compound 56)

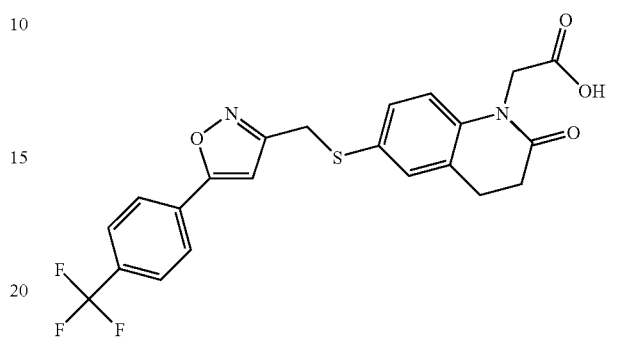

Step 1. Preparation of {2-Oxo-6-[5-(4-trifluoromethyl-phenyl)-isoxazol-3-ylmethylsulfanyl]-3,4-dihydro-2H-quinolin-1-yl}-acetic acid methyl ester (Compound 56A)

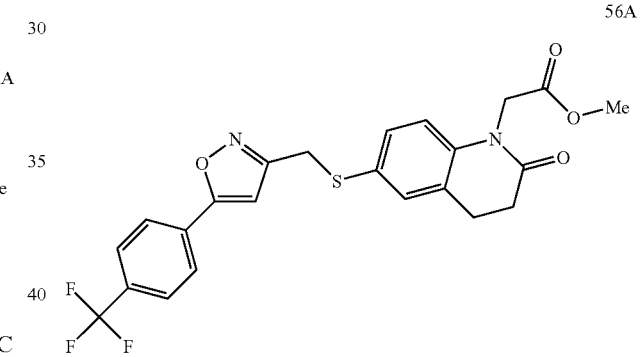

The title compound was made from example 49C and 13C in the manner analogous to example 5F. MS m/z 477 (M+1).

Step 2. Preparation of {2-Oxo-6-[5-(4-trifluoromethyl-phenyl)-isoxazol-3-ylmethylsulfanyl]-3,4-dihydro-2H-quinolin-1-yl}-acetic acid (Compound 56)

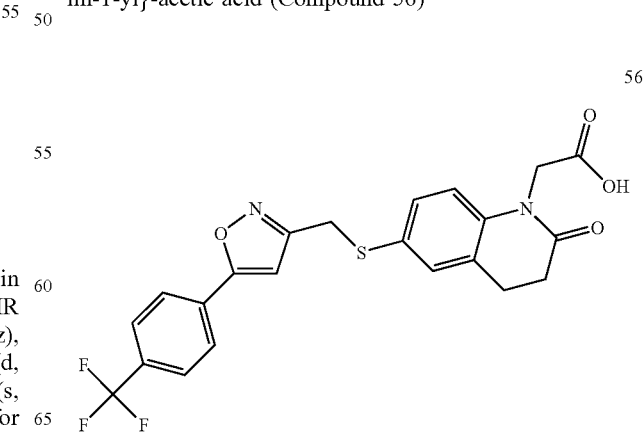

The title compound was prepared from compound 56A in a manner analogous to compound 1. 400 MHz ¹H NMR (DMSO-d₆) δ 8.02 (d, 2H, J=8.1 Hz), 7.83 (d, 2H, J=8.1 Hz), 7.27 (s, 1H), 7.20 (d, 1H, J=10.8 Hz), 7.14 (s, 1H), 6.83 (d, 1H, J=8.5 Hz), 4.48 (s, 2H), 4.23 (s, 2H), 2.80 (t, 2H, J=6.6 Hz), 2.50 (t, 2H, J=6.6 Hz); MS m/z 463 (M+1). Anal. Calc'd for $C_{22}H_{17}F_3N_2O_4S_1$ C, 57.14; H, 3.71; found: C, 57.04; H, 3.55.

EXAMPLE 57

Synthesis of {6-[5-(4-Chloro-phenyl)-isoxazol-3-ylmethylsulfanyl]-2-oxo-3,4-dihydro-2H-Quinolin-1-yl}-acetic acid (Compound 57)

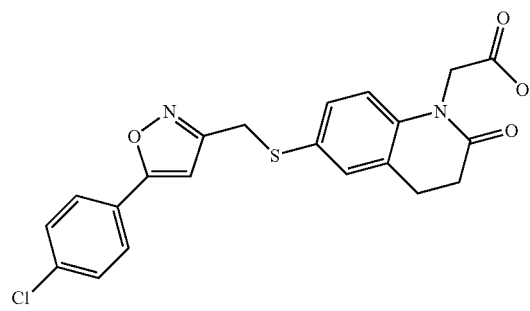

57

Step 1. Preparation of {6-[5-(4-Chloro-phenyl)-isoxazol-3-ylmethylsulfanyl]-2-oxo-3,4-dihydro-2H-quinolin-1-yl}-acetic acid methyl ester (Compound 57A)

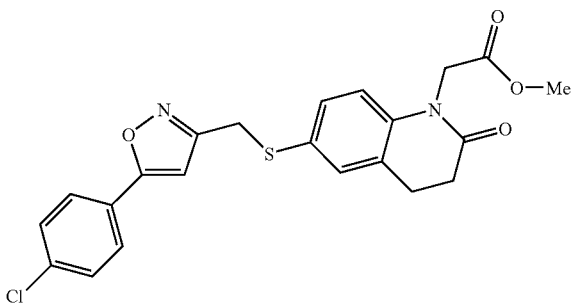

57A

The title compound was made from example 49C and commercially available 3-chloromethyl-5-(4-chloro-phenyl)-isoxazole in the manner analogous to example 5F. MS m/z 443 (M+1).

Step 2. Preparation of {6-[5-(4-Chloro-phenyl)-isoxazol-3-ylmethylsulfanyl]-2-oxo-3,4-dihydro-2H-quinolin-1-yl}-acetic acid (Compound 57)

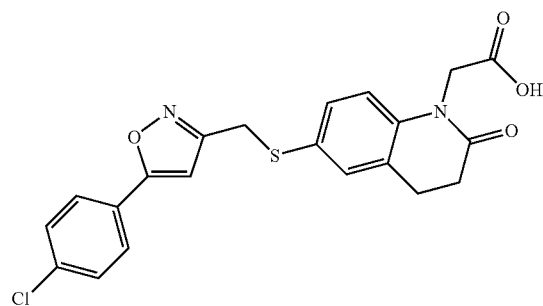

57

The title compound was prepared from compound 57A in a manner analogous to compound 1. 400 MHz ¹H NMR (DMSO-d₆) δ 7.82 (d, 2H, J=8.8 Hz), 7.53 (d, 2H, J=8.8 Hz), 7.26 (s, 1H), 7.20 (d, 1H, J=10.8 Hz), 6.99 (s, 1H), 6.83 (d, 1H, J=8.6 Hz), 4.48 (s, 2H), 4.20 (s, 2H), 2.80 (t, 2H, J=6.6 Hz), 2.50 (t, 2H, J=6.6 Hz); MS m/z 463 (M+1). MS m/z 429 (M+1). Anal. Calc'd for $C_{25}H_{19}F_3O_4S_1 \cdot 0.1H_2F_0$ C, 58.56; H, 4.03; found: C, 58.33; H, 3.92.

There are no Examples 58–61.

EXAMPLE 62

Synthesis of {5-[5-(4-Trifluoromethyl-phenyl)-isoxazol-3-ylmethoxy]-indol-1-yl}-acetic acid (Compound 62)

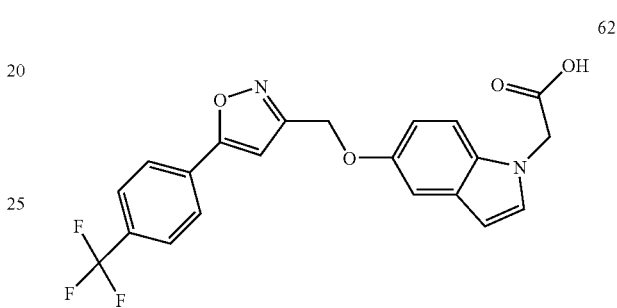

62

Step 1. Preparation of {5-[5-(4-Trifluoromethyl-phenyl)-isoxazol-3-ylmethoxy]-indol-1-yl}-acetic acid methyl ester (Compound 62A)

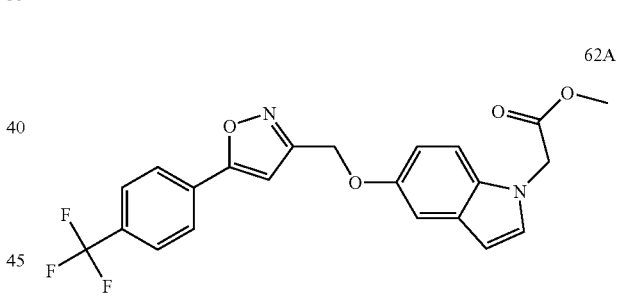

62A

Compound 13C and Compound 72B were reacted in a manner analogous to Compound 59C to give the title product. MS m/z 431 (M+1).

Step 2. Preparation of {5-[5-(4-Trifluoromethyl-phenyl)-isoxazol-3-ylmethoxy]-indol-1-yl}-acetic acid (Compound 62)

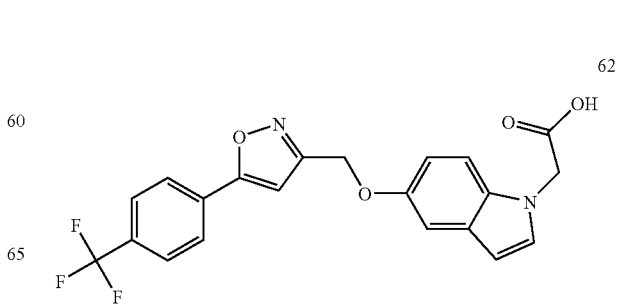

62

Compound 62A was reacted in a manner analogous to Compound 59 to give the title product. 400 MHz $^1$H NMR (DMSO-$d_6$) δ ppm 4.9 (s, 1H) 5.2 (s, 1H) 6.3 (d, J=3.2 Hz, 1H) 6.8 (dd, J=8.9, 2.3 Hz, 1H) 7.2 (d, J=2.4 Hz, 1H) 7.3 (m, 1H) 7.3 (s, 1H) 7.9 (d, J=8.3 Hz, 1H) 8.1 (d, J=8.1 Hz, 1H)). MS m/z 417 (M+1).

EXAMPLE 63

Synthesis of {5-Methoxy-2-methyl-4-[3-(methyl-pyridin-2-yl-amino)-propylsulfanyl]-phenoxy}-acetic acid (Compound 63)

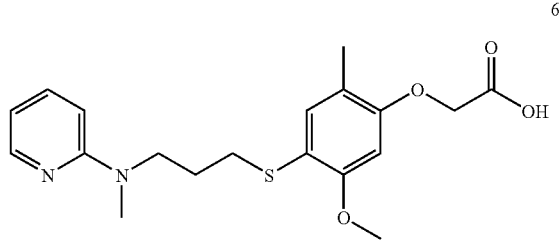

Step 1. Preparation of {5-Methoxy-2-methyl-4-[2-(methyl-pyridin-2-yl-carbamoyl)-ethylsulfanyl]-phenoxy}-acetic acid methyl ester (Compound 63A)

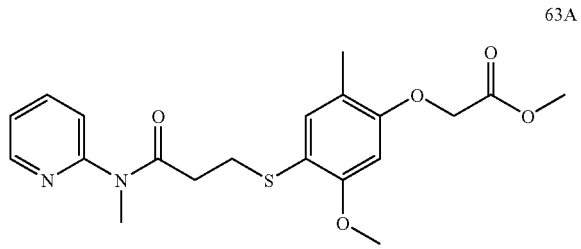

Methyl-pyridin-2-yl-amine (2 g, 18.5 mmol) and 3.8 ml triethylamine were dissolved in 30 ml ethyl acetate and cooled to −78 C. Acryloyl chloride (2.8 g, 27.7 mmol) was added and then removed from the dry ice bath. A yellow precipitate formed and the reaction was allowed to warm to room temp. 10 ml water was added and allowed to stir 1 minute. The organic layer was removed, dried over anhydrous sodium sulfate, decanted and concentrated. The N-methyl-N-pyridin-2-yl-acrylamide and Compound TA were added to 10 ml chloroform. 1 drop triethylamine was added and allowed to stir for 3 days. The reaction was concentrated and chromatographed to give the title compound as a clear colorless oil. MS m/z 405 (M+1).

Step 2. Preparation of {5-Methoxy-2-methyl-4-[3-(methyl-pyridin-2-yl-amino)-propylsulfanyl]-phenoxy}-acetic acid methyl ester (Compound 63B)

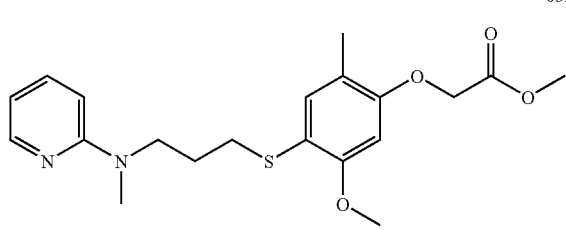

Compound 63A was dissolved POCl3 (250 mg, 1.6 mmol) and stirred for 15 minutes. The reaction was concentrated by blowing with nitrogen followed by concentration under vacuum. The intermediate was dissolved in 5 ml dimethoxyethane and cooled to ca. 5 C. Sodium borohydride (20 mg, 0.53 mmol) was added followed by warming to room temp. After 3 h 25 ml 2N HCl was added and heated to boiling for 1 minute. Saturated sodium bicarbonate was added to pH ca. 7–8. The crude product was extracted with 2×20 ml ethyl acetate, dried over anhydrous sodium sulfate, decanted and concentrated. Liquid chromatography gave the title product as a clear colorless oil. MS m/z 391 (M+1).

Step 4. Preparation of {5-Methoxy-2-methyl-4-[3-(methyl-pyridin-2-yl-amino)-propylsulfanyl]-phenoxy}-acetic acid (Compound 63)

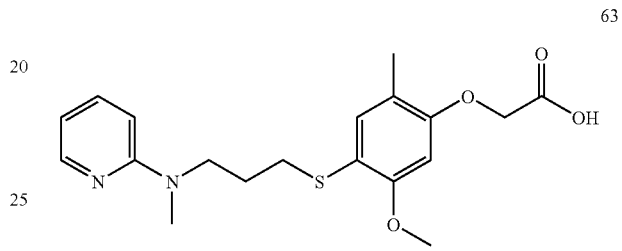

Compound 63B was reacted in a manner analogous to Compound 59 to give the title product. 400 MHz $^1$H NMR (DMSO-$d_6$) δ ppm 1.6 (m, 2H) 2.0 (s, 3H) 2.7 (t, J=7.1 Hz, 2H) 2.9 (s, 2H) 3.5 (t, J=7.1 Hz, 2H) 3.7 (s, 2H) 4.7 (s, 2H) 6.5 (dd, J=6.7, 5.2 Hz, 1H) 6.5 (t, J=4.3 Hz, 2H) 7.0 (s, 1H) 7.4 (ddd, J=8.8, 7.0, 2.1 Hz, 1H) 8.0 (dd, J=4.9, 1.2 Hz, 1H). MS m/z 377 (M+1).

EXAMPLE 64

Synthesis of (4-{3-[Ethyl-(5-phenyl-pyridin-2-yl)-amino]-propylsulfanyl}-5-methoxy-2-methyl-phenoxy)-acetic acid (Compound 64)

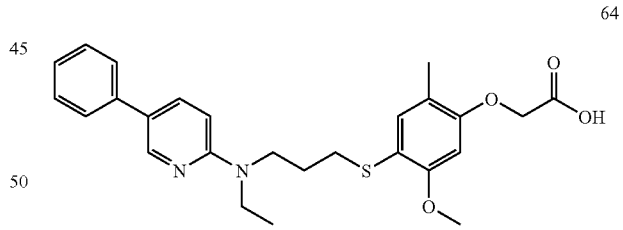

Step 1. Preparation of [5-Methoxy-2-methyl-4-(3-oxo-propylsulfanyl)-phenoxy]-acetic acid methyl ester (Compound 64A)

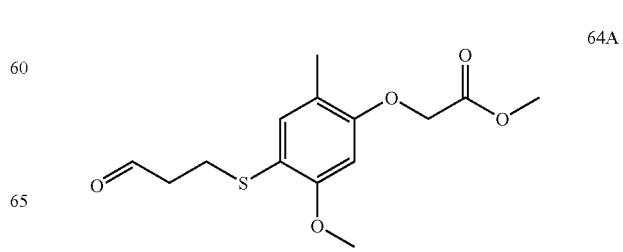

Compound TA (1 g, 4.13 mmol) was dissolved in 15 ml chloroform. Acrolein (255 mg, 4.5 mmol) was added followed by 4 drops of triethylamine. The reaction was stirred for 2 h. The reaction was filtered through silica and eluted with 50 ml dichloromethane. The filtrate was concentrated to give a clear, colorless oil which formed a white solid on standing. This was used for the next step without further purification. MS m/z 299 (M+1).

Step 2. Preparation of {5-Methoxy-2-methyl-4-[3-(5-phenyl-pyridin-2-ylamino)-propylsulfanyl]-phenoxy}-acetic acid methyl ester (Compound 64B)

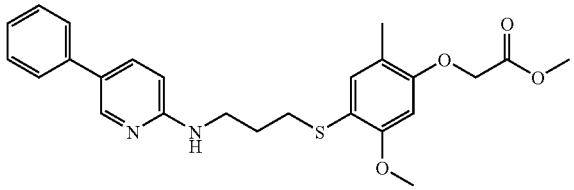

64B

Commercially available 5-phenyl-pyridin-2-ylamine (631 mg, 3.7 mmol) and Compound 64A were dissolved in 20 ml methanol with catalytic p-TsOH (ca. 20 mg) and stirred at 25 C for 18 h to give a yellow solution. NaH3CN was added and the reaction was allowed to stir for 1 h. 2N HCl was added to pH<3 and stirred 5 minutes. Saturated sodium bicarbonate was added and the product was extracted in to 100 ml ethyl acetate, dried over anhydrous sodium sulfate, decanted and concentrated. Liquid chromatography gave the title compound as a white solid. MS m/z 453 (M+1).

Step 3. Preparation of (4-{3-[Ethyl-(5-phenyl-pyridin-2-yl)-amino]-propylsulfanyl}-5-methoxy-2-methyl-phenoxy)-acetic acid methyl ester (Compound 64C)

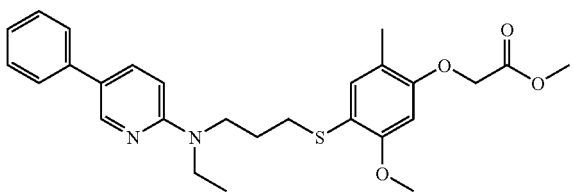

64C

Compound 64B (300 mg, 0.66 mmol), acetaldehyde (32 mg, 0.73 mmol), sodium triacetoxyborohydride (211 mg, 0.994 mmol), and 57 □l acetic acid were added to 5 ml dichloroethane and stirred at room temperature for 3 days. 1 eq more of aldehyde, sodium triacetoxyborohydride, and acetic acid were added and stirred 3 h more. 10 ml 2N HCl was added followed by saturated sodium bicarbonate to pH ca. 8. The product was extracted into 20 ml, dried over sodium sulfate, decanted, concentrated. Liquid chromatography give the title compound as a white solid. MS m/z 481 (M+1).

Step 4. Preparation of {4-[3-(Biphenyl-4-yl-ethyl-amino)-propylsulfanyl]-5-methoxy-2-methyl-phenoxy}-acetic acid (Compound 64)

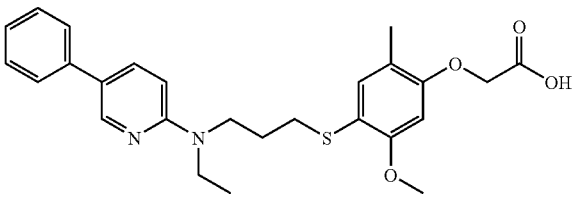

64

Compound 64C was reacted in a manner analogous to Compound 59 to give the title product. 400 MHz $^1$H NMR (DMSO-$d_6$) δ ppm 1.0 (t, J=7.0 Hz, 2H) 1.7 (m, 2H) 2.0 (s, 2H) 2.7 (t, J=7.0 Hz, 2H) 3.5 (m, 3H) 4.3 (s, 2H) 6.4 (s, 1H) 6.6 (d, J=8.3 Hz, 1H) 7.0 (s, 1H) 7.2 (m, 1H) 7.3 (m, 2H) 7.5 (m, 2H) 7.7 (dd, J=8.9, 2.6 Hz, 1H) 8.3 (d, J=2.0 Hz, 1H). MS m/z $^{467}$ (M+1).

EXAMPLE 66

Synthesis of (5-Methoxy-2-methyl-4-{3-[methyl-(5-phenyl-pyridin-2-yl)-amino]-propylsulfanyl}-phenoxy)-acetic acid (Compound 66)

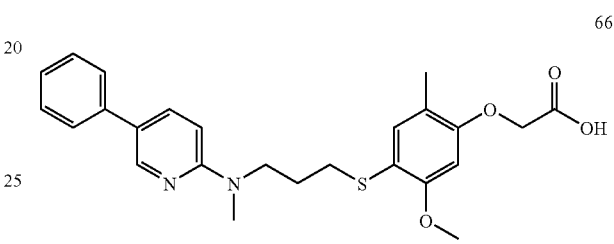

66

Step 1. Preparation of (5-Methoxy-2-methyl-4-{3-[methyl-(5-phenyl-pyridin-2-yl)-amino]-propylsulfanyl}-phenoxy)-acetic acid methyl ester (Compound 66A)

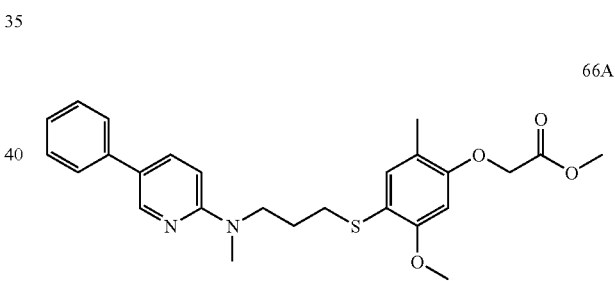

66A

Compound 64B was reacted with paraformaldehyde in a manner analogous to Compound 64C to give the title product. MS m/z 467 (M+1).

Step 2. Preparation of (5-Methoxy-2-methyl-4-{3-[methyl-(5-phenyl-pyridin-2-yl)-amino]-propylsulfanyl}-phenoxy)-acetic acid (Compound 66)

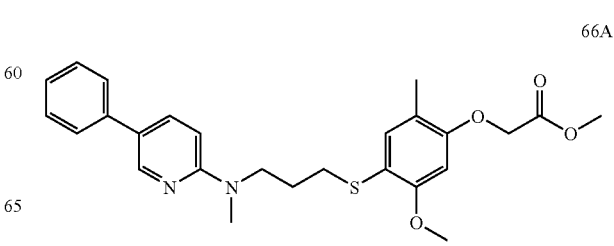

66A

Compound 66A was reacted in a manner analogous to Compound 59 to give the title product; 400 MHz ¹H NMR (DMSO-d₆) δ ppm 1.7 (m, 2H) 2.0 (s, 3H) 2.7 (t, 2H) 3.0 (s, 3H) 3.6 (t, 2H) 3.7 (s, 2H) 4.7 (s, 2H) 6.5 (s, 1H) 6.6 (d, J=8.3 Hz, 1H) 7.0 (s, 1H) 7.2 (m, 1H) 7.4 (m, 2H) 7.5 (m, 2H) 7.7 (dd, J=9.0, 2.7 Hz, 1H) 8.3 (d, J=2.0 Hz, 1H) 12.2 (br(s), 1H). MS m/z 453 (M+1).

EXAMPLE 67

Synthesis of {4-[3-(Benzyl-ethyl-amino)-propylsulfanyl]-5-methoxy-2-methyl-phenoxy}-acetic acid (Compound 67)

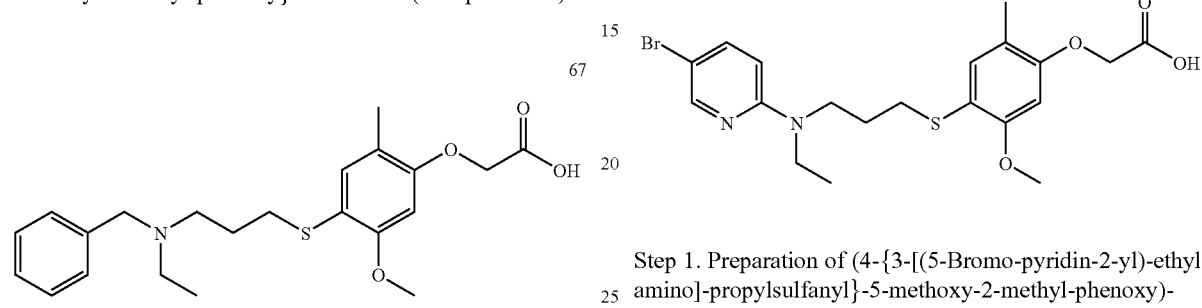

Step 1. Preparation of {4-[3-(Benzyl-ethyl-amino)-propylsulfanyl]-5-methoxy-2-methyl-phenoxy}-acetic acid methyl ester (Compound 67A)

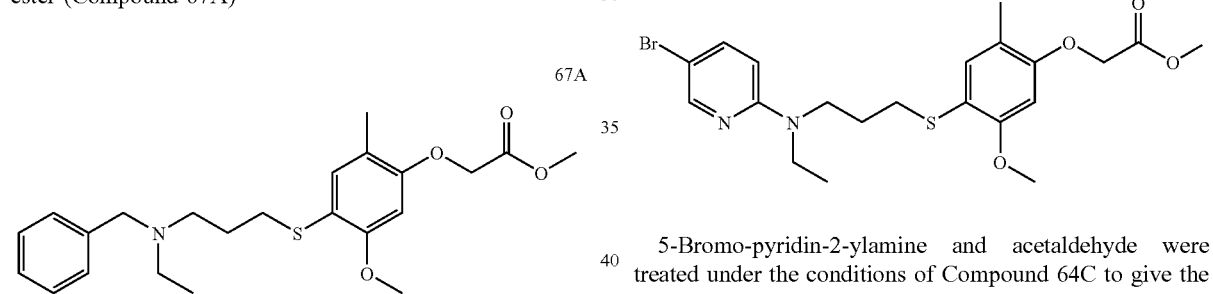

Compound 64A and benzyl-ethyl-amine were reacted in a manner analogous to Compound 64C to give the title product. MS m/z 418 (M+1).

Step 3. Preparation of {4-[3-(Benzyl-ethyl-amino)-propylsulfanyl]-5-methoxy-2-methyl-phenoxy}-acetic acid (Compound 67)

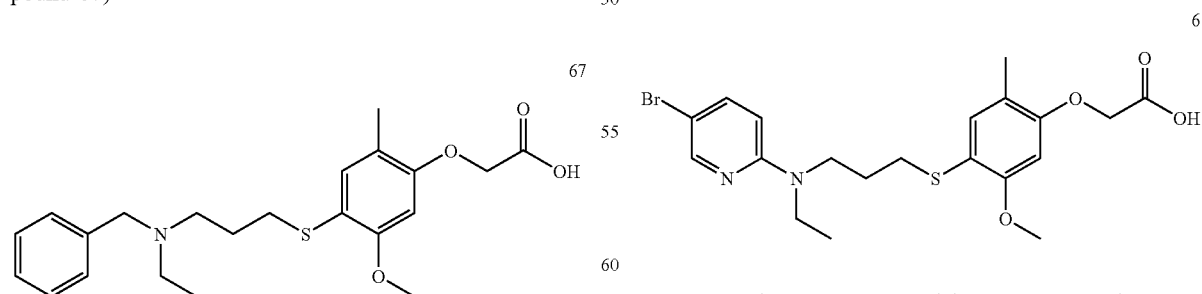

Compound 67A was reacted in a manner analogous to Compound 59 to give the title product. 400 MHz ¹H NMR (DMSO-d₆) δ ppm 0.9 (t, J=7.1 Hz, 3H) 1.5 (m, 2H) 2.0 (s, 3H) 2.3 (q, J=6.9 Hz, 2H) 2.4 (t, 2H), 2.7 (t, J=7.2 Hz, 2H) 3.4 (s, 2H) 3.7 (s, 3H) 4.5 (m, 2H) 6.5 (s, 1H) 7.0 (s, 1H) 7.2 (m, 1H) 7.2 (m, 4H). MS m/z 404 (M+1).

EXAMPLE 68

Synthesis of (4-{3-[(5-Bromo-pyridin-2-yl)-ethyl-amino]-propylsulfanyl}-5-methoxy-2-methyl-phenoxy)-acetic acid (Compound 68)

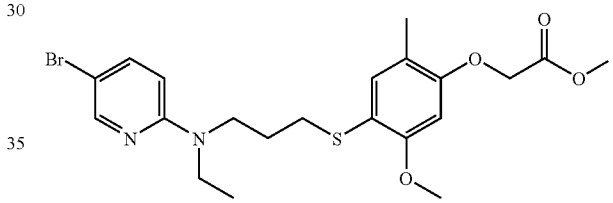

Step 1. Preparation of (4-{3-[(5-Bromo-pyridin-2-yl)-ethyl-amino]-propylsulfanyl}-5-methoxy-2-methyl-phenoxy)-acetic acid methyl ester (Compound 68A)

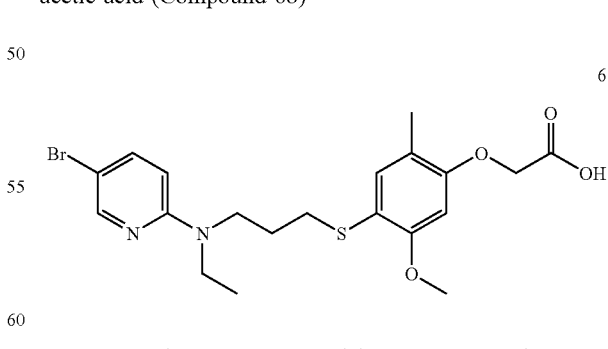

5-Bromo-pyridin-2-ylamine and acetaldehyde were treated under the conditions of Compound 64C to give the intermediate (5-bromo-pyridin-2-yl)-ethyl-amine. This was then reacted with Compound 64A to give the title product. MS m/z 481 (M+1).

Step 2. Preparation of (4-{3-[(5-Bromo-pyridin-2-yl)-ethyl-amino]-propylsulfanyl}-5-methoxy-2-methyl-phenoxy)-acetic acid (Compound 68)

Compound 68A was reacted in a manner analogous to Compound 59 to give the title product. 400 MHz ¹H NMR (DMSO-d₆) δ ppm 1.0 (t, J=7.0 Hz, 3H) 1.6 (m, 2H) 2.0 (s, 3H) 2.7 (t, J=7.0 Hz, 2H) 3.4 (m, 4H) 3.7 (s, 3H) 4.2 (s, 2H) 6.4 (s, 1H) 6.5 (d, J=9.0 Hz, 1H) 7.0 (s, 1H) 7.5 (dd, J=9.2, 2.6 Hz, 1H) 8.0 (d, J=2.2 Hz, 1H). MS m/z 471 (M+2)

EXAMPLE 69

Synthesis of {4-[2-(3-Fluoro-phenyl)-benzooxazol-5-ylmethylsulfanyl]-5-methoxy-2-methyl-phenoxy}-acetic acid (Compound 69)

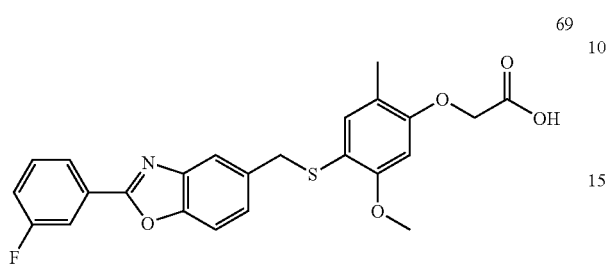

Step 1. Preparation of 2-(3-Fluoro-phenyl)-benzooxazole-5-carboxylic acid methyl ester (Compound 69A)

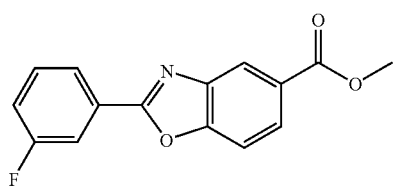

3-Fluoro-benzoic acid (7.0 g, 50 mmol), 3-amino-4-hydroxy-benzoic acid methyl ester (8.3 g, 50 mmol) were added portionwise to 50 ml polyphosphoric acid which was heated to 130° C. The reaction was stirred for 2 h at 130° C. and turned into a thick black syrup. The reaction was poured into water with rapid stirring until a pale white suspension was formed. This solution was extract 2×200 ml ethyl acetate, washed 1×50 ml brine, dried over sodium sulfate, decanted and concentrated to give the crude product as a light pink solid. MS m/z 272 (M+1).

Step 2. Preparation of [2-(3-Fluoro-phenyl)-benzooxazol-5-yl]-methanol (Compound 69B)

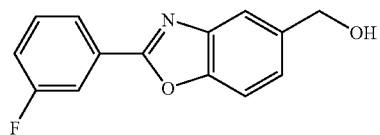

Lithium aluminum hydride was added to 100 ml THF and stirred for 10 minutes and cooled in an ice bath. A solution of Compound 69A (9.06 g, 33.4 mmol) in 200 ml THF was added dropwise over ½ hr to the lithium aluminum hydride solution and stirred for 2 h. A saturated solution of water/sodium sulfate decahydrate was added until gas evolution ceased and a heavy white precipitate formed. The reaction was stirred for 30 minutes more and filtered through Celite®, extracted into 2×200 ml ethyl acetate, washed with 1×50 ml brine dried over anhydrous sodium sulfate, and filtered through silica. The product was eluted with 300 ml ethyl acetate and concentrated to give a cream colored solid. MS m/z 244 (M+1).

Step 3. Preparation 5-Chloromethyl-2-(3-fluoro-phenyl)-benzooxazole (Compound 69C)

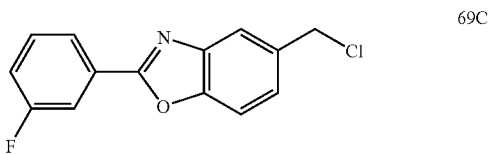

Compound 69B was suspended in 100 ml dichloromethane. SOCl2 was added and allowed to stir for 2 h. 20 ml Saturated sodium bicarbonate was added followed by 20 ml water and stirred for 5 minutes. The dichloromethane layer was seperated and dried over anhydrous sodium sulfate. The dichloromethane solution was filtered through silica and eluted with dichloromethane until clear. Concentration of the filtrate gave a pink solid. MS m/z 262 (M+1).

Step 4. Preparation {4-[2-(3-Fluoro-phenyl)-benzooxazol-5-ylmethylsulfanyl]-5-methoxy-2-methyl-phenoxy}-acetic acid methyl ester (Compound 69D)

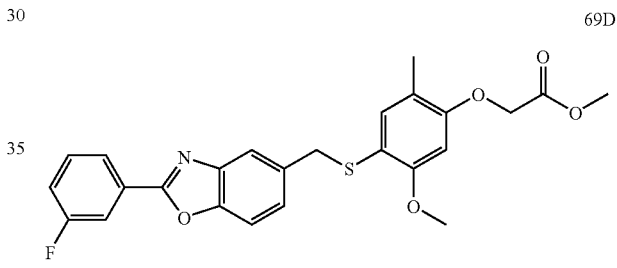

Compound 69C and Compound TA were reacted in a manner analogous to Compound 59A to give the title product. MS m/z 464 (M+1).

Step 5. Preparation of {4-[2-(3-Fluoro-phenyl)-benzooxazol-5-ylmethylsulfanyl]-5-methoxy-2-methyl-phenoxy}-acetic acid (Compound 69)

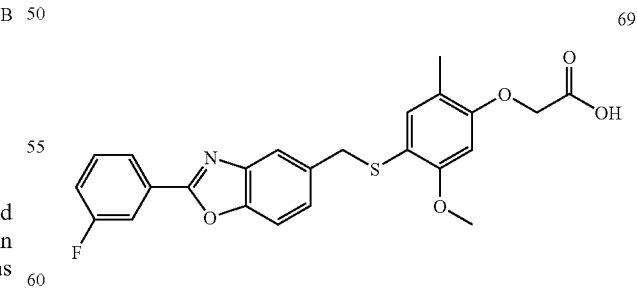

Compound 69D was reacted in a manner analogous to Compound 59 to give the title product. 400 MHz $^1$H NMR (DMSO-$d_6$) δ ppm 2.0 (s, 3H) 3.7 (s, 3H) 4.1 (s, 2H) 4.7 (s, 2H) 6.5 (s, 1H) 7.0 (s, 1H) 7.3 (dd, J=8.4, 1.8 Hz, 1H) 7.4 (m, 1H) 7.6 (m, 3H) 7.9 (ddd, J=9.5, 2.4, 1.5 Hz, 1H) 8.0 (dt, J=8.1, 1.1 Hz, 1H). MS m/z 454 (M+1).

EXAMPLE 70

Synthesis of [4-(3-{Ethyl-[5-(4-fluoro-phenyl)-pyridin-2-yl]-amino}-propylsulfanyl)-5-methoxy-2-methyl-phenoxy]-acetic acid (Compound 70)

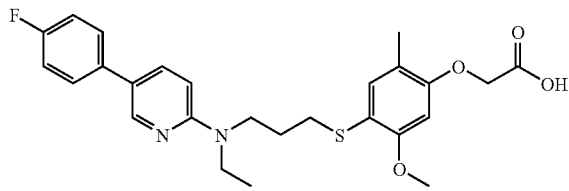

Step 1. Synthesis of 5-(4-Fluoro-phenyl)-pyridin-2-ylamine (Compound 70A)

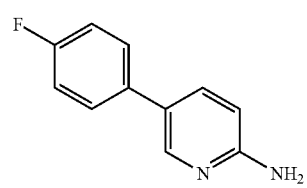

5-Bromo-pyridin-2-ylamine (2.00 g, 11.6 mmol) and 4-fluorophenylboronic acid (1.8 g, 12.7 mmol), $Na_2CO_3$ (2.45 g, 23 mmol), 210 µl water, were added to 20 ml degassed DME and heated to 80 deg. C. for 5 h. The reaction was cooled and poured into 100 ml ether, washed 2×50 ml water, 1×50 ml brine, dried over anhydrous sodium sulfate, decanted and concentrated. The crude product was dissolved in 1:1 dichloromethane/hexanes and filtered through silica gel and eluted with 200 ml 1:1 dichloromethane/hexanes. The filtrate was concentrated to a white solid. 400 MHz $^1$H NMR (DMSO-$d_6$) δ ppm 6.0 (s, 2H) 6.5 (dd, J=8.8, 1.0 Hz, 1H) 7.2 (t, J=9.0 Hz, 2H) 7.5 (m, 3H) 8.2 (d, J=2.0 Hz, 1H).

Step 2. Synthesis of Ethyl-[5-(4-fluoro-phenyl)-pyridin-2-yl]-amine (Compound 70B)

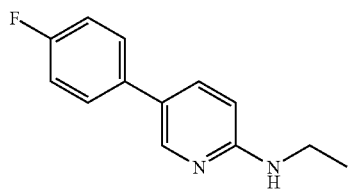

Compound 70A was reacted with acetaldehyde in a manner analogous to Compound 63C to give the title product. 400 MHz $^1$H NMR (DMSO-$d_6$) δ ppm 1.1 (t, 3H) 3.2 (q, 2H) 6.6 (m, 2H) 7.2 (m, 2H) 7.5 (m, 3H) 8.2 (d, J=2.0 Hz, 1H).

Step 3. Preparation of [4-(3-{Ethyl-[5-(4-fluoro-phenyl)-pyridin-2-yl]-amino}-propylsulfanyl)-5-methoxy-2-methyl-phenoxy]-acetic acid methyl ester (Compound 70C)

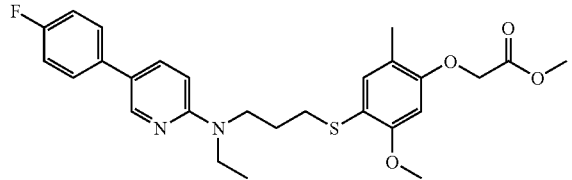

Compound 70B and Compound 64A were reacted in a manner analogous to Compound 63C to give the title product. MS m/z 499 (M+1).

Step 5. Preparation [4-(3-{Ethyl-[5-(4-fluoro-phenyl)-pyridin-2-yl]-amino}-propylsulfanyl)-5-methoxy-2-methyl-phenoxy]-acetic acid (Compound 70)

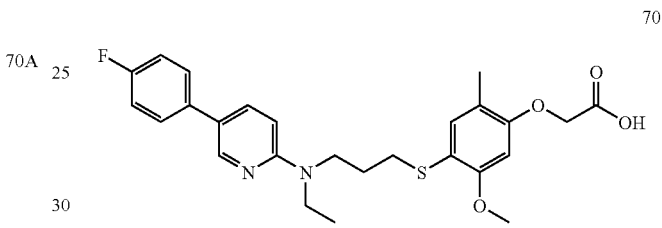

Compound 70C was reacted in a manner analogous to Compound 59 to give the title product. 400 MHz $^1$H NMR (DMSO-$d_6$) δ ppm 1.0 (t, 3H) 1.7 (m, 2H) 2.7 (t, J=7.1 Hz, 2H) 3.5 (m, 4H) 4.1 (s, 2H) 6.4 (s, 1H) 6.6 (d, J=8.3 Hz, 1H) 7.0 (s, 1H) 7.2 (m, 2H) 7.6 (m, 2H) 7.7 (dd, J=9.0, 2.7 Hz, 1H) 8.3 (d, J=2.2 Hz, 1H). MS m/z 485 (M+1)

EXAMPLE 71

Synthesis of {7-[2-(3-Fluoro-phenyl)-benzooxazol-5-ylmethylsulfanyl]-indan-4-yloxy}-acetic acid (Compound 71)

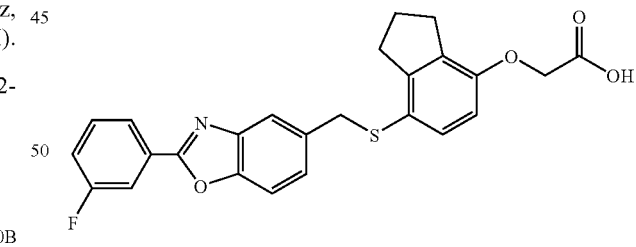

Step 1. Preparation of {7-[2-(3-Fluoro-phenyl)-benzooxazol-5-ylmethylsulfanyl]-indan-4-yloxy}-acetic acid methyl ester (Compound 71A)

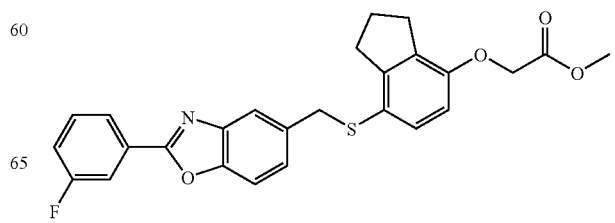

Compound 69C and Compound 1D were reacted in a manner analogous to Compound 59A to give the title product. MS m/z 464 (M+1).

Step 2. Preparation of {7-[2-(3-Fluoro-phenyl)-benzooxazol-5-ylmethylsulfanyl]-indan-4-yloxy}-acetic acid (Compound 71)

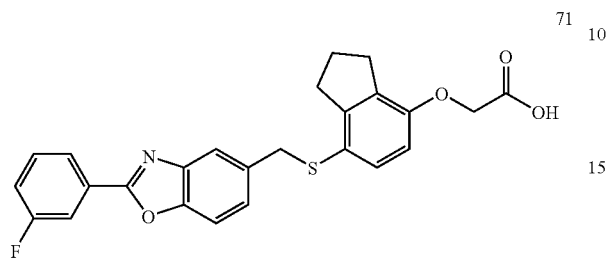

Compound 71A was reacted in a manner analogous to Compound 59 to give the title product. 400 MHz $^1$H NMR (DMSO-$d_6$) δ 1.9 (m, 2H) 2.7 (m, 4H) 4.2 (s, 2H) 4.6 (s, 2H) 6.6 (d, J=8.5 Hz, 1H) 7.1 (d, J=8.5 Hz, 1H) 7.3 (dd, J=8.5, 1.7 Hz, 1H) 7.4 (m, 1H) 7.6 (m, 3H) 7.9 (m, 1H) 8.0 (dt, J=8.1, 1.1 Hz, 1H) 12.9 (br(s), 1H). MS m/z 450 (M+1).

EXAMPLE 72

Synthesis of {5-[2-(3-Fluoro-phenyl)-benzooxazol-5-ylmethylsulfanyl]-indol-1-yl}-acetic acid (Compound 72)

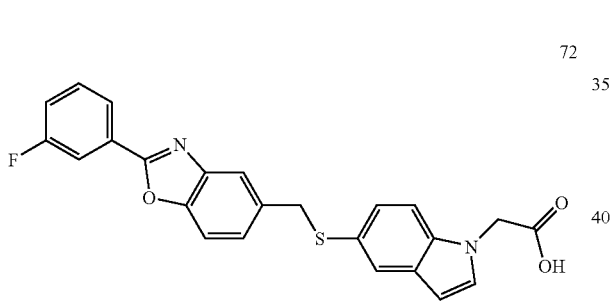

Step 1. Preparation of (5-Benzyloxy-indol-1-yl)-acetic acid methyl ester (Compound 72A)

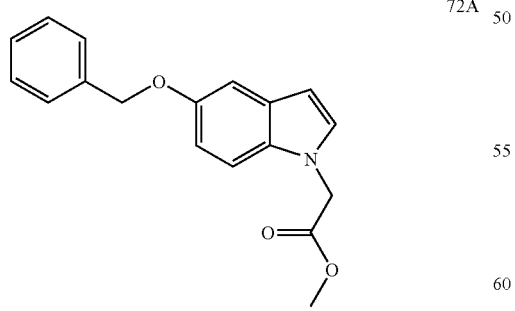

5-Benzyloxy-1H-indole (20 g, 89.6 mmol) was dissolved in 50 ml DMF. NaH (2.3 g, 94 mmol) was added and allowed to stir 10 minutes. Bromo-acetic acid methyl ester (15.1 g, 98.5 mmol) was then added followed by stirring for 2 h. 30 ml 2N HCl was added followed by extraction with 2×100 ml diethyl ether. The ether extracts were washed 1×100 ml water, 1×100 ml brine, dried over anhydrous sodium sulfate, decanted and concentrated. Purification by liquid chromatography gave the title product as a white solid. MS m/z 296 (M+1).

Step 2. Preparation of (5-Hydroxy-indol-1-yl)-acetic acid methyl ester (Compound 72B)

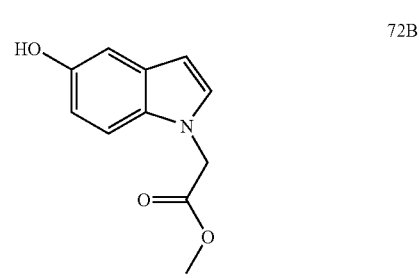

Compound 72A (18.9 g, 64 mmol) was dissolved in 100 ml 1:1 ethyl acetate/ethanol. 200 mg 10% Pd/C was added followed by purging with hydrogen. The reaction was stirred vigorously under balloon pressure for 16 h. The reaction was filtered through Celite® and concentrated to an oil which was filtered through 0.45 uM filter to give a pale yellow oil which crystallized on standing. MS m/z 206 (M+1).

Step 3. Preparation of (5-Dimethylthiocarbamoyloxy-indol-1-yl)-acetic acid methyl ester (Compound 72C)

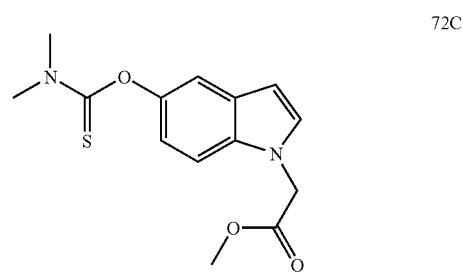

Compound 72B (9.12 g, 44.4 mmol) was dissolved in 50 ml DMF. NaH was added portionwise over 5 minutes. After stirring for 15 minutes a solution of thiocarbamoyl chloride (5.8 g, 46.7 mmol) in 25 ml DMF was added and allowed to stir for 2 h. 50 ml 2N HCl was added and the reaction was extracted 2×100 ml ether, washed 2×100 ml water, 1×100 ml brine, and filtered through silica. The product was eluted with 200 ml diethyl ether and concentrated. The precipitate was filtered and dried under vacuum for 16 h. MS m/z 293 (M+1).

Step 4. Preparation of (5-Dimethylcarbamoylsulfanyl-indol-1-yl)-acetic acid methyl ester (Compound 72D)

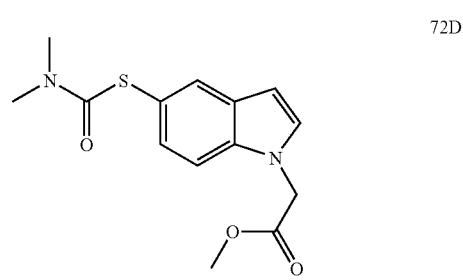

30 ml Diphenyl ether was heated to 260° C. A solution of Compound 72C (5.09 g, 17.4 mmol) in 20 ml diphenyl ether was added and allowed to heat at 260 C for 24 h The reaction became dark brown after 5 h. The reaction mixture was filtered through silica and eluted with 500 ml 9:1 hexanes/dichloromethane. The clear, yellow filtrate was concentrated to a dark orange oil and was used for the next step without further purification. MS m/z 293 (M+1).

Step 5. Preparation of (5-Mercapto-indol-1-yl)-acetic acid methyl ester (Compound 72E)

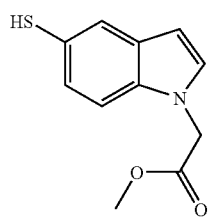

72E

Compound 72D (4.04 g, 13.8 mmol) was dissolved in 200 ml methanol. Nitrogen was bubbled for 5 minutes followed by the addition of a 2N NaOH solution (1.4 g/17 ml water). The solution was heated at reflux and tuned brown after 10 minutes. The reaction was concentrated to ca. 50 ml under vacuum and acidified to pH<4 with 2N HCl. The product was extracted into ethyl acetate 2×100 ml, dried over anhydrous sodium sulfate, decanted and concentrated. The crude acid was dissolved into 100 ml anhydrous methanol followed by 5 drops concentrated sulfuric acid. This was heated at reflux for 3 h then cooled to room temp. 500 mg dithiothreitol was added followed by 100 mg sodium borohydride. This was stirred for 1 h and concentrated to an oil. The crude thiol ester was dissolved into 100 ml dichloromethane, filtered through silica and eluted with 300 ml dichloromethane. The filtrate was concentrated and purified by liquid chromatography to give the title product as a yellow oil. MS m/z 222 (M+1).

Step 6. Preparation of {5-[2-(3-Fluoro-phenyl)-benzooxazol-5-ylmethylsulfanyl]-indol-1-yl}-acetic acid methyl ester (Compound 72F)

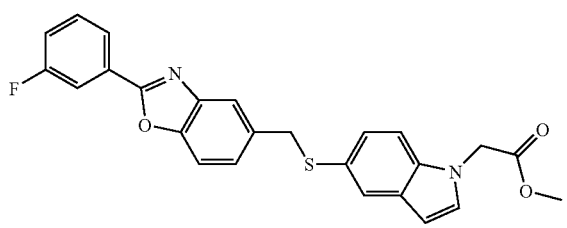

72F

Compound 70C and Compound 72E were reacted in a manner analogous to Compound 59A to give the title product. MS m/z 417 (M+1).

Step 7. Preparation of {5-[2-(3-Fluoro-phenyl)-benzooxazol-5-ylmethylsulfanyl]-indol-1-yl}-acetic acid (Compound 72)

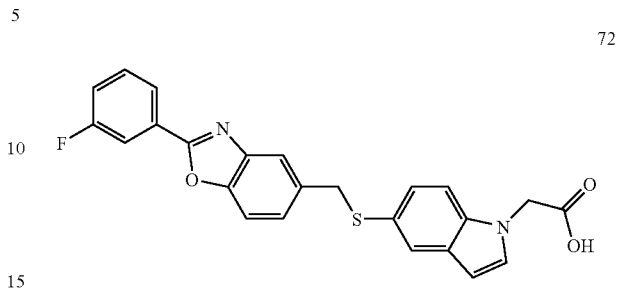

72

Compound 72F was reacted in a manner analogous to Compound 59 to give the title product. 400 MHz $^1$H NMR (DMSO-$d_6$) δ ppm 4.9 (s, 2H) 5.2 (s, 2H) 6.3 (d, J=3.2, 1.0 Hz, 1H) 6.8 (dd, J=8.8, 2.2 Hz, 1H) 7.1 (d, J=2.2 Hz, 1H) 7.2 (m, 2H) 7.5 (m, 2H) 7.6 (m, 1H) 7.8 (d, J=8.3 Hz, 1H) 7.9 (m, 2H) 8.0 (dt, J=8.1, 1.1 Hz, 1H) 12.8 (br(s), 1H).

EXAMPLE 73

Synthesis of {6-[2-(3-Fluoro-phenyl)-benzooxazol-5-ylmethoxy]-benzo[b]thiophen-3-yl}-acetic acid (Compound 73)

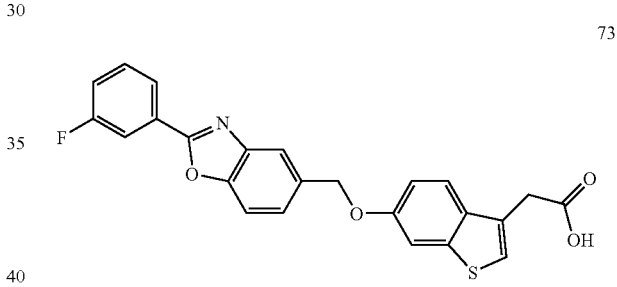

73

Compound 69C and Compound 5C were reacted in a manner analogous to Compound 59A to give {6-[2-(3-Fluoro-phenyl)-benzooxazol-5-ylmethoxy]-benzo[b]thiophen-3-yl}-acetic acid methyl ester. This was reacted in a manner analogous to Compound 59 to give the title product. 400 MHz $^1$H NMR (DMSO-$d_6$) δ ppm 3.7 (s, 2H) 5.3 (s, 2H) 7.1 (dd, J=8.8, 2.4 Hz, 1H) 7.3 (s, 1H) 7.5 (m, 1H) 7.5 (dd, J=8.3, 1.7 Hz, 1H) 7.6 (m, 3H) 7.8 (d, J=8.3 Hz, 1H) 7.9 (m, 2H) 8.0 (dt, J=8.1, 1.1 Hz, 1H).

EXAMPLE 74

Synthesis of {4-[2-(4-Fluoro-phenyl)-benzooxazol-5-ylmethylsulfanyl]-5-methoxy-2-methyl-phenoxy}-acetic acid (Compound 74)

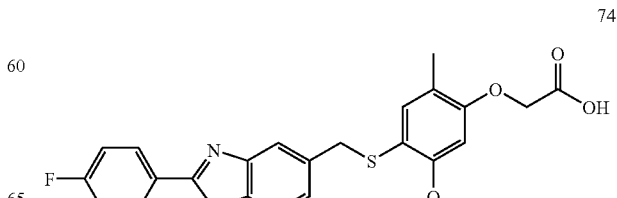

74

Step 1. Preparation of 2-(4-Fluoro-phenyl)-benzooxazole-5-carboxylic acid methyl ester (Compound 74A)

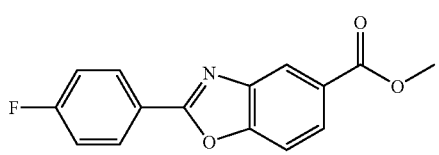

4-Fluoro-benzoic acid and 3-amino-4-hydroxy-benzoic acid methyl ester were reacted in a manner analogous to Compound 69A to give the title product. MS m/z 272 (M+1).

Step 2. Preparation of [2-(4-Fluoro-phenyl)-benzooxazol-5-yl]-methanol (Compound 74B)

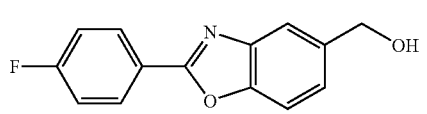

Compound 74A was reacted in a manner analogous to Compound 69B to give the title product. MS m/z 244 (M+1).

Step 3. Preparation of 5-Chloromethyl-2-(4-fluoro-phenyl)-benzooxazole (Compound 74C)

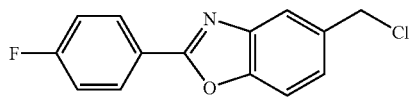

Compound 74B was reacted in a manner analogous to Compound 69C to give the title product. 400 MHz $^1$H NMR (DMSO-$d_6$) δ □ ppm 4.9 (s, 2H) 7.4 (t, J=9.0 Hz, 2H) 7.5 (dd, J=8.4, 1.8 Hz, 1H) 7.7 (d, J=9.0 Hz, 1H) 7.8 (d, J=1.2 Hz, 1H) 8.2 (dd, J=9.0, 5.4 Hz, 2H).

Step 4. Preparation of {4-[2-(4-Fluoro-phenyl)-benzooxazol-5-ylmethylsulfanyl]-5-methoxy-2-methyl-phenoxy}-acetic acid methyl ester (Compound 74C)

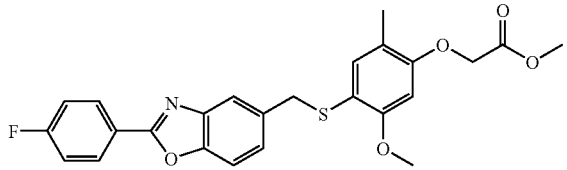

Compound 74C and Compound TA were reacted in a manner analogous to Compound 59A to give the title product. MS m/z 468 (M+1).

Step 5. Preparation of {4-[2-(3-Fluoro-phenyl)-benzooxazol-5-ylmethylsulfanyl]-5-methoxy-2-methyl-phenoxy}-acetic acid (Compound 74)

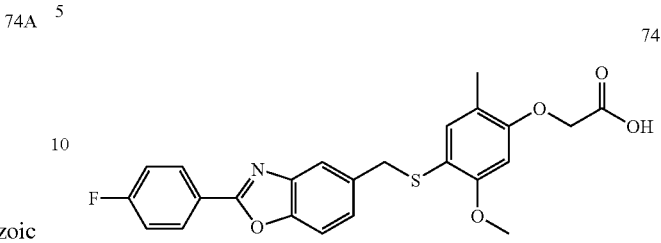

Compound 74C was reacted in a manner analogous to Compound 59 to give the title product; 400 MHz $^1$H NMR (DMSO-$d_6$) δ ppm 2.0 (s, 3H) 3.7 (s, 3H) 4.1 (s, 2H) 4.7 (s, 2H) 6.5 (s, 1H) 7.0 (s, 1H) 7.3 (dd, J=8.3, 1.7 Hz, 1H) 7.4 (ddd, J=8.8, 6.8, 2.2 Hz, 2H) 7.6 (m, 2H) 8.2 (m, 2H) 12.92 (br(s), 1H). MS m/z 454 (M+1).

EXAMPLE 75

Synthesis of {4-[2-(2-Fluoro-phenyl)-benzooxazol-5-ylmethylsulfanyl]-5-methoxy-2-methyl-phenoxy}-acetic acid (Compound 75)

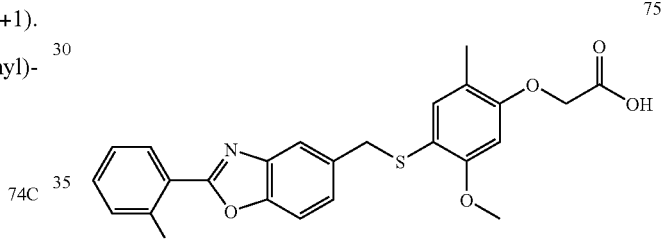

Step 1. Preparation of 2-(2-Fluoro-phenyl)-benzooxazole-5-carboxylic acid methyl ester (Compound 75A)

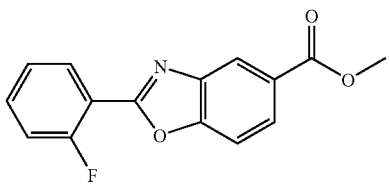

2-Fluoro-benzoic acid and 3-amino-4-hydroxy-benzoic acid methyl ester were reacted in a manner analogous to Compound 69A to give the title product. 400 MHz $^1$H NMR (DMSO-$d_6$) δ ppm 3.8 (s, 3H) 7.9 (d, J=8.5 Hz, 1H) 8.0 (dd, J=8.5, 1.7 Hz, 1H) 8.2 (dd, J=9.0, 5.4 Hz, 2H) 8.3 (d, J=1.7 Hz, 1H).

Step 2. Preparation of [2-(2-Fluoro-phenyl)-benzooxazol-5-yl]-methanol (Compound 75B)

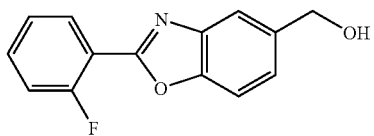

Compound 75A was reacted in a manner analogous to Compound 69B to give the title product. MS m/z 244 (M+1).

Step 3. Preparation of 5-Chloromethyl-2-(2-fluoro-phenyl)-benzooxazole (Compound 75C)

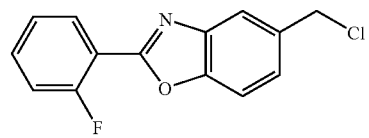

75C

Compound 75B was reacted in a manner analogous to Compound 69C to give the title product. MS m/z 262 (M+1).

Step 4. Preparation of {4-[2-(2-Fluoro-phenyl)-benzooxazol-5-ylmethylsulfanyl]-5-methoxy-2-methyl-phenoxy}-acetic acid methyl ester (Compound 75D)

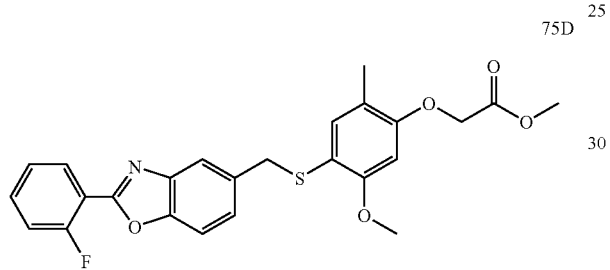

75D

Compound 75C and Compound TA were reacted in a manner analogous to Compound 59A to give the title product. MS m/z 454 (M+1).

Step 5. Preparation of {4-[2-(3-Fluoro-phenyl)-benzooxazol-5-ylmethylsulfanyl]-5-methoxy-2-methyl-phenoxy}-acetic acid (Compound 75)

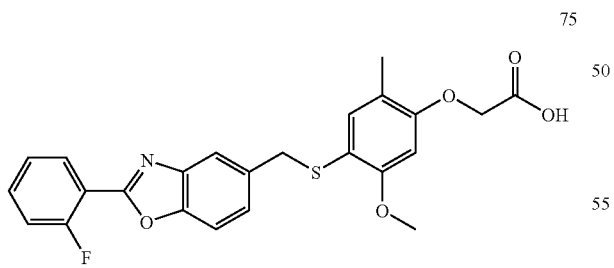

75

Compound 75D was reacted in a manner analogous to Compound 59 to give the title product; 400 MHz $^1$H NMR (DMSO-d$_6$) δ 12.94 (s(br), 1H), ppm 2.0 (s, 3H) 3.7 (s, 3H) 4.1 (s, 2H) 4.7 (s, 2H) 6.5 (s, 1H) 7.0 (s, 1H) 7.3 (dd, J=8.5, 1.7 Hz, 1H) 7.4 (m, 2H) 7.6 (m, 3H) 8.2 (td, J=7.7, 1.7 Hz, 1H). MS m/z 454 (M+1).

EXAMPLE 76

Synthesis of {2-Oxo-6-[3-(4-trifluoromethyl-benzyloxy)-benzylsulfanyl]-benzooxazol-3-yl}-acetic acid (Compound 76)

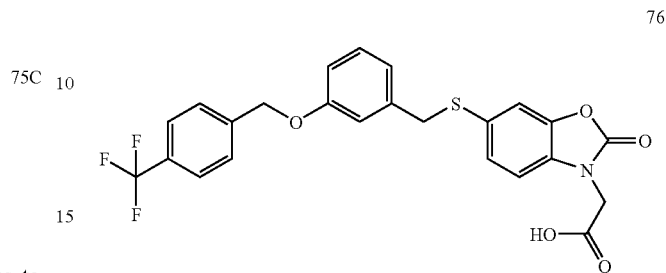

76

Step 1. Preparation of (2-Oxo-benzooxazol-3-yl)-acetic acid (Compound 76A)

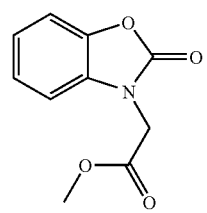

76A

Compound 76A was prepared analogously to compound 49A using 3H-benzooxazol-2-one. Yield was 89%. 400 MHz $^1$H NMR (CDCl$_3$) δ 7.1–7.22 (m, 3H), 6.85 (d, 1H), 4.54 (s, 2H), 3.76 (s, 3H).

Step 2. Preparation of (6-Chlorosulfonyl-2-oxo-benzooxazo-3-yl)-acetic acid methyl ester (Compound 76B)

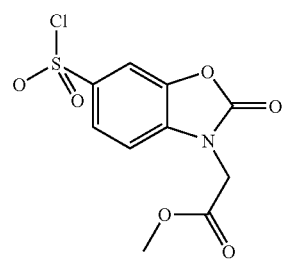

76B

Compound 76B, a pink oil was prepared analogously to compound 21B using the product prepared from compound 76A. Yield was 95%. 400 MHz $^1$H NMR (CDCl$_3$) δ 7.89 (d, 1H), 7.85 (s, 1H), 7.01 (d, 1H), 4.59 (s, 2H), 3.77 (s, 3H).

Step 3. Preparation of (6-Mercapto-2-oxo-benzooxazol-3-yl)-acetic acid methyl ester (Compound 76C)

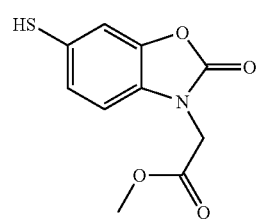

76C

Compound 76C was prepared analogously to compound 21C using the product prepared from compound 76B. Yield was 65%. MS m/z 238 (M−1).

Step 4. Preparation of {2-Oxo-6-[3-(4-trifluoromethyl-benzyloxy)-benzylsulfanyl]-benzooxazol-3-yl}-acetic acid methyl ester (Compound 76D)

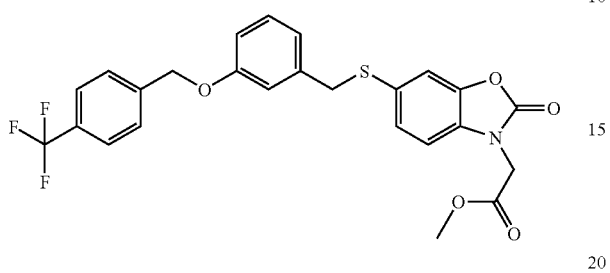

76D

Compound 76D was prepared analogously to compound 21D using the product prepared from compound 76C and 6B. Yield was 25% after flash column purification. MS m/z 504 (M+1). 400 MHz $^1$H NMR (DMSO-$d_6$) δ 7.61–6.71 (m, 1H), 5.05 (s, 2H), 4.50 (s, 2H), 3.99 (s, 2H), 3.74 (s, 3H).

Step 5. Synthesis of {2-Oxo-6-[3-(4-trifluoromethyl-benzyloxy)-benzylsulfanyl]-benzooxazol-3-yl}-acetic acid (Compound 76).

Compound 76 was prepared analogously to compound 21 in 95% yield. MS m/z 488 (M−1). 400 MHz $^1$H NMR (CD$_3$OD) δ 7.58–6.75 (m, 1H), 5.25 (s, 2H), 5.07 (s, 2H), 4.25 (s, 2H).

EXAMPLE 77

Synthesis of {7-[5-(4-Chloro-phenyl)-isoxazol-3-ylmethoxy]-benzo[b]thiophen-3-yl}-acetic acid (Compound 77)

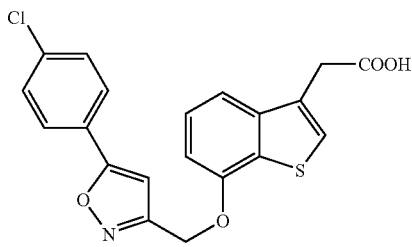

77

Step 1. Preparation of (7-Methoxybenzo[b]thiophen-3-yl) acetic acid methyl ester (Compound 77A)

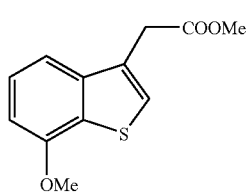

77A

A solution of compound 5A (5.7 g, 22 mmol) in ~30 mL of dichloromethane was added dropwise to 20 mL of methanesulfonic acid, stirred at room temp. After 45 min the mixture was poured over ~300 g of ice, stirred for an hour, then extracted twice with EtOAc. The combined extracts were washed with water, then saturated brine, then dried over MgSO$_4$. The solvent was removed in vacuo. The residue was chromatographed on a column of silica gel in CHCl$_3$/EtOAc (95:5) to afford 4.5 g of clear amber oil, suitable for use without further purification.

Step 2. Preparation of (7-Hydroxy-benzo[b]thiophen-3-yl) acetic acid methyl ester (Compound 77B)

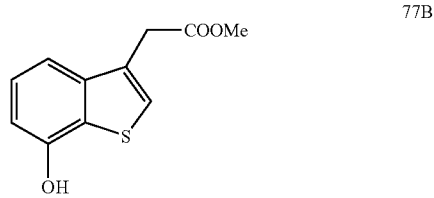

77B 29 mL of boron tribromide (1M in dichloromethane) was added slowly dropwise to a stirred solution of compound 77A from the preceding step (4.5 g, 19 mmol) in 100 mL of dichloromethane under N$_2$ at icebath temperature. An hour after the addition, 60 mL of 15% aq NH$_4$Cl was added slowly dropwise, the mixture was stirred for an additional 30 min, then the layers allowed to separate. The organic layer was washed with water, then sat brine, then dried over MgSO$_4$. The solvent was removed in vacuo, and the residue was chromatographed on a silica gel column in CHCl$_3$/EtOAc (9:1) to afford a clear, amber oil. Crystallization began after several hours under vacuum. The product was recrystallized from 55–60 mL of chloroform/hexanes (1:1). After filtration to remove the first crop of regio-isomeric material, the mother liquor was stripped of solvent in vacuo, and the residue recrystallized from chloroform to yield 0.14 g (3% yield) of the title compound as a white powder, mp 147–148° C., of sufficient purity for use in the next step.

Step 3. Preparation of {7-[5-(4-Chloro-phenyl)-isoxazol-3-ylmethoxy]-benzo[b]thiophen-3-yl}-acetic acid methyl ester (Compound 77C)

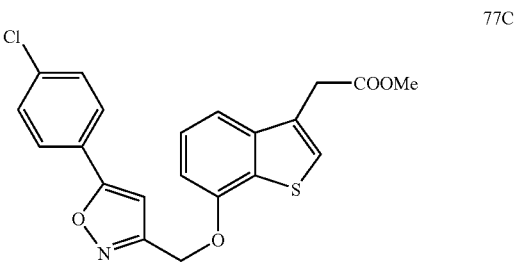

77C

Cesium carbonate (0.31 g, 90 mmol) was added to a stirred solution of compound 77B from the preceding step (0.14 g, 0.63 mmol) and commercially available 3-chloromethyl-5-(4-chloro-phenyl)-isoxazole (0.14 g, 0.63 mmol) in 15–20 mL of acetonitrile at room temp. After 20 hours the mixture was stripped of solvent in vacuo. The residue was dissolved in dichloromethane and filtered through a short column of Celite® over silica gel, eluting with several column volumes of solvent. The filtrate was stripped of solvent in vacuo, and the residue recrystallized from DMF to afford 0.1 g (38% yield) of the title compound as a snow-white solid; mp 155–156° C. Calc for C21H16ClNO4S: C 60.94; H 3.90; N 3.38 found: C, 60.67, H, 3.72, N, 3.41

Step 4. Preparation of {7-[5-(4-Chloro-phenyl)-isoxazol-3-ylmethoxy]-benzo[b]thiophen-3-yl}-acetic acid (Compound 77D)

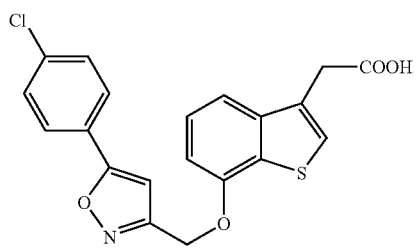

77D

Lithium hydroxide (0.024 g, 0.58 mmol) was added to a stirred suspension of compound 77C from the preceding step (0.06 g, 0.15 mmol) in 8 mL of tetrahydrofuran/water (3:2) at room temperature. After 18 hours the resulting clear solution was diluted with 75 mL of water, stirred, and acidified with aq HCl. After ~1 hour the precipitate was filtered off, rinsed 3× with water, and dried to afford 0.04 g (69% yield) of the title compound as a white solid; mp 229–230° C. (dec).

Calc for C20H14ClNO4S: C 60.08; H 3.53; N 3.50 found: C, 59.44, H, 3.44, N, 3.29

EXAMPLE 78

Synthesis of {5-Methyl-6-[2-(4-trifluoromethyl-benzyloxy)-benzyloxy]-benzo[b]-thiophen-3-yl}-acetic acid (Compound 78)

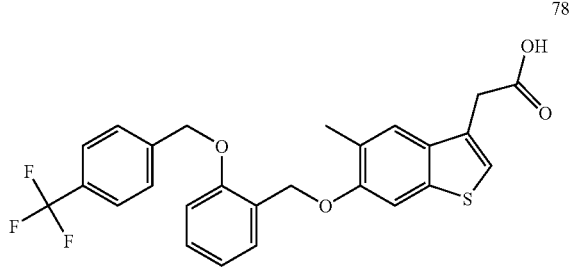

78

Step 1. Preparation of 4-(3-Methoxy-phenylsulfanyl)-3-oxo-butyric acid methyl ester (Compound 78A)

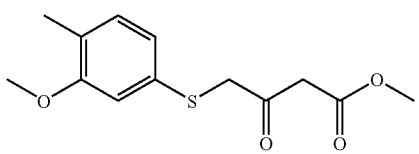

78A

Cesium carbonate (21.0 g, 63 mmol) was added to a stirred solution of commercially available 3-methoxy-4-methyl-benzenethiol (6.5 g, 42 mmol) and commercially available 4-chloro-3-oxo-butyric acid methyl ester (6.4 g, 42.5 mmol) in 100 mL of acetonitrile under N₂. After 18 hours the mixture was filtered through Celite®, the residue was washed with acetonitrile, and the filtrate and washings were stripped of solvent in vacuo. The residue was dissolved in ethyl acetate and filtered through a short column of silica gel, eluting with several volumes of solvent. The effluent was stripped of solvent in vacuo, leaving the title compound as a clear, amber oil of sufficient purity for use in the next step.

Step 2. Preparation of (6-Methoxy-5-methyl-benzo[b]thiophen-3-yl)-acetic acid methyl ester (Compound 78B)

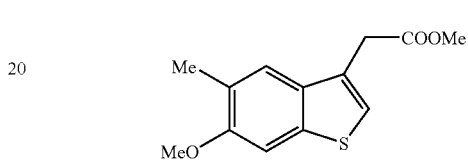

78B

A solution of compound 78A from the preceding step (8.6 g, 32 mmol) in 30 mL of dichloromethane was added dropwise to 30 mL of methanesulfonic acid stirred under N₂ at icebath temperature. The mixture was allowed to warm gradually to room temperature. After an hour 200 mL of icewater was cautiously added (vigorous reaction!), then the mixture was partitioned between a total of 300 mL of water and 350–400 mL of dichloro-methane. The organic layer was drawn off and washed with water, then 0.5M aq NaHCO₃, and dried over MgSO₄. The solvent was removed in vacuo, and the residue dissolved in a minimum of CHCl₃/EtOAc (24:1) and passed slowly through a column of silica gel, eluting with several column volumes of the same solvent. The effluent was stripped of solvent in vacuo to leave the title compound as a clear amber syrup, contaminated with the other possible regio-isomer, but of sufficient purity for the next step.

Step 3. Preparation of (6-Hydroxy-5-methyl-benzo[b]thiophen-3-yl)-acetic acid methyl ester (Compound 78C)

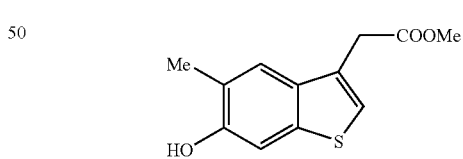

78C 10 mL of boron tribromide (1.0M in CH₂Cl₂) was added dropwise to a stirred solution of compound 78B from the preceding step (2.1 g, 8.4 mmol) in 15–20% L of dichloromethane under N₂ at icebath temperature. The mixture was allowed to warm gradually to room temperature. After 18 hours 20 mL of sat aq NH₄Cl was added dropwise with icebath cooling, and followed after several minutes by 100 mL of water. The mixture was extracted with dichloromethane (100, 50, 50 mL), and the combined extracts washed with water then sat brine, and dried over MgSO₄.

The solvent was removed in vacuo. The residue was chromatographed on a short column of silica gel in chloroform to afford 0.4 g (20%) of the title compound as a yellow, crystalline solid of sufficient purity for further reactions.

Step 4. Preparation of {5-Methyl-6-[2-(4-trifluoromethyl-benzyloxy)-benzyloxy]-benzo[b]thiophen-3-yl}-acetic acid methyl ester (Compound 78D)

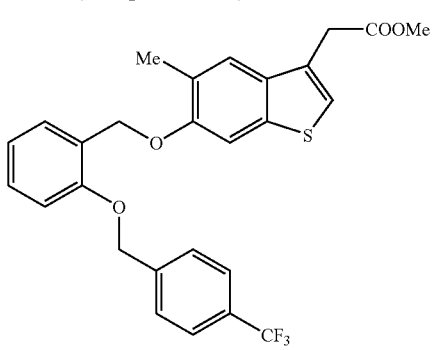

The title compound was prepared using compound 78C from the preceding step and compound 7A in a manner analogous to compound 77B. Thus, recrystallization from methanol afforded 0.42 g (43% yield) of the title compound as a cream-colored powder, mp 108–109° C. Calc for $C_{27}H_{23}F_3O_4S$: C 64.79; H 4.63; found: C, 64.64, H, 4.46.

Step 5. Preparation of {5-Methyl-6-[2-(4-trifluoromethyl-benzyloxy)-benzyloxy]-benzo[b]thiophen-3-yl}-acetic acid (Compound 78)

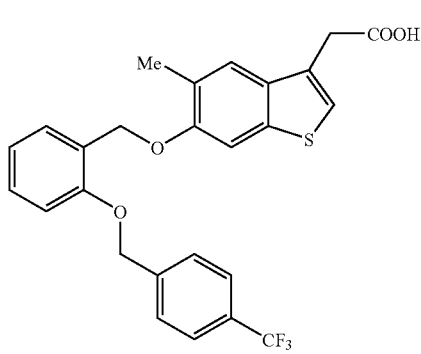

The title compound was prepared using compound 78D from the preceding step and compound 7A in a manner analogous to compound 77. Thus, chromatography on silica gel in ethyl acetate followed by trituration in ethanol afforded 0.16 g (86% yield) of the title compound as a white solid; mp 157–158° C. Calc for $C_{26}H_{21}F_3O_4S$: C 64.19; H 4.35; found: C, 63.43, H, 4.04

EXAMPLE 79

Synthesis of {5-Methyl-6-[5-(4-chloro-phenyl)-isoxazol-3-ylmethoxy]-benzo-[b]thiophen-3-yl}-acetic acid (Compound 79)

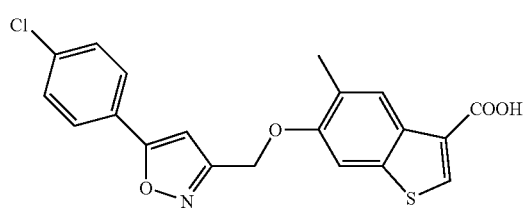

Step 1. Preparation of {5-Methyl-6-[5-(4-chloro-phenyl)-isoxazol-3-ylmethoxy]-benzo[b]thiophen-3-yl}-acetic acid methyl ester (Compound 79A)

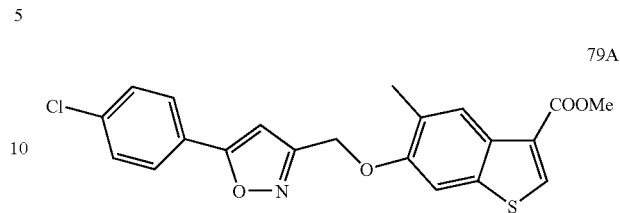

The title compound was prepared from commercially available 3-chloromethyl-5-(4-chloro-phenyl)-isoxazole and compound 78C in a manner analogous to compound 77C.

Thus, chromatography on silica gel in an ethyl acetate/hexanes gradient afforded 0.01 g (34% yield) of the title compound as a crystalline solid; mp 135–139° C. Calc for $C_{22}H_{18}ClNO_4S$: C 61.75; H 4.24; N 3.27; found: C, 61.77, H, 4.36, N, 3.05.

Step 2. Preparation of {5-Methyl-6-[5-(4-chloro-phenyl)-isoxazol-3-ylmethoxy]-benzo[b]thiophen-3-yl}-acetic acid (Compound 79)

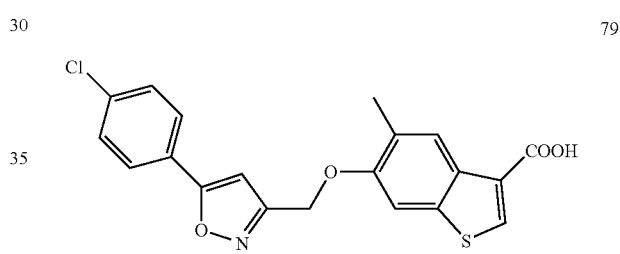

Compound 79A (0.03 g, 0.07 mmol) from the preceding step was dissolved in 2–3 mL of tetrahydrofuran, an equal volume of 2N KOH was added, and the mixture stirred at room temp. After 18 hours 75 mL of icewater was added and the mixture was acidified with $H_3PO_4$. After ~30 min the precipitate was filtered off, rinsed 3× with water, and dried. The product was triturated in 4N HCl, allowed to stand for an hour, then filtered off, rinsed with water then ethanol, and dried to afford 0.01 g (99%) of the title compound as a white powder; mp 198–200° C. (dec). MS m/z 413 (M).

Synthesis of {6-[5-(4-Trifluoromethyl-phenyl)-isoxazol-3-ylmethoxy]-benzofuran-3-yl}-acetic acid (Compound 80)

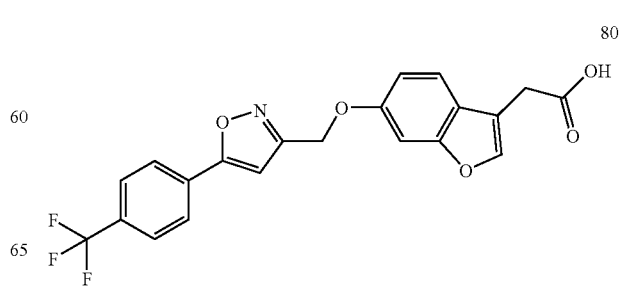

Step 1. Preparation of {6-[5-(4-Trifluoromethyl-phenyl)-isoxazol-3-ylmethoxy]-benzofuran-3-yl}-acetic acid methyl ester (Compound 80A)

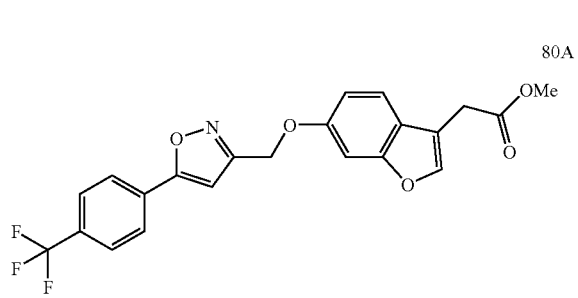

80A

A solution of (6-hydroxy-benzofuran-3-yl)-acetic acid methyl ester (0.60 g, 2.9 mmol) and 3-chloromethyl-5-(4-trifluoromethyl-phenyl)-isoxazole (0.77 g, 2.9 mmol) (13C) were combined in 20 ml of acetonitrile. The mixture was stirred at room temperature for 64 hours and then heated at 50° C. for three hours. The mixture was filtered, and the insoluble material was washed on the funnel several times with fresh acetonitrile. The bulk of the solvent was evaporated, and the residue was partitioned between 300 ml of ethyl acetate and 150 ml of brine. The layers were separated, and the aqueous layer was extracted with fresh ethyl acetate (2×100 ml). The combined organic layers were back-washed with brine (2×250 ml), then dried over anhydrous sodium sulfate and concentrated. The crude product was purified by normal phase chromatography. mp 127–128° C.; MS m/z 432 (M+1).

Step 2. Preparation of {6-[5-(4-Trifluoromethyl-phenyl)-isoxazol-3-ylmethoxy]-benzofuran-3-yl}-acetic acid (Compound 80)

The title compound was prepared in the manner analogous to example 24 using {6-[5-(4-trifluoromethyl-phenyl)-isoxazol-3-ylmethoxy]-benzofuran-3-yl}-acetic acid methyl ester (80A) and lithium hydroxide. mp 201° C. (decompose); IR (thin film) cm$^{-1}$: 1711, 1600, 1433, 1319, 1228, 1143; 400 MHz $^1$H NMR (DMSO-d$_6$) ☐12.40 (br s, 1H), 8.08 (d, 2H, J=8.1 Hz), 7.86 (d, 2H, J=8.1 Hz), 7.74 (s, 1H), 7.45 (d, 1H, J=8.6. Hz), 7.35 (s, 1H), 7.30 (d, 1H, J=2.0 Hz), 6.93 (dd, 1H, J=6.3, 2.2 Hz), 5.27 (s, 2H), 3.60 (s, 2H); MS m/z 416 (M−1). Anal. Calc'd for C$_{21}$H$_{14}$F$_3$NO$_5$: C, 60.44; H, 3.38; N, 3.36; found: 60.49; H, 3.23; N, 3.34.

Synthesis of {6-[3-(4-Trifluoromethyl-benzyloxy)-benzyloxy]-benzofuran-3-yl}-acetic acid (Compound 81)

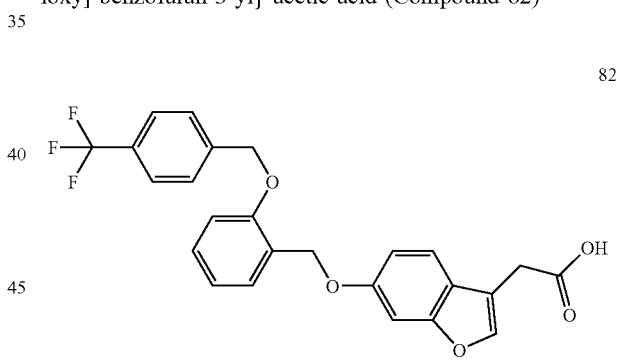

81

Step 1. Preparation of {6-[3-(4-Trifluoromethyl-benzyloxy)-benzyloxy]-benzofuran-3-yl}-acetic acid methyl ester (Compound 81A)

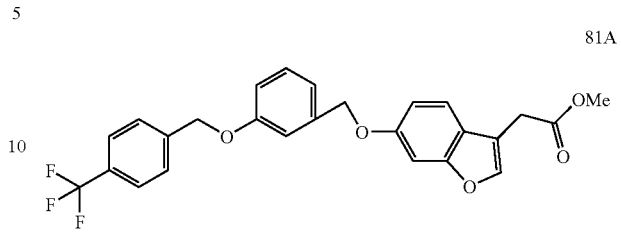

81A

The title compound was prepared in the manner analogous to step 1 of Example 80 using (6-hydroxy-benzofuran-3-yl)-acetic acid methyl ester and 1-(4-trifluoromethyl-benzyloxy)-3-chloromethyl-benzene. MS m/z 471 (M+1).

Step 2. Preparation of {6-[3-(4-Trifluoromethyl-benzyloxy)-benzyloxy]-benzofuran-3-yl}-acetic acid (Compound 81)

The title compound was prepared in the manner analogous to example 24 using {6-[3-(4-trifluoromethyl-benzyloxy)-benzyloxy]-benzofuran-3-yl}-acetic acid methyl ester and lithium hydroxide. mp 155–157° C.; IR (thin film) cm$^{-1}$: 1722, 1585, 1492, 1319, 1157, 1114; 400 MHz $^1$H NMR (DMSO-d$_6$) ☐12.39 (br s, 1H), 7.69–7.71 (m, 3H), 7.62 (d, 2H, J=8.1 Hz), 7.41 (d, 1H, J=8.5 Hz), 7.26 (t, 1H, J=7.9 Hz), 7.18 (d, 1H, J=2.2 Hz), 7.08–7.09 (m, 1H), 7.00 (d, 1H, J=7.8 Hz), 6.88–6.94 (m, 2H), 5.19 (s, 2H), 5.08 (s, 2H), 3.58 (s, 2H); MS m/z 455 (M−1). Anal. Calc'd for C$_{25}$H$_{19}$F$_3$O$_5$: C, 65.79; H, 4.20; found: C, 65.60; H, 4.08.

Synthesis of {6-[2-(4-Trifluoromethyl-benzyloxy)-benzyloxy]-benzofuran-3-yl}-acetic acid (Compound 82)

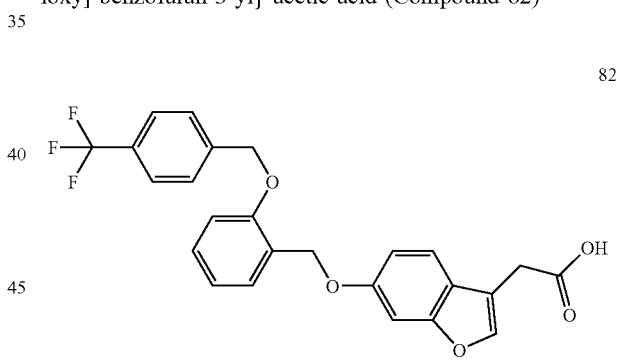

82

Step 1. Preparation of {6-[2-(4-Trifluoromethyl-benzyloxy)-benzyloxy]-benzofuran-3-yl}-acetic acid methyl ester (Compound 82A)

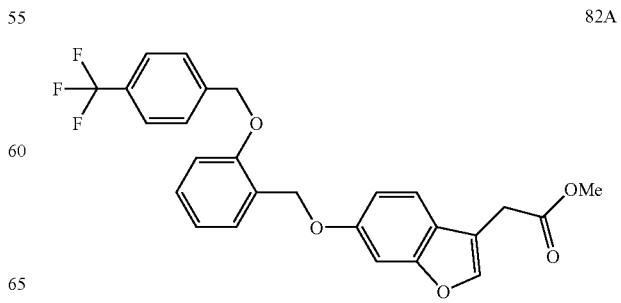

82A

The title compound was prepared in the manner analogous to step 1 of Example 80 using (6-hydroxy-benzofuran-3-yl)-acetic acid methyl ester and 1-(4-trifluoromethyl-benzyloxy)-2-chloromethyl-benzene. MS m/z 471 (M+1).

Step 2. Preparation of {6-[2-(4-Trifluoromethyl-benzyloxy)-benzyloxy]-benzofuran-3-yl}-acetic acid (Compound 82)

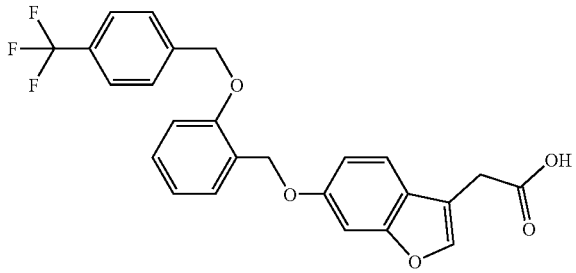

The title compound was prepared in the manner analogous to example 24 using {6-[2-(4-trifluoromethyl-benzyloxy)-benzyloxy]-benzofuran-3-yl}-acetic acid methyl ester and lithium hydroxide. mp 126–127° C.; IR (thin film) cm$^{-1}$: 1716, 1624, 1494, 1320, 1231, 1109; 400 MHz $^1$H NMR (DMSO-d$_6$) ☐12.39 (br s, 1H), 7.71 (s, 1H), 7.61–7.67 (m, 4H), 7.39–7.42 (m, 2H), 7.24–7.29 (m, 1H), 7.20 (d, 1H, J=2.0 Hz), 7.06 (d, 1H, J=7.6 Hz), 6.90–6.95 (m, 2H), 5.27 (s, 2H), 5.15 (s, 2H), 3.59 (s, 2H); MS m/z 455 (M−1). Anal. Calc'd for C$_{25}$H$_{19}$F$_3$O$_5$: C, 65.79; H, 4.20; found: C, 65.75; H, 4.02.

Compounds of the present invention may be prepared using combinatorial chemistry methods. In particular, compounds of Examples 101–207 were prepared using combinatorial chemistry analagous to the previously described Examples above. The combinatorial chemistry methods useful in the present invention include those where an activated alcohol or alkyl halide is contacted with a thiol followed by saponification of the resulting ester to afford the desired products. Such methods are illustrated by the previously described schemes, for example, Schemes 10 and 11.

EXAMPLES 101–207

| Example No. | Name | MS m/z | m |
|---|---|---|---|
| 101 | {4-[4-(2,4-Dichloro-phenoxy)-butylsulfanyl]-5-methoxy-2-methyl-phenoxy}-acetic acid | 445.22 | m + 1 |
| 102 | {4-[3-(Biphenyl-4-yl-ethyl-amino)-propylsulfanyl]-5-methoxy-2-methyl-phenoxy)-acetic acid | 466.36 | m + 1 |
| 103 | [5-Methoxy-2-methyl-4-(3-naphthalen-2-yl-propylsulfanyl)-phenoxy]-acetic acid | 395.42 | m − 1 |
| 104 | {4-[4-(2,4-Dichloro-phenoxy)-butylsulfanyl]-2-methyl-phenoxy}-acetic acid | 413.18 | m − 1 |
| 105 | [5-Methoxy-2-methyl-4-(3-methyl-4-pentyl-benzylsulfanyl)-phenoxy]-acetic acid | 403.33 | m + 1 |
| 106 | {4-[2-(Biphenyl-4-yl-ethyl-amino)-ethylsulfanyl]-5-methoxy-2-methyl-phenoxy}-acetic acid | 452.34 | m + 1 |
| 107 | {5-Methoxy-2-methyl-4-[2-(2,4,5-trichloro-phenoxy)-ethylsulfanyl]-phenoxy}-acetic acid | 452.15 | m + 1 |
| 108 | {4-[2-(2,4-Dichloro-phenoxy)-ethylsulfanyl]-5-methoxy-2-methyl-phenoxy}-acetic acid | 415.3 | m − 1 |
| 109 | {4-[2-(4-Chloro-phenylsulfanyl)-ethylsulfanyl]-5-methoxy-2-methyl-phenoxy}-acetic acid | 397.35 | m − 1 |
| 110 | {4-[4-(4-Bromo-phenyl)-4-oxo-butylsulfanyl]-2,5-dimethyl-phenoxy}-acetic acid | 437.31 | m + 1 |
| 111 | {4-[3-(4-Fluoro-phenyl)-propylsulfanyl]-5-methoxy-2-methyl-phenoxy}-acetic acid | 363.44 | m − 1 |
| 112 | {4-[4-(4-Bromo-phenyl)-4-oxo-butylsulfanyl]-2-methyl-phenoxy}-acetic acid | 423.29 | m + 1 |
| 113 | [2-Methyl-4-(3-naphthalen-2-yl-propylsulfanyl)-phenoxy]-acetic acid | 365.45 | m − 1 |
| 114 | {4-[2-(Biphenyl-4-yl-propyl-amino)-ethylsulfanyl]-2-methyl-phenoxy}-acetic acid | 436.35 | m + 1 |
| 115 | {5-Methoxy-2-methyl-4-[2-(5-phenyl-naphthalen-1-yloxy)-ethylsulfanyl]-phenoxy}-acetic acid | 473.31 | m − 1 |
| 116 | (4-{2-[(4-Benzyl-phenyl)-ethyl-amino]-ethylsulfanyl}-5-methoxy-2-methyl-phenoxy)-acetic acid | 466.36 | m + 1 |
| 117 | {4-[4-(2,5-Dimethyl-phenyl)-4-oxo-butylsulfanyl]-2,5-dimethyl-phenoxy}-acetic acid | 387.26 | m + 1 |
| 118 | [5-Methoxy-2-methyl-4-(5-methyl-2-pentyl-benzylsulfanyl)-phenoxy]-acetic acid | 403.31 | m + 1 |
| 119 | {4-[2-(4-Benzoyl-phenoxy)-ethylsulfanyl]-2-methyl-phenoxy}-acetic acid | 423.24 | m + 1 |
| 120 | {4-[4-(Biphenyl-4-yl-ethyl-amino)-butylsulfanyl]-5-methoxy-2-methyl-phenoxy}-acetic acid | 480.38 | m + 1 |
| 121 | {4-[4-(4-Bromo-phenyl)-4-oxo-butylsulfanyl]-2,6-dimethyl-phenoxy}-acetic acid | 437.29 | m + 1 |
| 122 | [4-(7-Benzyloxy-heptylsulfanyl)-5-methoxy-2-methyl-phenoxy]-acetic acid | 433.36 | m + 1 |

-continued

| Example No. | Name | MS m/z | m |
|---|---|---|---|
| 123 | {4-[2-(2,4-Dichloro-phenyl)-ethylsulfanyl]-2-methyl-phenoxy}-acetic acid | 369.35 | m − 1 |
| 124 | {4-[3-(4-Fluoro-phenyl)-propylsulfanyl]-2-methyl-phenoxy}-acetic acid | 333.45 | m − 1 |
| 125 | {4-[4-(4-Bromo-phenyl)-4-oxo-butylsulfanyl]-5,6,7,8-tetrahydro-naphthalen-1-yloxy}-acetic acid | 463.33 | m + 1 |
| 126 | {4-[2-(4-Benzoyl-phenoxy)-ethylsulfanyl]-5-methoxy-2-methyl-phenoxy}-acetic acid | 453.27 | m + 1 |
| 127 | {4-[2-(2,4-Dichloro-phenyl)-ethylsulfanyl]-5-methoxy-2-methyl-phenoxy}-acetic acid | 401.14 | m + 1 |
| 128 | {4-[4-(4-Bromo-phenyl)-4-oxo-butylsulfanyl]-phenoxy}-acetic acid | 409.09 | m + 1 |
| 129 | {4-[2-(4-sec-Butyl-phenoxy)-ethylsulfanyl]-5-methoxy-2-methyl-phenoxy}-acetic acid | 403.31 | m − 1 |
| 130 | [4-(5-Chloro-benzo[b]thiophen-3-ylmethylsulfanyl)-5,6,7,8-tetrahydro-naphthalen-1-yloxy}-acetic acid | 417.29 | m − 1 |
| 131 | [4-(9H-Fluoren-1-ylmethylsulfanyl)-5-methoxy-2-methyl-phenoxy]-acetic acid | 407.25 | m + 1 |
| 132 | {4-[2-(Biphenyl-4-yl-ethyl-amino)-ethylsulfanyl]-2-methyl-phenoxy}-acetic acid | 422.29 | m + 1 |
| 133 | {4-[2-(4-Bromo-phenoxy)-ethylsulfanyl]-2,6-dimethyl-phenoxy}-acetic acid | 409.08 | m − 1 |
| 134 | [2-Methyl-4-(2-naphthalen-2-yl-ethylsulfanyl)-phenoxy]-acetic acid | 351.46 | m − 1 |
| 135 | {4-[2-(4-tert-Butyl-phenoxy)-ethylsulfanyl]-5-methoxy-2-methyl-phenoxy}-acetic acid | 403.47 | m − 1 |
| 136 | {2-Methyl-4-[2-(2,4,5-trichloro-phenoxy)-ethylsulfanyl]-phenoxy}-acetic acid | 420.13 | m + 1 |
| 137 | [2-Methyl-4-(4-trifluoromethyl-benzylsulfanyl)-phenoxy]-acetic acid | 355.3 | m − 1 |
| 138 | (4-{2-[4-(1,1-Dimethyl-propyl)-phenoxy]-ethylsulfanyl}-5-methoxy-2-methyl-phenoxy)-acetic acid | 417.48 | m − 1 |
| 139 | [4-(4-tert-Butyl-benzylsulfanyl)-2-methyl-phenoxy]-acetic acid | 343.38 | m − 1 |
| 140 | {4-[2-(Butyl-naphthalen-1-ylmethyl-amino)-ethylsulfanyl]-5-methoxy-2-methyl-phenoxy}-acetic acid | 468.38 | m + 1 |
| 141 | [4-(2,6-Dichloro-benzylsulfanyl)-5,6,7,8-tetrahydro-naphthalen-1-yloxy]-acetic acid | 397.25 | m + 1 |
| 142 | {4-[2-(4-Chloro-phenyl)-2-oxo-ethylsulfanyl]-5,6,7,8-tetrahydro-naphthalen-1-yloxy}-acetic acid | 391.28 | m + 1 |
| 143 | {4-[3-(2-Chloro-phenoxy)-propylsulfanyl]-2-methyl-phenoxy}-acetic acid | 365.39 | m − 1 |
| 144 | [4-(3,4-Dichloro-benzylsulfanyl)-2-methyl-phenoxy]-acetic acid | 355.24 | m − 1 |
| 145 | {4-[2-(4-sec-Butyl-phenoxy)-ethylsulfanyl]-2-methyl-phenoxy}-acetic acid | 373.27 | m − 1 |
| 146 | (4-{2-[Ethyl-(3-trifluoromethyl-phenyl)-amino]-ethylsulfanyl}-5-methoxy-2-methyl-phenoxy)-acetic acid | 444.3 | m + 1 |
| 147 | [2,5-Dimethyl-4-(4-phenoxy-butylsulfanyl)-phenoxyl-acetic acid | 359.4 | m − 1 |
| 148 | [4-(2-Trifluoromethoxy-benzylsulfanyl)-5,6,7,8-tetrahydro-naphthalen-1-yloxy]-acetic acid | 411.34 | m − 1 |
| 149 | (4-{2-[(4-Benzyl-phenyl)-ethyl-amino]-ethylsulfanyl}-2-methyl-phenoxy)-acetic acid | 436.33 | m + 1 |
| 150 | [4-(3-Trifluoromethylsulfanyl-benzylsulfanyl)-5,6,7,8-tetrahydro-naphthalen-1-yloxy]-acetic acid | 429.31 | m − 1 |
| 151 | [2,5-Dimethyl-4-(4-trifluoromethyl-benzylsulfanyl)-phenoxy]-acetic acid | 369.32 | m − 1 |
| 152 | {4-[2-(4-tert-Butyl-phenyl)-ethylsulfanyl]-5-methoxy-2-methyl-phenoxy}-acetic acid | 389.28 | m + 1 |
| 153 | [2-Methyl-4-(naphthalen-2-ylmethylsulfanyl)-phenoxy]-acetic acid | 337.35 | m − 1 |
| 154 | {5-Methoxy-2-methyl-4-[2-(2-phenyl-benzimidazol-1-yl)-ethylsulfanyl]-phenoxy}-acetic acid | 449.28 | m + 1 |
| 155 | [4-(3,4-Dichloro-benzylsulfanyl)-2,5-dimethyl-phenoxy]-acetic acid | 369.25 | m − 1 |
| 156 | {4-[2-(4-Isopropyl-2-methyl-phenyl)-ethylsulfanyl]-2-methyl-phenoxy}-acetic acid | 357.49 | m − 1 |
| 157 | [4-(6-Chloro-1,3-benzodioxol-5-ylmethylsulfanyl)-5,6,7,8-tetrahydro-naphthalen-1-yloxy]-acetic acid | 405.32 | m − 1 |
| 158 | [5-Methoxy-2-methyl-4-(2-naphthalen-2-yl-ethylsulfanyl)-phenoxy]-acetic acid | 383.23 | m + 1 |
| 159 | [4-(4-tert-Butyl-benzylsulfanyl)-2,5-dimethyl-phenoxy]-acetic acid | 357.4 | m − 1 |
| 160 | [2-Methyl-4-(3-trifluoromethylsulfanyl-benzylsulfanyl)-phenoxy]-acetic acid | 387.26 | m − 1 |

-continued

| Example No. | Name | MS m/z | m |
|---|---|---|---|
| 161 | [4-(3,4-Dichloro-benzylsulfanyl)-5,6,7,8-tetrahydro-naphthalen-1-yloxy]-acetic acid | 395.28 | m − 1 |
| 162 | [4-(3,4-Dimethyl-benzylsulfanyl)-5,6,7,8-tetrahydro-naphthalen-1-yloxy]-acetic acid | 355.38 | m − 1 |
| 163 | {4-[2-(4-tert-Butyl-phenoxy)-ethylsulfanyl]-2-methyl-phenoxy}-acetic acid | 373.1 | m − 1 |
| 164 | {4-[5-(7-Chloro-quinolin-4-ylamino)-pentylsulfanyl]-5-methoxy-2-methyl-phenoxy}-acetic acid | 475.25 | m + 1 |
| 165 | [4-(3,4-Dimethyl-benzylsulfanyl)-2-methyl-phenoxy]-acetic acid | 315.36 | m − 1 |
| 166 | [2,5-Dimethyl-4-(3-trifluoromethylsulfanyl-benzylsulfanyl)-phenoxy]-acetic acid | 401.28 | m − 1 |
| 167 | [5-Methoxy-2-methyl-4-(2-naphthalen-1-yl-ethylsulfanyl)-phenoxy]-acetic acid | 381.44 | m − 1 |
| 168 | [2,5-Dimethyl-4-(naphthalen-2-ylmethylsulfanyl)-phenoxy]-acetic acid | 351.37 | m − 1 |
| 169 | [4-(Naphthalen-2-ylmethylsulfanyl)-5,6,7,8-tetrahydro-naphthalen-1-yloxy]-acetic acid | 377.38 | m − 1 |
| 170 | [4-(5-Chloro-benzo[b]thiophen-3-ylmethylsulfanyl)-2-methyl-phenoxy]-acetic acid | 377.23 | m − 1 |
| 171 | {4-[4-(2,5-Dimethyl-phenyl)-4-oxo-butylsulfanyl]-2,6-dimethyl-phenoxy}-acetic acid | 385.25 | m − 1 |
| 172 | [4-(5-Chloro-benzo[b]thiophen-3-ylmethylsulfanyl)-2,6-dimethyl-phenoxy]-acetic acid | 391.26 | m − 1 |
| 173 | [2,5-Dimethyl-4-(2-trifluoromethylsulfanyl-benzylsulfanyl)-phenoxy]-acetic acid | 401.17 | m − 1 |
| 174 | (4-{2-[Ethyl-(3-trifluoromethyl-phenyl)-amino]-ethylsulfanyl}-2-methyl-phenoxy)-acetic acid | 414.26 | m + 1 |
| 175 | {2,5-Dimethyl-4-(3-phenoxy-propylsulfanyl)-phenoxy}-acetic acid | 345.34 | m − 1 |
| 176 | [4-(6-Chloro-1,3-benzodioxol-5-ylmethylsulfanyl)-2-methyl-phenoxy]-acetic acid | 365.28 | m − 1 |
| 177 | {4-[4-(4-Ethyl-phenyl)-4-oxo-butylsulfanyl]-phenoxy}-acetic acid | 359.19 | m + 1 |
| 178 | [4-(3-Benzyloxy-propylsulfanyl)-5,6,7,8-tetrahydro-naphthalen-1-yloxy]-acetic acid | 387.36 | m + 1 |
| 179 | [4-(3-Phenyl-propylsulfanyl)-5,6,7,8-tetrahydro-naphthalen-1-yloxy]-acetic acid | 357.28 | m + 1 |
| 180 | [2-Methyl-4-(3-methyl-4-pentyl-benzylsulfanyl)-phenoxy]-acetic acid | 371.28 | m − 1 |
| 181 | [2,5-Dimethyl-4-(3-phenyl-propylsulfanyl)-phenoxy]-acetic acid | 331.37 | m + 1 |
| 182 | [4-(4-tert-Butyl-benzylsulfanyl)-5,6,7,8-tetrahydro-naphthalen-1-yloxy]-acetic acid | 383.42 | m − 1 |
| 183 | [4-(2-Trifluoromethoxy-benzylsulfanyl)-phenoxy]-acetic acid | 357.29 | m − 1 |
| 184 | [2,5-Dimethyl-4-(2-naphthalen-1-yl-ethylsulfanyl)-phenoxy]-acetic acid | 367.36 | m + 1 |
| 185 | (2-Methyl-4-{2-[3-(2-phenyl-quinazolin-4-ylamino)-propylsulfanyl]-ethylsulfanyl}-phenoxy)-acetic acid | 520.33 | m + 1 |
| 186 | [4-(3-Trifluoromethyl-benzylsulfanyl)-5,6,7,8-tetrahydro-naphthalen-1-yloxy]-acetic acid | 397.32 | m + 1 |
| 187 | [2-Methyl-4-(5-methyl-2-pentyl-benzylsulfanyl)-phenoxy]-acetic acid | 371.28 | m − 1 |
| 188 | [4-(5-Chloro-benzo[b]thiophen-3-ylmethylsulfanyl)-2,5-dimethyl-phenoxy]-acetic acid | 391.26 | m − 1 |
| 189 | [4-(3-Methoxy-benzylsulfanyl)-5,6,7,8-tetrahydro-naphthalen-1-yloxy]-acetic acid | 359.32 | m + 1 |
| 190 | [4-(6-Chloro-1,3-benzodioxol-5-ylmethylsulfanyl)-2,5-dimethyl-phenoxy]-acetic acid | 379.31 | m − 1 |
| 191 | [2,5-Dimethyl-4-(4-methyl-naphthalen-1-ylmethylsulfanyl)-phenoxy]-acetic acid | 365.38 | m − 1 |
| 192 | [4-(4-Trifluoromethyl-benzylsulfanyl)-5,6,7,8-tetrahydro-naphthalen-1-yloxy]-acetic acid | 395.34 | m − 1 |
| 193 | [4-(3,4-Dimethyl-benzylsulfanyl)-2,5-dimethyl-phenoxy]-acetic acid | 329.38 | m − 1 |
| 194 | [4-(2-Fluoro-4-trifluoromethyl-benzylsulfanyl)-2,6-dimethyl-phenoxy]-acetic acid | 387.16 | m − 1 |
| 195 | {4-[4-(2,5-Dimethoxy-3,4,6-trimethyl-phenyl)-butylsulfanyl]-5-methoxy-2-methyl-phenoxy}-acetic acid | 461.39 | m − 1 |
| 196 | {4-[2-(4-Chloro-phenyl)-2-oxo-ethylsulfanyl]-2-methyl-phenoxy}-acetic acid | 351.25 | m − 1 |
| 197 | [2,5-Dimethyl-4-(2-trifluoromethoxy-benzylsulfanyl)-phenoxy]-acetic acid | 385.32 | m − 1 |
| 198 | [2,5-Dimethyl-4-(2-oxo-2-p-tolyl-ethylsulfanyl)-phenoxy]-acetic acid | 345.35 | m + 1 |

-continued

| Example No. | Name | MS m/z | m |
|---|---|---|---|
| 199 | {4-[2-(2-Methoxy-phenyl)-2-oxo-ethylsulfanyl]-2-methyl-phenoxy}-acetic acid | 347.32 | m + 1 |
| 200 | [2-Methyl-4-(4-methyl-naphthalen-1-ylmethylsulfanyl)-phenoxy]-acetic acid | 351.36 | m − 1 |
| 201 | {4-[2-(4-tert-Butyl-phenylsulfanyl)-ethylsulfanyl]-2-methyl-phenoxy}-acetic acid | 389.24 | m − 1 |
| 202 | [4-(2,6-Dichloro-benzylsulfanyl)-2-methyl-phenoxy]-acetic acid | 369.24 | m − 1 |
| 203 | {4-[2-(2-Methoxy-phenyl)-2-oxo-ethylsulfanyl]-5,6,7,8-tetrahydro-naphthalen-1-yloxy}-acetic acid | 385.37 | m − 1 |
| 204 | [2,6-Dimethyl-4-(4-trifluoromethyl-benzylsulfanyl)-phenoxy]-acetic acid | 369.31 | m − 1 |
| 205 | {4-[2-(4-Acetyl-phenyl)-ethylsulfanyl]-2,5-dimethyl-phenoxy}-acetic acid | 359.35 | m + 1 |
| 206 | [2,6-Dimethyl-4-(2-oxo-2-p-tolyl-ethylsulfanyl)-phenoxy]-acetic acid | 343.32 | m − 1 |
| 207 | {4-[5-(7-Chloro-quinolin-4-ylamino)-pentylsulfanyl]-2-methyl-phenoxy}-acetic acid | 445.21 | m + 1 |

The preparation of Examples 101–207 is further described below.

Preparation of Thiols Used in Combinatorial Methods

Thiol A

Step 1. Preparation of 5-Methoxy-2-methyl-phenol (Compound TAA)

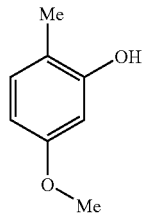

TAA

2-Hydroxy-4-methoxy-benzaldehyde (3 g, 19.7 mmol), ammonium formate (6.2 g, 99 mmol) and palladium/carbon (900 mg @ 10%) were added to 26 ml glacial acetic acid and heated at 110° C. for 1 h. The reaction was cooled, filtered, and diluted with water (100 ml). The crude product was extracted with chloroform (3×50 ml), washed with water, brine, and dried over anhydrous sodium sulfate. The resulting solution was concentrated and used for the next step without further purification. MS m/z 139 (M+1).

Step 2. Preparation of 5-Methoxy-2-methyl-4-thiocyanato-phenol (Compound TAB)

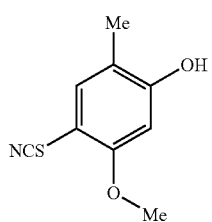

TAB

The product from Example TAA (3.5 g, 25 mmol), sodium thiocyanate (6.48 g, 80 mmol), and sodium bromide (2.6 g, 25 mmol) were dissolved in 30 ml anhydrous methanol. Bromine (4.4 g, 28 mmol) was added drop wise over 15 minutes and allowed to stir at ambient temperature for 1 h. Brine was added (50 ml) and the crude product was extracted into ethyl acetate (3×100 ml). The combined organic extracts were washed with brine, dried over anhydrous sodium sulfate, decanted, and concentrated to afford the title product in good purity. 400 MHz $^1$H NMR (DMSO-$d_6$) δ 10.13 (s, 1H), 7.25 (s, 1H), 6.54 (s, 1H), 3.77 (s, 3H), 2.0 (s, 3H); MS m/z 196 (M+1).

Step 3. Preparation of (5-Methoxy-2-methyl-4-thiocyanato-phenoxy)-acetic acid methyl ester (Compound TAC)

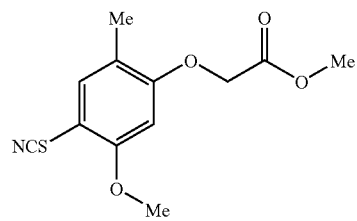

TAC

The product from Example TAB (620 mg, 3.2 mmol), methyl bromoacetate (854 mg, 3.5 mmol), and cesium carbonate (3.1 g, 9.6 mmol) were stirred in 10 ml anhydrous acetonitrile at ambient temperature for 1 h. The reaction was filtered through Celite®, concentrated, and purified using normal phase chromatography. 400 MHz $^1$H NMR (DMSO-$d_6$) δ 7.33 (s, 1H), 6.72 (s, 1H), 4.93 (s, 2H), 3.84 (s, 3H), 3.66 (s, 3H), 2.09 (s, 3H); MS m/z 268 (M+1).

Step 4. Preparation of (4-Mercapto-5-methoxy-2-methyl-phenoxy)-acetic acid methyl ester (Compound TA)

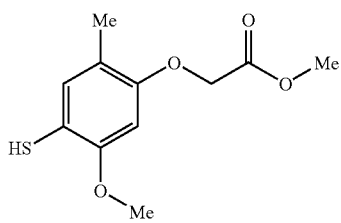

TA

The product from Example TAC (1.1 g, 4.1 mmol) and dithiothreitol (824 mg, 5.4 mmol) were dissolved in 20 ml methanol with 2.5 ml water. The solution was refluxed for 4 h, cooled, concentrated, and purified by normal phase chromatography. 400 MHz $^1$H NMR (DMSO-$d_6$) δ 7.02 (s, 1H), 6.54 (s, 1H), 4.79 (s, 2H), 4.41 (s, 1H), 3.72 (s, 3H), 3.64 (s, 3H), 2.02 (s, 3H); MS m/z 243 (M+1).

Thiol B

Step 1. Preparation of 2-Methyl-4-thiocyanato-phenol (Compound TBA)

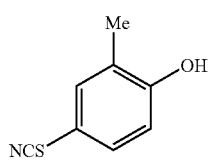

TBA

The title compound was prepared in a manner analogous to Example TAB from 2-methylphenol. 400 MHz $^1$H NMR (DMSO-$d_6$) δ 10.09 (s, 1H), 7.36 (s, 1H), 7.30 (d, 1H, J=8.1 Hz), 6.83 (d, 1H, J=8.1 Hz), 2.08 (s, 3H); MS m/z 166 (M+1).

Step 2. Preparation of (2-Methyl-4-thiocyanato-phenoxy)-acetic acid methyl ester (Compound TBB)

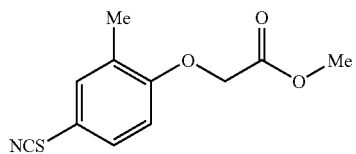

TBB

The title compound was prepared from Example TBA in a manner analogous to Example TAC. 400 MHz $^1$H NMR (DMSO-$d_6$) δ 7.46 (s, 1H), 6.95 (d, 1H, J=8.5 Hz), 6.80 (d, 1H, J=8.5 Hz), 4.86 (s, 2H), 3.65 (s, 3H), 2.17 (s, 3H); MS m/z 238 (M+1).

Step 3. Preparation of (4-Mercapto-2-methyl-phenoxy)-acetic acid methyl ester (Compound TB)

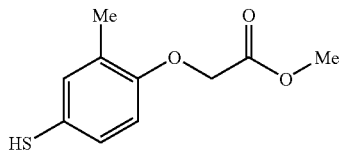

TB

The title compound was prepared from (2-methyl-4-thiocyanato-phenoxy)-acetic acid methyl ester in a manner analogous to Example TA. 400 MHz $^1$H NMR (DMSO-$d_6$) δ 7.05 (s, 1H), 7.00 (d, 1H, J=10.3 Hz), 6.70 (d, 1H, J=10.3 Hz), 5.00 (s, 1H), 4.73 (s, 1H), 3.63 (s, 3H), 2.09 (s, 3H); MS m/z 213 (M+1).

Thiol C

Preparation of 2,5-Dimethyl-4-thiocyanato-phenol (Compound TCA)

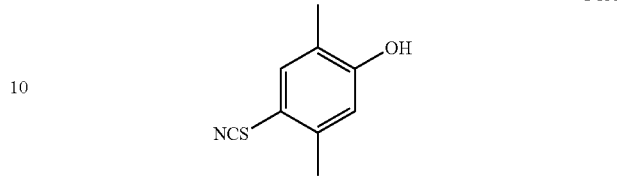

The title compound was prepared in a manner analogous to compound TAB. 400 MHz $^1$H NMR (DMSO-$d_6$) δ 10.0 (s, 1H), 7.35 (s, 1H), 6.73 (s, 1H), 2.3 (s, 3H), 2.04 (s, 3H); MS m/z 180 (m+1).

Preparation of (2,5-Dimethyl-4-thiocyanato-phenoxy)-acetic acid methyl ester (Compound TCB)

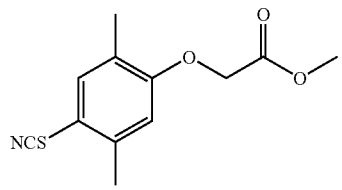

TCB

The title compound was prepared from compound TCA in a manner analogous to compound TAC. 400 MHz $^1$H NMR (DMSO-$d_6$) δ 7.07 (s, 1H), 6.50 (s, 1H), 4.56 (s, 2H), 3.76 (s, 3H), (s, 1H), 2.26 (s, 3H), 2.17 (s, 3H); MS m/z 252 (m+1).

Preparation of (4-Mercapto-2,5-dimethyl-phenoxy)-acetic acid methyl ester (Compound TC)

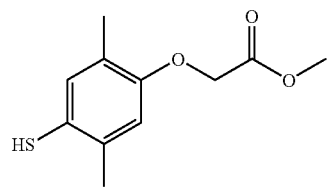

TC

The title compound was prepared from compound TCB in a manner analogous to compound TA 400 MHz $^1$H NMR (DMSO-$d_6$) δ 7.07 (s, 1H), 6.50 (s, 1H), 4.56 (s, 2H), 3.76 (s, 3H), 3.07 (s, 1H), 2.26 (s, 3H), 2.17 (s, 3H); MS m/z 227 (M+1).

Thiol D

Preparation of 2,6-Dimethyl-4-thiocyanato-phenol (Compound DA)

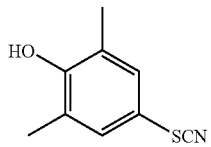

TDA

Compound TDA was prepared from 2,6-dimethylphenol in a similar manner as described for compound TAB. 400 MHz $^1$H NMR (DMSO-d$_6$) δ 8.96 (s, 1H), 7.22 (s, 2H), 2.13 (s, 6H).

Preparation of (2,6-Dimethyl-4-thiocyanato-phenoxy)-acetic acid methyl ester (Compound TDB)

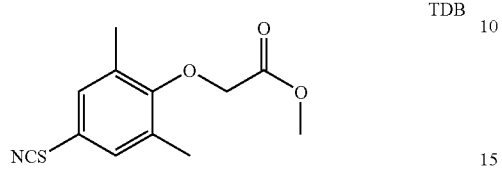

Compound TDB was prepared from compound TDA in a similar manner as described for compound TAC to give 2.5 g (46%) of the title compound pure enough for subsequent use. 400 MHz $^1$H NMR (DMSO-d$_6$) δ 7.11 (s, 2H), 4.41 (s, 2H), 3.63 (s, 3H), 2.14 (s, 6H).

Preparation of (4-Mercapto-2,6-dimethyl-phenoxy)-acetic acid methyl ester (Compound TD)

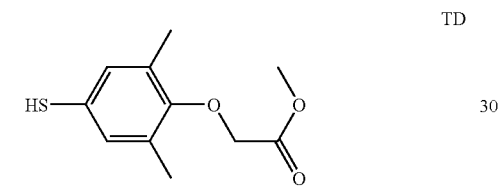

Compound TD was prepared from compound TDB in a similar manner as described for compound TA to give, after purification by flash column chromatography (gradient elution: 100% hexanes to 30% EtOAc/hexanes), 1.8 g (82%) of the title compound. 400 MHz $^1$H NMR (DMSO-d$_6$) δ 6.90 (s, 2H), 5.51 (s, 1H), 4.39 (s, 2H), 3.66 (s, 3H), 2.10 (s, 6H); MS m/z 225 (M−1).

Thiol E

Preparation of 4-Thiocyanato-5,6,7,8-tetrahydro-naphthalen-1-ol (Compound TEA)

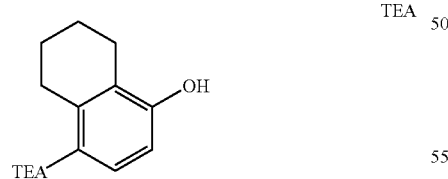

5,6,7,8-Tetrahydro-naphthalen-1-ol (1 g, 6.8 mmol) was dissolved in 25 ml acetonitrile. Sodium thiocyanate (1.76 g, 22 mmol) and sodium bromide (0.7 g, 6.8 mmol) were added and stirred for 5 minutes at ambient temperature. Bromine (1.2 g, 7.48 mmol) was added drop wise over 5 minutes. The orange solution was allowed to stir two hours. Brine was added and the crude product was extracted twice into ethyl acetate. The combined organic extracts were washed once with brine, dried over anhydrous sodium sulfate, decanted and concentrated. Normal phase chromatography afforded the title product, 1.28 g, 92%. 400 MHz $^1$H NMR (DMSO-d$_6$) δ 11.1 (s, 1H), 7.40 (d, 1H, J=8.8 Hz), 6.61 (d, 1H, 8.8 Hz), 2.78 (m, 2H), 2.59 (m, 2H), 1.70 (m, 4H). MS m/z 278 (m+1)

Preparation of (4-Thiocyanato-5,6,7,8-tetrahydro-naphthalen-1-yloxy)-acetic acid methyl ester (Compound TEB)

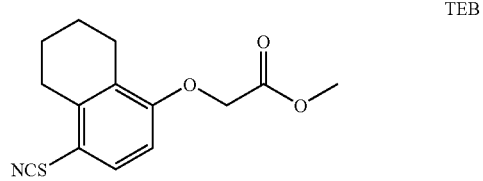

The title compound was prepared in the manner analogous to example TAC utilizing compound TEA. 400 MHz $^1$H NMR (DMSO-d$_6$) δ 7.4 (d, 1H, J=8.8 Hz), 6.80 (d, 1H, 8.8 Hz), 4.84 (s, 2H), 3.64 (s, 3H), 2.78 (m, 2H), 2.59 (m, 2H), 1.70 (m, 4H). MS m/z 278 (m+1).

Preparation of (4-Mercapto-5,6,7,8-tetrahydro-naphthalen-1-yloxy)-acetic acid methyl ester (Compound TE)

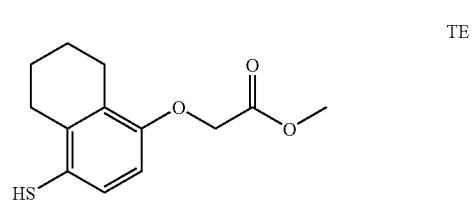

The title compound was prepared in the manner analogous to example TA utilizing compound TEB. 400 MHz $^1$H NMR (DMSO-d$_6$) δ 7.08 (d, 1H, J=8.8 Hz), 6.55 (d, 1H, 8.8 Hz), 4.71 (s, 1H), 4.70 (s, 2H), 3.63 (s, 3H), 2.45 (m, 2H), 2.44 (m, 2H), 1.65 (m, 4H). MS m/z 253 (M+1).

Thiol F

Preparation of 4-Thiocyanato-phenol (Compound TFA)

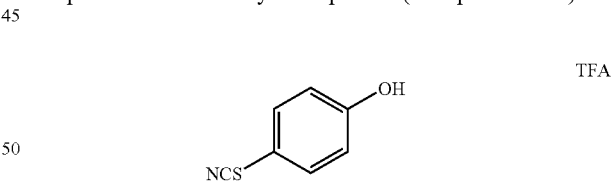

The title compound was prepared in the manner analogous to Example TAB using phenol. MS m/z 152 (M+1)

Preparation of [(4-Thiocyanato-phenoxy)-acetic acid methyl ester (Compound TFB)

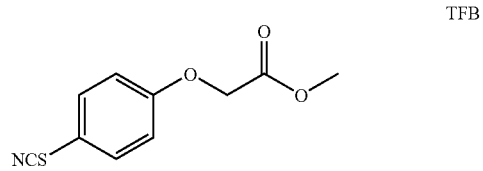

The title compound was prepared in the manner analogous to Example TAC using TFA. MS m/z 224 (M+1)

Preparation of (4-Mercapto-phenoxy)-acetic acid methyl ester (Compound TF)

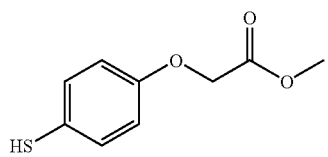

TF

The title compound was prepared in the manner analogous to Example A using TFB. MS m/z 197 (M−1)

Preparation of Examples 101–207

Alcohol Preparation:

The appropriate alcohols in the salt form (0.65 mmol) were dissolved in 3.0 mL of low water MeOH. MP-CO$_3$ (3.21 mmol/g, 3.70 equivalents to alcohol, 2.41 mmol) was then added to each vial containing the alcohol and shaken at ambient temperature for 3 h. The samples were then filtered into tared vials and concentrated.

Alcohol Activation:

Each alcohol sample was then diluted to 0.15M with DCM and 1.0 mL of each delivered to a reaction tube. PS-morpholine (4.0 mmol/g, 2 equivalents to alcohol, 0.3 mmol) and 25 µL methanesulfonyl chloride was then added to each reaction tube. The reaction tubes were shaken at ambient temperature for 16 h. The samples were then filtered into collection tubes, the resin rinsed with two 1.0 mL aliquots of DCM, and concentrated.

Alkylation:

Examples 101–207 were synthesized in the following fashion using either the thio]products TA-TF and the appropriate activated alcohol or alkyl halide. Each thiol was diluted to 0.15M with CH$_3$CN and each activated alcohol diluted to 0.15M with CH$_3$CN. 1.0 mL aliquots of each thiol (0.15 mmol) and 1.0 mL of each activated alcohol (1.0 equivalents, 0.15 mmol) were then delivered to a reaction tube and 100 mg Cs$_2$CO$_3$ (2 equivalents, 0.3 mmol) was added. The reaction tubes were shaken at 60° C. for 2.5 h. The reaction mixtures were filtered into collection tubes, the resin rinsed with two 1.0 mL aliquots of CH$_3$CN, and concentrated.

Saponification:

Examples 101–207 were synthesized in the following fashion using the products from the alkylation step discussed above. Each alkylation product was diluted with 3.0 mL of 0.5M LiOH in 4:1 methoxyethanol:H$_2$O, shaken at 60° C. for 4 h and cooled to ambient temperature. To each reaction, was then added 1.0 mL 1N HCl and 1.0 mL brine. Each reaction was extracted twice with 2.0 mL EtOAc, and the organic layers concentrated to afford the desired products.

Biological Assays

The compounds of the present invention have demonstrated PPAR modulating activity in the standard assays commonly employed by those skilled in the art. Accordingly, such compounds and formulations comprising such compounds are useful for treating, preventing or controlling dyslipidemia in a mammal.

A. Selectivity Measurements

1. Test A. Transient Transfections Assay Using the HepG2 Hepatoma Cell Line.

HepG2 cells were transiently transfected with an expression plasmids encoding hPPARα, hPPARβ or mPPARγ chimeric receptors and a reporter containing the yeast upstream activating sequence (UAS) upstream of the viral E1B promoter controlling a luciferase reporter gene. In addition, the plasmid pRSVβ-gal was used to control for transfection efficiency. HepG2 cells were grown in DMEM supplemented with 10% FBS and 1 µM non-essential amino acid. On the first day, cells were split into 100 mm dishes at 2.5×10$^6$/dish and incubated overnight at 37C.°/5% CO$_2$. On the second day the cells were transiently transfected with plasmid DNA encoding a chimeric receptor, the luciferase reporter gene; and β-gal. For each 100 mm dish, 15 µg of luciferase reporter (PG5E1b) DNA, 15 µg of Gal4-PPAR chimeric receptor DNA, and 1.5 µg of β-gal plasmid DNA were mixed with 1.4 ml of opti-MEM in the tube. 281 µl of LipoFectamine-2000 reagent was added to 1.4 ml of opti-MEM in the tube, and incubate for 5 min at RT. The diluted Lipofectamine-2000 reagent was combined with the DNA mixture, and incubate for 20 min at RT. After fresh medium was added to each 100 mm dish of cells, 2.8 ml of Lipofectamine2000-DNA mixture was added dropwise to the 100 mm dish containing 14 ml of medium, and incubate 37° C. overnight. On day three cells were trypsinized off the 100 mm dishes and re-plated on 96 well plates. Cells were plated at 2.5×10$^4$ cells per well in 150 µl of media and 5011 of compound diluted by media was added. The concentrations of reference agents and test compound added were in the range from 50 µM to 50 µM. After addition of compounds, the plates were incubated at 37C° for 24 hours. Subsequently cells were washed once with 100 µl of PBS, lysed, and processed for measuring luciferase and β-gal activity using Dual-Light luciferase kit from Tropix®, according to the manufacturer's recommendations, on an EG&G Bethold MicroLumat LB96P luminometer. Hep G2-hBeta EC$_{50}$ values ("EC$_{50}$β") and Hep G2-hAlpha EC$_{50}$. values, ("EC$_{50}$α") were obtained using the GraphPad Prism™ program. EC$_{50}$ is the concentration at which the PPAR mediated transcriptional response reaches one-half of its maximal response. Surprisingly, the compounds of the present invention exhibit activity for both PPARα and PPARβ. Accordingly, the compounds of the present invention should find considerable therapeutic applications for inter alia hypercholesterolemia and hyperlipidemia.

Compounds of the invention exhibit a range of EC$_{50}$β values of less than about 21,650 nM. Preferred compounds of the invention exhibit a range of EC$_{50}$β values of less than about 12,410 nM. See, for example, Compound 10-Example 10 which has an EC$_{50}$β of 6660 nM. more preferred compounds of the invention exhibit a range EC$_{50}$β values of less than about 1073 nM. See, for example, Compound 21-Example 21 which has an EC$_{50}$β of 303 nM. Compounds of the present invention exhibit a range of EC$_{50}$α values of less than about 15,000 nM. See, for example, Compound 36-Example 36 which has an EC$_{50}$α of 1962 nM. Further, compounds of the invention exhibit a range of α/β (EC$_{50}$α/EC$_{50}$β) selectivity values of between about 0.2 and about 1,000.

2. Test B. Radioligand Binding Assay

The ability of a compound to interact with PPARβ can be determined using a competition-based receptor binding assay that employs a radiolabeled PPARβ ligand together with a fragment of the PPARβ receptor containing the ligand binding domain (LBD) fused to the protein glutathione-S-transferase (GST).

[1] Preparation of PPARβ LBD-GST fusion protein. The ligand binding domain of the human PPARβ LBD-GST fusion protein can be expressed in *E. coli* and purified as outlined below. DNA encoding the LBD of human PPARβ is amplified via PCR and inserted in-frame into the bacterial expression vector pGEX-2t PPARβ LBD-GST fusion proteins are expressed in BL21(DE3)pLysS cells. After a 1–2 hr incubation with up to 1 mM IPTG, the cells are lysed by freeze-thaw in buffer containing 50 mM Tris (pH=8), 250 mM KCl, 10 mM DTT, 1 mM PMSF, and 1% triton X-100. After room temperature DNAse and RNAse treatment for 15 min and centrifugation for 1 hr at 50,000×g, 1.5 ml of a glutathione-Sepharose 4B slurry in PBS is added to the resulting supernatant and the mixture is incubated at room temperature for 30 min. PPARβ LBD-GST fusion protein glutathione-Sepharose 4B complexes are collected by centrifugation and washed twice in buffer containing 10 mM Tris (pH=8), 50 mM KCl, and 1 mM DTT. PPARβ LBD-GST fusion proteins are eluted from the glutathione-Sepharose 4B with glutathione-elution buffer.

[2] Assessment of the ability of a compound to interact with PPARβ. A competition-based receptor binding assay for measuring interaction of a compound with PPARβ can be conducted as outlined below. Volumes of 99 μl of buffer (50 mM Tris, 10% Glycerol, 10 mM Na-Molybdate, pH 7.6) containing 50 nM $^3$ of radiolabelled compound, tritiated 4-(3-(2-propyl-3-hydroxy-4-acetyl-phenoxy)propyloxy)-phenoxy acetic acid (34Ci/mmol), 0.2 mg rabbit anti-beads, 0.24 μg rabbit anti-GST and 0.2 μg purified GST/PPARβhLBD are placed into the wells of Corning 96-well tissue culture plates. To each well are then added 1 μL of DMSO (control), or 1 μl of DMSO containing 20 μM of non-radiolabeled compound, 4-(3-(2-propyl-3-hydroxy-4-acetyl-phenoxy)propyloxy)-phenoxy acetic acid, for assessment of nonspecific binding, or 1 μl of DMSO containing a test compound at a concentration sufficient to give a final assay concentration of between 1 nM and 100 μM. After incubation with shaking at room temperature for 30 minutes, radioactivity bound to the PPARβ LBD-GST fusion protein/anti-GST/SPA antibody-binding bead complex is assessed using a Wallac MicroBeta plate reader. The potency of interaction of a compound with the PPARβ LBD is determined as the concentration that inhibits 50% of the interaction between the PPARβ LBD and the radiolabeled ligand ("$IC_{50}β$"). A similar procedure was used to asses the ability of a compound to interact with PPARαLBD ("$IC_{50}α$").

Compounds of the present invention exhibit a range of $IC_{50}β$ values of less than about 9344 nM. Preferred compounds of the invention exhibit a range of $IC_{50}β$ values of less than about 2528 nM. See, for example, Compound 21-Example 21 which has an $IC_{50}β$ of 449 nM. more preferred compounds of the invention exhibit a range of $IC_{50}β$ values of less than about 43 nM. See, for example, Compound 31-Example 31 which has an $IC_{50}β$ of 6.8 nM. Compounds of the invention exhibit a range of $IC_{50}α$ of less than about 15,000 nM. See, for example, Compound 27-Example 27 which has an $IC_{50}α$ of 3537 nM. Further, compounds of the invention exhibit a range of α/β ($IC_{50}α/IC_{50}β$) selectivity values of between about 0.3 and about 1,000.

Formulations

The compounds of the present invention including those exemplified herein and all compounds of Formulas I through IV, hereafter referred to as "compound(s)" can be administered alone or in combination with one or more therapeutic agents. These include, for example, other agents for treating, preventing or controlling dyslipidemia, non-insulin dependent diabetes mellitus, obesity, hyperglycemia, hypercholesteremia, hyperlipidemia, atherosclerosis, hypertriglyceridemia, or hyperinsulinemia.

The compounds are thus well suited to formulation for convenient administration to mammals for the prevention and treatment of such disorders.

The following examples further illustrate typical formulations of the compounds provided by the invention.

Formulation 1

| Ingredient | Amount |
| --- | --- |
| compound | 0.5 to 800 mg |
| sodium benzoate | 5 mg |
| isotonic saline | 1000 mL |

The above ingredients are mixed and dissolved in the saline for IV administration to a patient.

Formulation 2

| Ingredient | Amount |
| --- | --- |
| compound | 0.5 to 800 mg |
| cellulose, microcrystalline | 400 mg |
| stearic acid | 5 mg |
| silicon dioxide | 10 mg |
| sugar, confectionery | 50 mg |

The ingredients are blended to uniformity and pressed into a tablet that is well suited for oral administration to a patient.

Formulation 3

| Ingredient | Amount |
| --- | --- |
| compound | 0.5 to 800 mg |
| starch, dried | 250 mg |
| magnesium stearate | 10 mg |

The ingredients are combined and milled to afford material suitable for filling hard gelatin capsules administered to a patient.

Formulation 4

| Ingredient | Amount % wt./(total wt.) |
|---|---|
| compound | 1 to 50 |
| Polyethylene glycol 1000 | 32 to 75 |
| Polyethylene glycol 4000 | 16 to 25 |

The ingredients are combined via melting and then poured into molds containing 2.5 g total weight.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound having a Formula (I),

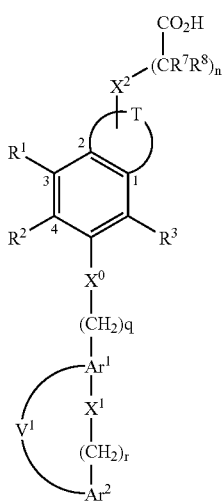

Formula I a pharmaceutically acceptable salt, ester, amide or prodrug thereof, or a pharmaceutically acceptable salt of the prodrug wherein:

$X^0$ and $X^1$ are each independently absent, O, S, $NR^4$, —$CH_2$—$CH_2$—, —CH=CH, or —C≡C—;

$Ar^1$ and $Ar^2$ are each independently absent or unsubstituted or substituted aryl or heteroaryl,

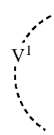

is absent; or when present,

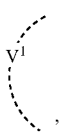

is a saturated or unsaturated hydrocarbon chain which is substituted or unsubstituted, wherein said chain has from 1 to 4 atoms so that

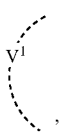

$Ar^1$, $X^1$, $(CH_2)_r$ and $Ar^2$, together form a five to eight membered ring;

T is a saturated or unsaturated, substituted or unsubstituted hydrocarbon chain or hydrocarbon-heteroatom chain having from 3 to 6 atoms wherein the carbon atom of position 1 is connected to the carbon atom of position 2 to form a five to eight member ring wherein the

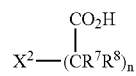

is attached to a substitutionally available position of said ring;

$X^2$ is absent, O, S, or $NR^4$;

$R^1$, $R^2$, and $R^3$ are independently hydrogen, lower alkyl, lower alkoxy, lower thioalkoxy, —$O(CH_2)_pCF_3$, halogen, nitro, cyano, —OH, —SH, —$CF_3$, $S(O)_p$Alkyl, $S(O)_p$Aryl, —$(CH_2)_mOR^4$, or —$(CH_2)_mNR^5R^6$, $COR^4$, —$CONR^5R^6$, —$CO_2R^4$, or —$NR^5R^6$ or $R^1$ and $R^2$ are joined together to form a substituted or unsubstituted, saturated or unsaturated cyloalkyl or heterocycloalkyl ring;

$R^4$ is hydrogen, alkyl, alkenyl, alkynyl, acyl, $SO_2$Aryl, $SO_2$Alkyl or aryl;

$R^5$ and $R^6$ are independently hydrogen, alkyl, alkenyl, alkynyl, cycloalkyl, $SO_2$Alkyl aryl or $SO_2$Aryl, or joined together to form a 4 to 7 member ring having 0 to 3 heteroatoms;

$R^7$ and $R^8$ are independently H, lower alkyl, halo, or $R^7$ and $R^8$ taken together form a 3–6 membered hydrocarbon ring, optionally containing a heteroatom;

m is an integer from 0 to 5;

n is an integer from 0 to 5;

p is an integer from 0 to 2;

q is an integer from 0 to 10; and r is an integer from 0 to 10.

2. A compound having a Formula II,

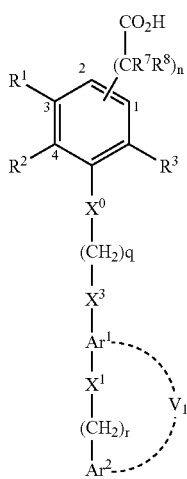
Formula (II)

a pharmaceutically acceptable salt, ester, amide or prodrug thereof or a pharmaceutically acceptable salt of the prodrug wherein:

$X^3$ is O, C=O, S, CHOR$^{11}$ where R$^{11}$ is lower alkyl, aryl, acyl, —SO$_2$alkyl- or —SO$_2$aryl, absent or NR$^4$; R$^1$, R$^2$, and R$^3$ are independently hydrogen, lower alkyl, lower alkoxy, lower thioalkoxy, —O(CH$_2$)$_p$CF$_3$, halogen, nitro, cyano, —OH, —SH, —CF$_3$, S(O)$_p$Alkyl, S(O)$_p$Aryl, —(CH$_2$)$_m$OR$^4$, or —(CH$_2$)$_m$NR$^5$R$^6$, COR$^4$, —CONR$^5$R$^6$, —CO$_2$R$^4$, or —NR$^5$R$^6$ or R$^1$ and R$^2$ are joined together to form a substituted or unsubstituted, saturated or unsaturated cyloalkyl or heterocycloalkyl ring;

R$^4$ is hydrogen, alkyl, alkenyl, alkynyl, acyl, SO$_2$Aryl, SO$_2$Alkyl or aryl;

R$^5$ and R$^6$ are independently hydrogen, alkyl, alkenyl, alkynyl, cycloalkyl, SO$_2$Alkyl aryl or SO$_2$Aryl, or joined together to form a 4 to 7 member ring having 0 to 3 heteroatoms;

R$^7$ and R$^8$ are independently H, lower alkyl, halo, or R$^7$ and R$^8$ taken together form a 3–6 membered hydrocarbon ring, optionally containing a heteroatom;

$X^0$ and $X^1$ are each independently absent, O, S, NR$^4$, —CH$_2$—CH$_2$—, —CH=CH, or —C≡C—; $X^2$ is absent, O, S, or NR$^4$;

Ar$^1$ and Ar$^2$ are each independently absent or unsubstituted or substituted aryl or heteroaryl,

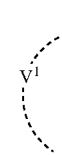

is absent; or when present,

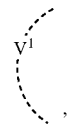

is a saturated or unsaturated hydrocarbon chain which is substituted or unsubstituted, wherein said chain has from 1 to 4 atoms so that

Ar$^1$, X$^1$, (CH$_2$)$_r$ and Ar$^2$, together form a five to eight membered ring;

n is an integer from 0 to 5; q is an integer from 0 to 10; and r is an integer from 0 to 10.

3. A compound of claim 1, the pharmaceutically acceptable salt, ester, amide or prodrug thereof, or the pharmaceutically acceptable salt of the prodrug, wherein:

$X^0$ is S or O;

$X^1$ is absent, O or S;

Ar$^1$ and Ar$^2$ are each independently absent, or unsubstituted or substituted aryl or heteroaryl;

is absent;

q is 1; and r is 0 or 1.

4. A compound of claim 1, the pharmaceutically acceptable salt, ester, amide or prodrug thereof, or the pharmaceutically acceptable salt of the prodrug, wherein: $X^0$ is S or O; $X^1$ is O or absent; and Ar$^1$ and Ar$^2$ are each independently unsubstituted or substituted aryl or heteroaryl.

5. A compound of claim 1, the pharmaceutically acceptable salt, ester, amide or prodrug thereof, or the pharmaceutically acceptable salt of the prodrug, wherein:

T is —CH$_2$CH$_2$CO—O—, —CH$_2$—CH$_2$—O—CO—, —CH$_2$—CH$_2$—CH$_2$—CH$_2$—, —HC=CH—HC=CH—, —N=CH—HC=CH—, —HC=N—HC=CH—, —HC=CH—N=CH—, —HC=CH—HC=N—, —CH$_2$—CH$_2$—CH$_2$—, —CH$_2$—CH$_2$—O—CH$_2$—, —CH$_2$—HC=CH—, —CH$_2$CH$_2$—NH—CH$_2$—, —COCH=CH—O—, —O—CH=CH—CO—, —O—CH=CH—, —CH=CH—O—, —O—CH$_2$—CH=CH—, —CH=CH—CH$_2$—O—, —CH$_2$—CH$_2$—CO—NR$^4$, —CH$_2$—CH$_2$—CO—CH$_2$—, —CH$_2$—CH$_2$—NR$^4$—CH$_2$—, —CH$_2$—NR$^4$—CH$_2$—CH$_2$—, —CH=CH—NR$^4$—, —NR$^4$—CH=CH—, —CH=CH—CH$_2$—, —CH$_2$—CH$_2$—NR$^4$—, —NR$^4$—CH$_2$—CH$_2$—, —O—CH$_2$—CH$_2$—, —O—CH$_2$—CH$_2$—CH$_2$—, —CH$_2$—CH$_2$—O—, —CH$_2$—CH$_2$—CH$_2$—O—, —O—CH(CH$_3$)—CH$_2$—CH$_2$—, —CH$_2$—CH$_2$—CH(CH$_3$)—O—, —CH$_2$—CH$_2$—CH$_2$—NR$^4$—, —NR$^4$—CH$_2$—CH$_2$—CH$_2$—, —CH$_2$—CH$_2$—CO—NR$^4$—, —NR$^4$—CO—CH$_2$—CH$_2$—, —O—NR$^4$—CO—, —CO—NR$^4$—O—, —O—CH$_2$—CH$_2$—CH$_2$—, —CH$_2$—CH$_2$—CH$_2$—

O—, —CH$_2$—CH$_2$—NR$^4$—CO—, —CH$_2$—CH$_2$—CH$_2$—CO—, —CO—CH$_2$—CH$_2$—CH$_2$—, —NR$^4$—CO—CH$_2$—CH$_2$—, —CO—NR$^4$—CH$_2$—CH$_2$—, —CH$_2$—CH$_2$—CO—, —CH$_2$—CO—CH$_2$—, —CO—CH$_2$—CH$_2$—, —S—C=C—, —C=C—S—, —S—C—C—, —C—C—S—, —S—C—C—, —C—C—C—S—, —C=C—C—S—, —C—C=C—S—, —S—C=C—C—, or —S—C—C=C—.

6. A compound of claim 1, the pharmaceutically acceptable salt, ester, amide or prodrug thereof, or the pharmaceutically acceptable salt of the prodrug, wherein:
X$^0$ is S;
X$^1$ is absent;
Ar$^1$ is substituted phenyl;
Ar$^2$ is phenyl;

V$^1$ is absent;
q is 1; and
r is 0 or 1.

7. A compound of claim 3, the pharmaceutically acceptable salt, ester, amide or prodrug thereof, or the pharmaceutically acceptable salt of the prodrug, wherein:
T is substituted with 1 or more substituents selected from the group consisting of lower alkyl, lower alkoxy, lower thioalkoxy, —O(CH$_2$)$_{0-2}$CF$_3$, halogen, nitro, cyano, =O, =S, —OH, —SH, —CF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$; and
R' and R" are independently alkyl, akenyl, alkynyl, aryl, or joined together to form a 4 to 7 member ring.

8. A compound of claim 1, the pharmaceutically acceptable salt, ester, amide or prodrug thereof, or the pharmaceutically acceptable salt of the prodrug, wherein q is 1.

9. A compound of claim 1, the pharmaceutically acceptable salt, ester, amide or prodrug thereof, or the pharmaceutically acceptable salt of the prodrug, wherein Ar$^1$ is substituted or unsubstituted phenyl.

10. A compound of claim 1, the pharmaceutically acceptable salt, ester, amide or prodrug thereof, or the pharmaceutically acceptable salt of the prodrug, wherein Ar$^2$ is 4-trifluoromethylphenyl.

11. A compound of claim 1, the pharmaceutically acceptable salt, ester, amide or prodrug thereof, or the pharmaceutically acceptable salt of the prodrug, wherein

V$^1$ is absent.

12. A compound of claim 1, the pharmaceutically acceptable salt, ester, amide or prodrug thereof, or the pharmaceutically acceptable salt of the prodrug, wherein

V$^1$ is (CH$_2$)$_t$ and t is an integer from 1 to 4.

13. A compound of claim 1, the pharmaceutically acceptable salt, ester, amide or prodrug thereof, or the pharmaceutically acceptable salt of the prodrug, wherein

V$^1$ is substituted with at least one substituent selected from the group consisting of lower alkyl, lower alkoxy, lower thioalkoxy, —O(CH$_2$)$_{0-2}$CF$_3$, halogen, nitro, cyano, =O, =S, —OH, —SH, —CF$_3$, —OCF$_3$, —CO$_2$H, —CO$_2$C$_1$–C$_6$ alkyl, —NH$_2$, —NHC$_1$–C$_6$ alkyl, —CONR'R", or —N(C$_1$–C$_6$alkyl)$_2$ where R' and R" are independently alkyl, akenyl, alkynyl, aryl, or joined together to form a 4 to 7 member ring.

14. A pharmaceutical composition comprising a compound of claim 1, the pharmaceutically acceptable salt, ester, amide or prodrug thereof or the pharmaceutically acceptable salt of the prodrug; or a compound of claim 2, the pharmaceutically acceptable salt, ester, amide or prodrug thereof, or the pharmaceutically acceptable salt of the prodrug; and a pharmaceutically acceptable carrier, diluent, or vehicle.

15. A method of treating, preventing or controlling non-insulin dependent diabetes mellitus in a mammal comprising administering to the mammal in need thereof a therapeutically effective amount of a compound of claim 1, the pharmaceutically acceptable salt, ester, amide or prodrug thereof, or the pharmaceutically acceptable salt of the prodrug; or a compound of claim 2, the pharmaceutically acceptable salt, ester, amide or prodrug thereof, or the pharmaceutically acceptable salt of the prodrug.

16. A method of treating, preventing or controlling obesity in a mammal comprising administering to the mammal in need thereof a therapeutically effective amount of a compound of claim 1, the pharmaceutically acceptable salt, ester, amide or prodrug thereof, or the pharmaceutically acceptable salt of the prodrug; or a compound of claim 2, the pharmaceutically acceptable salt, ester, amide or prodrug thereof, or the pharmaceutically acceptable salt of the prodrug.

17. A method of treating, preventing or controlling hyperglycemia in a mammal comprising administering to the mammal in need thereof a therapeutically effective amount of a compound of claim 1, the pharmaceutically acceptable salt, ester, amide or prodrug thereof, or the pharmaceutically acceptable salt of the prodrug; or a compound of claim 2, the pharmaceutically acceptable salt, ester, amide or prodrug thereof, or the pharmaceutically acceptable salt of the prodrug.

18. A method of treating, preventing or controlling hyperlipidemia in a mammal comprising administering to the mammal in need thereof a therapeutically effective amount of a compound of claim 1, the pharmaceutically acceptable salt, ester, amide or prodrug thereof, or the pharmaceutically acceptable salt of the prodrug; or a compound of claim 2, the pharmaceutically acceptable salt, ester, amide or prodrug thereof, or the pharmaceutically acceptable salt of the prodrug.

19. A method of treating, preventing or controlling hypercholesteremia in a mammal comprising administering to the mammal in need thereof a therapeutically effective amount of a compound of claim 1, the pharmaceutically acceptable salt, ester, amide or prodrug thereof, or the pharmaceutically acceptable salt of the prodrug; or a compound of claim 2, the pharmaceutically acceptable salt, ester, amide or prodrug thereof, or the pharmaceutically acceptable salt of the prodrug.

20. A method of treating, preventing or controlling atherosclerosis in a mammal comprising administering to the mammal in need thereof a therapeutically effective amount of a compound of claim 1, the pharmaceutically acceptable salt, ester, amide or prodrug thereof, or the pharmaceutically acceptable salt of the prodrug; or a compound of claim 2, the pharmaceutically acceptable salt, ester, amide or prodrug thereof, or the pharmaceutically acceptable salt of the prodrug.

21. A method of treating, preventing or controlling hypertriglyceridemia in a mammal comprising administering to the mammal in need thereof a therapeutically effective amount of a compound of claim 1, the pharmaceutically acceptable salt, ester, amide or prodrug thereof, or the pharmaceutically acceptable salt of the prodrug; or a compound of claim 2, the pharmaceutically acceptable salt, ester, amide or prodrug thereof, or the pharmaceutically acceptable salt of the prodrug.

22. A method of treating, preventing or controlling hyperinsulinemia in a mammal comprising administering to the mammal in need thereof a therapeutically effective amount of a compound of claim 1, the pharmaceutically acceptable salt, ester, amide or prodrug thereof, or the pharmaceutically acceptable salt of the prodrug; or a compound of claim 2, the pharmaceutically acceptable salt, ester, amide or prodrug thereof, or the pharmaceutically acceptable salt of the prodrug.

23. A method of treating a patient exhibiting glucose disorders associated with circulating glucocorticoids, growth hormone, catecholamines, glucagon, or parathyroid hormone, comprising administering to the patient a therapeutically effective amount of a compound of claim 1, the pharmaceutically acceptable salt, ester, amide or prodrug thereof, or the pharmaceutically acceptable salt of the prodrug; or a compound of claim 2, the pharmaceutically acceptable salt, ester, amide or prodrug thereof, or the pharmaceutically acceptable salt of the prodrug.

24. A compound of claim 2, the pharmaceutically acceptable salt, ester, amide or prodrug thereof, or the pharmaceutically acceptable salt of the prodrug, wherein $X^3$ is $NR^4$ or $C=O$.

25. A compound of claim 2, the pharmaceutically acceptable salt, ester, amide or prodrug thereof, or the pharmaceutically acceptable salt of the prodrug, wherein $Ar^2$ is chloro-phenyl, dichloro-phenyl-, trichlorophenyl, fluorophenyl-, difluorophenyl, trifluorophenyl, trifluoromethylphenyl, or fluoro-trifluoromethyl-phenyl-; and wherein $Ar^1$ is absent.

26. A compound of claim 1 having Formula 1a, Formula 1b, Formula 1c, Formula 1d, Formula 1e, Formula 1f, Formula 1g, or Formula 1h,

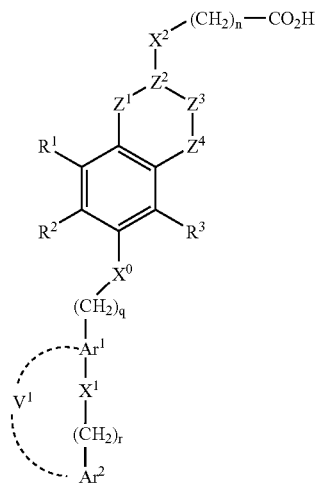

1a

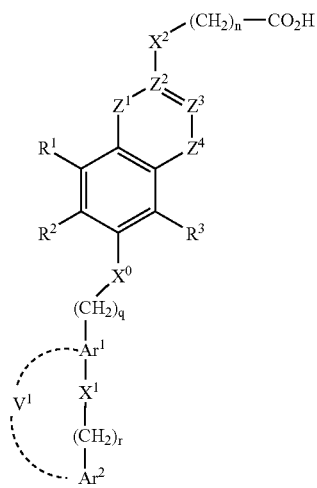

1b

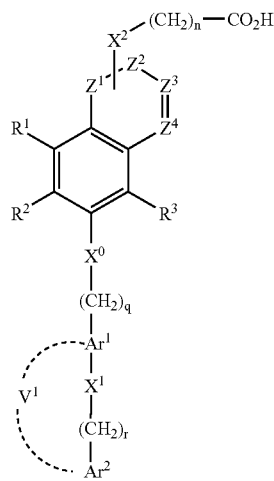

1c

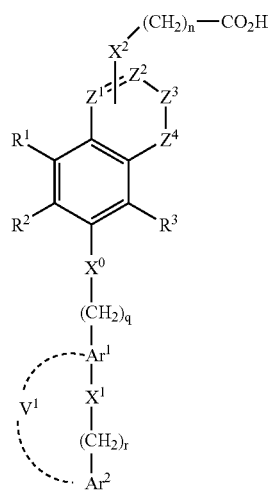

1d

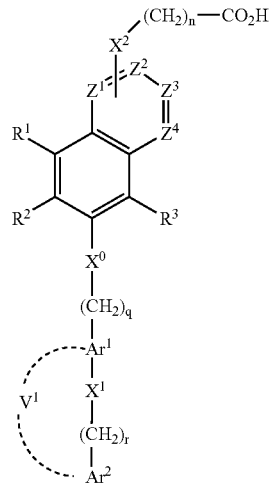

1e

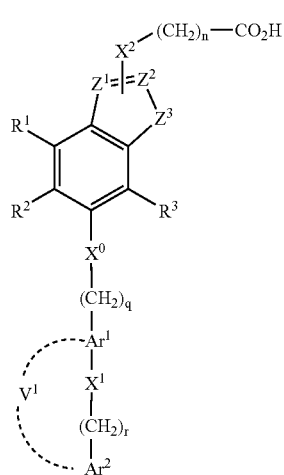

1f

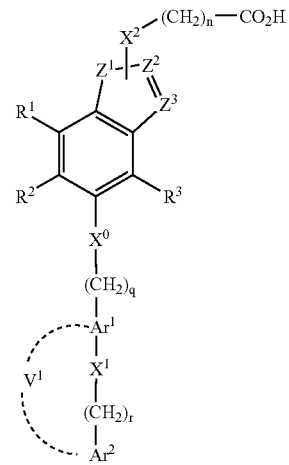

1g

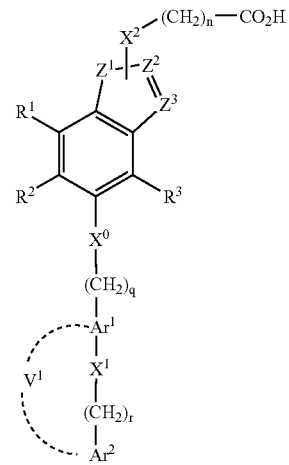

1h or the pharmaceutically acceptable salt, ester, amide or prodrug thereof, or the pharmaceutically acceptable salt of the prodrug wherein:

$X^0$ is O or S;

$X^2$ is absent, O, S, or $NR^4$;

$R^1$, $R^2$, and $R^3$ are independently hydrogen, lower alkyl, lower alkoxy, lower thioalkoxy, —$O(CH_2)_pCF_3$, halogen, nitro, cyano, —OH, —SH, —$CF_3$, $S(O)_p$Alkyl, $S(O)_p$Aryl, —$(CH_2)_mOR^4$, or —$(CH_2)_mNR^5R^6$, $COR^4$, —$CO_2H$, —$CO_2R^4$, or —$NR^5R^6$ or $R^1$ and $R^2$ are joined together to form a substituted or unsubstituted, saturated or unsaturated cyloalkyl or heterocycloalkyl ring;

$R^4$ is hydrogen, alkyl, alkenyl, alkynyl, or aryl;

$R^5$ and $R^6$ are independently hydrogen, alkyl, alkenyl, alkynyl, cycloalkyl, $SO_2$Alkyl or, $SO_2$Aryl, or joined together to form a 4 to 7 member ring having 0 to 3 heteroatoms;

m is an integer from 0 to 5;

n is an integer from 0 to 5;

p is an integer from 0 to 2, $Z^1$, $Z^2$, $Z^3$, and $Z^4$ are independently O, S, $CR^5R^6$, $NR^{11}$, or N;

$R^{11}$ is lower alkyl, acyl, aralkyl, —$SO_2$alkyl, or —$SO_2$Ar, and wherein $Z^1$, $Z^2$, $Z^3$, and $Z^4$ are bonded to a sufficient number of hydrogen atoms or substituents to complete the valency of each atom with the proviso that $Z^1$, $Z^2$, $Z^3$, and $Z^4$ are not all heteroatoms and that not more than two adjacent atoms in $Z^1$, $Z^2$, $Z^3$, and $Z^4$ are heteroatoms and that in Formulae 1b, 1c, 1d, 1f, and 1g, $Z^1$, $Z^2$, $Z^3$, and $Z^4$ are not all carbon atoms; and $X^1$, $Ar^1$, $Ar^2$, $$\overset{\curvearrowleft}{\underset{\cdot\cdot}{V^1}}\,,$$

r and q are as defined in claim 1.

27. A compound of claim 1, the pharmaceutically acceptable salt, ester, amide or prodrug thereof, or the pharmaceutically acceptable salt of the prodrug, wherein:

$R^1$, $R^2$, and $R^3$ are independently hydrogen, alkyl, or alkoxy.

28. A compound of claim 1, the pharmaceutically acceptable salt, ester, amide or prodrug thereof, or the pharmaceutically acceptable salt of the prodrug, wherein:

$R^1$ and $R^3$ are hydrogen; and $R^2$ is alkyl or alkoxy.

29. A compound of claim 1, the pharmaceutically acceptable salt, ester, amide or prodrug thereof, or the pharmaceutically acceptable salt of the prodrug, wherein:

$R^1$ and $R^3$ are hydrogen; and $R^2$ is alkoxy.

30. A compound of claim 1, the pharmaceutically acceptable salt, ester, amide or prodrug thereof, or the pharmaceutically acceptable salt of the prodrug, wherein:

$R^1$ and $R^3$ are independently hydrogen, methyl, ethyl, isopropyl, n-propyl, t-butyl, n-butyl, or isobutyl; and $R^2$ is methyoxy, ethoxy, isopropoxy, n-propoxy, t-butoxy, n-butoxy, or isobutoxy.

31. A compound selected from the group consisting of: [6-(4'-Trifluoromethyl-biphenyl-4-ylmethylsulfanyl)-chroman-2-yl]-acetic acid; {6-[4-(5-Trifluoromethyl-pyridin-2-yl)-benzylsulfanyl]-chroman-2-yl}-acetic acid; {6-[4-(2,5-Dichloro-benzyloxy)-benxylsulfanyl}-chroman-2-yl}-acetic acid; {6-[4-(4-Trifluoromethyl-benzyloxy)-benzylsulfanyl]-chroman-2-yl}-acetic acid; {6-[5-(4-Trifluoromethyl-phenyl)-isoxazol-3-ylmethylsulfany]-chroman-2-yl}-acetic acid; {6-[3-(4-Trifluoromethyl-benzyloxy)-benzylsulfanyl]-chroman-2yl}-acetic acid; {6-[2-(4-Trifluoromethyl-phenyl)-thiazol-4-ylmethoxy]-benzo[b]thiophen-3-yl}-acetic acid; {6-[4-(4-Trifluoromethyl-benzyloxy)-benzyloxy]-benzo[b]thiophen-3-yl}-acetic acid; {6-[2-(4-Trifluoromethyl-benzyloxy)-benzyloxy]-benzo[b]thiophen-3-yl}-acetic acid; and pharmaceutically acceptable salts thereof.

32. A compound having a formula (IA),

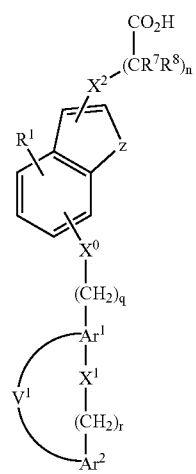

Formula (IA)

a pharmaceutically acceptable salt, ester, amide, or prodrug thereof, or a pharmaceutically acceptable salt of the prodrug wherein:

Z=S, O or $NR^4$, $Ar^1$ and $Ar^2$ are each independently absent or unsubstituted or substituted aryl or heteroaryl, $$\overset{\curvearrowleft}{\underset{\cdot\cdot}{V^1}}$$

is absent; or when present, $$\overset{\curvearrowleft}{\underset{\cdot\cdot}{V^1}}$$

is a saturated or unsaturated hydrocarbon chain which is substituted or unsubstituted, wherein said chain has from 1 to 4 atoms so that $$\overset{\curvearrowleft}{\underset{\cdot\cdot}{V^1}}\,,$$

$Ar^1$, $X^1$, $(CH_2)_r$ and $Ar^2$, together form a five to eight membered ring;

$X^0$ and $X^1$ are each independently absent, O, S, $NR^4$, —$CH_2$—$CH_2$—, —CH=CH, or —C≡C—; $X^2$ is absent, O, S, or $NR^4$; $R^1$ is independently hydrogen, lower alkyl, lower alkoxy, lower thioalkoxy, —$O(CH_2)_p$ $CF_3$, halogen, nitro, cyano, —OH, —SH, —$CF_3$, $S(O)_p$Alkyl, $S(O)_p$Aryl, —$(CH_2)_m OR^4$, —$(CH_2)_m NR^5R^6$, $COR^4$, —$CONR^5R^6$, —$CO_2R^4$, or —$NR^5R^6$;

R⁴ is hydrogen, alkyl, alkenyl, alkynyl, acyl, SO₂Aryl, SO₂Alkyl or aryl;

R⁵ and R⁶ are independently hydrogen, alkyl, alkenyl, alkynyl, cycloalkyl, SO₂Alkyl aryl or SO₂Aryl, or joined together to form a 4 to 7 member ring having 0 to 3 heteroatoms;

R⁷ and R⁸ are independently H, lower alkyl, halo, or R⁷ and R⁸ taken together form a 3–6 membered hydrocarbon ring, optionally containing a heteroatom;

n is an integer from 0 to 5;

q is an integer from 0 to 10; and r is an integer from 0 to 10.

33. A compound selected from the group consisting of: {6-[4-(4-Trifluoromethyl-benzyloxy)-benzyloxy]-benzo[b]thiophen 3-yl}-acetic acid; {6-[5-(4-Trifluoromethyl-phenyl)-isoxazol-3-ylmethoxy]-benzo[b]thiophen-3-yl}-acetic acid; {6-[3-(4-Trifluoromethyl-benzyloxy)-benzyloxy]-benzo[b]thiphen-3-yl}-acetic acid; {6-[2-(4-Trifluoromethyl-phenyl)-thiazol-4-ylmethoxy]-benzo[b]thiophen-3-yl}-acetic acid; {6-[5-(4-Chloro-phenyl)-isoxazol-3-ylmethoxy]-benzo[b]thiophen-3-yl}-acetic acid; and pharmaceutically acceptable salts thereof.

34. A compound of claim 32, the pharmaceutically acceptable amide ester or prodrug thereof, or the pharmaceutically acceptable salt of the prodrug wherein:

X⁰ is oxygen;

X¹ is absent or O;

Ar¹ is a substituted or unsubstituted aryl or heteroaryl;

Ar² is a substituted phenyl;

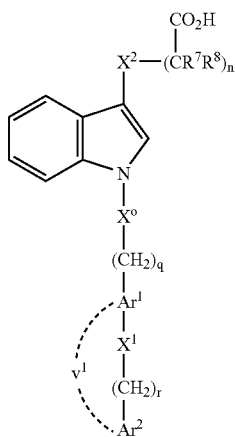

is absent;

X² is absent n is an integer from 0 to 5 q is an integer from 0 to 3; and r is an integer from 0 to 3.

35. A compound having a Formula III,

Formula (III)

a pharmaceutically salt, ester amide or prodrug thereof, or a pharmaceutically acceptable salt of the prodrug wherein:

Ar¹ and Ar² are each independently absent or unsubstituted or substituted aryl or heteroaryl, is absent; or when present, is a saturated or unsaturated hydrocarbon chain which is substituted or unsubstituted, wherein said chain has from 1 to 4 atoms so that Ar¹, X¹, (CH₂)ᵣ and Ar², together form a five to eight membered ring;

X⁰ and X¹ are each independently absent, O, S, NR⁴, —CH₂—CH₂—, —CH=CH, or —C≡C—; X² is absent, O, S, or NR⁴;

R⁴ is hydrogen alkyl, alkenyl, alkynyl, acyl, SO₂Aryl, SO₂Alkyl or aryl;

R⁷ and R⁸ are independently H, lower alkyl, halo, or R⁷ and R⁸ taken together form a 3–6 membered hydrocarbon ring, optionally containing a heteroatom;

n is an integer from 0 to 5;

q is an integer from 0 to 10; and r is an integer from 0 to 10.

36. A compound selected from the group consisting of: 3-{1-[3-(4-Trifluoromethyl-benzyloxy)-benzyl]-1H-indol-3yl}-propionic acid; 3-{1-[4-(4-Trifluoromethyl-benzyloxy)-benzyl]-1H-indol-3-yl}-propionic acid; 3-[1-(4'-Trifluoromethyl-biphenyl-4-ylmethyl)-1H-indol-3-yl]-propionic acid; {1-[3-(4-Trifluoromethyl-benzyloxy)-benzyl]-1H-indol-3-yl}-acetic acid, and pharmaceutically acceptable salts thereof.

37. A compound having a Formula IV,

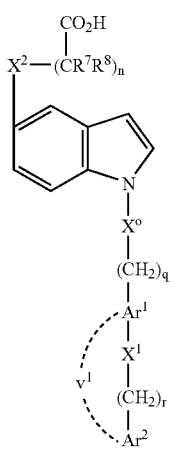

Formula (IV)

a pharmaceutically acceptable salt, ester, amide, or prodrug thereof, or a pharmaceutically acceptable salt of the prodrug wherein:

Ar$^1$ and Ar$^2$ are each independently absent or unsubstituted or substituted aryl or heteroaryl,

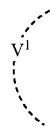

is absent; or when present,

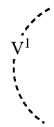

is a saturated or unsaturated hydrocarbon chain which is substituted or unsubstituted, wherein said chain has from 1 to 4 atoms so that

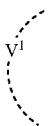

Ar$^1$, X$^1$, (CH$_2$)$_r$ and Ar$^2$, together form a five to eight membered ring;

X$^0$ and X$^1$ are each independently absent, O, S, NR$^4$, —CH$_2$—CH$_2$—, —CH═CH, or —C≡C—; X$^2$ is absent, O, S, or NR$^4$;

R$^4$ is hydrogen alkyl, alkenyl, alkynyl, acyl, SO$_2$Aryl, SO$_2$Alkyl or aryl;

R$^7$ and R$^8$ are independently H, lower alkyl, halo, or R$^7$ and R$^8$ taken together form a 3–6 membered hydrocarbon ring, optionally containing a heteroatom;

n is an integer from 0 to 5;

q is an integer from 0 to 10; and r is an integer from 0 to 10.

38. A compound selected from the group consisting of: [1-(4'-Trifluoromethyl-biphenyl-4-ylmethyl)-1H-indol-5-yloxyl]-acetc acid, [1-(4'-Trifluoromethyl-biphenyl-4-ylmethyl)-1H-indol-4-yloxy]-acetic acid; and pharmaceutically acceptable salts thereof.

39. A compound selected from the group consisting of: [6-(4'-Trifluoromethyl-biphenyl-4-ylmethylsulfanyl)-chroman-2-yl]-acetic acid; {6-[5-(4-Trifluoromethyl-phenyl)-isoxazol-3-ylmethylsulfany]-chroman-2-yl}-acetic acid; {6-[2-(4-Trifluoromethyl-phenyl)-thiazol-4-ylmethoxy]-benzo[b]thiophen-3-yl}-acetic acid; and pharmaceutically acceptable salts thereof.

40. A compound of claim 35, a pharmaceutically acceptable salt, amide, ester or prodrug thereof, or a pharmaceutically acceptable salt of the prodrug wherein:

X$^0$ is absent

X$^1$ is absent or O;

Ar$^1$ is a substituted or unsubstituted phenyl;

Ar$^2$ is 4-trifluoromethyl phenyl;

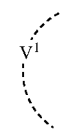

is absent;

X$^2$ is absent, 0, or S;

n is an integer from 0 to 5;

q is an integer from 0 to 3; and r is an integer from 0 to 3.

41. A compound of claim 37, a pharmaceutically acceptable salt, amide, ester, prodrug thereof, or a pharmaceutically acceptable salt of the prodrug, wherein:

X$^0$ and X$^1$ are absent;

Ar$^1$ is a substituted or unsubstituted phenyl;

Ar$^2$ is 4-trifluoromethylphenyl;

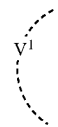

is absent;

X$^2$ is absent, 0 or S;

n is an integer from 0 to 5;

q is an integer from 0 to 3; and r is an integer from 0 to 3.

42. A compound of claim 34, a pharmaceutically acceptable salt, ester, amide or prodrug thereof, or a pharmaceutically acceptable salt of the prodrug, wherein Ar$^2$ is trifluoromethyl-phenyl.

43. A method of making a compound of claim 1 having the Formula (I):

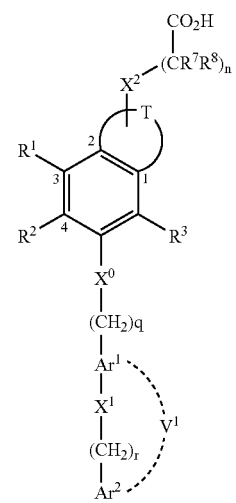

Formula (I)

wherein X$^0$, X$^1$, Ar$^1$, Ar$^2$,

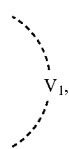

T, $X^2$, $R^1$, $R^2$, $R^3$, $R^4$, $R^5$, $R^6$, $R^7$, $R^8$, m, n, p, q and r are as defined in claim 1, comprising:

reacting a compound of Formula A,

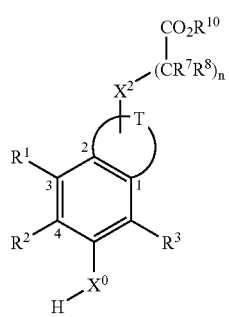

Formula (A)

wherein $R^{10}$ is a lower alkyl, with a compound of Formula B,

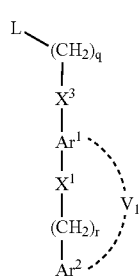

Formula (B)

wherein L is an appropriate leaving group and $X^3$ is absent, to form a compound having a Formula C,

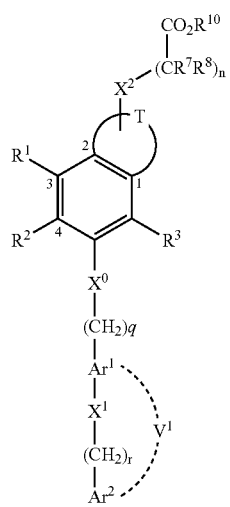

Formula (C)

and subsequently saponifying the compound having a Formula C to form the compound having the Formula I.

44. A compound of claim 32 having the Formula IIB,

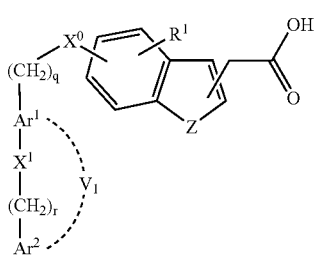

Formula (IIB)

a pharmaceutically acceptable salt, ester, or amide thereof, or a pharmaceutically acceptable salt of the prodrug wherein:

Z is $NR^4$, S, or O; and $R^1$, $R^4$, $X^0$, $X^1$, $Ar^1$, $Ar^2$,

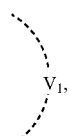

q and r are as defined in claim 32.

45. A method of making a compound of claim 44 having the Formula IIB

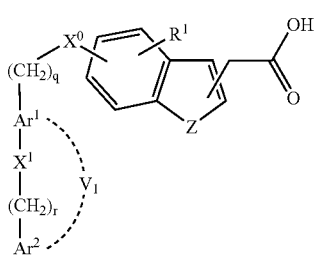

Formula (IIB)

wherein Z, $R^1$, $R^4$, $X^0$, $X^1$, $Ar^1$, $Ar^2$,

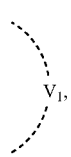

q and r are as defined in claim 45, comprising reacting a compound of Formula H wherein $R^{10}$ is a lower alkyl,

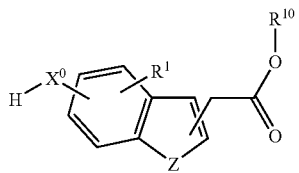

Formula (H)

with a compound of Formula B:

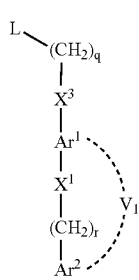

Formula (B)

L = leaving group wherein L is an appropriate leaving group, to form a compound of Formula J:

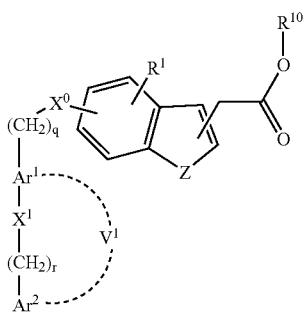

Formula (J)

and subsequently saponifying the compound of Formula J to form the compound IIB.

46. A compound selected from the group consisting of:
{6-[5-(4-Methoxymethyl-phenyl)-isoxazol-3-yl-methoxy]-benzo[b]thiophen-3-yl}-acetic acid;
{6-[5-(3-Methoxymethyl-phenyl)-isoxazol-3-yl-methoxy]-benzo[b]thiophen-3-yl}-acetic acid;
{6-[5-(4-Methanesulfonyloxy-phenyl)-isoxazol-3-yl-methoxy]-benzo[b]thiophen-3-yl}-acetic acid;
{6-[5-(3-Methanesulfonyloxy-phenyl)-isoxazol-3-yl-methoxy]-benzo[b]thiophen-3-yl}-acetic acid;
{6-[5-(4-Methoxymethyl-phenyl)-isoxazol-3-yl-methoxy]-4-methyl-benzo[b]thiophen-3-yl}-acetic acid;
{6-[5-(3-Methoxymethyl-phenyl)-isoxazol-3-yl-methoxy]-4-methyl-benzo[b]thiophen-3-yl}-acetic acid;
{6-[5-(4-Methanesulfonyloxy-phenyl)-isoxazol-3-yl-methoxy]-4-methyl-benzo[b]thiophen-3-yl}-acetic acid;
{6-[5-(3-Methanesulfonyloxy-phenyl)-isoxazol-3-yl-methoxy]-4-methyl-benzo[b]thiophen-3-yl}-acetic acid;
{5-Methoxy-6-[5-(4-methoxymethyl-phenyl)-isoxazol-3-ylmethoxy]-benzo[b]thiophen-3-yl}-acetic acid;
{5-Methoxy-6-[5-(3-methoxymethyl-phenyl)-isoxazol-3-ylmethoxy]-benzo[b]thiophen-3-yl}-acetic acid;
{6-[5-(4-Methanesulfonyloxy-phenyl)-isoxazol-3-yl-methoxy]-5-methoxy-benzo[b]thiophen-3-yl}-acetic acid;
{6-[5-(3-Methanesulfonyloxy-phenyl)-isoxazol-3-yl-methoxy]-5-methoxy-benzo[b]thiophen-3-yl}-acetic acid;
{6-[5-(4-Methoxymethyl-phenyl)-isoxazol-3-yl-methoxy]-benzofuran-3-yl}-acetic acid;
{6-[5-(3-Methoxymethyl-phenyl)-isoxazol-3-yl-methoxy]-benzofuran-3-yl}-acetic acid;
{6-[5-(4-Methanesulfonyloxy-phenyl)-isoxazol-3-yl-methoxy]-benzofuran-3-yl}-acetic acid;
{6-[5-(3-Methanesulfonyloxy-phenyl)-isoxazol-3-yl-methoxy]-benzofuran-3-yl}-acetic acid;
{6-[5-(4-Methoxymethyl-phenyl)-isoxazol-3-yl-methoxy]-4-methyl-benzofuran-3-yl}-acetic acid;
{6-[5-(3-Methoxymethyl-phenyl)-isoxazol-3-yl-methoxy]-4-methyl-benzofuran-3-yl}-acetic acid;
{6-[5-(4-Methanesulfonyloxy-phenyl)-isoxazol-3-yl-methoxy]-4-methyl-benzofuran-3-yl}-acetic acid;
{6-[5-(3-Methanesulfonyloxy-phenyl)-isoxazol-3-yl-methoxy]-4-methyl-benzofuran-3-yl}-acetic acid;
{5-Methoxy-6-[5-(4-methoxymethyl-phenyl)-isoxazol-3-ylmethoxy]-benzofuran-3-yl}-acetic acid;
{5-Methoxy-6-[5-(3-methoxymethyl-phenyl)-isoxazol-3-ylmethoxy]-benzofuran-3-yl}-acetic acid;
{6-[5-(4-Methanesulfonyloxy-phenyl)-isoxazol-3-yl-methoxy]-5-methoxy-benzofuran-3-yl}-acetic acid;
{6-[5-(3-Methanesulfonyloxy-phenyl)-isoxazol-3-yl-methoxy]-5-methoxy-benzofuran-3-yl}-acetic acid;
{7-[5-(4-Methoxymethyl-phenyl)-isoxazol-3-yl-methoxy]-indan-4-yloxy}-acetic acid;
{7-[5-(3-Methoxymethyl-phenyl)-isoxazol-3-yl-methoxy]-indan-4-yloxy}-acetic acid;
{7-[5-(4-Methanesulfonyloxy-phenyl)-isoxazol-3-yl-methoxy]-indan-4-yloxy}-acetic acid;
{7-[5-(3-Methanesulfonyloxy-phenyl)-isoxazol-3-yl-methoxy]-indan-4-yloxy}-acetic acid;
{4-[5-(4-Methoxymethyl-phenyl)-isoxazol-3-yl-methoxy]-2-methyl-phenoxy}-acetic acid;
{4-[5-(3-Methoxymethyl-phenyl)-isoxazol-3-yl-methoxy]-2-methyl-phenoxy}-acetic acid;
{4-[5-(4-Methanesulfonyloxy-phenyl)-isoxazol-3-yl-methoxy]-2-methyl-phenoxy}-acetic acid;
{4-[5-(3-Methanesulfonyloxy-phenyl)-isoxazol-3-yl-methoxy]-2-methyl-phenoxy}-acetic acid; and pharmaceutically acceptable salts thereof.

* * * * *